US008063032B2

(12) United States Patent
Chytil et al.

(10) Patent No.: US 8,063,032 B2
(45) Date of Patent: Nov. 22, 2011

(54) HISTAMINE H3 INVERSE AGONISTS AND ANTAGONISTS AND METHODS OF USE THEREOF

(75) Inventors: Milan Chytil, Clinton, MA (US); Qun Kevin Fang, Wellesley, MA (US); Kerry L. Spear, Concord, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 12/704,460

(22) Filed: Feb. 11, 2010

(65) Prior Publication Data
US 2010/0204214 A1    Aug. 12, 2010

Related U.S. Application Data

(60) Provisional application No. 61/151,817, filed on Feb. 11, 2009, provisional application No. 61/241,840, filed on Sep. 11, 2009.

(51) Int. Cl.
*A61K 31/33* (2006.01)
*A61K 31/55* (2006.01)
*C07D 257/10* (2006.01)
*C07D 487/12* (2006.01)

(52) U.S. Cl. ........ 514/183; 514/219; 514/220; 540/474; 540/554; 540/555; 540/562

(58) Field of Classification Search .................. None
See application file for complete search history.

(56) References Cited

U.S. PATENT DOCUMENTS

| | | | |
|---|---|---|---|
| 2,479,152 A | 8/1949 | Brooker | |
| 3,642,778 A | 2/1972 | Helsley et al. | |
| 4,252,816 A | 2/1981 | Saari et al. | |
| 4,490,463 A | 12/1984 | Gilbert | |
| 5,013,748 A | 5/1991 | Radtke et al. | |
| 5,845,025 A | 12/1998 | Garito et al. | |
| 5,852,191 A | 12/1998 | Karandikar et al. | |
| 5,856,384 A | 1/1999 | Garito et al. | |
| 6,410,550 B1 | 6/2002 | Coe et al. | |
| 6,413,956 B1 | 7/2002 | Albaugh et al. | |
| 6,451,520 B1 | 9/2002 | Odenwalder et al. | |
| 6,515,122 B1 | 2/2003 | Lang et al. | |
| 6,605,610 B1 | 8/2003 | Coe et al. | |
| 7,056,942 B2 * | 6/2006 | Hildesheim et al. | 514/411 |
| 2002/0002161 A1 | 1/2002 | Ennis et al. | |
| 2005/0026910 A1 | 2/2005 | Roush et al. | |
| 2005/0096342 A1 | 5/2005 | Zefirov et al. | |
| 2005/0239767 A1 | 10/2005 | Chan et al. | |
| 2006/0090269 A1 | 5/2006 | Lagrange | |
| 2006/0217370 A1 | 9/2006 | Burstein et al. | |
| 2007/0117834 A1 | 5/2007 | Hung | |
| 2007/0225316 A1 | 9/2007 | Bachurin et al. | |
| 2008/0234310 A1 | 9/2008 | Bachurin et al. | |
| 2009/0042873 A1 | 2/2009 | Dubois et al. | |
| 2009/0163545 A1 | 6/2009 | Goldfarb | |
| 2009/0186879 A1 | 7/2009 | Aso et al. | |
| 2009/0221627 A1 | 9/2009 | Aksinenko et al. | |
| 2009/0239854 A1 | 9/2009 | Hung et al. | |
| 2009/0270412 A1 | 10/2009 | Hung et al. | |
| 2010/0022580 A1 | 1/2010 | Hung et al. | |
| 2010/0056790 A1 | 3/2010 | Aksinenko et al. | |
| 2010/0099667 A1 | 4/2010 | Hung et al. | |
| 2010/0099700 A1 | 4/2010 | Hung | |
| 2010/0120792 A1 | 5/2010 | Ivashchenko et al. | |
| 2010/0152108 A1 | 6/2010 | Hung et al. | |
| 2010/0152163 A1 | 6/2010 | Hung et al. | |
| 2010/0152225 A1 | 6/2010 | Hung | |
| 2010/0178277 A1 | 7/2010 | Hung et al. | |
| 2010/0216814 A1 | 8/2010 | Hung et al. | |
| 2010/0252823 A1 | 10/2010 | Kambe et al. | |
| 2010/0273778 A1 | 10/2010 | Cowart et al. | |
| 2010/0278811 A1 | 11/2010 | Wrasidlo et al. | |
| 2010/0286188 A1 | 11/2010 | Bachurin et al. | |
| 2010/0298287 A1 | 11/2010 | Aso et al. | |
| 2011/0065694 A1 | 3/2011 | Chytil et al. | |

FOREIGN PATENT DOCUMENTS

| | | |
|---|---|---|
| DE | 2231560 | 1/1974 |
| EP | 1990355 | 3/2008 |
| GB | 618889 | 3/1949 |
| JP | 04149180 | 5/1992 |
| JP | 2001022129 | 1/2001 |
| JP | 2005033185 A | 2/2005 |
| JP | 2009203311 | 9/2009 |
| WO | WO 96/29331 | 9/1996 |
| WO | WO 98/43649 | 10/1998 |
| WO | WO 01/98263 | 12/2001 |
| WO | WO 2005/040144 | 5/2005 |
| WO | WO 2006/084833 | 8/2006 |
| WO | WO 2007/065820 | 6/2007 |
| WO | WO 2007/117180 | 10/2007 |
| WO | WO 2008073231 | 6/2008 |

(Continued)

OTHER PUBLICATIONS

Agundez et al., 2008, "Nonsynonymous Polymorphisms of Histamine-Metabolising Enzymes in Patients with Parkinson's Disease," Neuromol. Med., 10, 10-16.

Alcalde et al., 1992, "Heterocyclic Betaines, Novel Ethyleneimidazolium Benzimidazolate Inner Salts. Synthesis, Characterization, and Transformation into 2-Vinyl-1H-benzimidazoles," Chem. Lett., 2357-60.

Alcalde et al., 1996, "Synthesis of Dipolar Ethyleneimidazolium Benzimidazolate Inner Salts and Their Transformation to 2-Vinylbenzimidazoles Through a Type of β-Elimination Reaction," Heterocycles, 43(3), 567-80.

(Continued)

*Primary Examiner* — Noble Jarrell

(57) ABSTRACT

Provided herein are fused imidazolyl compounds, methods of synthesis, and methods of use thereof. The compounds provided herein are useful for the treatment, prevention, and/or management of various disorders, such as neurological disorders and metabolic disorders. Compounds provided herein inhibit the activity of histamine H3 receptors and modulate the release of various neurotransmitters, such as histamine, acetylcholine, norepinephrine, and dopamine (e.g. at the synapse). Pharmaceutical formulations containing the compounds and their methods of use are also provided herein.

58 Claims, No Drawings

FOREIGN PATENT DOCUMENTS

| | | |
|---|---|---|
| WO | WO 2009005771 | 1/2009 |
| WO | WO 2009017836 | 2/2009 |
| WO | WO 2009039420 | 3/2009 |
| WO | WO 2009111540 | 9/2009 |
| WO | WO 2009135091 | 11/2009 |
| WO | WO 2010/062065 | 6/2010 |
| WO | WO 2010/093425 | 8/2010 |
| WO | PCT/US2010/048199 | 9/2010 |
| WO | PCT/US2010/048201 | 9/2010 |
| WO | WO 2010127177 | 11/2010 |
| WO | WO 2010144571 | 12/2010 |
| WO | WO 2011/014695 | 2/2011 |
| WO | WO 2011/019417 | 2/2011 |
| WO | WO 2011031816 | 3/2011 |
| WO | WO 2011031818 | 3/2011 |

OTHER PUBLICATIONS

Anichtchik et al., 2000, "Modulation of Histamine H3 Receptors in the Brain of 6-Hydroxydopamine-Lesioned Rats," Eur. J. Neuroscience, 12, 3823-32.

Anichtchik et al., 2001, "Distribution and Modulation of Histamine H3 Receptors in Basal Ganglia and Frontal Cortex of Healthy Controls and Patients with Parkinson's Disease," Neurobio. Disease, 8, 707-16.

Barbier et al., 2004, "Acute Wake-Promoting Actions of JNJ-5207852, a Novel, Diamine-Based H3 Antagonist," Brit. J. Pharm., 143, 649-61.

Bertaccini et al., 1995, "An Update on Histamine H3 Receptors and Gastrointestinal Functions," Digestive Disease & Sciences, 40(9), 2052-63.

Breunig et al., 2007, "Histamine Excites Neurons in the Human Submucous Plexus Through Activation of H1, H2, H3 and H4 Receptors," J. Physiol., 583(2), 731-42.

Brown et al., 2001, "The Physiology of Brain Histamine," Prog. Neurobio., 63, 637-72.

Laurence L. Brunton et al., Goodman & Gilman's The Pharmacological Basis of Therapeutics 629-51 (11th ed. 2006).

Chavez et al., 2005, "Histamine (H3) Receptors Modulate the Excitatory Amino Acid Receptor Response of the Vestibular Afferents," Brain Research, 1064(1-2), 1-9.

Cherkaoui et al., 1991, "Heterocyclization of the 2-Aminoalkyl (and aryl) Benzimidazoles Under Phase Transfer Catalysis Conditions," Bulletin de la Societe Chimique de France, 255-59.

Clapham et al., 1994, "Thioperamide, the Selective Histamine H3 Receptor Antagonist, Attenuates Stimulant-Induced Locomotor Activity in the Mouse," Eur. J. Pharm., 259, 107-14.

Claramunt et al., 1998, "Conformational Analysis of Heterocyclic Analogues of 5,6,11,12-Tetrahydrodibenzo[a,e]cyclooctene: 6,7,14,15-Tetrahydrobisbenzimidazo[1,2-a:1',2'-e][1,5]diazocine and 6,7,13,14-Tetrahydrobispyrido[1,2-a:1',2'-e]diazocinediium Dibromide," Tetrahedron, 54, 9569-80.

Day et al., 2007, "Differential Effects of Ciproxifan and Nicotine on impulsivity and Attention Measures in the 5-Choice Serial Reaction Time Test," Biochem. Pharm., 73, 1123-34.

El Abbassi et al., 1990, "Synthesis of Pyrozolo[2',3':1,7][1,4]diazepino[4,5-a]benzimidazoles and of 1-Alkyl-2-[(5-methyl-3-pyrazolyl)methyl]benzimidazoles," Bulletin de la Societe Chimique de France, (1), 117-28.

Elguero et al., 1976, "Synthesis, Spectra, and Crystal Structure of 6,7,14,15-Tetrahydrobisbenzimidazo[1,2-a:1',2'-e][1,5]diazocine," J.C.S. Perkin Trans I, (3), 312-15.

Ennis et al., 2003, "2,3,4,5-Tetrahydro-and 2,3,4,5,11,11 a-Hexahydro-1H-[1,4]diazepino[1,7-a]indoles: New Templates for 5HT2C Agonists," Bioorg. Med. Chem. Lett., 13, 2369-72.

Esbenshade et al., 2004, "Pharmacological and Behavioral Properties of A-349821, a Selective and Potent Human Histamine H3 Receptor Antagonist," Biochem. Pharm., 68, 933-45.

Esbenshade et al., 2006, "Histamine H3 Receptor Antagonists: Preclinical Promise for Treating Obesity and Cognitive Disorders," Molecular Interventions, 6(2), 77-88.

Esbenshade et al., 2008, "The Histamine H3 Receptor: An Attractive Target for the Treatment of Cognitive Disorders," Brit. J. Pharm., 154(6), 1166-81.

Fox et al., 2002, "Effects of Histamine H3 Receptor Ligands GT-2331 and Ciproxifan in a Repeated Acquisition Avoidance Response in the Spontaneously Hypertensive Rat Pup," Behavioural Brain Research, 131, 151-61.

Fox et al., 2003, "Two Novel and Selective Nonimidazole H3 Receptor Antagonists A-304121 and A-317920: II. In Vivo Behavioral and Neurophysiological Characterization," J. Pharm. Exp. Ther., 305(3), 897-908.

Fox et al., 2005, "Pharmacological Properties of ABT-239: II. Neurophysiological Characterization and Broad Preclinical Efficacy in Cognition and Schizophrenia of a Potent and Selective Histamine H3 Receptor Antagonist," J. Pharm. Exp. Ther., 313(1), 176-90.

Gomez-Ramirez et al., 2006, "Histamine H3 Receptor Agonists Reduce L.-Dopa-Induced Chorea, But Not Dystonia, in the MPTP-Lesioned Nonhuman Primate Model of Parkinson's Disease," Movement Disorders, 21(6), 839-46.

Haas et al., 2008, "Histamine in the Nervous System," Physiol. Rev., 88, 1183-241.

Hancock et al., 2004, "Antiobesity Effects of A-331440, a Novel Non-Imidazole Histamine H3 Receptor Antagonist," Eur. J. Pharm., 487, 183-97.

Herbert et al, 1988, "2H-Benzimidazoles (Isobenzimidazoles). Part 3. Thermal Isomerisation of Substituted 2H-Benzimidazoles to 1H-Benzimidazoles," J.C.S. Perkin Trans I, (5), 991-97.

Huff et al., 1982, "Convenient and Regioselective Synthesis of Substituted 2,3,4,5-Tetrahydro-1H[1,4]diazepino[1,7-a]benzimidazoles," J. Org. Chem., 47, 582-85.

Ishizuka et al., 2008, "Comparison of the Effect of an H3-Inverse Agonist on Energy Intake and Hypothalamic Histamine Release in Normal Mice and Leptin Resistant Mice with High Fat Diet-Induced Obesity," Behavioural Brain Research, 188, 250-54.

Komater et al., 2003, "H3 Receptor Blockade by Thioperamide Enhances Cognition in Rats without Inducing Locomotor Sensitization," Psychopharm., 167, 363-72.

Ledesma et al., 2008, "The Nonsynonymous Thr105Ile Polymorphism of the Histamine N-Methyltransferase is Associated to the Risk of Developing Essential Tremor," Neuromol. Med., 10(4), 356-61.

Lin et al., 1990, "Involvement of Histaminergic Neurons in Arousal Mechanisms Demonstrated with H3-Receptor Ligands in the Cat," Brain Research, 523, 325-30.

Lin et al., 2008, "An Inverse Agonist of the Histamine H3 Receptor Improves Wakefulness in Narcolepsy: Studies in Orexin -/- Mice and Patients," Neurobio. Disease, 30, 74-83.

Lovenberg et al., 1999, "Cloning and Functional Expression of the Human Histamine H3 Receptor," Mol. Pharm., 55, 1101-07.

Malmlof et al., 2006, "Increase of Neuronal Histamine in Obese Rats Is Associated with Decreases in Body Weight and Plasma Triglycerides," Obesity, 14(12), 2154-62.

Masaki et al., 2007, "Neuronal Histamine and its Receptors in Obesity and Diabetes," Current Diabetes Reviews, 3, 212-16.

Medhurst et al., 2007, "Structurally Novel Histamine H3 Receptor Antagonists GSK207040 and GSK334429 Improve Scopolamine-Induced Memory Impairment and Capsaicin-Induced Secondary Allodynia in Rats," Biochem. Pharm., 73, 1182-94.

Medhurst et al., 2007, "GSK189254, a Novel H3 Receptor Antagonist That Binds to Histamine H3 Receptors in Alzheimer's Disease Brain and Improves Cognitive Performance in Preclinical Models," J. Pharm. Exp. Ther., 321(3), 1032 45.

Medhurst et al., 2008, "Novel Histamine H3 Receptor Antagonists GSK189254 and GSK334429 are Efficacious in Surgically-Induced and Virally-Induced Rat Models of Neuropathic Pain," Pain, 138, 61-69.

Munzar et al., 2004, "Histamine H3 Receptor Antagonists Potentiate Methamphetamine Self-Administration and Methamphetamine-Induced Accumbal Dopamine Release," Neuropsychopharm., 29, 705-17.

Perez-Garcia et al., 1999, "Effects of Histamine H3 Receptor Ligands in Experimental Models of Anxiety and Depression," Psychopharm., 142, 215-20.

Preuss et al., 1998, "Human Histamine N-Methyltransferase Pharmacogenetics: Common Genetic Polymorphisms that Alter Activity," Mol. Pharm., 53, 708-17.

Rizk et al., 2004, "Anxiety and Cognition in Histamine H3 Receptor -/- Mice," Eur. J. Neuroscience, 19, 1992-96.

Sander et al., 2008, "Histamine H3 Receptor Antagonists Go to Clinics," Biol. Pharm. Bull., 31(12), 2163-81.

Singh et al., 1997, "The Physiological Role of Histamine in the Exocrine Pancreas," Inflammation Research, 46, 159-65.

Vohora et al., 2000, "Thioperamide, a Selective Histamine H3 Receptor Antagonist, Protects Against PTZ-Induced Seizures in Mice," Life Sciences, 66(22), PL 297-301.

Vohora et al., 2001, "Histamine and Selective H3-Receptor Ligands: A Possible Role in the Mechanism and Management of Epilepsy," Pharm. Biochem. Behavior, 68, 735-41.

Zhang et al., 2003, "Effects of Clobenpropit on Pentylenetetrazole-Kindled Seizures in Rats," Eur. J. Pharm., 482, 169-75.

Zhang et al., 2005, "Lack of Cataleptogenic Potentiation with Non-Imidazole H3 Receptor Antagonists Reveals Potential Drug-Drug Interactions between Imidazole-Based H3 Receptor Antagonists and Antipsychotic Drugs," Brain Res., 1045, 142-49.

International Search Report and Written Opinion of the International Searching Authority for PCT/US2010/000335, filed Feb. 11, 2010, published under WO 2010/093425.

CAS Registry Records, STN, 1984, 2000, & 2001.

U.S. Appl. No. 12/878,887, filed Sep. 9, 2010, Chytil et al.

N.A. Parris, 1984, Instrumental Liquid Chromatography, in Journal of Chromatography Library, vol. 27, Second Edition, 135-174.

* cited by examiner

HISTAMINE H3 INVERSE AGONISTS AND ANTAGONISTS AND METHODS OF USE THEREOF

This application claims priority to U.S. Provisional Patent Application No. 61/151,817, filed on Feb. 11, 2009, the content of which is hereby incorporated by reference herein in its entirety. This application also claims priority to U.S. Provisional Patent Application No. 61/241,840, filed on Sep. 11, 2009.

I. FIELD

Provided herein are compounds useful as histamine H3 receptor inverse agonists or antagonists, compositions comprising the compounds, and methods of their use.

II. BACKGROUND

Histamine producing cells locate in the tuberomammillary nucleus (TMN) and project throughout the brain and the spinal cord to form a histamine neurotransmitter system. Four histamine receptors, histamine H1, H2, H3, and H4 receptors, have been identified to date. The human H3 receptor was cloned in 1999. See, e.g., Lovenberg et al., Mol. Pharmacol. 55(6): 1101-07 (1999).

Histamine H3 receptors (also referred to as H3 receptors or H3 herein) are expressed on neurons throughout the CNS, particularly the forebrain. H3 receptors are primarily localized at the pre-synaptic site of the neurons and act as autoreceptors to regulate neurotransmitter release. H3 receptor is a G-protein coupled receptor (GPCR) that signals primarily through the Gi/o pathway. Activation of the pre-synaptic H3 receptors located on histaminergic neurons leads to a decrease in histamine release; whereas inhibition of H3 receptors with an antagonist or inverse agonist leads to an increase in histamine at the synapse. Thus H3 receptor ligands are capable of modifying histaminergic neurotransmission in the brain: agonists decrease it, and antagonists or inverse agonists increase it. H3 receptors from the brain have significant constitutive activity in the absence of agonists. Consequently, inverse agonists will reduce receptor activity, increase histamine release, and activate histaminergic neurons. See, e.g., Goodman & Gilman's Pharmacological Basis of Therapeutics, 629 (11$^{th}$ Ed. 2006).

H3 receptors are also found on the terminals of other neurotransmitter producing neurons, where they serve as pre-synaptic hetero-receptors to regulate the release of other neurotransmitters. H3 receptor antagonists have been shown to increase acetylcholine, norepinephrine, and dopamine in the extra-cellular fluid. The ability for H3 receptors to modulate the release of a variety of neurotransmitters suggests a wide range of therapeutic indications for H3 antagonists and inverse agonists.

H3 receptor antagonists or inverse agonists that cross the blood-brain barrier have a range of central effects through the activation of histaminergic neurons. For example, in animal experiments, H3 antagonists or inverse agonists induced marked arousal and wakefulness, improved attention and learning, and demonstrated beneficial effects in animal models of convulsions. Thus these compounds may be used to treat conditions such as cognitive impairment, pathological diurnal somnolence, and epilepsy without sedative side effects. The ability of these compounds to improve wakefulness could also lead to an improved sleep pattern, and therefore H3 antagonists or inverse agonists may also be useful in treating sleeping disorders, such as insomnia.

Preclinical research with H3 antagonists and inverse agonists suggests that this class of ligands may offer novel treatments for a variety of disorders, including but not limited to, cognitive impairments (such as those associated with Alzheimer's and Parkinson's diseases), schizophrenia, attention deficit hyperactivity disorder (ADHD), pain, and obesity. Additionally, these ligands have been shown to possess wake-promoting properties in both pre-clinical and clinical studies and may be useful in disorders associated with excessive daytime sleepiness. Additional uses of H3 ligands include, but are not limited to, disorders of the mood such as anxiety and depression, seizures, vertigo, movement disorders, and gastrointestinal (GI) motility disorders.

In addition, it is reported that H3 receptors may be associated with other various neurological disorders. Therefore, there is a great need for effective H3 inverse agonists and antagonists as therapeutics for treatment of various disorders, such as neurological disorders.

III. SUMMARY

Provided herein are compounds of formula (I), or pharmaceutically acceptable salt, solvate, or stereoisomer thereof:

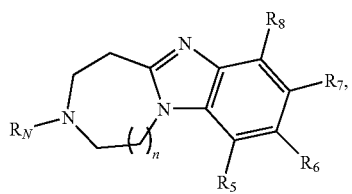

I wherein $R_N$, $R_5$, $R_6$, $R_7$, $R_8$, and n are defined herein elsewhere. The compounds are useful as histamine H3 receptor inverse agonists or antagonists.

Also provided herein are compositions and dosage forms comprising compounds provided herein. Compositions and dosage forms provided herein may comprise one or more additional active ingredients.

Also provided herein are methods for the treatment, prevention, and/or management of various disorders using the compounds and compositions provided herein. Also provided herein are uses of the compounds and compositions provided herein in the manufacture of a medicament for the treatment, prevention, and/or management of various disorders provided herein. Also provided herein are compounds and compositions for use in the treatment, prevention, and/or management of various disorders provided herein. Disorders that may be treated, prevented, and/or managed include, but are not limited to, neurological disorders; neurodegenerative diseases; schizophrenia; Alzheimer's disease; Parkinson's disease; affective disorders; attention deficit hyperactivity disorder (ADHD); psychosis; convulsion; seizures; vertigo; epilepsy; narcolepsy; pain (e.g. neuropathic pain); sensitization that accompanies many neuropathic pain disorders; mood disorders such as depression and anxiety; excessive daytime sleepiness such as that seen in narcolepsy, Parkinson's disease, multiple sclerosis, shift workers, and jet lag, or as a relief of side effects of other medications; insomnia; substance abuse; cognitive impairments such as those associated with Alzheimer's disease, Parkinson's disease, schizophrenia, and ADHD; metabolic disorders such as diabetes and obesity; disorders related to satiety and gastric activity, or as a side effects of other medications; diseases affecting the enteric system, such as acid secretion, digestion, and gut motility; and movement disorders such as Parkinson's disease, restless leg syndrome (RLS), Huntington's disease; and any other neurological disorders described herein elsewhere.

In another embodiment, provided herein is a method of inhibiting or reducing the activity of histamine H3 receptors. The method comprises contacting the H3 receptor with a compound provided herein.

Also provided herein is a method of regulating the release of neurotransmitters, including but not limited to, histamine, acetylcholine, norepinephrine, and dopamine, at the synapse. The method comprises contacting the cell with a compound provided herein. In an exemplary embodiment, the cell is a brain cell, such as, for example, a neuronal cell or a glial cell.

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

As used herein, and unless otherwise indicated, the term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-4}$ carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$, or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$, or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the term "cycloalkyl" refers to a cyclic saturated bridged and/or non-bridged monovalent hydrocarbon radical, which may be optionally substituted one or more substituents as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

As used herein, and unless otherwise specified, the term "heteroalkyl" refers to a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms are optionally oxidized and the nitrogen heteroatom can optionally be quaternized. The heteroatom(s) O, N and S may be placed at any interior position of the heteroalkyl group. The heteroatom Si can be placed at any position of the heteroalkyl group, including the position at which the alkyl group is attached to the remainder of the molecule. The heteroatom O, N, or S cannot be placed at the position at which the alkyl group is attached to the remainder of the molecule. The heteroatom O, N, or S can be placed at the external position distal to where the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms can be consecutive, such as, for example, —$CH_2$—NH—$OCH_3$ and —$CH_2$—O—Si($CH_3$)$_3$. Also included in the term "heteroalkyl" are those radicals described as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. Still further, for heteroalkylene linking groups, as well as all other linking group provided herein, no orientation of the linking group is implied.

As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

As used herein, and unless otherwise specified, the term "arylalkyl" or "aralkyl" refers to a monovalent alkyl group substituted with aryl. In certain embodiments, both alkyl and aryl may be optionally substituted with one or more substituents.

As used herein, and unless otherwise specified, the term "heteroaryl" refers to a monocyclic aromatic group and/or multicyclic aromatic group that contain at least one aromatic ring, wherein at least one ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may be optionally substituted with one or more substituents.

As used herein, and unless otherwise specified, the term "heterocycloalkyl," "heterocyclyl," or "heterocyclic" refers to a monocyclic non-aromatic ring system and/or multicyclic ring system that contains at least one non-aromatic ring, wherein at least one ring contains one or more heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may be optionally substituted with one or more substituents.

As used herein, and unless otherwise specified, the term "halogen", "halide" or "halo" refers to fluorine, chlorine, bromine, and/or iodine.

As used herein, and unless otherwise specified, the term "hydrogen" encompasses proton ($^1H$), deuterium ($^2H$), tritium ($^3H$), and/or mixtures thereof.

As used herein, and unless otherwise specified, the term "optionally substituted" is intended to mean that a group, such as an alkyl, alkenyl, alkynyl, cycloalkyl, heteroalkyl, aryl, aralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—$NO_2$), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In some embodiments, the salt is formed from hydrochloric, hydrobromic, phosphoric, or sulfuric acid. In one embodiment, the salt is formed from hydrochloride salt.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) or (−), is not related to the absolute configuration of the molecule, R or S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "histamine receptor ligand" refers to any compound, which binds to a histamine receptor. Unless otherwise specified, the histamine receptor includes, but is not limited to, histamine H3 receptor. Ligands include endogenous ligands for a given histamine receptor as well as drug molecules and other compounds, such as synthetic molecules known to bind to a particular histamine receptor. In one example, the ligands include those labeled with one or more radioisotopes, such as tritium, or otherwise (e.g., fluorescently) labeled. It is within the abilities of the skilled person to select an appropriate ligand for a given histamine receptor. For example, known ligands for the histamine receptor include histamine, R-γ-Me-histamine, imetit, thioperamide, clobenpropit, and the like.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. In one embodiment, a method of treating a neurodegenerative disorder includes methods of treating loss of memory and/or loss of cognition associated with a neurodegenerative disorder. In one embodiment, a method of treating a neurodegenerative disorder includes methods of treating cognitive function, memory performance, learning performance, speed of reaction, and/or time to respond associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD) and dysthymia. "Major depressive disorder" is used herein interchangeably with "unipolar depression" and "major depression." "Depression" may also includes any condition commonly associated with depression, such as all forms of fatigue (e.g., chronic fatigue syndrome) and cognitive deficits.

As used herein, and unless otherwise specified, the terms "obsessive-compulsive disorder," "substance abuse," "premenstrual syndrome," "anxiety," "eating disorders" and "migraine" are used herein in a manner consistent with their accepted meanings in the art. See, e.g., DSM-IV™. For example, the term "eating disorder," as used herein, refers to abnormal compulsions to avoid eating or uncontrollable impulses to consume abnormally large amounts of food. These disorders may affect not only the social well-being, but also the physical well-being of sufferers. Examples of eating disorders include, but are not limited to, anorexia nervosa, bulimia, and binge eating.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes. As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (MIN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

B. Compounds

In one embodiment, provided herein is a compound of formula (I):

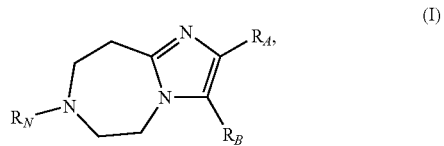

or a pharmaceutically acceptable salt, solvate, or stereoisomer thereof, wherein $R_N$ is a bond, hydrogen, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, or (5 to 10 membered) heteroaryl, each of which is optionally substituted with one or more R;

each occurrence of R' is independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_2$; or two R' substituents together may form a 3 to 10 membered ring optionally substituted with one or more $R_2$;

$R_A$ and $R_B$ are independently hydrogen, halogen, cyano, $(C_1-C_{10})$alkyl, $(C_1-C_{10})$ alkenyl, $(C_3-C_{10})$cyclo alkyl, (6 to 10 membered)aryl, $(C_1-C_{10})$heteroalkyl, $(C_3-C_{10})$ heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more R"; or $R_A$ and $R_B$ together may form a ring (e.g. phenyl and pyridyl) optionally substituted with one or more R";

each occurrence of R" is independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or two R" substituents together may form a 3 to 10 membered ring optionally substituted with one or more $R_1$;

each occurrence of $R_1$ is independently hydrogen, halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, —$S(O)_2NR_3R_4$, $(C_1-C_{10})$alkyl optionally substituted with one or more $R_2$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$;

each occurrence of $R_2$ is independently hydrogen, $(C_1-C_6)$alkyl optionally substituted with one or more $R_3$, $(C_3-C_6)$cycloalkyl optionally substituted with one or more $R_3$, halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, or —$S(O)_2NR_3R_4$;

$R_3$ and $R_4$ are each independently hydrogen, $(C_1-C_6)$alkyl, $(C_3-C_6)$cycloalkyl, $(C_7-C_{10})$aralkyl; $(C_1-C_6)$heteroalkyl, ($C_3$-$C_6$)heterocycloalkyl, (6 to 10 membered)aryl, or (5 to 10 membered)heteroaryl; or $R_3$ and $R_4$ together may form a 3 to 10 membered ring; and m is 0, 1, or 2.

In another embodiment, provided herein is a compound of formula (Ia):

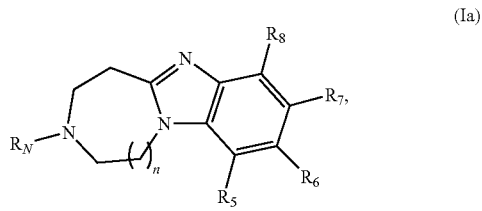

(Ia)

or a pharmaceutically acceptable salt, solvate, or stereoisomer thereof, wherein $R_N$ is a bond, hydrogen, ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$)heterocycloalkyl, or (5 to 10 membered) heteroaryl, each of which is optionally substituted with one or more R';

each occurrence of R' is independently hydrogen, halogen, cyano, ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$)heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_2$; or two R' substituents together may form a 3 to 10 membered ring optionally substituted with one or more $R_2$;

$R_5$, $R_6$, $R_7$, and $R_8$ are each independently (i) hydrogen, halogen, or cyano; (ii) ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$)heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; (iii) hydroxyl substituted with one or more $R_1$'; or (iv) two adjacent $R_5$, $R_6$, $R_7$, and $R_8$ together form a 3 to 10 membered ring optionally substituted with one or more $R_1$;

each occurrence of $R_1$ is independently hydrogen, halogen, cyano, $=O$, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, —$S(O)_2NR_3R_4$, ($C_1$-$C_{10}$)alkyl optionally substituted with one or more $R_2$, ($C_3$-$C_{10}$)cycloalkyl optionally substituted with one or more $R_2$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$;

each occurrence of $R_1$' is independently —$C(O)NR_3R_4$, —$C(O)R_3$, ($C_3$-$C_{10}$)cycloalkyl optionally substituted with one or more $R_2$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$;

each occurrence of $R_2$ is independently hydrogen, ($C_1$-$C_6$)alkyl optionally substituted with one or more $R_3$, ($C_3$-$C_6$)cycloalkyl optionally substituted with one or more $R_3$, halogen, cyano, $=O$, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, or —$S(O)_2NR_3R_4$;

$R_3$ and $R_4$ are each independently hydrogen, ($C_1$-$C_6$)alkyl, ($C_3$-$C_6$)cycloalkyl, ($C_7$-$C_{10}$)aralkyl; ($C_1$-$C_6$)heteroalkyl, ($C_3$-$C_6$)heterocycloalkyl, (6 to 10 membered)aryl, or (5 to 10 membered)heteroaryl; or $R_3$ and $R_4$ together may form a 3 to 10 membered ring;

m is 0, 1, or 2;

n is 1, 2, or 3; and when n is 1, (i) $R_5$, $R_6$, $R_7$, and $R_8$ cannot all be hydrogen; (ii) when one of $R_5$, $R_6$, $R_7$, and $R_8$ is halogen, the other three of $R_5$, $R_6$, $R_7$, and $R_8$ cannot all be hydrogen; and (iii) when $R_6$ is ($C_1$-$C_4$)alkyl or ($C_1$-$C_4$)alkoxyl optionally substituted with one or more halogen, $R_5$, $R_7$, and $R_8$ cannot all be hydrogen.

In one embodiment, $R_N$ is a bond. In another embodiment, $R_N$ is hydrogen. In another embodiment, $R_N$ is optionally substituted ($C_1$-$C_{10}$)alkyl. In another embodiment, $R_N$ is optionally substituted ($C_1$-$C_{10}$)alkenyl. In another embodiment, $R_N$ is optionally substituted ($C_3$-$C_{10}$)cycloalkyl. In another embodiment, $R_N$ is optionally substituted (6 to 10 membered)aryl. In another embodiment, $R_N$ is optionally substituted ($C_1$-$C_{10}$)heteroalkyl. In another embodiment, $R_N$ is optionally substituted ($C_3$-$C_{10}$) heterocycloalkyl. In another embodiment, $R_N$ is optionally substituted (5 to 10 membered)heteroaryl. Each $R_N$ may be substituted with one or more R'.

In one embodiment, $R_N$ is cyclopropyl optionally substituted with one or more R'. In another embodiment, $R_N$ is cyclobutyl optionally substituted with one or more R'. In another embodiment, $R_N$ is cyclopentyl optionally substituted with one or more R'. In another embodiment, $R_N$ is cyclohexyl optionally substituted with one or more R'.

In one embodiment, R' is hydrogen. In another embodiment, R' is halogen. In another embodiment, R' is cyano. In another embodiment, R' is optionally substituted ($C_1$-$C_{10}$) alkyl. In another embodiment, R' is optionally substituted ($C_1$-$C_{10}$)alkenyl. In another embodiment, R' is optionally substituted ($C_3$-$C_{10}$)cycloalkyl. In another embodiment, R' is optionally substituted (6 to 10 membered)aryl. In another embodiment, R' is optionally substituted ($C_1$-$C_{10}$)heteroalkyl. In another embodiment, R' is optionally substituted ($C_3$-$C_{10}$)heterocycloalkyl. In another embodiment, R' is optionally substituted (5 to 10 membered)heteroaryl. In another embodiment, R' is optionally substituted hydroxyl. In another embodiment, R' is optionally substituted alkoxyl. In another embodiment, R' is optionally substituted aminoalkyl. In another embodiment, R' is optionally substituted amino. In another embodiment, R' is optionally substituted imino. In another embodiment, R' is optionally substituted amido. In another embodiment, R' is optionally substituted carbonyl. In another embodiment, R' is optionally substituted thiol. In another embodiment, R' is optionally substituted sulfinyl. In another embodiment, R' is optionally substituted sulfonyl. In another embodiment, two R' substituents together form a 3 to 10 membered ring optionally substituted with one or more $R_2$. In another embodiment, two geminal R' substituents together form a 3 to 10 membered ring optionally substituted with one or more $R_2$. In another embodiment, two vicinal R' substituents together form a 3 to 10 membered ring optionally substituted with one or more $R_2$. Each occurrence of R' is optionally substituted with one or more $R_2$.

In one embodiment, $R_A$ is hydrogen. In another embodiment, $R_A$ is halogen. In another embodiment, $R_A$ is cyano. In another embodiment, $R_A$ is optionally substituted ($C_1$-$C_{10}$) alkyl. In another embodiment, $R_A$ is optionally substituted ($C_1$-$C_{10}$) alkenyl. In another embodiment, $R_A$ is optionally substituted $(C_3-C_{10})$cycloalkyl. In another embodiment, $R_A$ is optionally substituted (6 to 10 membered)aryl. In another embodiment, $R_A$ is optionally substituted $(C_1-C_{10})$heteroalkyl. In another embodiment, $R_A$ is optionally substituted $(C_3-C_{10})$heterocycloalkyl. In another embodiment, $R_A$ is optionally substituted (5 to 10 membered)heteroaryl. In another embodiment, $R_A$ is optionally substituted hydroxyl. In another embodiment, $R_A$ is optionally substituted alkoxyl. In another embodiment, $R_A$ is optionally substituted aminoalkyl. In another embodiment, $R_A$ is optionally substituted amino. In another embodiment, $R_A$ is optionally substituted imino. In another embodiment, $R_A$ is optionally substituted amido. In another embodiment, $R_A$ is optionally substituted carbonyl. In another embodiment, $R_A$ is optionally substituted thiol. In another embodiment, $R_A$ is optionally substituted sulfinyl. In another embodiment, $R_A$ is optionally substituted sulfonyl. Each occurrence of $R_A$ is optionally substituted with one or more R".

In one embodiment, $R_B$ is hydrogen. In another embodiment, $R_B$ is halogen. In another embodiment, $R_B$ is cyano. In another embodiment, $R_B$ is optionally substituted $(C_1-C_{10})$ alkyl. In another embodiment, $R_B$ is optionally substituted $(C_1-C_{10})$ alkenyl. In another embodiment, $R_B$ is optionally substituted $(C_3-C_{10})$cycloalkyl. In another embodiment, $R_B$ is optionally substituted (6 to 10 membered)aryl. In another embodiment, $R_B$ is optionally substituted $(C_1-C_{10})$heteroalkyl. In another embodiment, $R_B$ is optionally substituted $(C_3-C_{10})$heterocycloalkyl. In another embodiment, $R_B$ is optionally substituted (5 to 10 membered)heteroaryl. In another embodiment, $R_B$ is optionally substituted hydroxyl. In another embodiment, $R_B$ is optionally substituted alkoxyl. In another embodiment, $R_B$ is optionally substituted aminoalkyl. In another embodiment, $R_B$ is optionally substituted amino. In another embodiment, $R_B$ is optionally substituted imino. In another embodiment, $R_B$ is optionally substituted amido. In another embodiment, $R_B$ is optionally substituted carbonyl. In another embodiment, $R_B$ is optionally substituted thiol. In another embodiment, $R_B$ is optionally substituted sulfinyl. In another embodiment, $R_B$ is optionally substituted sulfonyl. Each occurrence of $R_B$ is optionally substituted with one or more R".

In one embodiment, $R_A$ and $R_B$ together form a ring, which is optionally substituted with one or more R". In another embodiment, $R_A$ and $R_B$ together form a phenyl ring, which is optionally substituted with one or more R". In another embodiment, $R_A$ and $R_B$ together form a thiophene ring, which is optionally substituted with one or more R". In another embodiment, $R_A$ and $R_B$ together form a furan ring, which is optionally substituted with one or more R". In another embodiment, $R_A$ and $R_B$ together form a pyrrole ring, which is optionally substituted with one or more R". In another embodiment, $R_A$ and $R_B$ together form a pyridine ring, which is optionally substituted with one or more R". In another embodiment, $R_A$ and $R_B$ together form a pyrimidine ring, which is optionally substituted with one or more R". In another embodiment, $R_A$ and $R_B$ together form a pyrazine ring, which is optionally substituted with one or more R". In another embodiment, $R_A$ and $R_B$ together form a tetrahydropyridine ring, which is optionally substituted with one or more R". In another embodiment, $R_A$ and $R_B$ together form a pyridone ring, which is optionally substituted with one or more R". In another embodiment, $R_A$ and $R_B$ together form a pyrimidone ring, which is optionally substituted with one or more R". In another embodiment, $R_A$ and $R_B$ together form a pyridazinone ring, which is optionally substituted with one or more R". In another embodiment, $R_A$ and $R_B$ together form a pyrazinone ring, which is optionally substituted with one or more R".

In one embodiment, R" is hydrogen. In another embodiment, R" is halogen. In another embodiment, R" is cyano. In another embodiment, R" is optionally substituted $(C_1-C_{10})$ alkyl. In another embodiment, R" is optionally substituted $(C_1-C_{10})$ alkenyl. In another embodiment, R" is optionally substituted $(C_3-C_{10})$cycloalkyl. In another embodiment, R" is optionally substituted (6 to 10 membered)aryl. In another embodiment, R" is optionally substituted $(C_1-C_{10})$heteroalkyl. In another embodiment, R" is optionally substituted $(C_3-C_{10})$heterocycloalkyl. In another embodiment, R" is optionally substituted (5 to 10 membered)heteroaryl. In another embodiment, R" is optionally substituted hydroxyl. In another embodiment, R" is optionally substituted alkoxyl. In another embodiment, R" is optionally substituted aminoalkyl. In another embodiment, R" is optionally substituted amino. In another embodiment, R" is optionally substituted imino. In another embodiment, R" is optionally substituted amido. In another embodiment, R" is optionally substituted carbonyl. In another embodiment, R" is optionally substituted thiol. In another embodiment, R" is optionally substituted sulfinyl. In another embodiment, R" is optionally substituted sulfonyl. In another embodiment, two R" substituents together form a 3 to 10 membered ring optionally substituted with one or more $R_1$. In another embodiment, two geminal R" substituents together form a 3 to 10 membered ring optionally substituted with one or more $R_1$. In another embodiment, two vicinal R" substituents together form a 3 to 10 membered ring optionally substituted with one or more $R_1$. Each occurrence of R" is optionally substituted with one or more $R_1$.

In one embodiment, $R_1$ is hydrogen. In another embodiment, $R_1$ is halogen. In another embodiment, $R_1$ is cyano. In another embodiment, $R_1$ is =O. In another embodiment, $R_1$ is —$OR_3$. In another embodiment, $R_1$ is —$NR_3R_4$. In another embodiment, $R_1$ is —$N(R_3)C(O)R_4$. In another embodiment, $R_1$ is —$C(O)NR_3R_4$. In another embodiment, $R_1$ is —$C(O)R_3$. In another embodiment, $R_1$ is —$C(O)OR_3$. In another embodiment, $R_1$ is —$OC(O)R_3$. In another embodiment, $R_1$ is —$S(O)_mR_3$. In another embodiment, $R_1$ is —$S(O)_2NR_3R_4$. In another embodiment, $R_1$ is $(C_1-C_{10})$alkyl optionally substituted with one or more $R_2$. In another embodiment, $R_1$ is $(C_3-C_{10})$ cycloalkyl optionally substituted with one or more $R_2$. In another embodiment, $R_1$ is $(C_6-C_{12})$aralkyl optionally substituted with one or more $R_2$. In another embodiment, $R_1$ is (6 to 10 membered)aryl optionally substituted with one or more $R_2$. In another embodiment, $R_1$ is $(C_1-C_{10})$heteroalkyl optionally substituted with one or more $R_2$. In another embodiment, $R_1$ is $(C_3-C_{10})$heterocycloalkyl optionally substituted with one or more $R_2$. In another embodiment, $R_1$ is (5 to 10 membered)heteroaryl optionally substituted with one or more $R_2$.

In one embodiment, $R_2$ is hydrogen. In another embodiment, $R_2$ is $(C_1-C_6)$ alkyl optionally substituted with one or more $R_3$. In another embodiment, $R_2$ is $(C_3-C_6)$ cycloalkyl optionally substituted with one or more $R_3$. In another embodiment, $R_2$ is halogen. In another embodiment, $R_2$ is cyano. In another embodiment, $R_2$ is =O. In another embodiment, $R_2$ is —$OR_3$. In another embodiment, $R_2$ is —$NR_3R_4$. In another embodiment, $R_2$ is —$N(R_3)C(O)R_4$. In another embodiment, $R_2$ is —$C(O)NR_3R_4$. In another embodiment, $R_2$ is —$C(O)R_3$. In another embodiment, $R_2$ is —$C(O)OR_3$. In another embodiment, $R_2$ is —$OC(O)R_3$. In another embodiment, $R_2$ is —$S(O)_mR_3$. In another embodiment, $R_2$ is —$S(O)_2NR_3R_4$.

In one embodiment, $R_3$ is hydrogen. In another embodiment, $R_3$ is $(C_1-C_6)$ alkyl. In another embodiment, $R_3$ is $(C_3-C_6)$cycloalkyl. In another embodiment, $R_3$ is $(C_7-C_{10})$aralkyl. In another embodiment, $R_3$ is $(C_1-C_6)$heteroalkyl. In another embodiment, $R_3$ is $(C_3-C_6)$heterocycloalkyl. In another embodiment, $R_3$ is (6 to 10 membered)aryl. In another embodiment, $R_3$ is (5 to 10 membered)heteroaryl.

In one embodiment, $R_4$ is hydrogen. In another embodiment, $R_4$ is $(C_1-C_6)$ alkyl. In another embodiment, $R_4$ is $(C_3-C_6)$cycloalkyl. In another embodiment, $R_4$ is $(C_7-C_{10})$aralkyl. In another embodiment, $R_4$ is $(C_1-C_6)$heteroalkyl. In another embodiment, $R_4$ is $(C_3-C_6)$heterocycloalkyl. In another embodiment, $R_4$ is (6 to 10 membered)aryl. In another embodiment, $R_4$ is (5 to 10 membered)heteroaryl.

In one embodiment, $R_3$ and $R_4$ together form a 3 to 10 membered ring. In another embodiment, two geminal instances of $R_3$ and $R_4$ together form a 3 to 10 membered ring. In another embodiment, two vicinal instances of $R_3$ and $R_4$ together form a 3 to 10 membered ring. In one embodiment, $R_3$ and $R_4$ together form a ring which is optionally substituted.

In one embodiment, $R_5$ is hydrogen. In another embodiment, $R_5$ is halogen. In another embodiment, $R_5$ is cyano. In another embodiment, $R_5$ is $(C_1-C_{10})$alkyl optionally substituted with one or more $R_1$. In another embodiment, $R_5$ is $(C_1-C_{10})$alkyl substituted with one or more $R_1'$. In another embodiment, $R_5$ is $(C_1-C_{10})$ alkenyl optionally substituted with one or more $R_1$. In another embodiment, $R_5$ is $(C_3-C_{10})$ cycloalkyl optionally substituted with one or more $R_1$. In another embodiment, $R_5$ is (6 to 10 membered)aryl optionally substituted with one or more $R_1$. In another embodiment, $R_5$ is $(C_1-C_{10})$heteroalkyl optionally substituted with one or more $R_1$. In another embodiment, $R_5$ is $(C_3-C_{10})$heterocycloalkyl optionally substituted with one or more $R_1$. In another embodiment, $R_5$ is (5 to 10 membered)heteroaryl optionally substituted with one or more $R_1$. In another embodiment, $R_5$ is hydroxyl optionally substituted with $R_1$. In another embodiment, $R_5$ is hydroxyl substituted with $R_1'$. In another embodiment, $R_5$ is alkoxyl optionally substituted with one or more $R_1$. In another embodiment, $R_5$ is alkoxyl substituted with one or more $R_1'$. In another embodiment, $R_5$ is aminoalkyl optionally substituted with one or more $R_1$. In another embodiment, $R_5$ is amino optionally substituted with one or more $R_1$. In another embodiment, $R_5$ is imino optionally substituted with one or more $R_1$. In another embodiment, $R_5$ is amido optionally substituted with one or more $R_1$. In another embodiment, $R_5$ is carbonyl optionally substituted with one or more $R_1$. In another embodiment, $R_5$ is thiol optionally substituted with one or more $R_1$. In another embodiment, $R_5$ is sulfinyl optionally substituted with one or more $R_1$. In another embodiment, $R_5$ is sulfonyl optionally substituted with one or more $R_1$. $R_1$ and $R_1'$ are defined herein elsewhere.

In one embodiment, $R_6$ is hydrogen. In another embodiment, $R_6$ is halogen. In another embodiment, $R_6$ is cyano. In another embodiment, $R_6$ is $(C_1-C_{10})$alkyl optionally substituted with one or more $R_1$. In another embodiment, $R_6$ is $(C_1-C_{10})$alkyl substituted with one or more $R_1'$. In another embodiment, $R_6$ is $(C_1-C_{10})$-alkenyl optionally substituted with one or more $R_1$. In another embodiment, $R_6$ is $(C_3-C_{10})$ cycloalkyl optionally substituted with one or more $R_1$. In another embodiment, $R_6$ is (6 to 10 membered)aryl optionally substituted with one or more $R_1$. In another embodiment, $R_6$ is $(C_1-C_{10})$heteroalkyl optionally substituted with one or more $R_1$. In another embodiment, $R_6$ is $(C_3-C_{10})$heterocycloalkyl optionally substituted with one or more $R_1$. In another embodiment, $R_6$ is (5 to 10 membered)heteroaryl optionally substituted with one or more $R_1$. In another embodiment, $R_6$ is hydroxyl optionally substituted with $R_1$. In another embodiment, $R_6$ is hydroxyl substituted with $R_1'$. In another embodiment, $R_6$ is alkoxyl optionally substituted with one or more $R_1$. In another embodiment, $R_6$ is alkoxyl substituted with one or more $R_1'$. In another embodiment, $R_6$ is aminoalkyl optionally substituted with one or more $R_1$. In another embodiment, $R_6$ is amino optionally substituted with one or more $R_1$. In another embodiment, $R_6$ is imino optionally substituted with one or more $R_1$. In another embodiment, $R_6$ is amido optionally substituted with one or more $R_1$. In another embodiment, $R_6$ is carbonyl optionally substituted with one or more $R_1$. In another embodiment, $R_6$ is thiol optionally substituted with one or more $R_1$. In another embodiment, $R_6$ is sulfinyl optionally substituted with one or more $R_1$. In another embodiment, $R_6$ is sulfonyl optionally substituted with one or more $R_1$. $R_1$ and $R_1'$ are defined herein elsewhere.

In one embodiment, $R_7$ is hydrogen. In another embodiment, $R_7$ is halogen. In another embodiment, $R_7$ is cyano. In another embodiment, $R_7$ is $(C_1-C_{10})$alkyl optionally substituted with one or more $R_1$. In another embodiment, $R_7$ is $(C_1-C_{10})$alkyl substituted with one or more $R_1'$. In another embodiment, $R_7$ is $(C_1-C_{10})$-alkenyl optionally substituted with one or more $R_1'$. In another embodiment, $R_7$ is $(C_3-C_{10})$ cycloalkyl optionally substituted with one or more $R_1$. In another embodiment, $R_7$ is (6 to 10 membered)aryl optionally substituted with one or more $R_1$. In another embodiment, $R_7$ is $(C_1-C_{10})$heteroalkyl optionally substituted with one or more $R_1$. In another embodiment, $R_7$ is $(C_3-C_{10})$heterocycloalkyl optionally substituted with one or more $R_1$. In another embodiment, $R_7$ is (5 to 10 membered)heteroaryl optionally substituted with one or more $R_1$. In another embodiment, $R_7$ is hydroxyl optionally substituted with $R_1$. In another embodiment, $R_7$ is hydroxyl substituted with $R_1'$. In another embodiment, $R_7$ is alkoxyl optionally substituted with one or more $R_1$. In another embodiment, $R_7$ is alkoxyl substituted with one or more $R_1'$. In another embodiment, $R_7$ is aminoalkyl optionally substituted with one or more $R_1$. In another embodiment, $R_7$ is amino optionally substituted with one or more $R_1$. In another embodiment, $R_7$ is imino optionally substituted with one or more $R_1$. In another embodiment, $R_7$ is amido optionally substituted with one or more $R_1$. In another embodiment, $R_7$ is carbonyl optionally substituted with one or more $R_1$. In another embodiment, $R_7$ is thiol optionally substituted with one or more $R_1$. In another embodiment, $R_7$ is sulfinyl optionally substituted with one or more $R_1$. In another embodiment, $R_7$ is sulfonyl optionally substituted with one or more $R_1$. $R_1$ and $R_1'$ are defined herein elsewhere.

In one embodiment, $R_8$ is hydrogen. In another embodiment, $R_8$ is halogen. In another embodiment, $R_8$ is cyano. In another embodiment, $R_8$ is $(C_1-C_{10})$alkyl optionally substituted with one or more $R_1$. In another embodiment, $R_8$ is $(C_1-C_{10})$alkyl substituted with one or more $R_1'$. In another embodiment, $R_8$ is $(C_1-C_{10})$alkyl optionally substituted with one or more $R_1$. In another embodiment, $R_8$ is $(C_1-C_{10})$-alkenyl optionally substituted with one or more $R_1$. In another embodiment, $R_8$ is $(C_3-C_{10})$cycloalkyl optionally substituted with one or more $R_1$. In another embodiment, $R_8$ is (6 to 10 membered)aryl optionally substituted with one or more $R_1$. In another embodiment, $R_8$ is $(C_1-C_{10})$heteroalkyl optionally substituted with one or more $R_1$. In another embodiment, $R_8$ is $(C_3-C_{10})$heterocycloalkyl optionally substituted with one or more $R_1$. In another embodiment, $R_8$ is (5 to 10 membered) heteroaryl optionally substituted with one or more $R_1$. In another embodiment, $R_8$ is hydroxyl optionally substituted with $R_1$. In another embodiment, $R_8$ is hydroxyl substituted with $R_1'$. In another embodiment, $R_8$ is alkoxyl optionally substituted with one or more $R_1$. In another embodiment, $R_8$ is alkoxyl substituted with one or more $R_1'$. In another embodiment, $R_8$ is aminoalkyl optionally substituted with one or more $R_1$. In another embodiment, $R_8$ is amino optionally substituted with one or more $R_1$. In another embodiment, $R_8$ is imino optionally substituted with one or more $R_1$. In another embodiment, $R_8$ is amido optionally substituted with one or more $R_1$. In another embodiment, $R_8$ is carbonyl optionally substituted with one or more $R_1$. In another embodiment, $R_8$ is thiol optionally substituted with one or more $R_1$. In another embodiment, $R_8$ is sulfinyl optionally substituted with one or more $R_1$. In another embodiment, $R_8$ is sulfonyl optionally substituted with one or more $R_1$. $R_1$ and $R_1'$ are defined herein elsewhere.

In one embodiment, $R_5$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_6$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_7$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered) heteroaryl optionally substituted with one or more $R_2$. In one embodiment, $R_8$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$.

In one embodiment, $R_5$ is hydroxyl substituted with one or more $-C(O)NR_3R_4$, $-C(O)R_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_6$ is hydroxyl substituted with one or more $-C(O)NR_3R_4$, $-C(O)R_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_7$ is hydroxyl substituted with one or more $-C(O)NR_3R_4$, $-C(O)R_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_8$ is hydroxyl substituted with one or more $-C(O)NR_3R_4$, $-C(O)R_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$.

In one embodiment, $R_5$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_6$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_7$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$. In one embodiment, $R_8$ is $(C_1-C_{10})$alkyl or alkoxyl, each of which is substituted with one or more cyano, $=O$, $-OR_3$, $-NR_3R_4$, $-N(R_3)C(O)R_4$, $-C(O)NR_3R_4$, $-C(O)R_3$, $-C(O)OR_3$, $-OC(O)R_3$, $-S(O)_mR_3$, $-S(O)_2NR_3R_4$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$.

In one embodiment, $R_5$ is hydroxyl substituted with one or more $-C(O)NR_3R_4$, $-C(O)R_3$, $(C_6-C_{12})$aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$) heterocycloalkyl optionally substituted with one or more $R_2$, or (5 to 10 membered)heteroaryl optionally substituted with one or more $R_2$. In one embodiment, $R_6$ is hydroxyl substituted with one or more —C(O)$NR_3R_4$, —C(O)$R_3$, ($C_6$-$C_{12}$) aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$. In one embodiment, $R_7$ is hydroxyl substituted with one or more —C(O)$NR_3R_4$, —C(O)$R_3$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered) heteroaryl optionally substituted with one or more $R_2$. In one embodiment, $R_8$ is hydroxyl substituted with one or more —C(O)$NR_3R_4$, —C(O)$R_3$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$.

In one embodiment, $R_5$ and $R_6$ together form a 3 to 10 membered ring, which is optionally substituted with one or more $R_1$. In another embodiment, $R_6$ and $R_7$ together form a 3 to 10 membered ring, which is optionally substituted with one or more $R_1$. In another embodiment, $R_7$ and $R_8$ together form a 3 to 10 membered ring, which is optionally substituted with one or more $R_1$. $R_1$ is defined herein elsewhere.

In one embodiment, $R_1'$ is —C(O)$NR_3R_4$. In another embodiment, $R_1'$ is —C(O)$R_3$. In another embodiment, $R_1'$ is ($C_3$-$C_{10}$)cycloalkyl optionally substituted with one or more $R_2$. In another embodiment, $R_1'$ is ($C_6$-$C_{12}$)aralkyl optionally substituted with one or more $R_2$. In another embodiment, $R_1'$ is (6 to 10 membered)aryl optionally substituted with one or more $R_2$. In another embodiment, $R_1'$ is ($C_1$-$C_{10}$)heteroalkyl optionally substituted with one or more $R_2$. In another embodiment, $R_1'$ is ($C_3$-$C_{10}$)heterocycloalkyl optionally substituted with one or more $R_2$. In another embodiment, $R_1'$ is (5 to 10 membered) heteroaryl optionally substituted with one or more $R_2$.

In one embodiment, m is 0. In another embodiment, m is 1. In another embodiment, m is 2.

In one embodiment, n is 1. In another embodiment, n is 2. In another embodiment, n is 3. In one embodiment, n is 1 or 2.

In one embodiment, when n is 1, $R_5$, $R_6$, $R_7$, and $R_8$ are not all hydrogen. In one embodiment, when n is 1 and when one of $R_5$, $R_6$, $R_7$, and $R_8$ is halogen, the other three of $R_5$, $R_6$, $R_7$, and $R_8$ are not all hydrogen. In one embodiment, when n is 1 and when $R_6$ is ($C_1$-$C_4$)alkyl or ($C_1$-$C_4$)alkoxyl optionally substituted with one or more halogen, $R_5$, $R_7$, and $R_8$ are not all hydrogen.

Any of the combinations of $R_A$, $R_B$, $R_N$, R', R", $R_1$, $R_2$, $R_3$, $R_4$, $R_5$, $R_6$, $R_7$, $R_8$, $R_1'$, m, and n are encompassed by this disclosure and specifically provided herein.

In one embodiment, provided herein is a compound of formula (IIa):

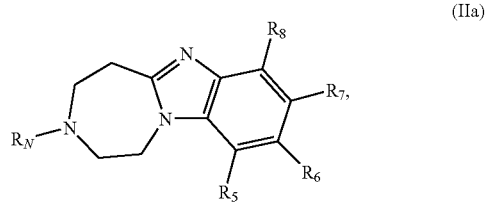

or a pharmaceutically acceptable salt, solvate, or stereoisomer thereof, wherein $R_5$, $R_6$, $R_7$, and $R_8$ are independently hydrogen, halogen, cyano, ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$)heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or two adjacent $R_5$, $R_6$, $R_7$, and $R_8$ may together form a 3 to 10 membered ring; and $R_N$ and $R_1$ are defined herein elsewhere.

In another embodiment, provided herein is a compound of formula (IIa), or a pharmaceutically acceptable salt, solvate, or stereoisomer thereof, wherein $R_5$, $R_6$, $R_7$, and $R_8$ are each independently (i) hydrogen, halogen, or cyano; (ii) ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$) heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; (iii) hydroxyl substituted with one or more $R_1'$; or (iv) two adjacent $R_5$, $R_6$, $R_7$, and $R_8$ together form a 3 to 10 membered ring optionally substituted with one or more $R_1$;

$R_5$, $R_6$, $R_7$, and $R_8$ cannot all be hydrogen;

when one of $R_5$, $R_6$, $R_7$, and $R_8$ is halogen, the other three of $R_5$, $R_6$, $R_7$, and $R_8$ cannot all be hydrogen;

when $R_6$ is ($C_1$-$C_4$)alkyl or ($C_1$-$C_4$)alkoxyl optionally substituted with one or more halogen, $R_5$, $R_7$, and $R_8$ cannot all be hydrogen; and $R_N$, $R_1$, and $R_1'$ are defined herein elsewhere.

In one embodiment, two adjacent $R_5$, $R_6$, $R_7$, and $R_8$ together form a 3 to 10 membered ring optionally substituted with one or more $R_1$. In one embodiment, two adjacent $R_5$, $R_6$, $R_7$, and $R_8$ together form a 5 to 6 membered ring optionally substituted with one or more $R_1$. In one embodiment, two adjacent $R_5$, $R_6$, $R_7$, and $R_8$ together form a partially saturated 5 to 6 membered heterocycloalkyl ring optionally substituted with one or more $R_1$. In one embodiment, the 5 to 6 membered ring contains at least one nitrogen ring atom. Specific examples include, but are not limited to, compounds of the following structure:

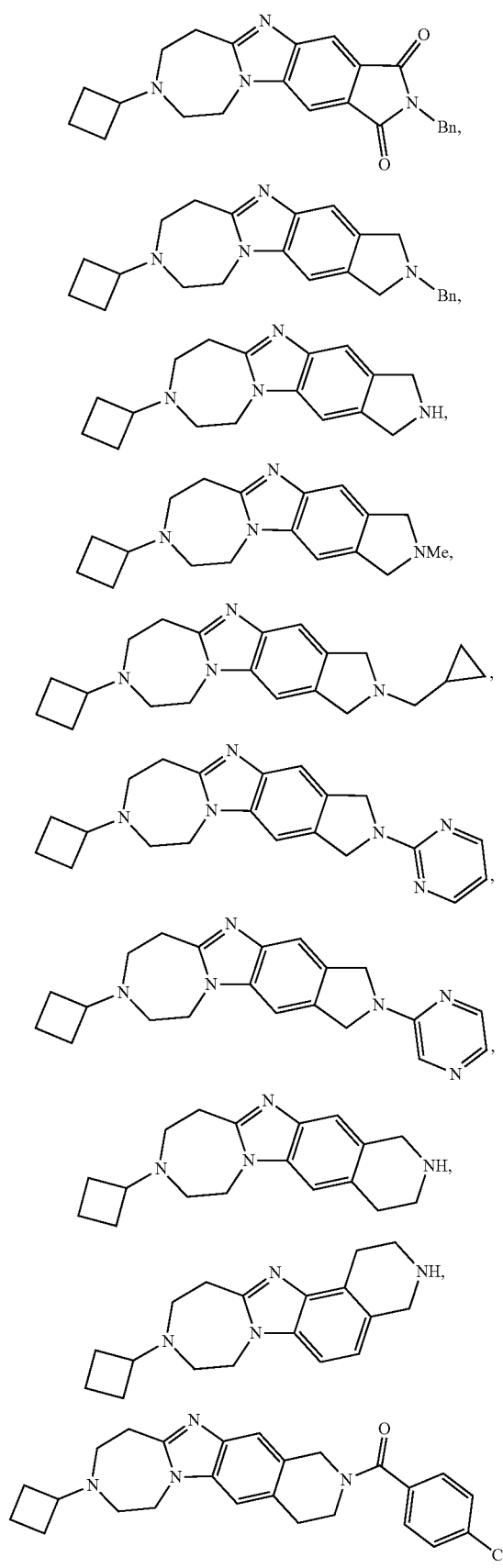
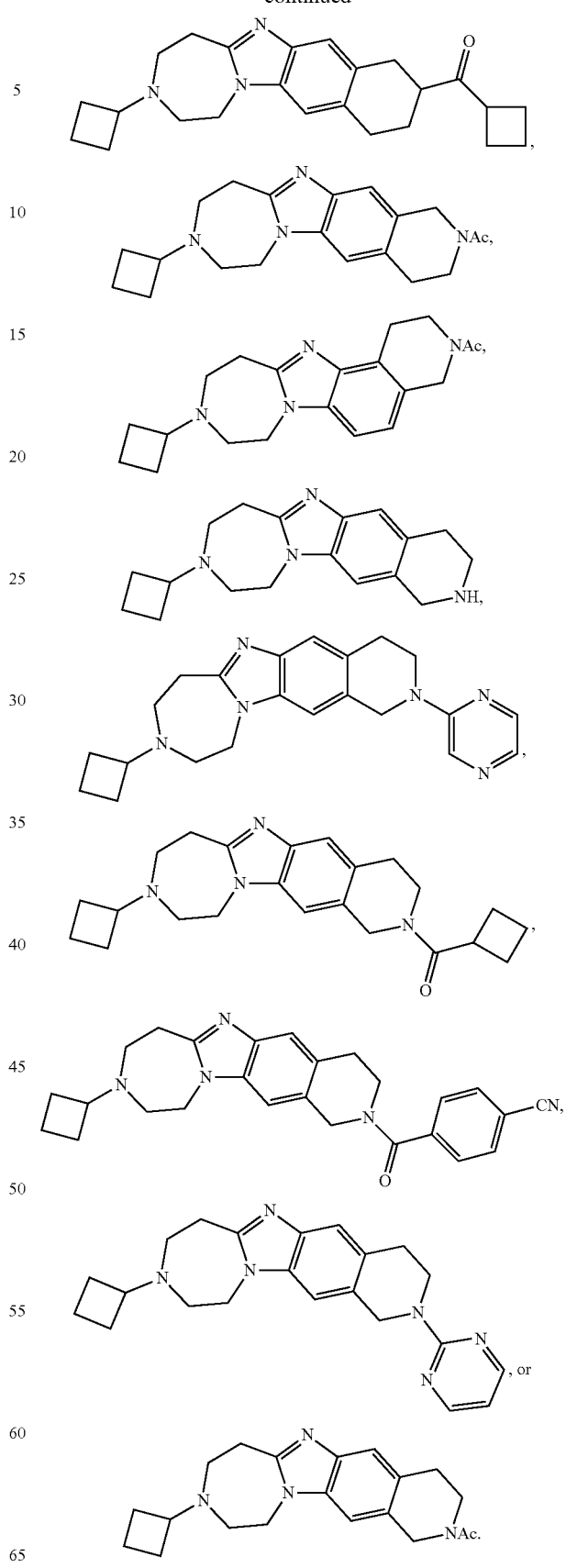

In another embodiment, provided herein is a compound of formula (IIb):

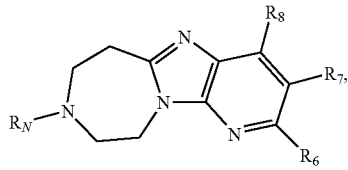
(IIb)

or a pharmaceutically acceptable salt, solvate, or stereoisomer thereof, wherein $R_6$, $R_7$, and $R_8$ are independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$-heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or two adjacent $R_6$, $R_7$, and $R_8$ may together form a 3 to 10 membered ring; and $R_N$ and $R_1$ are defined herein elsewhere.

In one embodiment, provided herein are compounds of formula (IIb), or a pharmaceutically acceptable salt, solvate, or stereoisomer thereof, wherein $R_N$ is $(C_3-C_{10})$cycloalkyl optionally substituted with one or more R'; $R_6$ and $R_8$ are hydrogen; and $R_7$ is hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocyclo alkyl, (5 to 10 membered)-heteroaryl, hydroxyl, alkoxyl, aminoalkyl, amino, imino, amido, carbonyl, thiol, sulfinyl, or sulfonyl, each of which is optionally substituted with one or more $R_1$. R' and $R_1$ are defined herein elsewhere. In one embodiment, $R_N$ is optionally substituted cyclobutyl. In one embodiment, $R_7$ is halogen. In another embodiment, $R_7$ is optionally substituted phenyl. In another embodiment, $R_7$ is optionally substituted pyridine. In another embodiment, $R_7$ is optionally substituted pyrimidine. In another embodiment, $R_7$ is optionally substituted pyrazine. In another embodiment, $R_7$ is optionally substituted five-membered heteroaryl. In another embodiment, $R_7$ is optionally substituted six-membered heteroaryl.

Specific examples include, but are not limited to, compounds of the following structures:

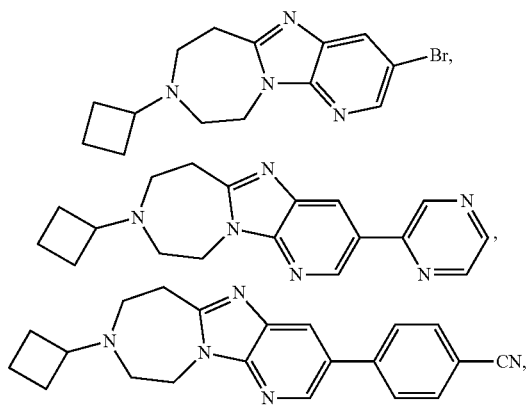

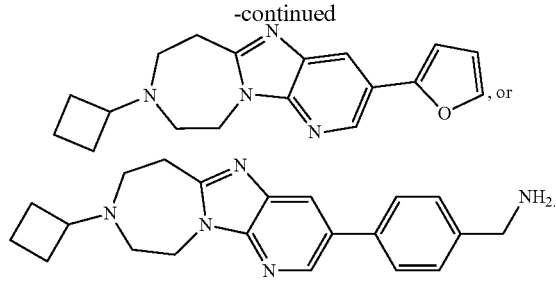

In another embodiment, provided herein is a compound of formula (IIc):

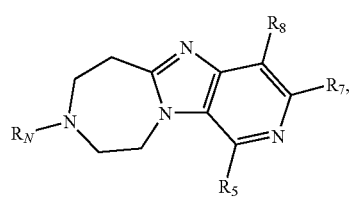
(IIc)

or a pharmaceutically acceptable salt, solvate, or stereoisomer thereof, wherein $R_5$, $R_7$, and $R_8$ are independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$-heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or $R_7$ and $R_8$ may together form a 3 to 10 membered ring; and $R_N$ and $R_1$ are defined herein elsewhere.

In another embodiment, provided herein is a compound of formula (IId):

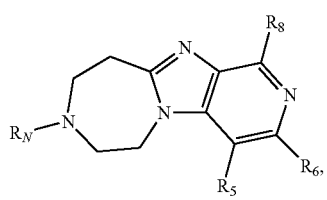
(IId)

or a pharmaceutically acceptable salt, solvate, or stereoisomer thereof, wherein $R_5$, $R_6$, and $R_8$ are independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$-heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or $R_5$ and $R_6$ may together form a 3 to 10 membered ring; and $R_N$ and $R_1$ are defined herein elsewhere.

In another embodiment, provided herein is a compound of formula (IIe):

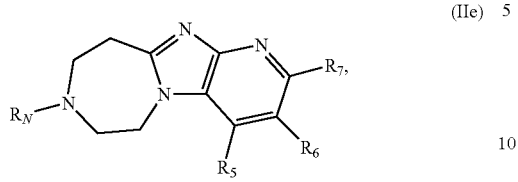

(IIe)

or a pharmaceutically acceptable salt, solvate, or stereoisomer thereof, wherein $R_5$, $R_6$, and $R_7$ are independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$-heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; or two adjacent $R_5$, $R_6$, and $R_7$ may together form a 3 to 10 membered ring; and $R_N$ and $R_1$ are defined herein elsewhere.

In one embodiment, provided herein is a compound of formula (IIf):

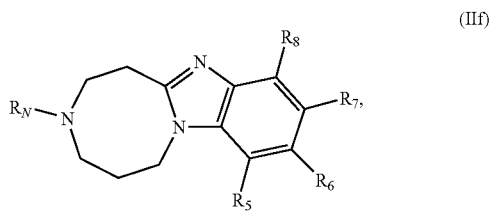

(IIf)

or a pharmaceutically acceptable salt, solvate, or stereoisomer thereof, wherein $R_5$, $R_6$, $R_7$, and $R_8$ are each independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; and $R_N$ and $R_1$ are defined herein elsewhere.

In another embodiment, provided herein is a compound of formula (IIf), or a pharmaceutically acceptable salt, solvate, or stereoisomer thereof, wherein $R_5$, $R_6$, $R_7$, and $R_8$ are each independently (i) hydrogen, halogen, or cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; (iii) hydroxyl substituted with one or more $R_1'$; or (iv) two adjacent $R_5$, $R_6$, $R_7$, and $R_8$ together form a 3 to 10 membered ring optionally substituted with one or more $R_1$; and $R_N$, $R_1$, and $R_1'$ are defined herein elsewhere.

In one embodiment, provided herein is a compound of formula (IIIa):

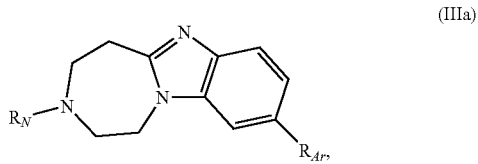

(IIIa)

or a pharmaceutically acceptable salt, solvate, or stereoisomer thereof, wherein $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1'$;

$R_{Ar}$ is not $(C_1-C_4)$alkyl or $(C_1-C_4)$alkoxyl optionally substituted with one or more halogen; and $R_N$, $R_1$, and $R_1'$ are defined herein elsewhere.

In one embodiment, $R_{Ar}$ is not $(C_1-C_4)$alkyl. In one embodiment, $R_{Ar}$ is not $(C_1-C_4)$alkyl optionally substituted with one or more halogen. In one embodiment, $R_{Ar}$ is not $(C_1-C_4)$alkyl optionally substituted with cycloalkyl. In one embodiment, $R_{Ar}$ is not $(C_1-C_4)$alkoxyl optionally substituted with one or more halogen. In one embodiment, $R_{Ar}$ is not $(C_1-C_4)$alkoxyl optionally substituted with cycloalkyl.

In one embodiment, $R_{Ar}$ is (i) cyano; (ii) (6 to 10 membered)aryl, $(C_1-C_{10})$heteroalkyl, $(C_3-C_{10})$heterocycloalkyl, (5 to 10 membered)heteroaryl, aminoalkyl, amino, amido, or carbonyl, each of which is optionally substituted with one or more $R_1$; or (iii) $(C_1-C_{10})$alkyl, alkoxyl, or hydroxyl, each of which is substituted with one or more $R_1'$.

In one embodiment, provided herein is a compound of formula (IIIb):

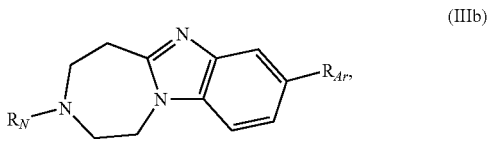

(IIIb)

or a pharmaceutically acceptable salt, solvate, or stereoisomer thereof, wherein $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1'$; and $R_N$, $R_1$, and $R_1'$ are defined herein elsewhere.

In one embodiment, $R_{Ar}$ is hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$.

In one embodiment, $R_{Ar}$ is $(C_1-C_{10})$alkyl or alkoxyl, each of which is substituted with one or more halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, —$S(O)_2NR_3R_4$, ($C_3$-$C_{10}$) cycloalkyl optionally substituted with one or more $R_2$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$.

In one embodiment, $R_{Ar}$ is ($C_1$-$C_{10}$)alkyl or alkoxyl, each of which is substituted with one or more halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, —$S(O)_2NR_3R_4$, ($C_6$-$C_{12}$)aralkyl optionally substituted with one or more $R_2$, (6 to 10 membered)aryl optionally substituted with one or more $R_2$, ($C_1$-$C_{10}$)heteroalkyl optionally substituted with one or more $R_2$, ($C_3$-$C_{10}$)heterocycloalkyl optionally substituted with one or more $R_2$, or (5 to 10 membered)heteroaryl optionally substituted with one or more $R_2$.

In one embodiment, $R_{Ar}$ is hydrogen. In another embodiment, $R_{Ar}$ is halogen. In another embodiment, $R_{Ar}$ is cyano. In another embodiment, $R_{Ar}$ is ($C_1$-$C_{10}$)alkyl optionally substituted with one or more $R_1$. In another embodiment, $R_{Ar}$ is ($C_1$-$C_{10}$)alkyl substituted with one or more $R_1'$. In another embodiment, $R_{Ar}$ is ($C_1$-$C_{10}$)alkenyl optionally substituted with one or more $R_1$. In another embodiment, $R_{Ar}$ is ($C_3$-$C_{10}$) cycloalkyl optionally substituted with one or more $R_1$. In another embodiment, $R_{Ar}$ is (6 to 10 membered)aryl optionally substituted with one or more $R_1$. In another embodiment, $R_{Ar}$ is ($C_1$-$C_{10}$)heteroalkyl optionally substituted with one or more $R_1$. In another embodiment, $R_{Ar}$ is ($C_3$-$C_{10}$)heterocycloalkyl optionally substituted with one or more $R_1$. In another embodiment, $R_{Ar}$ is (5 to 10 membered)heteroaryl optionally substituted with one or more $R_1$. In another embodiment, $R_{Ar}$ is hydroxyl optionally substituted with one or more $R_1$. In another embodiment, $R_{Ar}$ is hydroxyl substituted with one or more $R_1'$. In another embodiment, $R_{Ar}$ is alkoxyl optionally substituted with one or more $R_1$. In another embodiment, $R_{Ar}$ is alkoxyl substituted with one or more $R_1'$. In another embodiment, $R_{Ar}$ is aminoalkyl optionally substituted with one or more $R_1$. In another embodiment, $R_{Ar}$ is amino optionally substituted with one or more $R_1$. In another embodiment, $R_{Ar}$ is imino optionally substituted with one or more $R_1$. In another embodiment, $R_{Ar}$ is amido optionally substituted with one or more $R_1$. In another embodiment, $R_{Ar}$ is carbonyl optionally substituted with one or more $R_1$. In another embodiment, $R_{Ar}$ is thiol optionally substituted with one or more $R_1$. In another embodiment, $R_{Ar}$ is sulfinyl optionally substituted with one or more $R_1$. In another embodiment, $R_{Ar}$ is sulfonyl optionally substituted with one or more $R_1$. In one embodiment, $R_{Ar}$ is fluorine. In another embodiment, $R_{Ar}$ is chlorine. In another embodiment, $R_{Ar}$ is bromine. In another embodiment, $R_{Ar}$ is iodine. In another embodiment, $R_{Ar}$ is cyano. In another embodiment, $R_{Ar}$ is —$OR_1$. In another embodiment, $R_{Ar}$ is —$OR_1'$. In another embodiment, $R_{Ar}$ is —$OCH_2R_1$. In another embodiment, $R_{Ar}$ is $OCH_2R_1'$. In another embodiment, $R_{Ar}$ is —$NHR_1$. In another embodiment, $R_{Ar}$ is —$NHCH_2R_1$. In another embodiment, $R_{Ar}$ is —$N(R_1)_2$. In another embodiment, $R_{Ar}$ is —$C(O)R_1$. In another embodiment, $R_{Ar}$ is —$C(O)N(R_1)_2$. In another embodiment, $R_{Ar}$ is —$CH_2R_1$. In another embodiment, $R_{Ar}$ is —$CH_2R_1'$. In another embodiment, $R_{Ar}$ is —$CH_2N(R_1)_2$. In another embodiment, $R_{Ar}$ is —$CH_2OR_1$. In another embodiment, $R_{Ar}$ is —$CH_2OR_1'$. $R_1$ and $R_1'$ are defined herein elsewhere.

Any of the combinations of $R_{Ar}$, $R_N$, $R_1$ and $R_1'$ are encompassed by this disclosure and specifically provided herein.

In one embodiment, provided herein is a compound of formula (IIIa), or a pharmaceutically acceptable salt, solvate, or stereoisomer thereof, wherein $R_N$ is ($C_3$-$C_{10}$)cycloalkyl optionally substituted with one or more R'; and $R_{Ar}$ is halogen, cyano, ($C_1$-$C_{10}$)alkyl, (6 to 10 membered)aryl, ($C_1$-$C_{10}$) heteroalkyl, ($C_3$-$C_{10}$)heterocycloalkyl, (5 to 10 membered) heteroaryl, hydroxyl, alkoxyl, aminoalkyl, amino, amido, or carbonyl, each of which is optionally substituted with one or more $R_1$. R' and $R_1$ are defined herein elsewhere.

In one embodiment, provided herein is a compound of formula (IIIa), or a pharmaceutically acceptable salt, solvate, or stereoisomer thereof, wherein $R_N$ is ($C_3$-$C_{10}$)cycloalkyl or ($C_1$-$C_{10}$)alkyl, each of which is optionally substituted with one or more R'; $R_{Ar}$ is (i) cyano; (ii) ($C_1$-$C_{10}$)alkyl, (6 to 10 membered)aryl, ($C_1$-$C_{10}$)heteroalkyl, ($C_3$-$C_{10}$)heterocycloalkyl, (5 to 10 membered)heteroaryl, alkoxyl, aminoalkyl, amino, amido, or carbonyl, each of which is optionally substituted with one or more $R_1$; or (iii) hydroxyl substituted with one or more $R_1'$; $R_{Ar}$ is not ($C_1$-$C_4$)alkyl or ($C_1$-$C_4$)alkoxyl optionally substituted with one or more halogen; and R', $R_1$, and $R_1'$ are defined herein elsewhere.

In one embodiment, provided herein is a compound of formula (IIIa), or a pharmaceutically acceptable salt, solvate, or stereoisomer thereof, wherein $R_N$ is ($C_3$-$C_{10}$)cycloalkyl or ($C_1$-$C_{10}$)alkyl, each of which is optionally substituted with one or more R'; $R_{Ar}$ is (i) cyano; (ii) (6 to 10 membered)aryl, ($C_1$-$C_{10}$)heteroalkyl, ($C_3$-$C_{10}$)heterocycloalkyl, (5 to 10 membered)heteroaryl, aminoalkyl, amino, amido, or carbonyl, each of which is optionally substituted with one or more $R_1$; or (iii) ($C_1$-$C_{10}$)alkyl, alkoxyl, or hydroxyl, each of which is substituted with one or more $R_1'$; and R', $R_1$, and $R_1'$ are defined herein elsewhere.

In one embodiment, $R_N$ is optionally substituted cyclobutyl. In one embodiment, $R_N$ is optionally substituted t-butyl. In one embodiment, $R_{Ar}$ is fluorine. In another embodiment, $R_{Ar}$ is chlorine. In another embodiment, $R_{Ar}$ is bromine. In another embodiment, $R_{Ar}$ is iodine. In another embodiment, $R_{Ar}$ is cyano. In another embodiment, $R_{Ar}$ is optionally substituted phenyl. In another embodiment, $R_{Ar}$ is optionally substituted six-membered heteroaryl. In another embodiment, $R_{Ar}$ is optionally substituted five-membered heteroaryl. In another embodiment, $R_{Ar}$ is optionally substituted 8 to 10-membered heteroaryl. In another embodiment, $R_{Ar}$ is optionally substituted six-membered heterocycloalkyl. In another embodiment, $R_{Ar}$ is optionally substituted five-membered heterocycloalkyl. In another embodiment, $R_{Ar}$ is —$OR_1$. In another embodiment, $R_{Ar}$ is —$OR_1'$. In another embodiment, $R_{Ar}$ is —$OCH_2R_1$. In another embodiment, $R_{Ar}$ is —$OCH_2R_1'$. In another embodiment, $R_{Ar}$ is —$NHR_1$. In another embodiment, $R_{Ar}$ is —$NHCH_2R_1$. In another embodiment, $R_{Ar}$ is —$N(R_1)_2$. In another embodiment, $R_{Ar}$ is —$C(O)R_1$. In another embodiment, $R_{Ar}$ is —$C(O)N(R_1)_2$. In another embodiment, $R_{Ar}$ is —$CH_2R_1$. In another embodiment, $R_{Ar}$ is —$CH_2R_1'$. In another embodiment, $R_{Ar}$ is —$CH_2N(R_1)_2$. In another embodiment, $R_{Ar}$ is —$CH_2OR_1$. In another embodiment, $R_{Ar}$ is —$CH_2OR_1'$.

In one embodiment, $R_{Ar}$ is cyano, optionally substituted phenyl, optionally substituted six-membered heteroaryl, optionally substituted five-membered heteroaryl, optionally substituted (8 to 10)membered heteroaryl, optionally substituted six-membered heterocycloalkyl, optionally substituted five-membered heterocycloalkyl, —$OR_1'$, —$OCH_2R_1'$, —$NHR_1$, —$NHCH_2R_1$, —$N(R_1)_2$, —$C(O)R_1$, —$C(O)N(R_1)_2$, —$CH_2R_1'$, —$CH_2N(R_1)_2$, —$CH_2OH$, or —$CH_2OR_1'$.

Specific examples include, but are not limited to, compounds of the following structures:
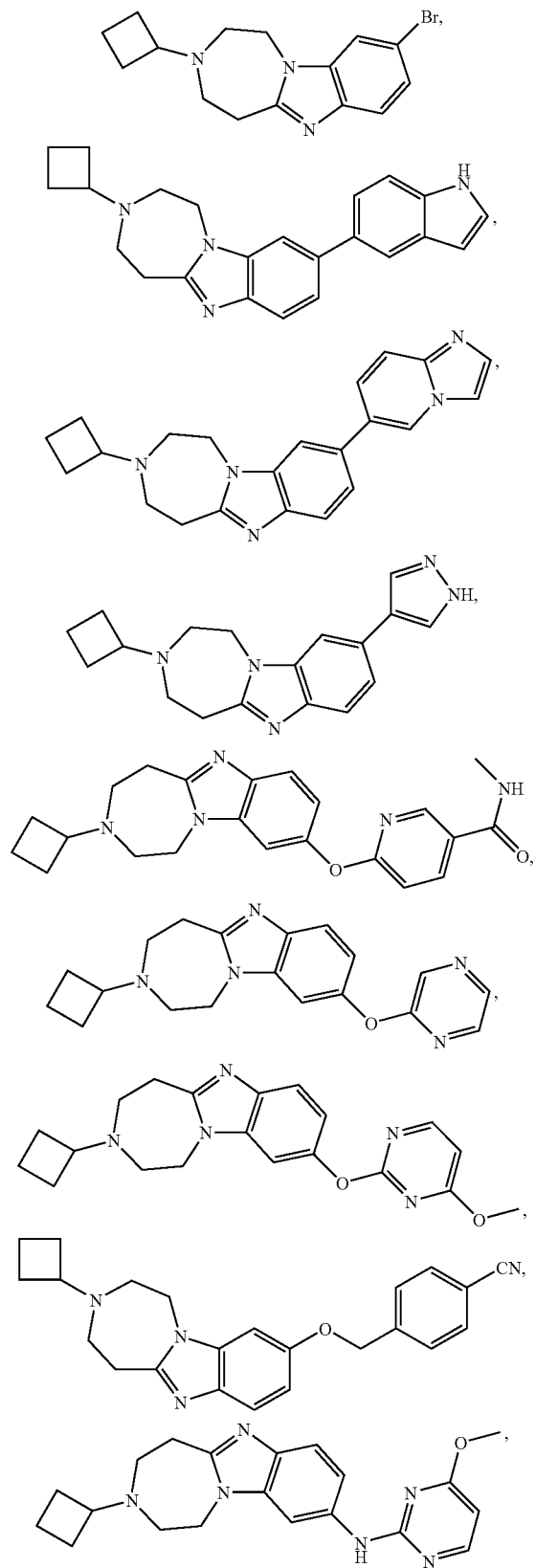
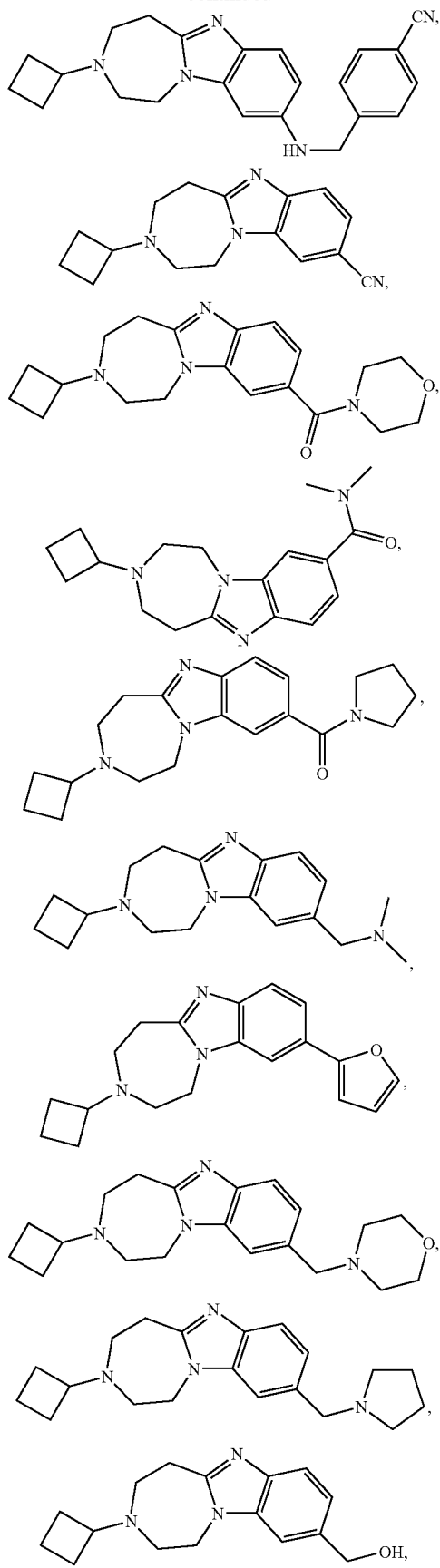

-continued

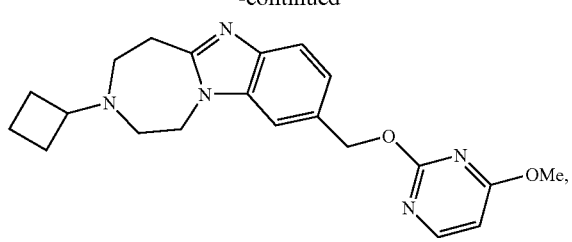

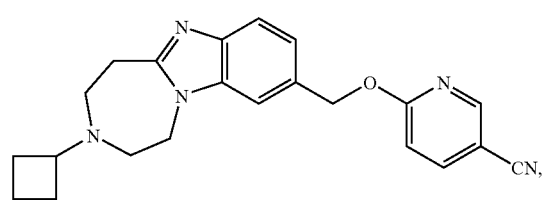

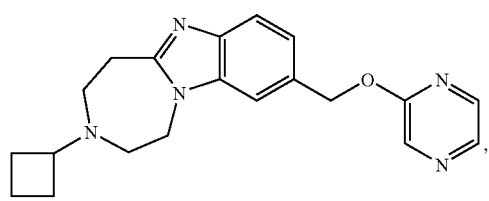

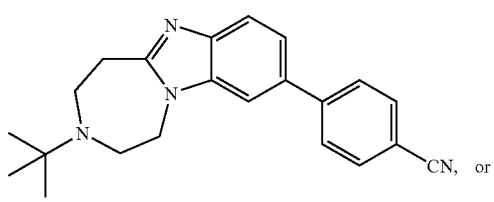

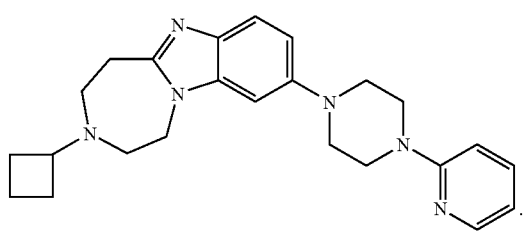

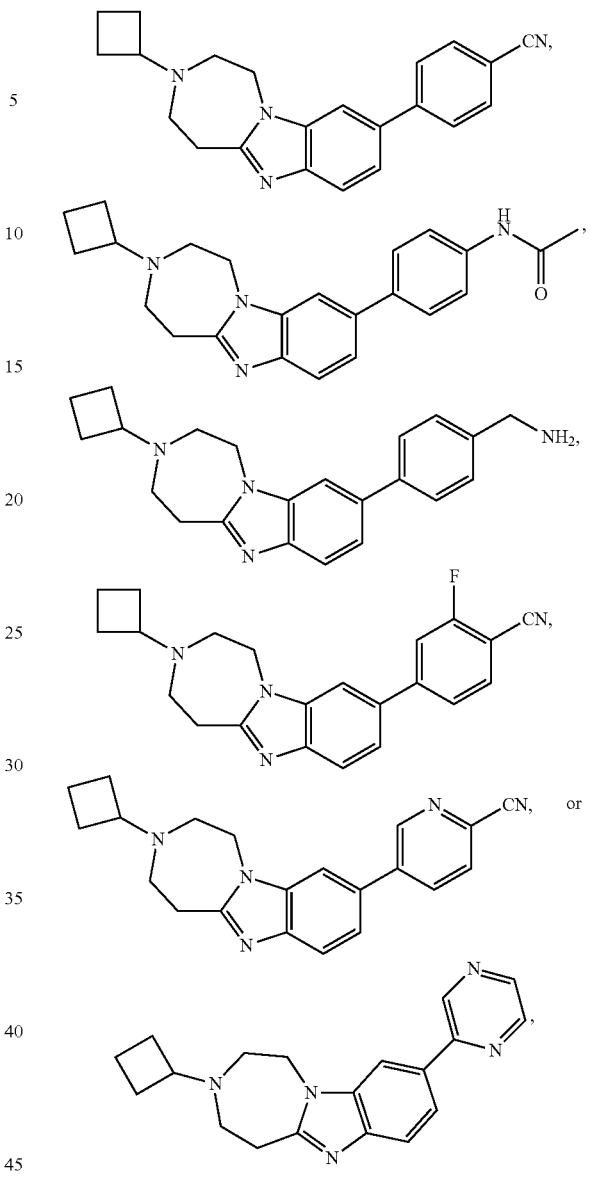

In one embodiment, provided herein is a compound of formula (IVa):

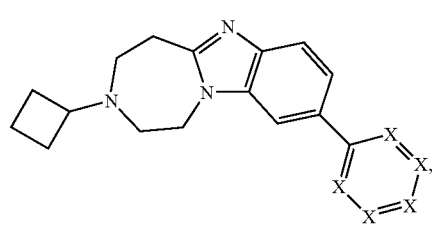

(IVa)

or a pharmaceutically acceptable salt, solvate, or stereoisomer thereof, wherein each occurrence of X is independently N, CH, or $CR_1$; and $R_1$ is defined herein elsewhere. Examples include, but are not limited to, the following compounds:

In one embodiment, provided herein is a compound of formula (IIIb), or a pharmaceutically acceptable salt, solvate, or stereoisomer thereof, wherein $R_N$ is $(C_1-C_{10})$alkyl optionally substituted with one or more R'; and $R_{Ar}$ is hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$. R' and $R_1$ are defined herein elsewhere.

In one embodiment, provided herein is a compound of formula (IIIb), or a pharmaceutically acceptable salt, solvate, or stereoisomer thereof, wherein $R_N$ is $(C_1-C_{10})$alkyl optionally substituted with one or more R'; and $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$;

or (iii) hydroxyl substituted with one or more $R_1'$. $R'$, $R_1$, and $R_1'$ are defined herein elsewhere.

In one embodiment, $R_{Ar}$ is (i) cyano; (ii) $(C_1$-$C_{10})$alkenyl, $(C_3$-$C_{10})$cycloalkyl, (6 to 10 membered)aryl, $(C_1$-$C_{10})$heteroalkyl, $(C_3$-$C_{10})$heterocycloalkyl, (5 to 10 membered)heteroaryl, aminoalkyl, amino, imino, amido, carbonyl, thiol, sulfinyl, or sulfonyl, each of which is optionally substituted with one or more $R_1$; or (iii) $(C_1$-$C_{10})$alkyl, hydroxyl, or alkoxyl, each of which is substituted with one or more $R_1'$. $R'$, $R_1$, and $R_1'$ are defined herein elsewhere.

Specific examples include, but are not limited to, compounds of the following structures:

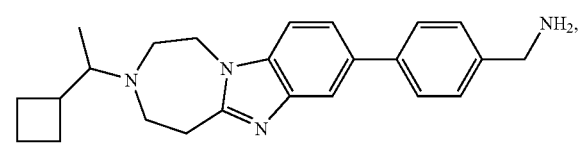

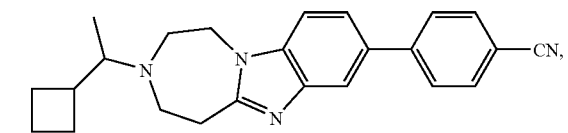

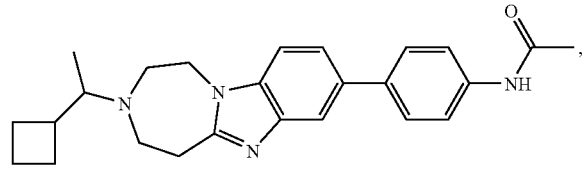

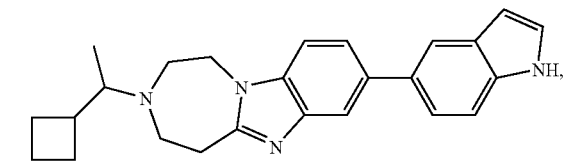

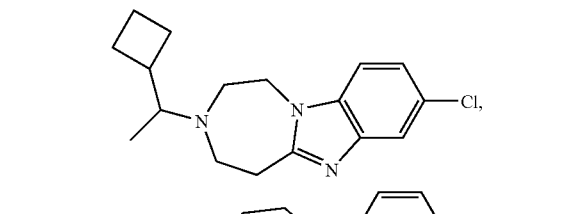

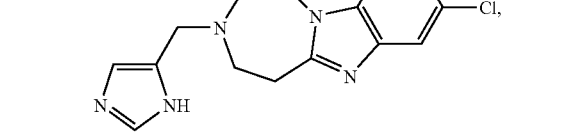

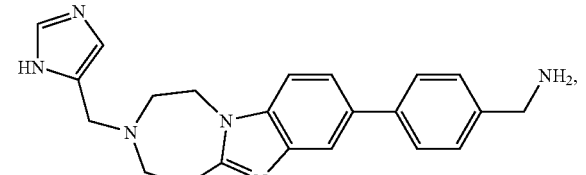

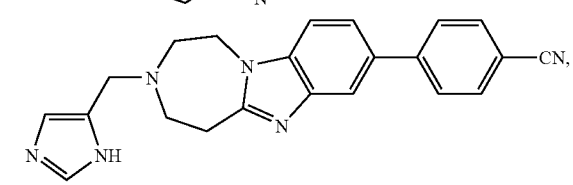

-continued

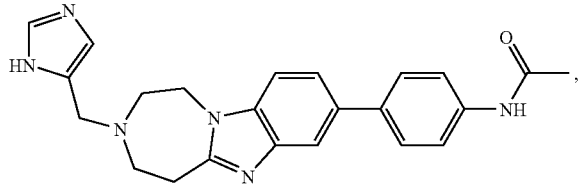

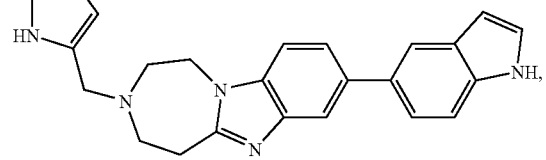

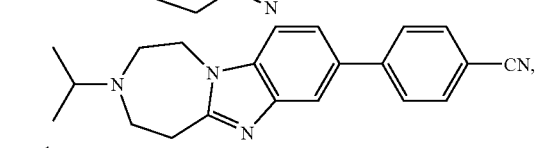

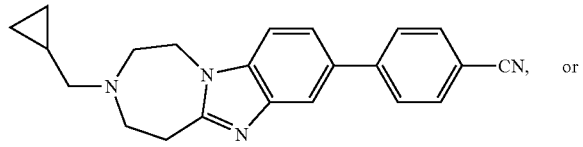

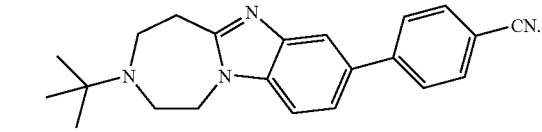

In another embodiment, provided herein are compounds of formula (IIIb), or a pharmaceutically acceptable salt, solvate, or stereoisomer thereof, wherein $R_N$ is $(C_3$-$C_{10})$heterocycloalkyl optionally substituted with one or more $R'$; and $R_{Ar}$ is hydrogen, halogen, cyano, $(C_1$-$C_{10})$alkyl, $(C_1$-$C_{10})$alkenyl, $(C_3$-$C_{10})$cycloalkyl, (6 to 10 membered)-aryl, $(C_1$-$C_{10})$heteroalkyl, $(C_3$-$C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$. $R'$ and $R_1$ are defined herein elsewhere.

In one embodiment, provided herein is a compound of formula (IIIb), or a pharmaceutically acceptable salt, solvate, or stereoisomer thereof, wherein $R_N$ is $(C_3$-$C_{10})$heterocycloalkyl optionally substituted with one or more $R'$; and $R_{Ar}$ is (i) cyano; (ii) $(C_1$-$C_{10})$alkyl, $(C_1$-$C_{10})$alkenyl, $(C_3$-$C_{10})$cycloalkyl, (6 to 10 membered)aryl, $(C_1$-$C_{10})$heteroalkyl, $(C_3$-$C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1'$. $R'$, $R_1$, and $R_1'$ are defined herein elsewhere.

In one embodiment, provided herein is a compound of formula (nib), or a pharmaceutically acceptable salt, solvate, or stereoisomer thereof, wherein $R_N$ is $(C_3$-$C_{10})$heterocycloalkyl optionally substituted with one or more $R'$; and $R_{Ar}$ is (i) cyano; (ii) $(C_1$-$C_{10})$alkenyl, $(C_3$-$C_{10})$cycloalkyl, (6 to 10 membered)aryl, $(C_1$-$C_{10})$heteroalkyl, $(C_3$-$C_{10})$heterocycloalkyl, (5 to 10 membered)heteroaryl, aminoalkyl, amino, imino, amido, carbonyl, thiol, sulfinyl, or sulfonyl, each of which is optionally substituted with one or more $R_1$; or (iii) $(C_1$-$C_{10})$alkyl, hydroxyl, or alkoxyl, each of which is substituted with one or more $R_1'$. $R'$, $R_1$, and $R_1'$ are defined herein elsewhere.

Specific examples include, but are not limited to, compounds of the following structures:

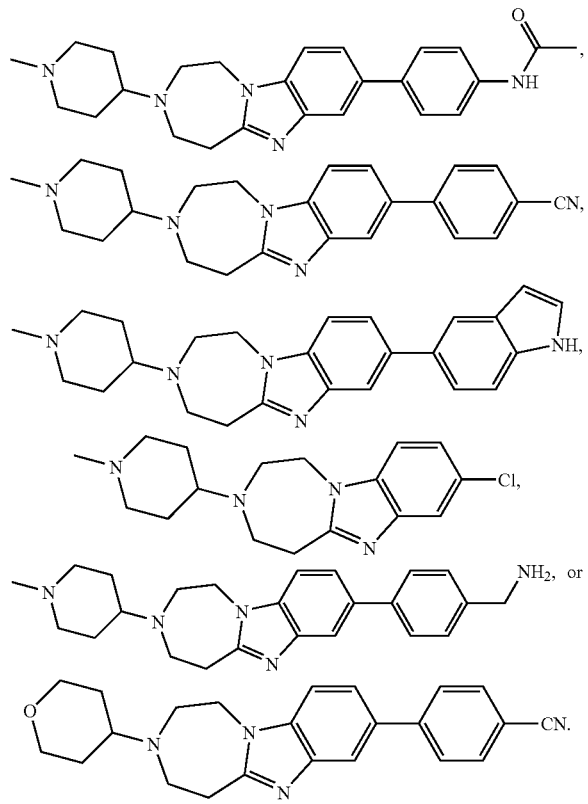

In one embodiment, provided herein is a compound of formula (IIIb), or a pharmaceutically acceptable salt, solvate, or stereoisomer thereof, wherein $R_N$ is $(C_3-C_{10})$cycloalkyl optionally substituted with one or more R'. In one embodiment, provided herein is a compound of formula (IIIb), or a pharmaceutically acceptable salt, solvate, or stereoisomer thereof, wherein $R_N$ is $(C_3-C_6)$cycloalkyl optionally substituted with one or more R'. In one embodiment, provided herein is a compound of formula (IIIb), or a pharmaceutically acceptable salt, solvate, or stereoisomer thereof, wherein $R_N$ is $(C_4-C_6)$cycloalkyl optionally substituted with one or more R'.

In another embodiment, provided herein is a compound of formula (IIIb), or a pharmaceutically acceptable salt, solvate, or stereoisomer thereof, wherein $R_N$ is cyclohexyl optionally substituted with one or more R'; and $R_{Ar}$ is hydrogen, halogen, cyano, $(C_1-C_{10})$alkyl, $(C_1-C_{10})$alkenyl, $(C_3-C_{10})$cycloalkyl, (6 to 10 membered)-aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$. R' and $R_1$ are defined herein elsewhere.

In one embodiment, provided herein is a compound of formula (IIIb), or a pharmaceutically acceptable salt, solvate, or stereoisomer thereof, wherein $R_N$ is cyclohexyl optionally substituted with one or more R'; and $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1$'. R', $R_1$, and $R_1$' are defined herein elsewhere.

In one embodiment, provided herein is a compound of formula (IIIb), or a pharmaceutically acceptable salt, solvate, or stereoisomer thereof, wherein $R_N$ is cyclohexyl optionally substituted with one or more R'; and $R_{Ar}$ is (i) cyano; (ii) $(C_1-C_{10})$alkenyl, $(C_3-C_{10})$cycloalkyl, (6 to 10 membered) aryl, $(C_1-C_{10})$heteroalkyl, $(C_3-C_{10})$heterocycloalkyl, (5 to 10 membered)heteroaryl, aminoalkyl, amino, imino, amido, carbonyl, thiol, sulfinyl, or sulfonyl, each of which is optionally substituted with one or more $R_1$; or (iii) $(C_1-C_{10})$alkyl, hydroxyl, or alkoxyl, each of which is substituted with one or more $R_1$'. R', $R_1$, and $R_1$' are defined herein elsewhere.

Specific examples include, but are not limited to, compounds of the following structures:

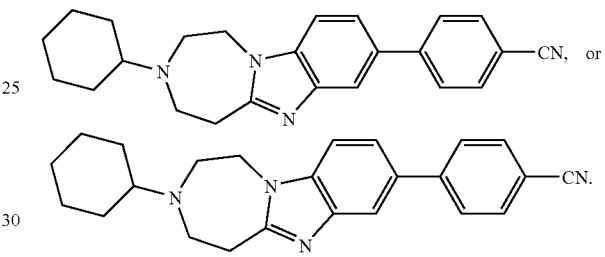

In another embodiment, provided herein is a compounds of formula (IIIb), or a pharmaceutically acceptable salt, solvate, or stereoisomer thereof, wherein $R_N$ is cyclopentyl optionally substituted with one or more R'; and $R_{Ar}$ is hydrogen, halogen, cyano, $(C_1-C_{10})$alkyl, $(C_1-C_{10})$alkenyl, $(C_3-C_{10})$cycloalkyl, (6 to 10 membered)-aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$. R' and $R_1$ are defined herein elsewhere.

In one embodiment, provided herein is a compound of formula (IIIb), or a pharmaceutically acceptable salt, solvate, or stereoisomer thereof, wherein $R_N$ is cyclopentyl optionally substituted with one or more R'; and $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1$'. R', $R_1$, and $R_1$' are defined herein elsewhere.

In one embodiment, provided herein is a compound of formula (IIIb), or a pharmaceutically acceptable salt, solvate, or stereoisomer thereof, wherein $R_N$ is cyclopentyl optionally substituted with one or more R'; and $R_{Ar}$ is (i) cyano; (ii) $(C_1-C_{10})$alkenyl, $(C_3-C_{10})$cycloalkyl, (6 to 10 membered) aryl, $(C_1-C_{10})$heteroalkyl, $(C_3-C_{10})$heterocycloalkyl, (5 to 10 membered)heteroaryl, aminoalkyl, amino, imino, amido, carbonyl, thiol, sulfinyl, or sulfonyl, each of which is optionally substituted with one or more $R_1$; or (iii) $(C_1-C_{10})$alkyl, hydroxyl, or alkoxyl, each of which is substituted with one or more $R_1$'. R', $R_1$, and $R_1$' are defined herein elsewhere.

Specific examples include, but are not limited to, compounds of the following structures:

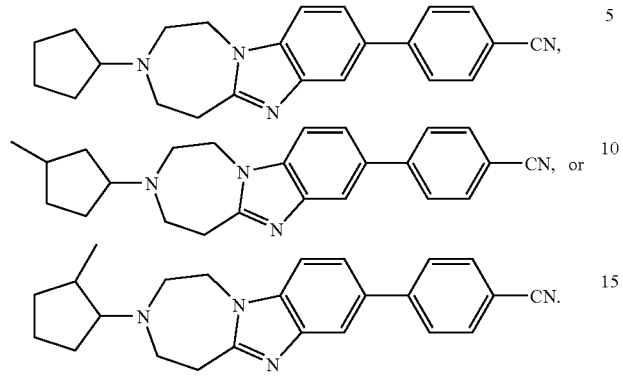

In one embodiment, provided herein is a compound of formula (IIIb), or a pharmaceutically acceptable salt, solvate, or stereoisomer thereof, wherein $R_{Ar}$ is a five-membered heteroaryl optionally substituted with one or more $R_1$. In one embodiment, provided herein is a compound of formula (IIIb), or a pharmaceutically acceptable salt, solvate, or stereoisomer thereof, wherein $R_N$ is cyclobutyl optionally substituted with one or more R', and $R_{AS}$ is a five-membered heteroaryl optionally substituted with one or more $R_1$. R' and $R_1$ are defined herein elsewhere. Specific examples include, but are not limited to, compounds of the following structures:

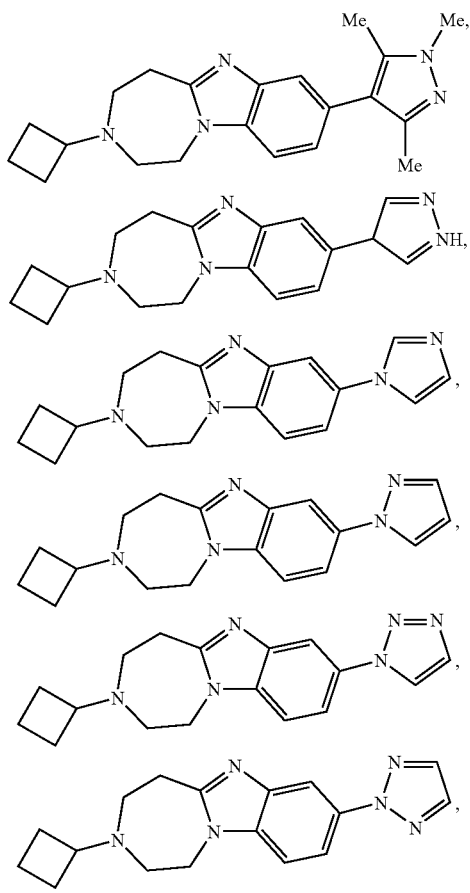

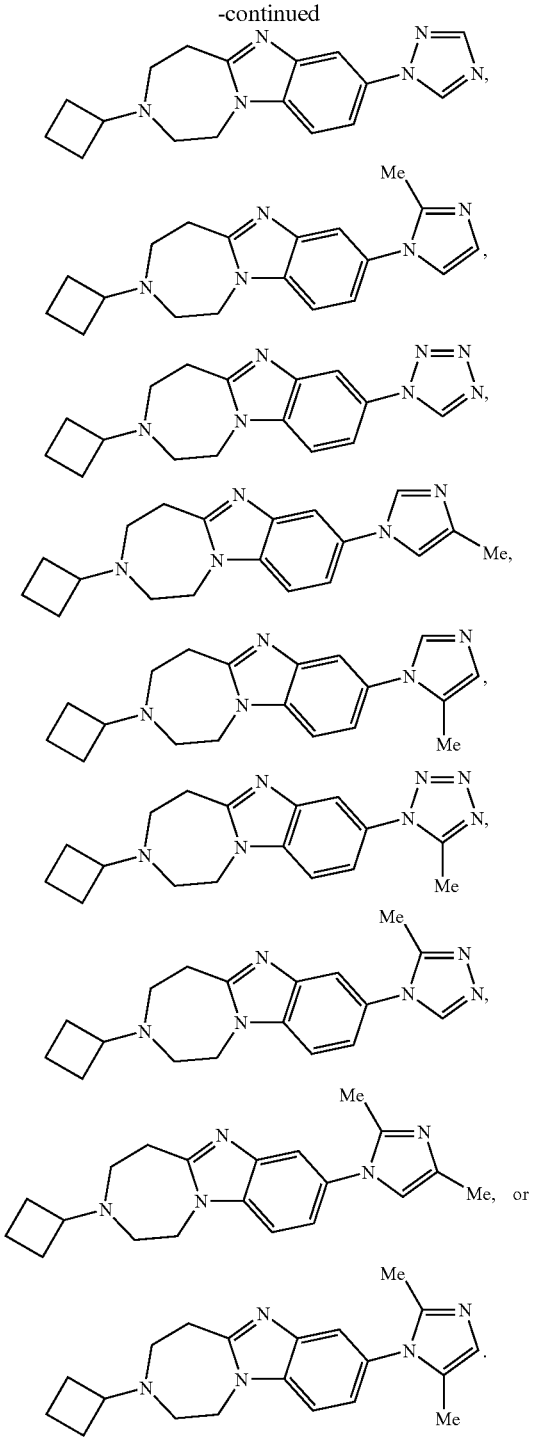

In one embodiment, provided herein is a compound of formula (IIIb), or a pharmaceutically acceptable salt, solvate, or stereoisomer thereof, wherein $R_{Ar}$ is 8 to 10 membered heteroaryl optionally substituted with one or more $R_1$. In one embodiment, provided herein is a compound of formula (IIIb), or a pharmaceutically acceptable salt, solvate, or stereoisomer thereof, wherein $R_N$ is cyclobutyl optionally substituted with one or more R', and $R_{Ar}$ is 8 to 10 membered heteroaryl optionally substituted with one or more $R_1$. R' and $R_1$ are defined herein elsewhere. In one embodiment, $R_{Ar}$ is an 9 to 10 membered heteroaryl optionally substituted with one or more $R_1$. In one embodiment, $R_{Ar}$ is an 9 membered heteroaryl optionally substituted with one or more $R_1$. Specific examples include, but are not limited to, compounds of the following structures:
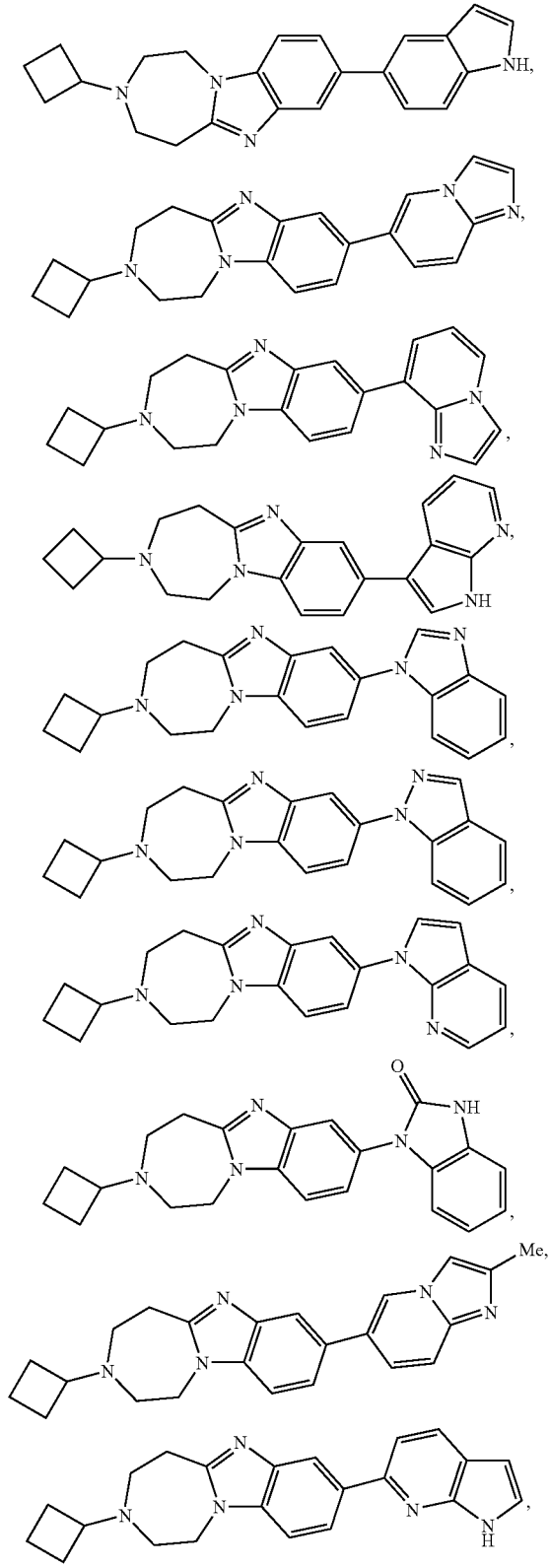
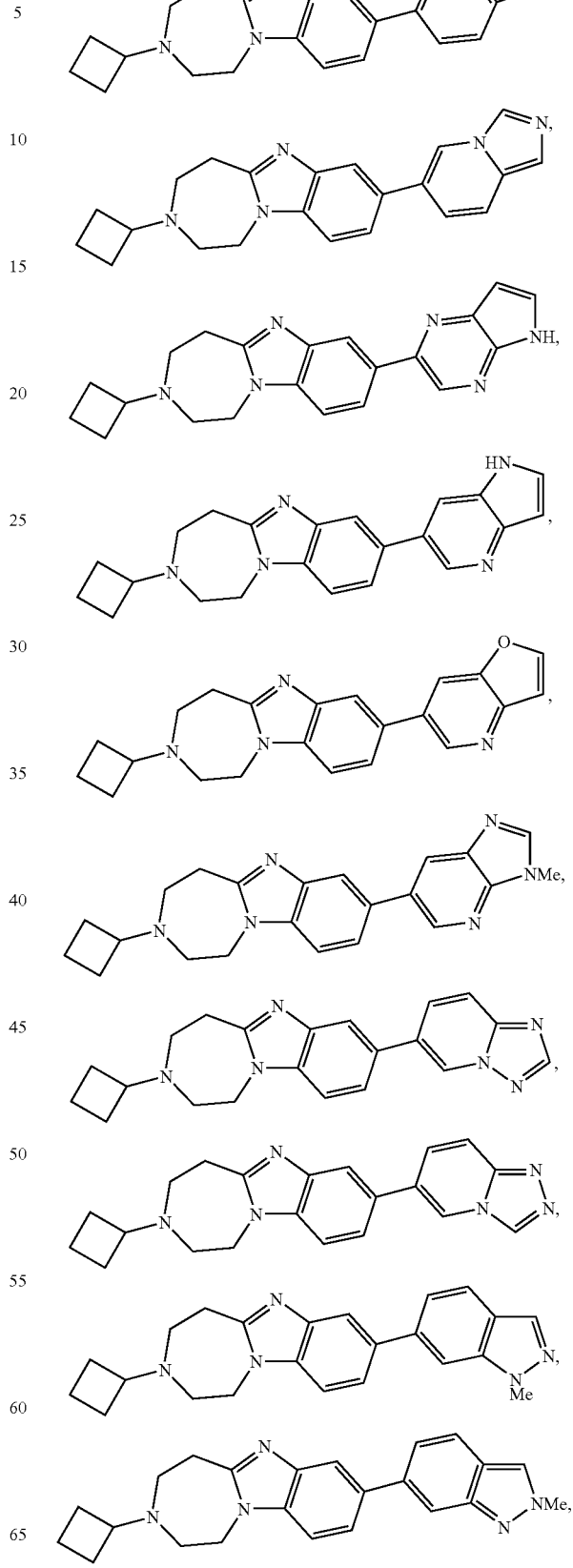

-continued

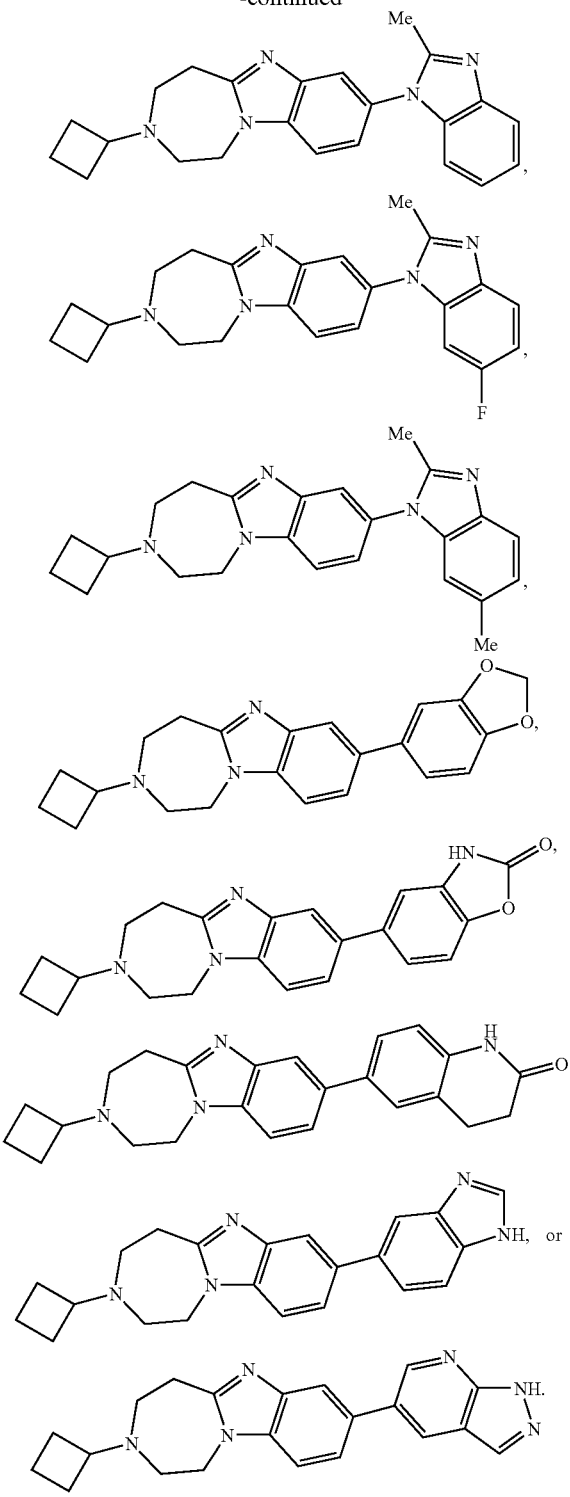

In one embodiment, provided herein is a compound of formula (IIIb), or a pharmaceutically acceptable salt, solvate, or stereoisomer thereof, wherein $R_{Ar}$ is $(C_3-C_{10})$ heterocycloalkyl optionally substituted with one or more $R_1$. In one embodiment, provided herein is a compound of formula (IIIb), or a pharmaceutically acceptable salt, solvate, or stereoisomer thereof, wherein $R_N$ is cyclobutyl optionally substituted with one or more R', and $R_{Ar}$ is $(C_3-C_{10})$ heterocycloalkyl optionally substituted with one or more $R_1$. R' and $R_1$ are defined herein elsewhere. In one embodiment, $R_{Ar}$ is 5 to 6 membered heterocycloalkyl optionally substituted with one or more $R_1$. In one embodiment, $R_{Ar}$ is 9 to 10 membered heterocycloalkyl optionally substituted with one or more $R_1$. Specific examples include, but are not limited to, compounds of the following structures:

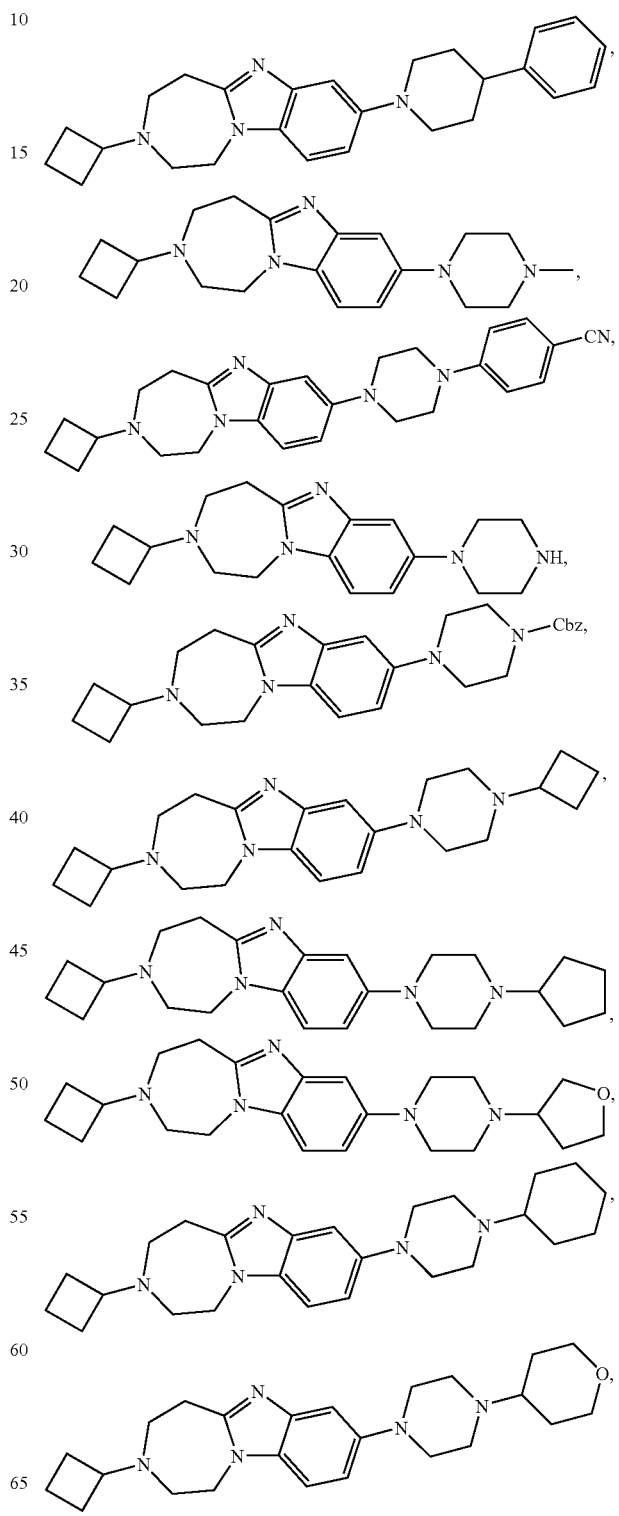

47
-continued
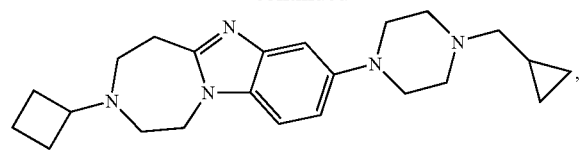,
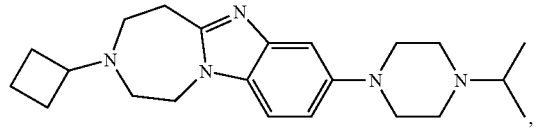,
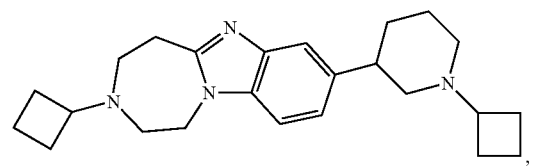,
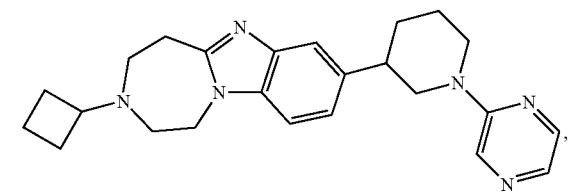,
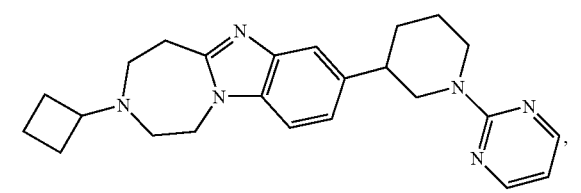,
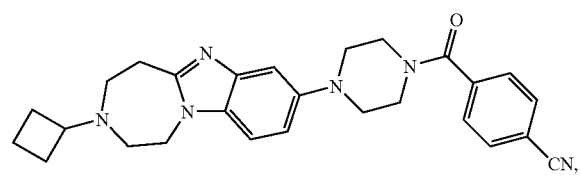,
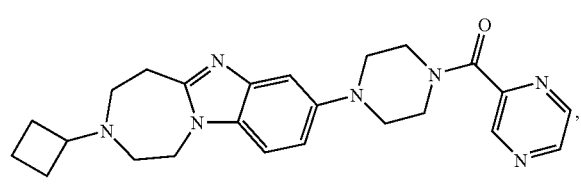,
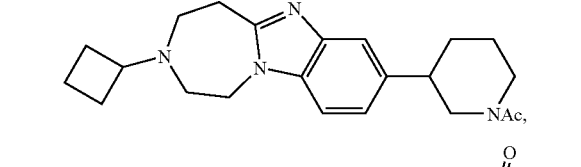,
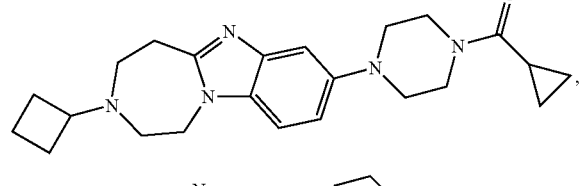,
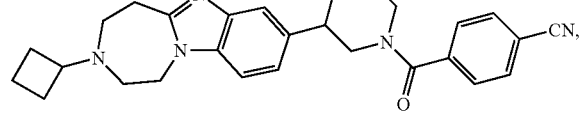,
48
-continued
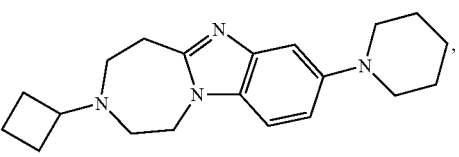,
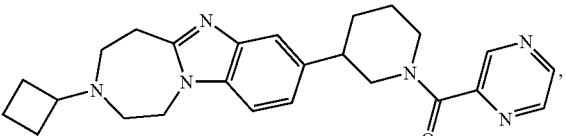,
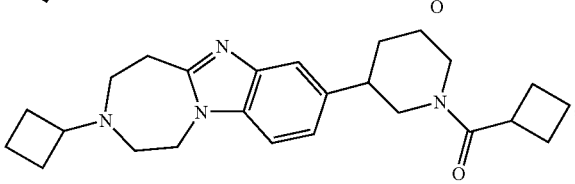,
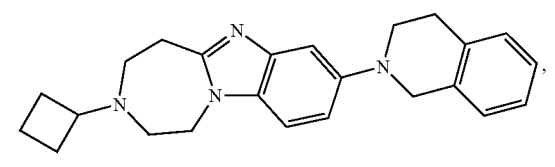,
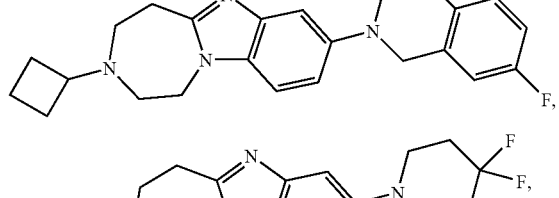,
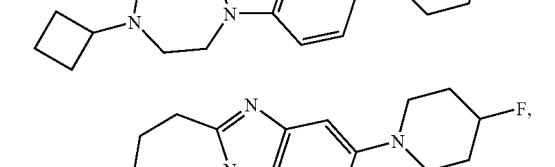,
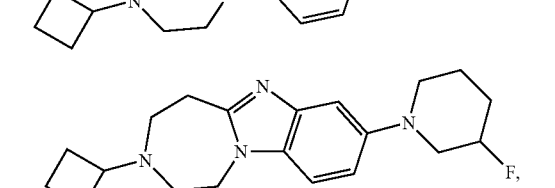,
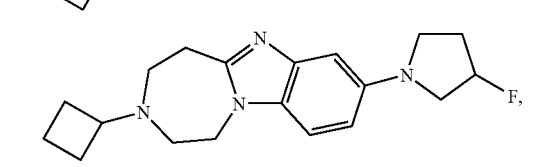,
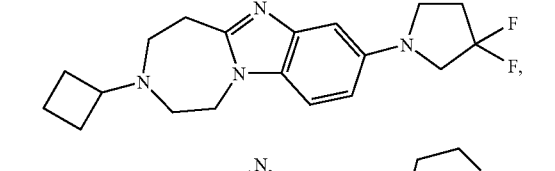,
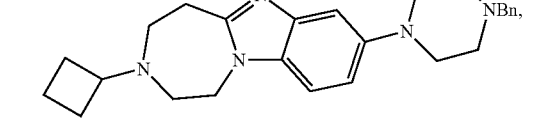, -continued

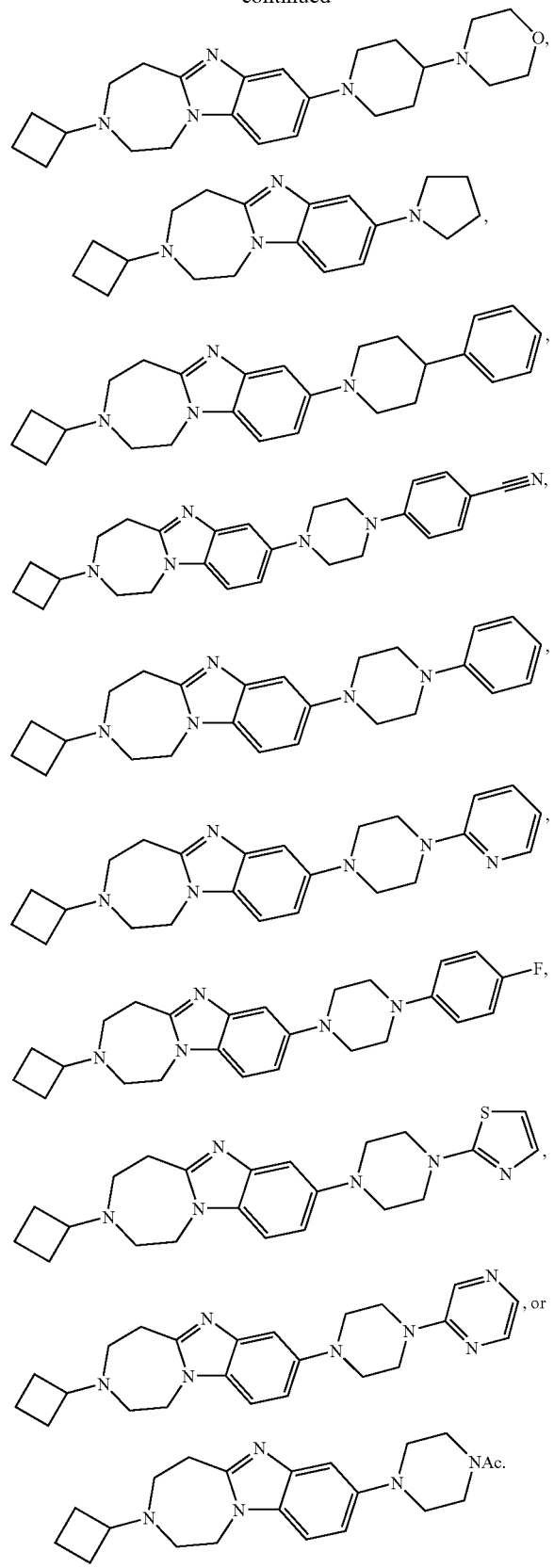

In another embodiment, provided herein is a compound of formula (IIIb), or a pharmaceutically acceptable salt, solvate, or stereoisomer thereof, wherein $R_N$ is cyclobutyl optionally substituted with one or more R'; and $R_{Ar}$ is halogen, cyano, $(C_1-C_{10})$alkyl, $(C_1-C_{10})$heteroalkyl, hydroxyl, alkoxyl, aminoalkyl, amino, amido, or carbonyl, each of which is optionally substituted with one or more $R_1$. R' and $R_1$ are defined herein elsewhere.

In one embodiment, provided herein is a compound of formula (IIIb), or a pharmaceutically acceptable salt, solvate, or stereoisomer thereof, wherein $R_{Ar}$ is (i) cyano; (ii) $(C_1-C_{10})$ alkyl, $(C_1-C_{10})$heteroalkyl, alkoxyl, aminoalkyl, amino, amido, or carbonyl, each of which is optionally substituted with one or more $R_1$; or (iii) hydroxyl substituted with one or more $R_1'$. In one embodiment, provided herein is a compound of formula (IIIb), or a pharmaceutically acceptable salt, solvate, or stereoisomer thereof, wherein $R_{Ar}$ is (i) cyano; (ii) $(C_1-C_{10})$heteroalkyl, aminoalkyl, amino, amido, or carbonyl, each of which is optionally substituted with one or more $R_1$; or (iii) $(C_1-C_{10})$alkyl, hydroxyl, or alkoxyl, each of which is substituted with one or more $R_1'$. In one embodiment, provided herein is a compound of formula (IIIb), or a pharmaceutically acceptable salt, solvate, or stereoisomer thereof, wherein $R_N$ is cyclobutyl optionally substituted with one or more R'; and $R_{Ar}$ is (i) cyano; (ii) $(C_1-C_{10})$alkyl, $(C_1-C_{10})$ heteroalkyl, alkoxyl, aminoalkyl, amino, amido, or carbonyl, each of which is optionally substituted with one or more $R_1$, or (iii) hydroxyl substituted with one or more $R_1'$. In one embodiment, provided herein is a compound of formula (IIIb), or a pharmaceutically acceptable salt, solvate, or stereoisomer thereof, wherein $R_N$ is cyclobutyl optionally substituted with one or more R'; and $R_{Ar}$ is (i) cyano; (ii) $(C_1-C_{10})$heteroalkyl, aminoalkyl, amino, amido, or carbonyl, each of which is optionally substituted with one or more $R_1$, or (iii) $(C_1-C_{10})$alkyl, hydroxyl, or alkoxyl, each of which is substituted with one or more $R_1'$. R', $R_1$, and $R_1'$ are defined herein elsewhere.

In one embodiment, $R_{Ar}$ is fluorine. In another embodiment, $R_{Ar}$ is chlorine. In another embodiment, $R_{Ar}$ is bromine. In another embodiment, $R_{Ar}$ is iodine.

In one embodiment, $R_{Ar}$ is cyano. In another embodiment, $R_{Ar}$ is $(C_1-C_{10})$ alkyl substituted with one or more $R_1$. In another embodiment, $R_{Ar}$ is $(C_1-C_{10})$ alkyl substituted with one or more $R_1'$. In another embodiment, $R_{Ar}$ is —$CH_2R_1$. In another embodiment, $R_{Ar}$ is —$CH_2R_1'$. In another embodiment, $R_{Ar}$ is —$CH(R_1)_2$. In another embodiment, $R_{Ar}$ is —$CH(R_1')_2$. In another embodiment, $R_{Ar}$ is —$CH(OH)R_1$. In another embodiment, $R_{Ar}$ is —$CH(OH)R_1'$. In another embodiment, $R_{Ar}$ is —$CH_2OR_1$. In another embodiment, $R_{Ar}$ is —$CH_2OR_1'$. In another embodiment, $R_{Ar}$ is —$CH_2OH$. In another embodiment, $R_{Ar}$ is hydroxyl or alkoxyl substituted with one or more $R_1$. In another embodiment, $R_{Ar}$ is hydroxyl or alkoxyl substituted with one or more $R_1^1$. In another embodiment, $R_{Ar}$ is —$OR_1$. In another embodiment, $R_{Ar}$ is —$OR_1'$. In another embodiment, $R_{Ar}$ is —$OCH_2R_1$. In another embodiment, $R_{Ar}$ is —$OCH_2R_1'$. In another embodiment, $R_{Ar}$ is amino, amido, or carbonyl, each of which is optionally substituted with one or more $R_1$. In another embodiment, $R_{Ar}$ is —$NHR_1$. In another embodiment, $R_{Ar}$ is —$NHCH_2R_1$. In another embodiment, $R_{Ar}$ is —$N(R_1)_2$. In another embodiment, $R_{Ar}$ is —$C(O)R_1$. In another embodiment, $R_{Ar}$ is —$C(O)N(R_1)_2$. In another embodiment, $R_{Ar}$ is —$CH_2N(R_1)_2$.

Specific examples include, but are not limited to, compounds of the following structures:
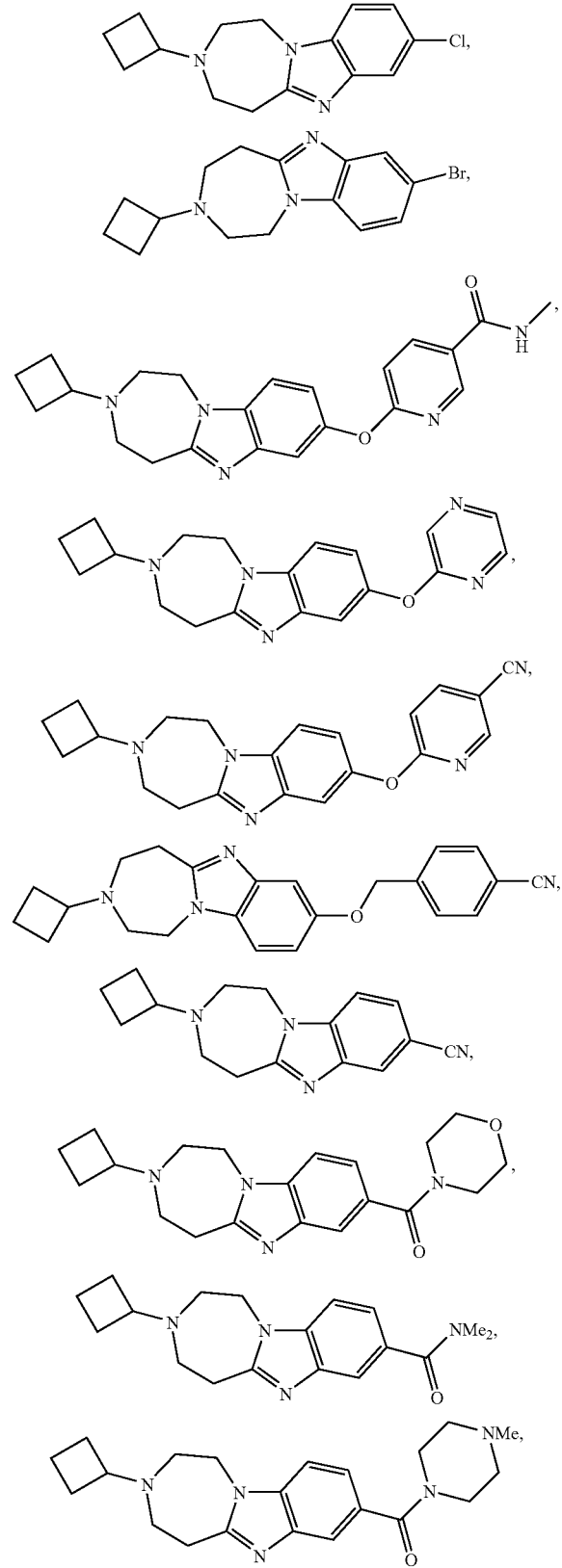
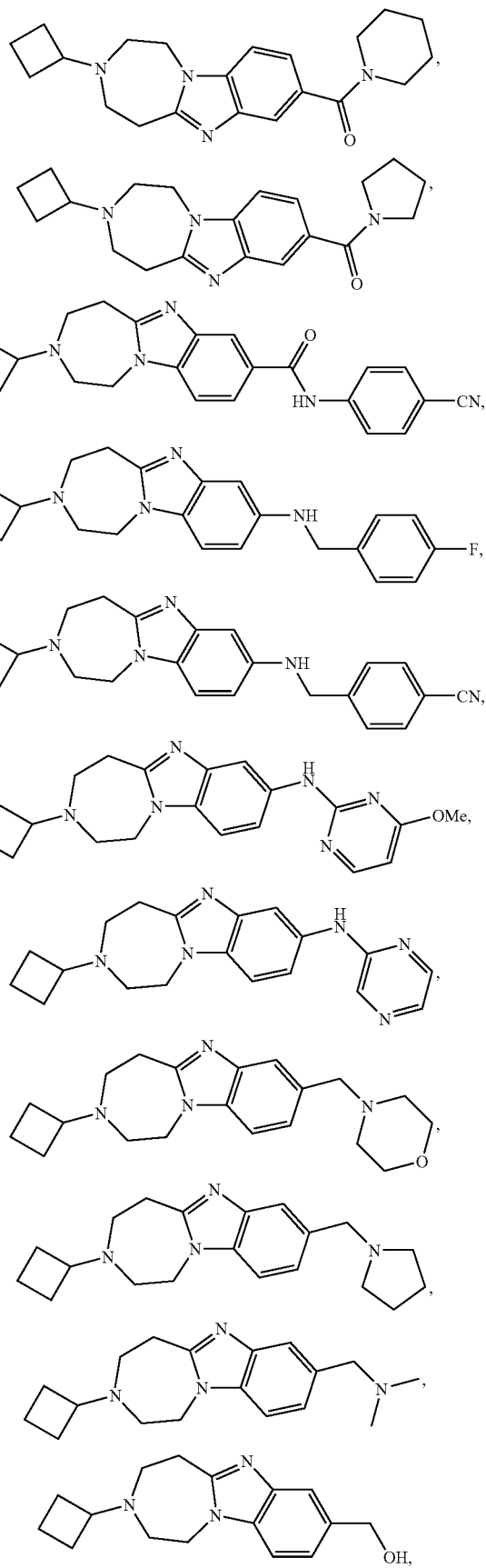

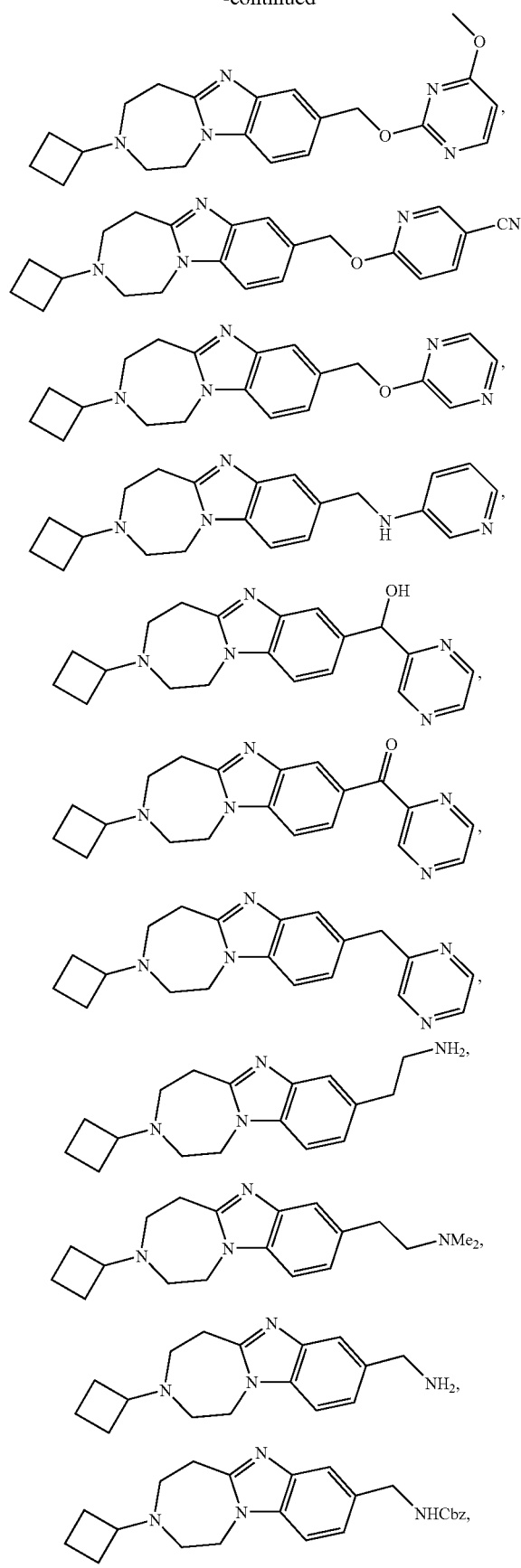
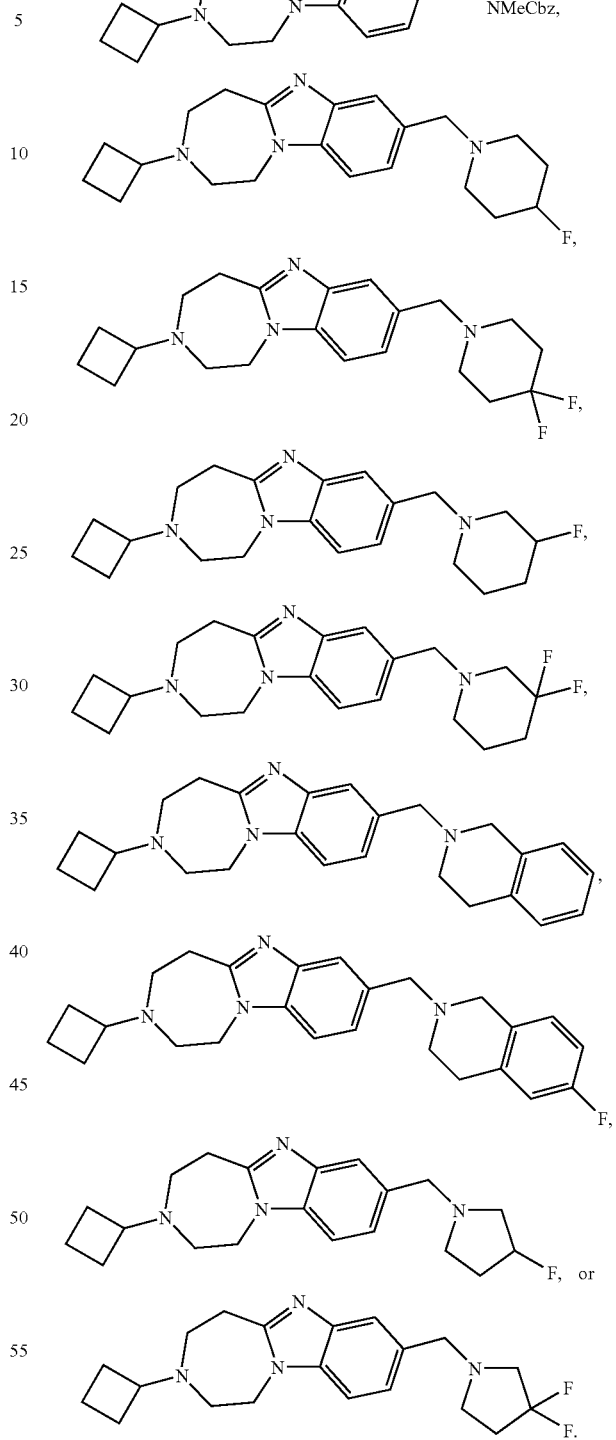

In another embodiment, provided herein is a compound of formula (IIIb), or a pharmaceutically acceptable salt, solvate, or stereoisomer thereof, wherein $R_N$ is cyclobutyl optionally substituted with one or more R'; and $R_{Ar}$ is 10-membered aryl optionally substituted with one or more $R_1$. In one embodiment, $R_{Ar}$ is naphthyl. Specific example includes, but is not limited to, a compound of the following structure:

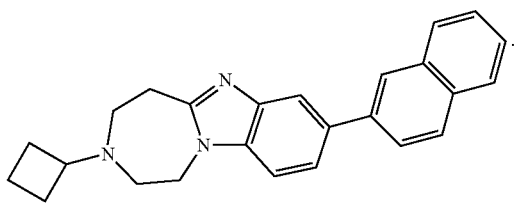

In one embodiment, provided herein is a compound of formula (IIIb), or a pharmaceutically acceptable salt, solvate, or stereoisomer thereof, wherein $R_{Ar}$ is phenyl or naphthyl, each of which is optionally substituted with one or more $R_1$. In one embodiment, provided herein is a compound of formula (IIIb), or a pharmaceutically acceptable salt, solvate, or stereoisomer thereof, wherein $R_{Ar}$ is six-membered heteroaryl, optionally substituted with one or more $R_1$.

In one embodiment, provided herein is a compound of formula (IVb):

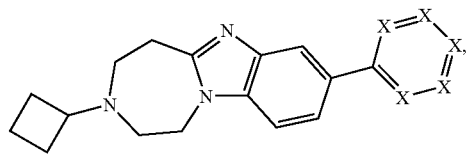

(IVb)

or a pharmaceutically acceptable salt, solvate, or stereoisomer thereof, wherein each occurrence of X is independently N, CH, or $CR_1$; and $R_1$ is defined herein elsewhere. Examples include, but are not limited to, the following compounds:

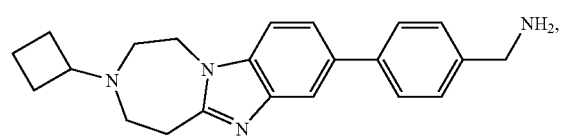

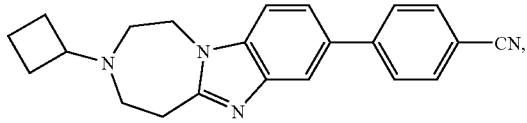

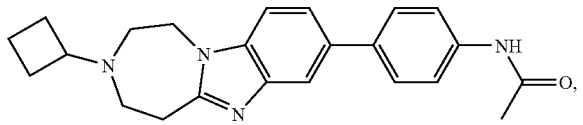

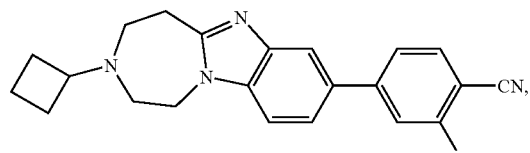

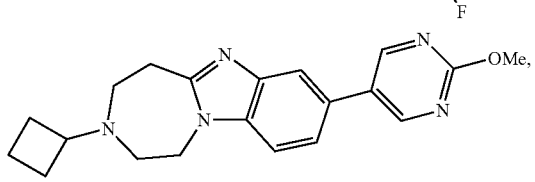

-continued

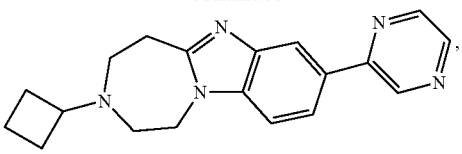

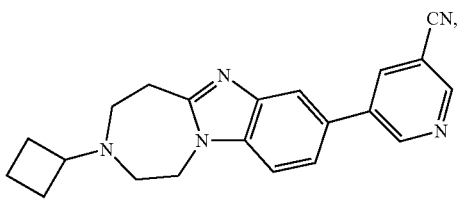

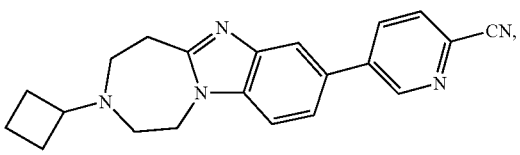

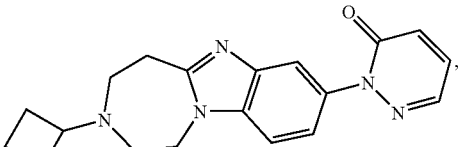

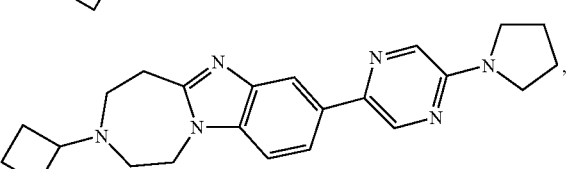

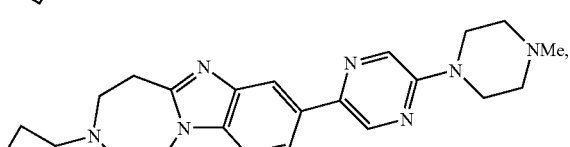

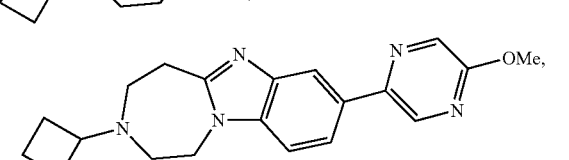

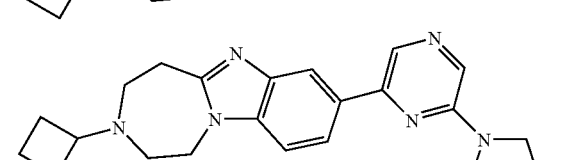

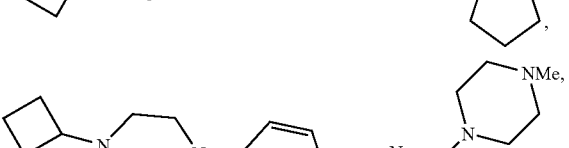

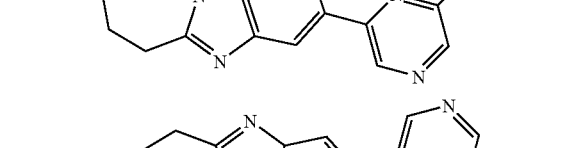

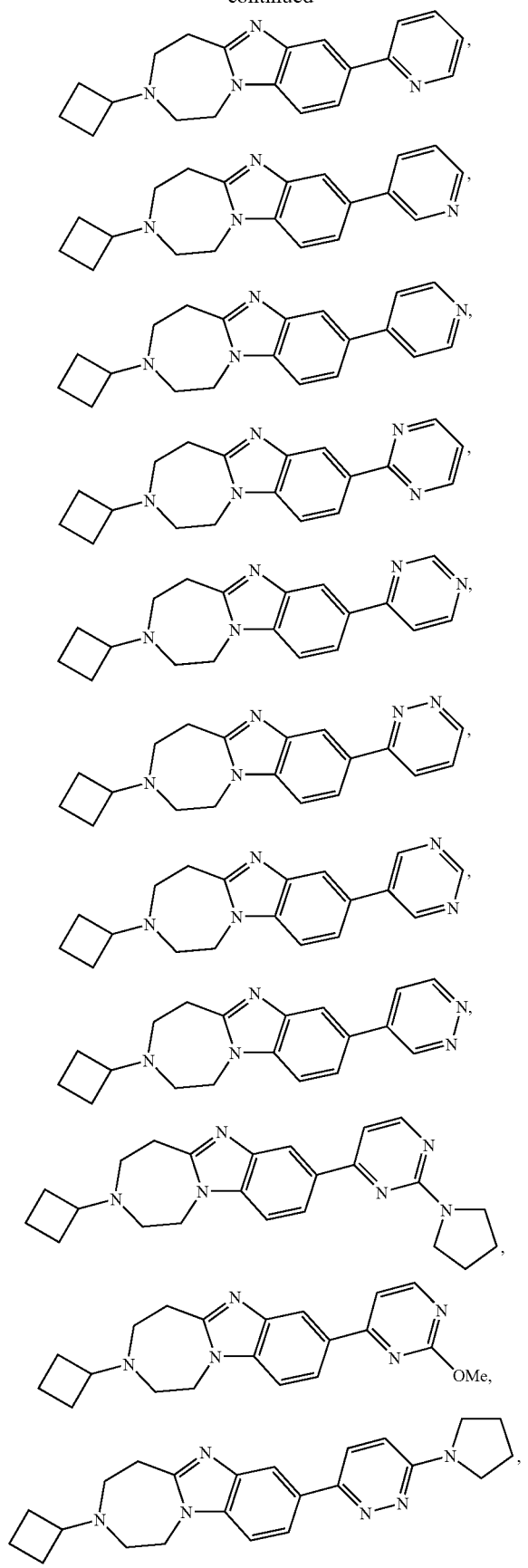

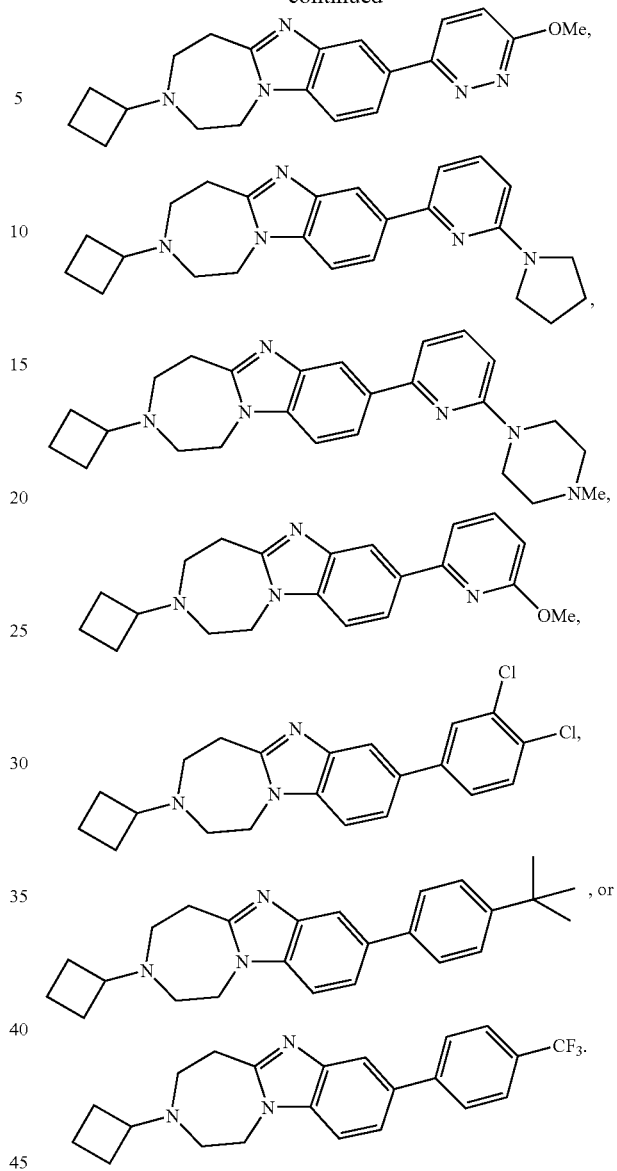

In one embodiment, provided herein is a compound of formula (V):

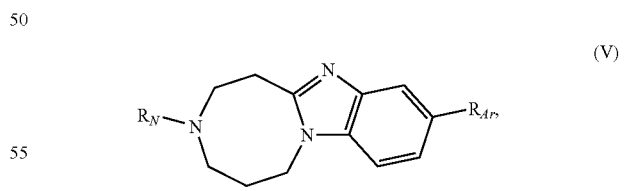

or a pharmaceutically acceptable salt, solvate, or stereoisomer thereof, wherein $R_{Ar}$ is hydrogen, halogen, cyano, $(C_1-C_{10})$alkyl, $(C_1-C_{10})$ alkenyl, $(C_3-C_{10})$ cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_1$; and $R_N$ and $R_1$ are defined herein elsewhere.

In one embodiment, provided herein is a compound of formula (V), or a pharmaceutically acceptable salt, solvate, or stereoisomer thereof, wherein $R_{Ar}$ is (i) hydrogen, halogen, or cyano; (ii) $(C_1-C_{10})$alkyl, $(C_1-C_{10})$alkenyl, $(C_3-C_{10})$cyclo alkyl, (6 to 10 membered) aryl, $(C_1-C_{10})$heteroalkyl, $(C_3-C_{10})$heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with one or more $R_1$; and $R_N$, $R_1$, and $R_1'$ are defined herein elsewhere.

In one embodiment, provided herein is a compound of formula (V), or a pharmaceutically acceptable salt, solvate, or stereoisomer thereof, wherein $R_{Ar}$ is (i) hydrogen, halogen, or cyano; (ii) $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, aminoalkyl, amino, imino, amido, carbonyl, thiol, sulfinyl, or sulfonyl, each of which is optionally substituted with one or more $R_1$; or (iii) $(C_1-C_{10})$allyl, hydroxyl, or alkoxyl, each of which is substituted with one or more $R_1$; and $R_N$, $R_1$, and $R_1'$ are defined herein elsewhere.

Specific examples include, but are not limited to, compounds of the following structure:

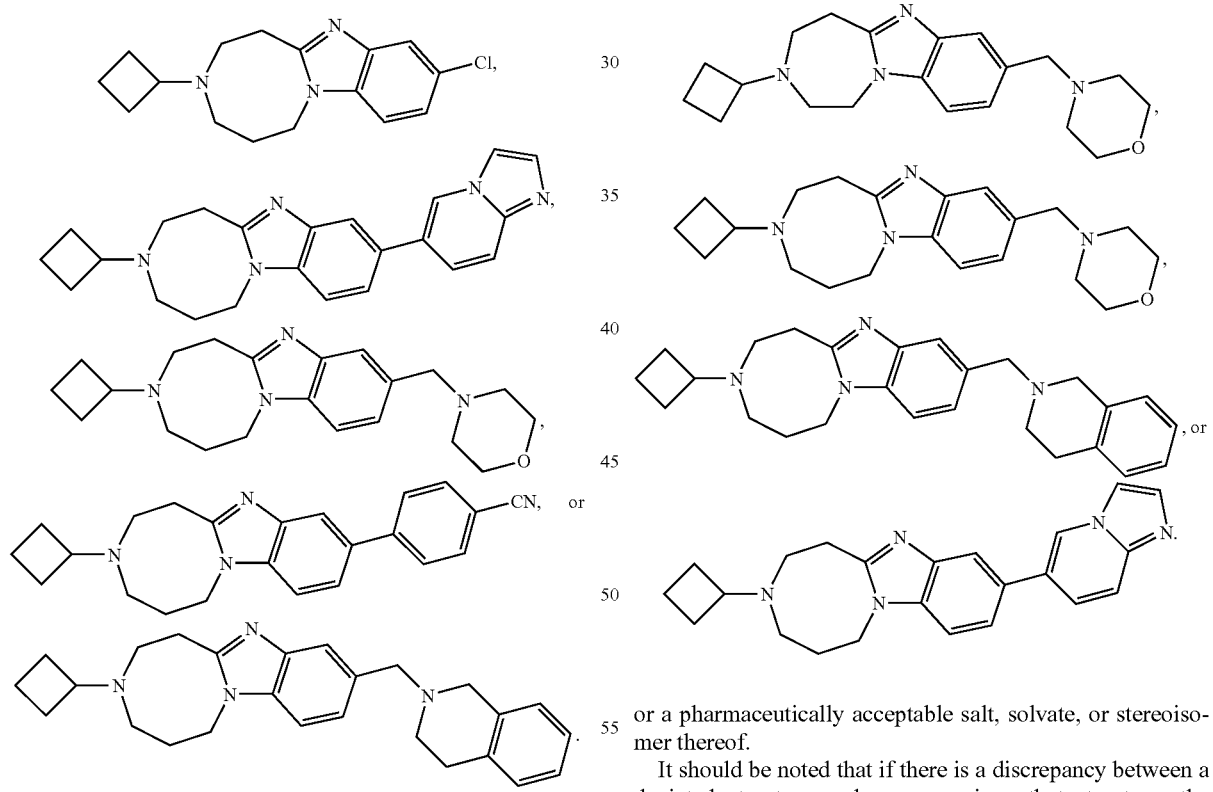
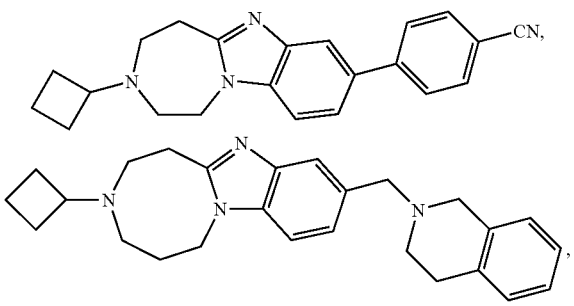
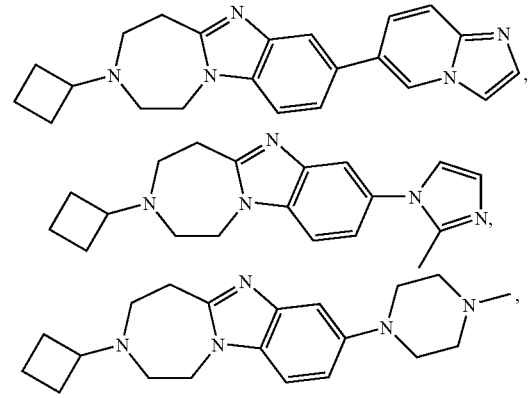
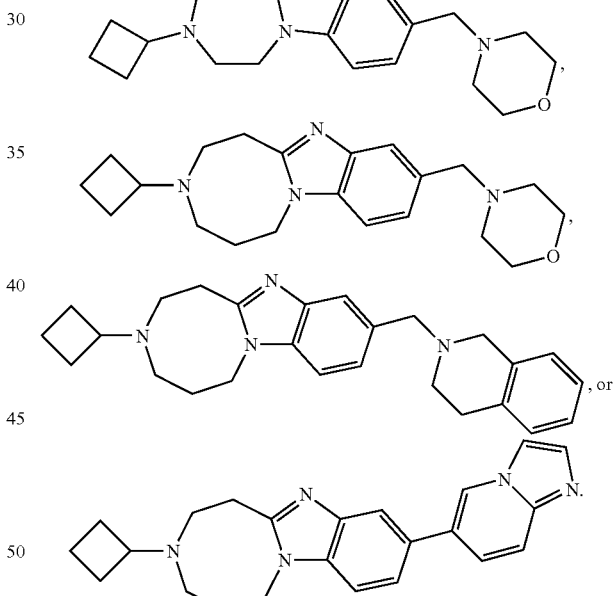

Any of the combinations of $R_N$ and $R_{Ar}$ are encompassed by this disclosure and specifically provided herein.

In one embodiment, provided here is a compound of formula (I), (Ia), (IIa), (IIb), (IIc), (IId), (He), (IIf), (IIIa), (IIIb), or (V), or a pharmaceutically acceptable salt, solvate, or stereoisomer thereof, wherein $R_N$ is cyclobutyl optionally substituted with one of more R'. In one embodiment, provided herein is a compound having the following structure:

or a pharmaceutically acceptable salt, solvate, or stereoisomer thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one or mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, e.g., Berge et al., *J. Pharm. Sci.* 1977, 66, 1-19; and *Handbook of Pharmaceutical Salts, Properties, and Use*, Stahl and Wermuth, ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In certain embodiments, the compounds provided herein are pharmacologically acceptable salts of the compounds with one or more of hydrochloric, sulfuric, phosphoric, acetic, citric, oxalic, malonic, salicylic, malic, fumaric, succinic, ascorbic, maleic, methanesulfonic, and isoethonic acids; or with one or more of potassium carbonate, sodium or potassium hydroxide, ammonia, triethylamine, and triethanolamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, e.g., Harper, *Progress in Drug Research* 1962, 4, 221-294; Morozowich et al. in Design of Biopharmaceutical Properties through Prodrugs and Analogs, Roche ed., APHA Acad. Pharm. Sci. 1977; Bioreversible Carriers in Drug in Drug Design, Theory and Application, Roche ed., APHA Acad. Pharm. Sci. 1987; Design of Prodrugs, Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in Transport Processes in Pharmaceutical Systems, Amidon et al., ed., Marcell Dekker, 185-218, 2000; Balant et al., *Eur. J. Drug Metab. Pharmacokinet.* 1990, 15, 143-53; Balimane & Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, a compound of formula (I) may be prepared following Scheme 1. Compound I-A may be available from a commercial source, or may be readily prepared following known literature procedures. Compound I-A is converted to I-B in one or more steps following standard procedures. Compound I-B is treated with TosCl under basic condition, such as TEA/DCM. Subsequently the Boc protecting group is removed using standard condition, such as treatment with TFA, to render I-C. Compound I-C is treated with base, such as $K_2CO_3$ in aqueous 2-propanol, to yield I-D. Compound I-D may be converted to I-E in one or more steps, such as, via reductive alkylation by ketones or aldehydes, or alkylation by alkyl halides. Optionally, further organic transformations may convert $R_A'$ and $R_B'$ to suitable $R_A$ and $R_B$ groups.

may be available from a commercial source, or may be readily prepared following known literature procedures. Compound I-A' is converted to I-B' in one or more steps following standard procedures. Compound I-B' is treated with TosCl under basic condition, such as TEA/DCM. Subsequently the Boc protecting group is removed using standard condition, such as treatment with TFA, to render I-C'. Compound I-C' is treated with base, such as $K_2CO_3$ in aqueous 2-propanol, to yield I-D'. Compound I-D' may be converted to I-E' in one or more steps, such as, via reductive alkylation by ketones or aldehydes, or alkylation by alkyl halides. Optionally, further organic transformations may convert $R_5$, $R_6$, $R_7$, and $R_8$ to other suitable embodiments of $R_5$, $R_6$, $R_7$, and $R_8$ provided herein.

Scheme 1:

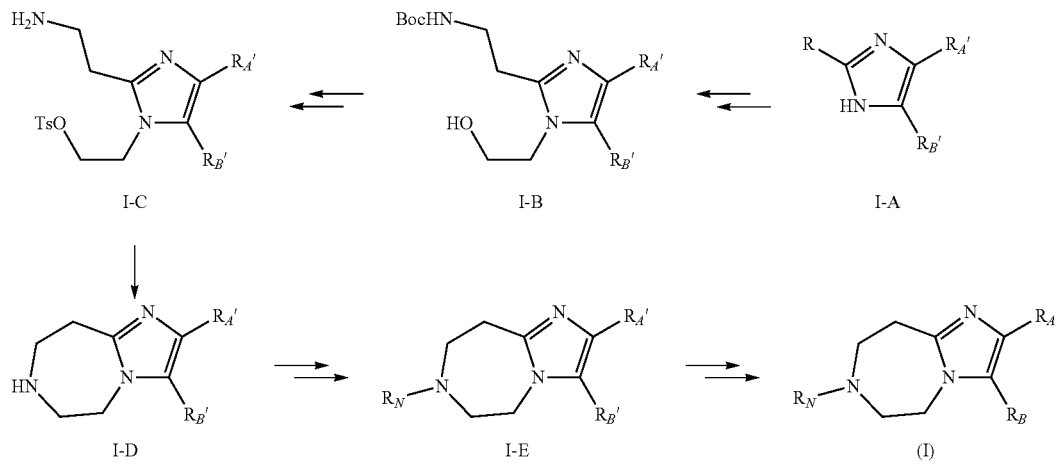

In one embodiment, a compound of formula (Ia) may be prepared following the steps in Scheme 1a. Compound I-A'

Scheme 1a:

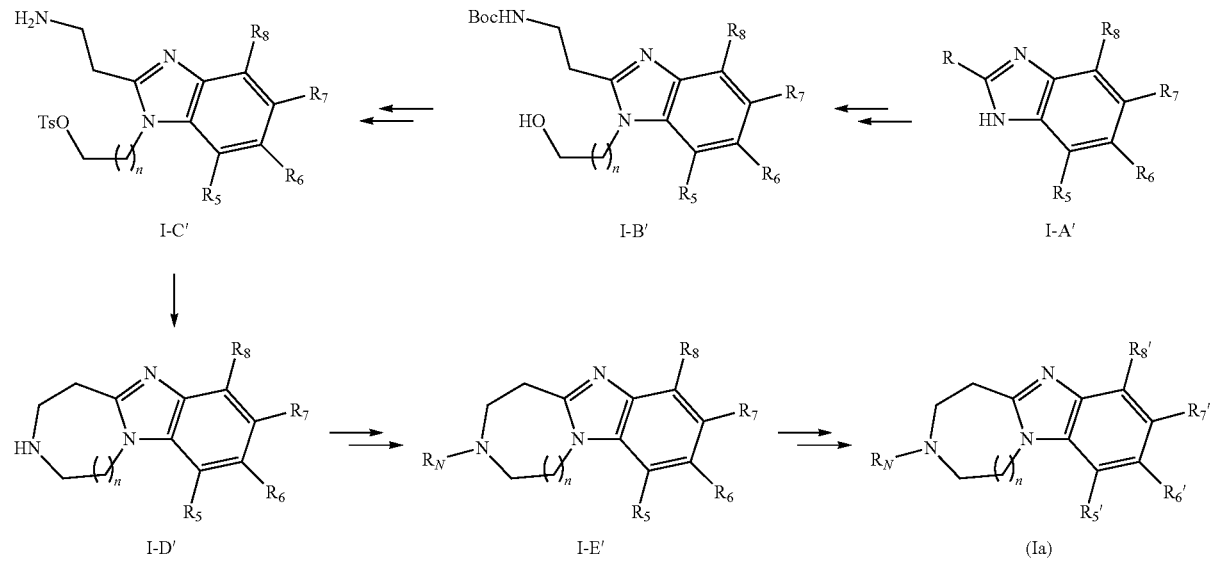

Specific schemes for preparing compounds provided herein are shown below. Detailed reaction conditions are provided for various specific examples herein below. One of ordinary skills of the art will understand that the following schemes may be modified with appropriate reagents, protecting groups, conditions, starting materials, or reaction sequences to suit the preparation of other embodiments provided herein.

In one embodiment, a compound of formula (IIIb) may be prepared following Scheme 2. 1,4-Dichloro-2-nitrobenzene (I-1) is treated with 2-aminoethanol in n-butanol to yield 2-(4-chloro-2-nitrophenylamino)ethanol (I-2). I-2 is reduced, such as with $Na_2S_2O_4$ in 40% ethanol to provide the corresponding aniline I-3. I-3 is coupled with 3-aminopropanoic acid and is cyclized under acid conditions, such as in 6N HCl, to yield benzimidazole I-4. The amino group in I-4 is protected, such as with the Boc protecting group, and subsequently the alcohol is converted to the corresponding tosylate, such as by treatment with TosCl in $Et_3N$ and DCM, to yield I-6. The Boc protecting group in I-6 is removed, such as by TFA, to yield I-7. I-7 is treated with base, such as $K_2CO_3$ in 20% aqueous 2-propanol, to render I-8. I-8 is converted to IIIb-A in one or more steps, such as, via reductive alkylation by ketones or aldehydes, or alkylation by alkyl halides. IIIb-A may be converted via one or more reactions to other IIIb with suitable $R_{Ar}$. The chloride in I-8 may also be converted via known reactions to other suitable $R_{Ar}$, and further converted to suitable IIIb, such as via alkylation. Specific examples of reactions and conditions converting IIIb-A to IIIb are provided herein below.

Scheme 2:

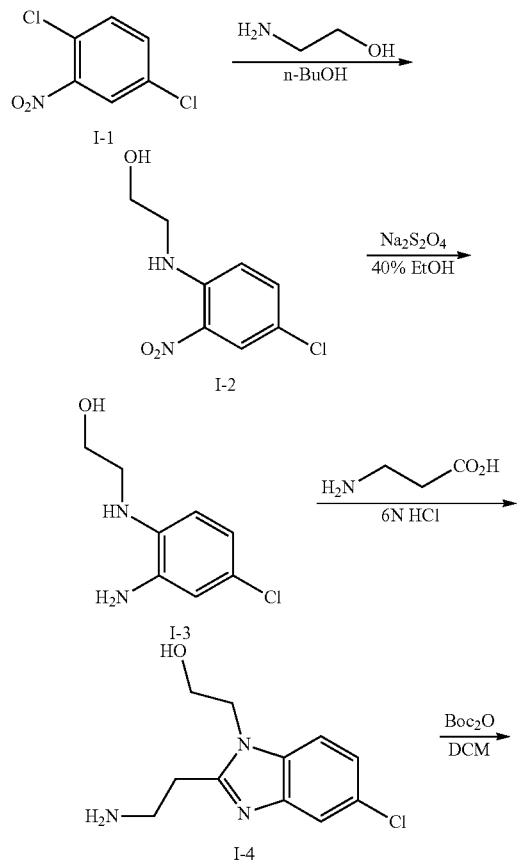

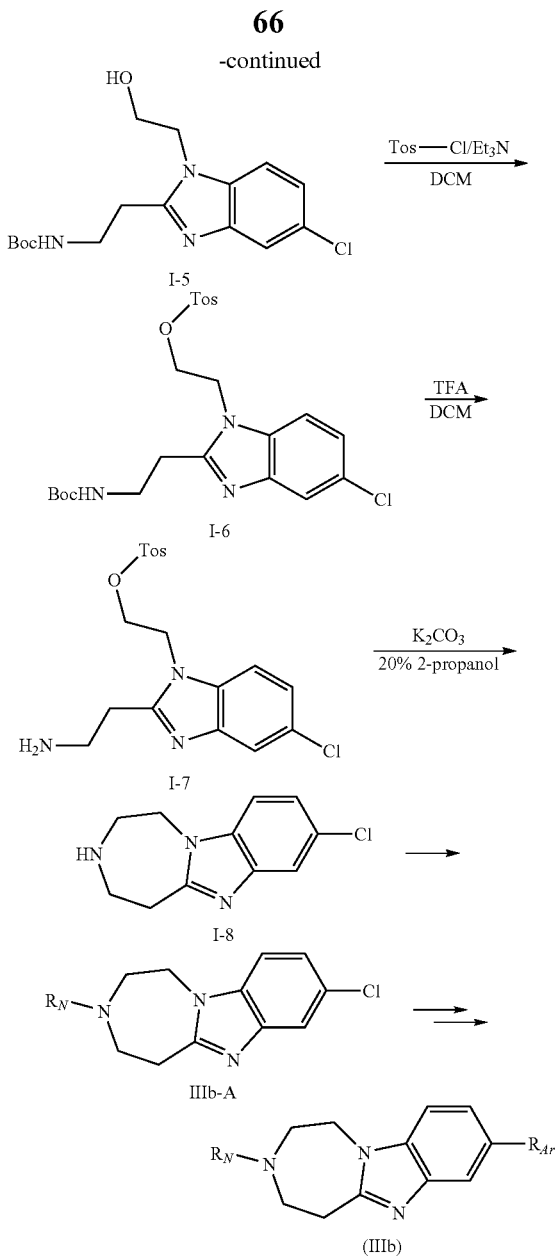

A compound of formula (IIIb) may also be prepared following Scheme 3. 4-Bromo-1-fluoro-2-nitrobenzene (I-9) is treated with 2-aminoethanol in n-butanol to yield 2-(4-bromo-2-nitrophenylamino)ethanol (I-10). I-10 is reduced, such as with hydrazine/Raney Nickel to provide the corresponding aniline I-11. I-11 is coupled with 3-(tent-butoxycarbonylamino)propanoic acid to yield amide I-12. I-12 is treated with acid, such as HOAc, and is cyclized to yield benzimidazole I-13. The alcohol in I-13 is converted to the corresponding tosylate, such as by treatment with TosCl in $Et_3N$ and DCM, to yield I-14. The Boc protecting group in I-14 is removed, such as by TFA, to yield I-15. I-15 is treated with base, such as $K_2CO_3$ in 20% aqueous 2-propanol, to render I-16. I-16 is converted to IIIb-B in one or more steps, such as, via reductive alkylation by ketones or aldehydes, or alkylation by alkyl halides. IIIb-B may be converted via one or more reactions to other IIIb with suitable $R_{Ar}$. The bromide in I-16 may also be converted via known reactions to other suitable $R_{Ar}$, and further converted to suitable IIIb, such as via alkylation. Specific examples of reactions and conditions converting IIIb-B to IIIb are provided herein below.

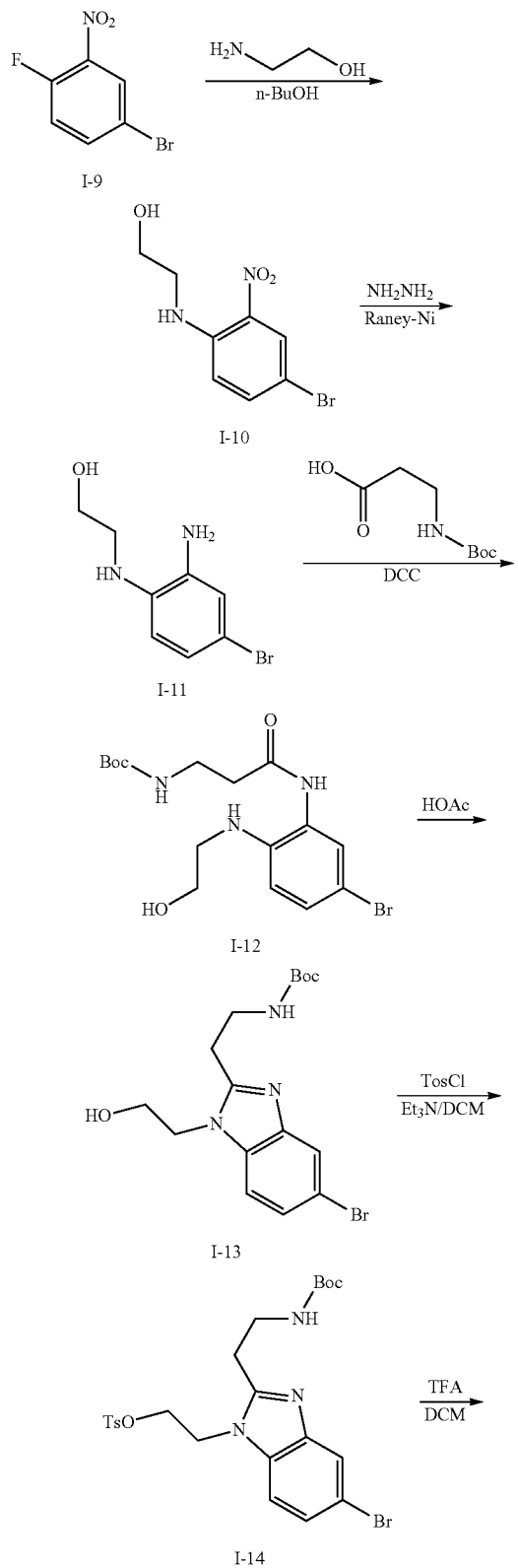

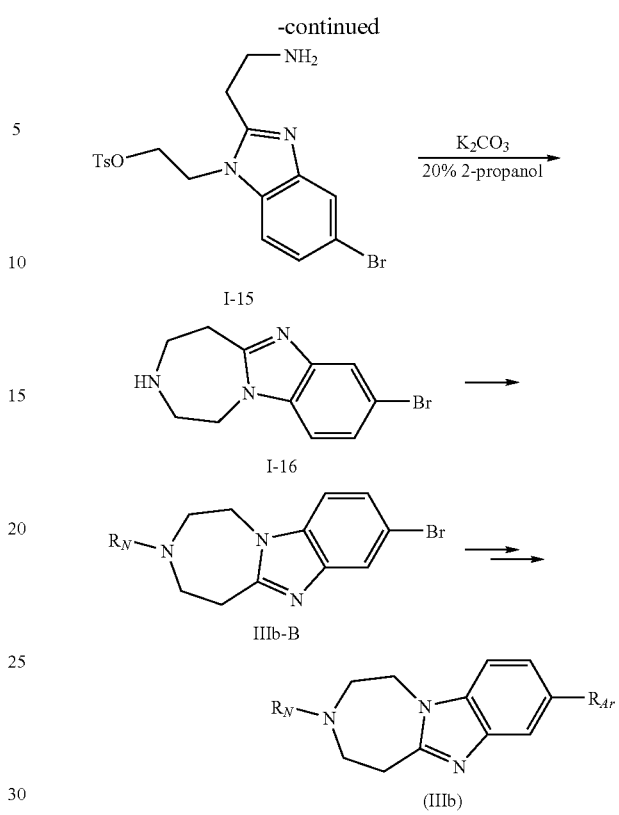

In one embodiment, A compound of formula (IIIa) may be prepared following Scheme 4. 4-Bromo-2-fluoro-1-nitrobenzene (I-19) is treated with 2-aminoethanol in n-butanol to yield I-20. I-20 is reduced, such as with hydrazine/Raney Nickel to provide the corresponding aniline I-21. I-21 is coupled with 3-(tert-butoxycarbonylamino)-propanoic acid to yield amide I-22. I-22 is treated with acid, such as HOAc, and is cyclized to yield benzimidazole I-23. The alcohol in I-23 is converted to the corresponding tosylate, such as by treatment with TosCl in Et$_3$N and DCM, to yield I-24. The Boc protecting group in I-24 is removed, such as by TFA, to yield I-25. I-25 is treated with base, such as K$_2$CO$_3$ in 20% aqueous 2-propanol, to render I-26. I-26 is converted to IIIa-A in one or more steps, such as, via reductive alkylation by ketones or aldehydes, or alkylation by alkyl halides. IIIa-A may be converted via one or more reactions to other IIIa with suitable $R_{Ar}$. The bromide in I-26 may also be converted via known reactions to other suitable $R_{Ar}$, and further converted to suitable IIIa, such as via alkylation. Specific examples of reactions and conditions converting IIIa-A to IIIa are provided herein below.

Scheme 4:

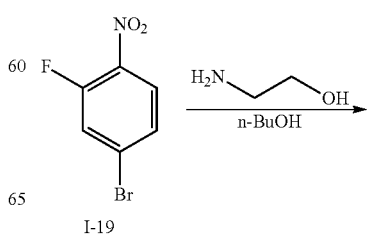

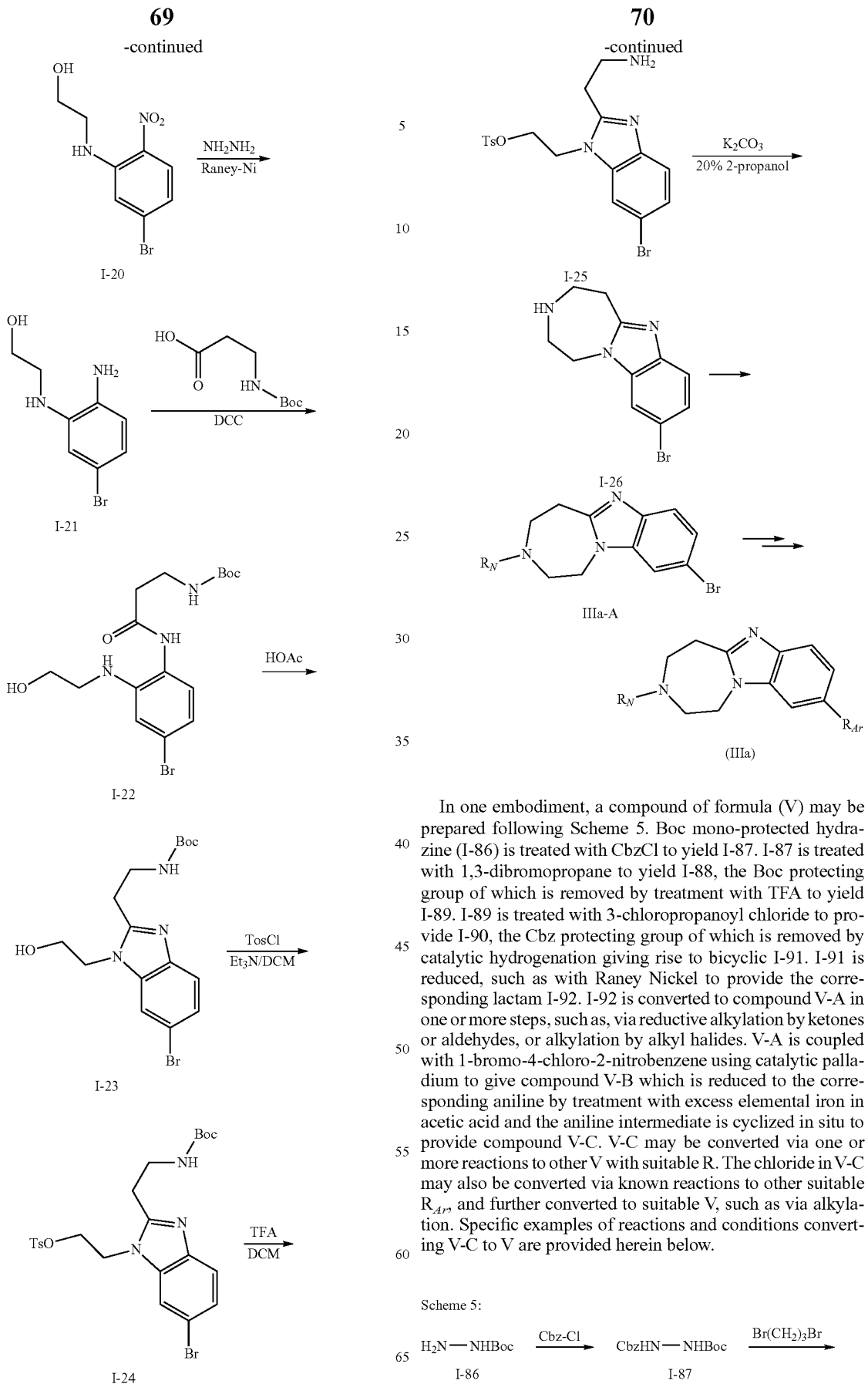

In one embodiment, a compound of formula (V) may be prepared following Scheme 5. Boc mono-protected hydrazine (I-86) is treated with CbzCl to yield I-87. I-87 is treated with 1,3-dibromopropane to yield I-88, the Boc protecting group of which is removed by treatment with TFA to yield I-89. I-89 is treated with 3-chloropropanoyl chloride to provide I-90, the Cbz protecting group of which is removed by catalytic hydrogenation giving rise to bicyclic I-91. I-91 is reduced, such as with Raney Nickel to provide the corresponding lactam I-92. I-92 is converted to compound V-A in one or more steps, such as, via reductive alkylation by ketones or aldehydes, or alkylation by alkyl halides. V-A is coupled with 1-bromo-4-chloro-2-nitrobenzene using catalytic palladium to give compound V-B which is reduced to the corresponding aniline by treatment with excess elemental iron in acetic acid and the aniline intermediate is cyclized in situ to provide compound V-C. V-C may be converted via one or more reactions to other V with suitable R. The chloride in V-C may also be converted via known reactions to other suitable $R_{Ar}$, and further converted to suitable V, such as via alkylation. Specific examples of reactions and conditions converting V-C to V are provided herein below.

Scheme 5:

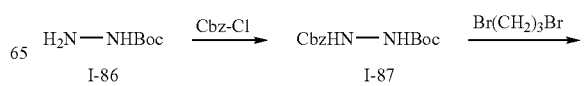

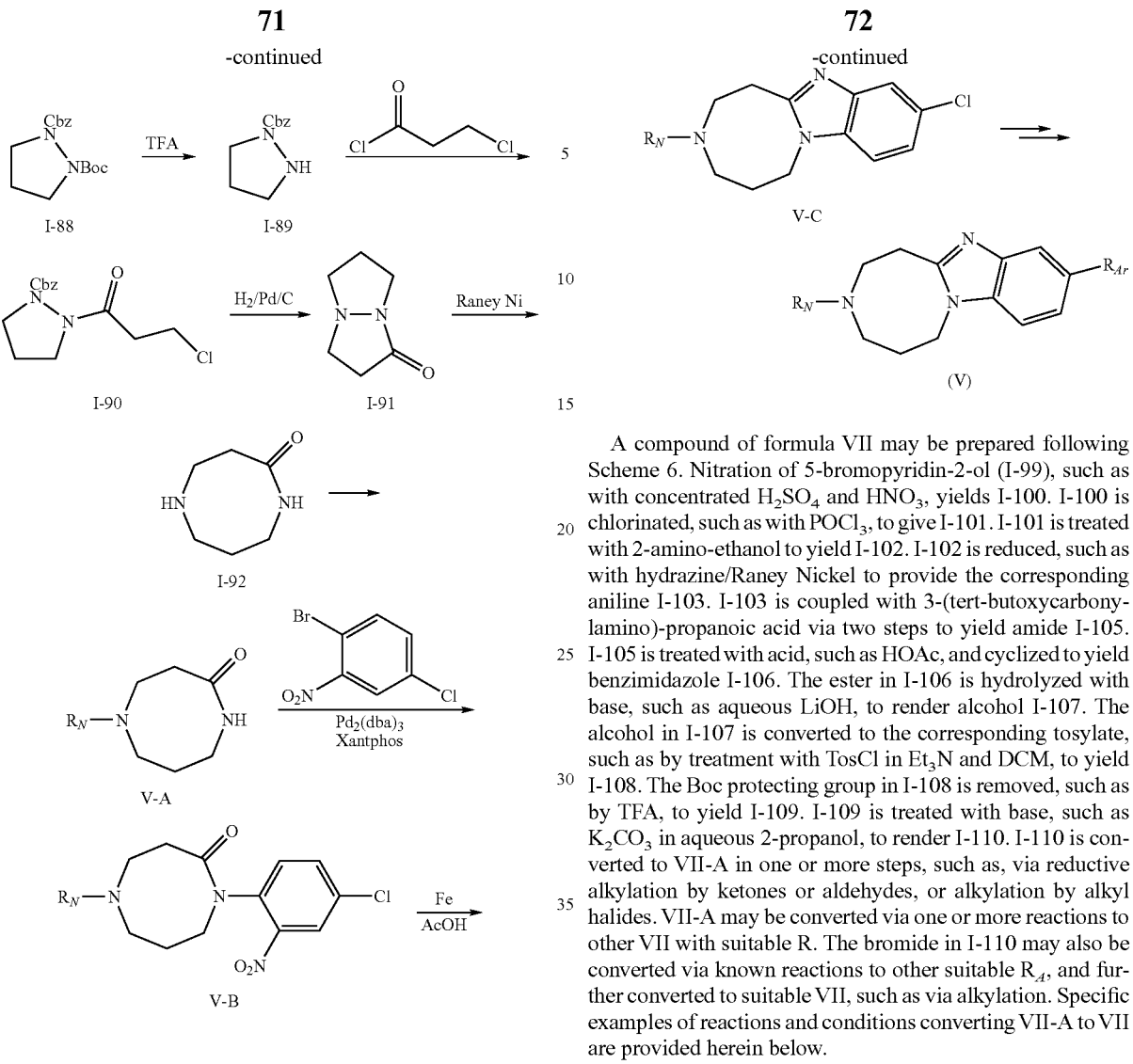

A compound of formula VII may be prepared following Scheme 6. Nitration of 5-bromopyridin-2-ol (I-99), such as with concentrated $H_2SO_4$ and $HNO_3$, yields I-100. I-100 is chlorinated, such as with $POCl_3$, to give I-101. I-101 is treated with 2-amino-ethanol to yield I-102. I-102 is reduced, such as with hydrazine/Raney Nickel to provide the corresponding aniline I-103. I-103 is coupled with 3-(tert-butoxycarbonylamino)-propanoic acid via two steps to yield amide I-105. I-105 is treated with acid, such as HOAc, and cyclized to yield benzimidazole I-106. The ester in I-106 is hydrolyzed with base, such as aqueous LiOH, to render alcohol I-107. The alcohol in I-107 is converted to the corresponding tosylate, such as by treatment with TosCl in $Et_3N$ and DCM, to yield I-108. The Boc protecting group in I-108 is removed, such as by TFA, to yield I-109. I-109 is treated with base, such as $K_2CO_3$ in aqueous 2-propanol, to render I-110. I-110 is converted to VII-A in one or more steps, such as, via reductive alkylation by ketones or aldehydes, or alkylation by alkyl halides. VII-A may be converted via one or more reactions to other VII with suitable R. The bromide in I-110 may also be converted via known reactions to other suitable $R_A$, and further converted to suitable VII, such as via alkylation. Specific examples of reactions and conditions converting VII-A to VII are provided herein below.

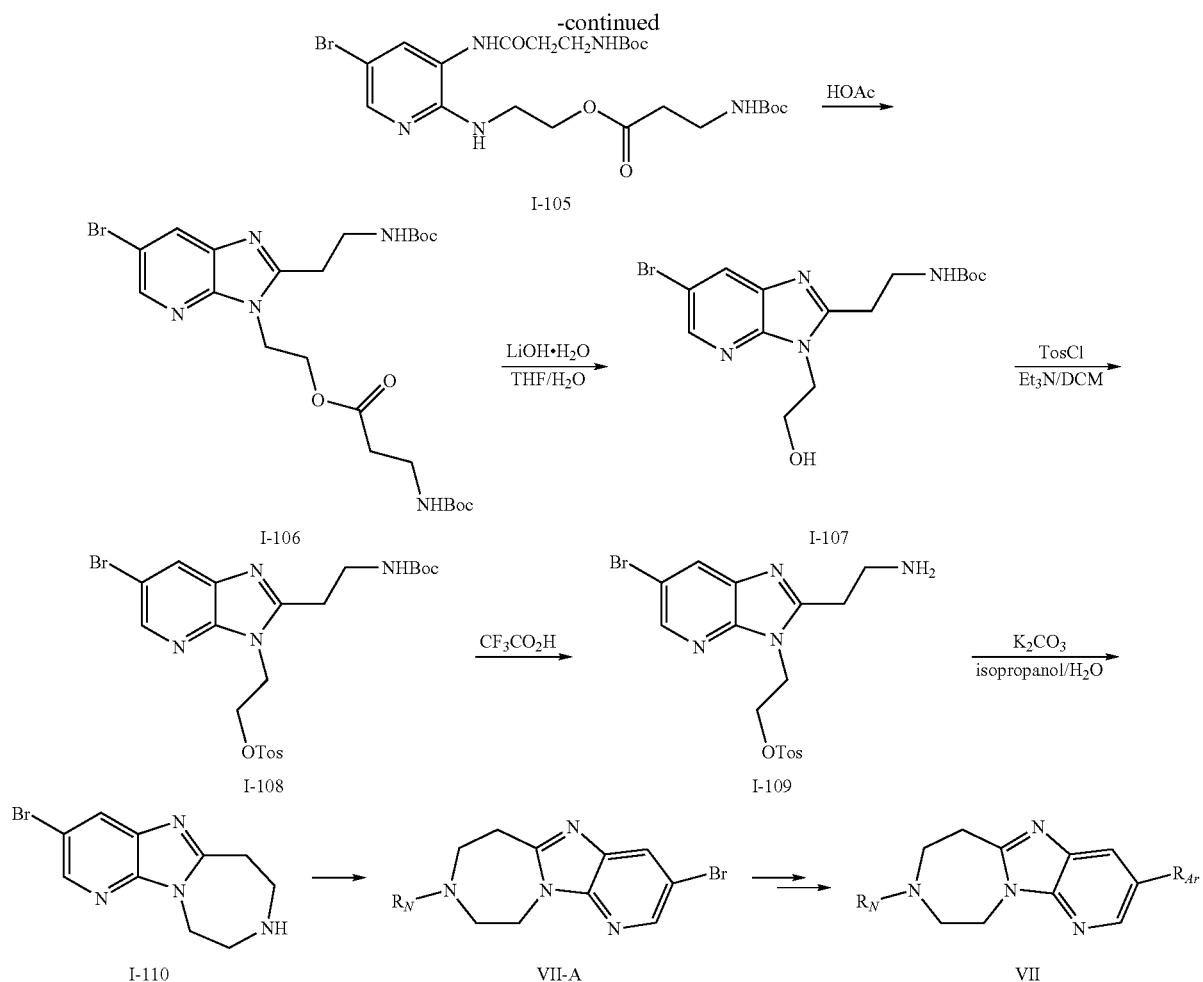

D. Methods of Treatment, Prevention, and/or Management

1. Binding to Histamine Receptor

In various embodiments, provided herein is a method of binding a compound provided herein to a histamine receptor, such as, a histamine H3 receptor. The method comprises contacting the histamine receptor with a compound provided herein.

In other embodiments, provided herein is a method of inhibiting the binding of a histamine receptor ligand to a histamine receptor, such as, a histamine H3 receptor. The method comprises contacting the histamine receptor with a compound provided herein. In one embodiment, the histamine receptor ligand is an endogenous ligand. In another embodiment, the ligand is a drug molecule or another small molecule known to have binding affinity to the histamine receptor. In another embodiment, the histamine receptor ligand is a radioactively labeled compound, known to bind to the histamine receptor. In another embodiment, the ligand is an agonist, partial agonist, antagonist, or inverse agonist of the histamine receptor.

In one embodiment, inhibition of ligand binding is assessed using an in vitro binding assay, such as those described herein. In another embodiment, the compound provided herein inhibits mean binding by about 1%, about 5%, about 10%, about 20%, about 30%, about 40%, about 50%, about 60%, about 70%, about 80%, about 90%, about 95%, about 99%, or more, as compared to vehicle. In one embodiment, the inhibition of mean binding is dose dependent.

2. Inhibition of Histamine Receptor Activity

In various embodiments, provided herein is a method of modulating (e.g., inhibiting or augmenting) the activity of a histamine receptor, such as a histamine H3 receptor. The method comprises contacting the histamine receptor, such as histamine H3 receptor, with a compound provided herein, in vitro or in vivo. In one embodiment, the histamine receptor, such as histamine H3 receptor, is contacted with a compound provided herein by administering to a subject a therapeutically effective amount of the compound provided herein, or a pharmaceutically acceptable salt or solvate thereof. The subject may be a human. In another embodiment, the histamine receptor is histamine H3 receptor.

In other embodiments, the compound provided herein inhibits or reduces the activity of a histamine receptor, such as histamine H3 receptor. Inhibition of histamine receptor activity may be measured using assays known in the art. In some embodiments, the activity of a histamine receptor is inhibited or reduced by about 1%, about 5%, about 10%, about 20%, about 30%, about 40%, about 50%, about 60%, about 70%, about 80%, about 90%, about 95%, about 99% or more, as compared with the activity obtained without contacting with the compounds provided herein. In one embodiment, the inhibition or reduction of receptor activity is dose dependent. Exemplary assay methods include, but are not limited to, in vitro functional assays. In one embodiment, the functional assay utilizes an appropriate cell-line expression a desired histamine receptor. In other embodiments, the functional assay utilizes synaptosomes isolated from brain tissue of an appropriate organism. In other embodiments, inhibition of histamine receptor activity may be assessed using receptor binding experiments know in the art, e.g. utilizing appropriate membrane preparations. In one embodiment, the assay involves treatment of a test subject (e.g., a rat) with a compound provided herein as well as a reference compound, followed by isolation of brain tissue and ex vivo analysis of receptor occupancy.

In certain embodiments, provided herein are methods of inhibiting or reducing the activity of a histamine receptor, e.g., H3 receptor, in a subject (e.g., human) comprising administering to the subject an effective amount of a compound provided herein. In some embodiments, the activity of histamine receptor is inhibited or reduced by about 1%, about 5%, about 10%, about 20%, about 30%, about 40%, about 50%, about 60%, about 70%, about 80%, about 90%, about 95%, about 99% or more, when measured using an assay described herein elsewhere.

In one embodiment, provided herein is a method of inhibiting or reducing the activity of a histamine receptor, such as a histamine I-13 receptor, by a histamine receptor ligand. In one embodiment, the method comprises contacting the histamine receptor with an antagonist or an inverse agonist of the histamine receptor. In another embodiment, an antagonist or an inverse agonist of the histamine receptor is a compound provided herein.

3. Modulation of Histamine Release

In some embodiments, provided herein is a method of inhibiting a histamine receptor to increase the histamine release by a cell. The method includes contacting the cell with a compound provided herein. In one embodiment, the cell is a brain cell, such as a neuron or a glial cell. In one embodiment, the histamine release occurs in vivo. Thus, in certain embodiments, provided herein are methods of increasing the level of histamine release comprising administering to a subject (e.g., human) an effective amount of a compound provided herein. In an organism, the histamine release may occur, for example, at the synapse. Thus, in one embodiment, the neuronal cell is in contact with the synapse of a mammal. In another embodiment, the histamine release occurs in vitro. In some embodiments, the cell may be a brain cell, such as a neuronal cell or a cell type which expresses a histamine receptor, such as a histamine H3 receptor.

Stimulation of histamine release can be shown, for example, by performing various in vitro functional assays utilizing a cell type which expresses a certain type of histamine receptor, such as a histamine H3 receptor, together with an appropriate labeled histamine receptor ligand. In some embodiments, inhibition of the histamine receptor is demonstrated when an antagonist or inverse agonist (e.g., a compound provided herein) has an $IC_{50}$ of, for example, between about 0.1 nM and about 10 µM, between about 1 nM and about 1 µM, between about 1 nM and about 500 nM, and between about 1 nM and about 100 nM, in a functional histamine receptor assay, such as those described herein.

4. Treatment, Prevention, and/or Management of H3 Receptor Related Disorders In one embodiment, provided herein are methods for the treatment, prevention, and/or management of a disorder related to histamine H3 receptor, such as a neurological disorder provided herein. In one embodiment, provided herein are uses of compounds and compositions provided herein in the manufacture of a medicament for the treatment, prevention, and/or management of a disorder related to histamine H3 receptor, such as a neurological disorder. In one embodiment, provided herein are compounds and compositions for use in the treatment, prevention, and/or management of a disorder related to histamine H3 receptor, such as a neurological disorder provided herein.

In some embodiments, provided herein is a method of treating, preventing, and/or managing a disorder related to histamine H3 receptor, such as a neurological disorder. Without being limited by a particular theory, the treatment, prevention, and/or management is done by inhibiting or reducing the activity of histamine H3 receptor. Histamine H3 receptors modulate the release of neurotransmitters, including but not limited to, histamine, acetylcholine, norepinephrine, and dopamine, implicating a wide range of therapeutic indications. See, e.g., Haas et al., *Physio. Rev.* 88: 1183-241 (2008); Brown et al., *Prog. Neurobio.* 63: 637-72 (2001); Esbenshade et al., *Mol. Interven.* 6(2): 77-88 (2006); Esbenshade et al., *British J. Pharmacol.* 154(6): 1166-81 (2008); Sander et al., *Bio. Pharm. Bull.* 21: 2163-81 (2008).

In one embodiment, the method comprises administering to a subject (e.g., human) a therapeutically or prophylactically effective amount of a composition or compound provided herein. In one embodiment, the subject is a human. In another embodiment, the compound provided herein inhibits the activity of a histamine receptor. In another embodiment, the compound provided herein inhibits the activity of histamine H3 receptor. In certain embodiments, the compounds provided herein are inverse agonists of histamine H3 receptor. In other embodiments, the compounds provided herein are antagonists of histamine H3 receptors. In certain embodiments, the compounds provided herein are selective for histamine H3 receptor over other CNS-related targets. In one embodiment, the compounds provided herein are highly brain penetrable in animals, such as rodents, and human. In some embodiments, inhibition of the histamine receptor activity may be assessed by functional assays as described herein elsewhere. In certain embodiments, the efficacious concentration of the compounds provided herein is less than 10 nM, less than 100 nM, less than 1 µM, less than 10 µM, less than 100 µM, or less than 1 mM. In other embodiments, compound's activity may be assessed in various art-recognized animal models as described herein elsewhere.

In some embodiments, provided herein is a method of treating, preventing, and/or managing a disorder associated with excessive daytime sleepiness, such as narcolepsy, Parkinson's disease, Multiple Sclerosis, shift workers, jet lag, relief of side effects of other medications, and the like, comprising administering to a subject an effective amount of a compound provided herein. For example, without being limited by a particular theory, H3 antagonists or inverse agonists may have wake promoting effects. See, e.g., Lin et al., *Br. Res.* 523: 325-30 (1990); Barbier et al., *Br. J. Pharm.* 143: 649-61 (2004); Lin et al., *Neurobiol. Dis.* 30(1): 74-83 (2008).

In another embodiment, provided herein is a method of treating, preventing, and/or managing a sleeping disorder, such as insomnia, comprising administering to a subject an effective amount of a compound provided herein. For example, without being limited by a particular theory, H3 antagonists or inverse agonists may improve wakefulness and lead to an improved sleep pattern, and therefore H3 antagonists or inverse agonists may be useful in treating insomnia.

In another embodiment, provided herein is a method of treating, preventing, and/or managing substance abuse, comprising administering to a subject an effective amount of a compound provided herein. For example, without being limited by a particular theory, H3 antagonists can alter methamphetamine self-administration in rats, and therefore H3 antagonists may ameliorate the craving for addictive drugs. See, e.g., Munzar et al, *Neuropsychopharmacology* 29:705-17 (2004).

In another embodiment, provided herein is a method of treating, preventing, and/or managing a disorder related to cognitive impairments, impairments of learning, impairments of memory, and/or impairments of attention, vigilance and/or speed of response, such as those associated with Alzheimer's disease, Parkinson's disease, schizophrenia, and attention deficit hyperactivity disorder (ADHD), and the like, comprising administering to a subject an effective amount of a compound provided herein. For example, without being limited by a particular theory, H3 antagonists or inverse agonists may have pro-cognitive effects, such as passive avoidance, novel object recognition, social recognition, and attention-set shifting. See, e.g., Medhurst et al., *JPET* 321: 1032-45 (2007); Medhurst et al., *Biochem. Pharmcol.* 73: 1182-94 (2007); Fox et al., *JPET* 313:176-190 (2005); Fox et al., *JPET* 305: 897-908 (2003). Further, without being limited by a particular theory, H3 receptor antagonists or inverse agonists may improve social memory, increase the acquisition of an environment, and reverse scopolamine-induced deficits. H3 antagonists or inverse agonists may also reverse scopolamine-induced deficits in a passive avoidance memory test.

In another embodiment, provided herein is a method of treating, preventing, and/or managing a disorder related to psychosis, schizophrenia, ADHD, and/or mood disorders such as depression and/or anxiety, comprising administering to a subject an effective amount of a compound provided herein. For example, without being limited by a particular theory, H3 antagonists or inverse agonists may improve the gating deficits of DBA/2 mice seen in the pre-pulse inhibition (PPI) test and reverse the methamphe-tamine-induced hyper-locomotor activity. See, e.g., Fox et al., *JPET* 313:176-190 (2005). Without being limited to a particular theory, H3 antagonists or inverse agonists may: 1) reverse the amphetamine-induced hyper-locomotor activity (See, e.g., Clapham et al., *Eur. J. Pharmacol.* 259: 107-14 (1994)); 2) be useful as antipsychotic agents and dosed sparing (See, e.g., Zhang et al., *Br. Res.* 1045: 142-49 (2005)); 3) improve attention and modulate impulsivity (See, e.g., Day et al., *Biochem. Pharmacol.* 73:1123-34 (2007)); 4) improve learning parameters in ADHD (See, e.g., Fox et al., *JPET* 313:176-90 (2005); Fox et al., *JPET* 305: 897-908 (2003); Fox et al., *Behav. Br. Res.* 131: 151-61 (2002); Komater et al., *Psychopharm.* 167: 363-72 (2003); Esbenshade et al., *Biochem. Pharmacol.* 68: 933-45 (2004)); 5) enhance learning ability and reduce anxiety in behavioral tests (See, e.g., Rizk et al., *Eur. J. Neurosci.* 19: 1992-96 (2004)); and 6) have an anti-depressant effect (See, e.g., Pérez-Garcia et al., *Psychopharm.* 142(2): 215-20 (1999)).

In another embodiment, provided herein is a method of using the compounds provided herein as psycho-stimulants, which may lack the abuse liabilities generally associated with other classes of psycho-stimulants. Without being limited by a particular theory, H3 antagonists or inverse agonists increase the levels of histamine, dopamine, norepinephrine, and acetylcholine in the prefrontal cortical area, which is consistent with their pro-cognitive effects and their wake promoting effects seen in animal models. For example, H3 antagonists or inverse agonists may increase dopamine in the frontal cortex but not the striatum. H3 antagonists or inverse agonists may not induce increased locomotor activity or sensitization that is associated with other psycho-stimulus. See, e.g., Komater et al., *Psychopharm.* 167: 363-72 (2003).

In another embodiment, provided herein is a method of treating, preventing, and/or managing a disorder such as convulsion (e.g. epilepsy), seizures, vertigo, and pain, comprising administering to a subject an effective amount of a compound provided herein. For example, without being limited by a particular theory, H3 antagonists or inverse agonists may be protective against pentylenetetrazole (PTZ) and electrical-induced seizures. See, e.g., Vohora et al., *Life Sci.* 22: 297-301 (2000); Vohora et al., *Pharmacol. Biochem. Behav.* 68(4): 735-41 (2001); Zhang et al., *Eur. J. Pharmacol.* 15(581): 169-75 (2003). H3 antagonists or inverse agonists may increase the seizure threshold in humans. See, e.g., WO 2006/084833. H3 antagonists or inverse agonists may decrease electrical discharge from afferent neurons in an inner ear preparation. See, e.g., Chavez et al., *Brain Res.* 1064(1-2): 1-9 (2005). Further, H3 receptors are localized on neurons in the dorsal horn of the spinal cord, an area important for the transmission of nociceptive information in humans, and have shown efficacy in preclinical pain models. Thus, without being limited by a particular theory, H3 receptor antagonists or inverse agonists may increase the threshold for neuropathic pain, which was shown in models such as the chronic constriction injure (CCI) model, herpes virus-induced model, and capsaicin-induced allodynia model. See, e.g., Medhurst et al., *Pain* 138: 61-69 (2008); Medhurst et al., *Biochem. Pharmacol.* 73: 1182-94 (2007). Therefore, in some embodiments, the compounds provided herein are employed for their analgesic effects to treat, prevent, and/or manage disorders involving pain and the sensitization that accompanies many neuropathic pain disorders.

In yet another embodiment, provided herein is a method of treating, preventing, and/or managing a disorder related to satiety, gastric activity, irritable bowel syndrome (IBS), chronic constipation (CC), and/or metabolic disorders such as diabetes and obesity, comprising administering to a subject an effective amount of a compound provided herein. In other embodiments, provided herein is a method of mitigating the weight gain associated with other therapeutic agents, comprising administering to a subject an effective amount of a compound provided herein. For example, without being limited to a particular theory, H3 receptor plays a role in satiety. See, e.g., Masaki et al., *Curr. Diabetes Rev.* 3: 212-16 (2007); Ishizuka et al., *Behav. Br. Res.* 188: 250-54 (2008). H3 antagonists or inverse agonists may decrease food intake, reduce weight gain, reduce plasma triglyceride levels, modulate energy expenditure, reduce body weight and body fat, and normalize insulin tolerance. See, e.g., Malmlof et al., *Obesity* 14: 2154-62 (2006); Hancock et al., *Eur J. Pharm.* 487: 183-97 (2004). H3 antagonists or inverse agonists may also block olanzepine-induced decrease in satiety. See, e.g., WO 2006/084833.

In another embodiment, provided herein is a method of treating, preventing, and/or managing a disorder of enteric system and/or exocrine pancreatic system, such as acid secretion, digestion, and gut motility, comprising administering to a subject an effective amount of a compound provided herein. See, e.g., Breunig et al., *J. Physiol.* 583(2): 731-42 (2007); Singh et al., *Inflamm. Res.* 46: 159-65 (1997); Bertaccini et al., *Dig. Dis. Sci.* 40: 2052-63 (1995).

In another embodiment, provided herein is a method of treating, preventing, and/or managing movement disorders, such as Parkinson's disease, restless leg syndrome (RLS), and Huntington's disease, comprising administering to a subject an effective amount of a compound provided herein. For example, without being limited by a particular theory, an increased expression of H3 receptors have been found in the postmortem brain of subjects with Parkinson's disease. See, e.g., Anichtchik et al., *Neurobiol. Dis.* 8: 707-16 (2001); Anichtchik et al., *Eur. J. Pharm.* 12: 3823-32 (2000). Further, it was reported that a polymorphism in the primary enzyme that metabolizes histamine in the brain, the Thr105Ile polymorphism, results in a functional alteration in activity of the enzyme. This polymorphism has been associated with movement disorders such as Parkinson's disease and essential tremor. See, e.g., Preuss et al., *JPET* 53: 708-17 (1998); Agundez et al., *Neuromol. Med.* 10(1): 10-16 (2008); Ledesma et al., *Neuromol. Med.* 10(4): 356-61 (2008). Thus, H3 antagonists or inverse agonists may be useful in the treatment of Parkinson's disease. See, e.g., Gomez-Ramirez et al., *Mov. Disord.* 21: 839-46 (2006).

In some embodiments, the compounds provided herein are active in at least one model, which can be used to measure the activity of the compounds and estimate their efficacy in treating a neurological disorder. For example, when the model is for depression (e.g., mean immobility), the compounds are active when they inhibit mean immobility of a test subject by about 5%, about 10%, about 20%, about 30%, about 40%, about 50%, about 60%, about 70%, about 80%, about 90%, about 95%, about 99%, or more, when compared to vehicle. In some embodiments, the compounds provided herein produce a similar disparity in measured endpoint between treated animals and animals administered vehicle.

In other embodiments, provided herein is a method of effecting a therapeutic effect as described herein elsewhere. The method comprises administering to a subject (e.g., a mammal) a therapeutically effective amount of a compound or composition provided herein. The particular therapeutic effects may be measured using any model system known in the art and described herein, such as those involving an animal model of a disease.

In some embodiments, the neurological disorder is: depression (e.g., major depressive disorder, bipolar disorder, unipolar disorder, dysthymia and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; or substance abuse or dependency (e.g., cocaine addiction, nicotine addiction). In another embodiment, the compounds provided herein are useful to treat, prevent, and/or manage two or more conditions/disorders, which are co-morbid, such as cognitive deficit and depression.

Neurological disorders include cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psychosexual dysfunction, including without limitation, inhibited sexual desire, inhibited sexual excitement, inhibited female orgasm, inhibited male orgasm, functional dyspareunia, functional vaginismus, and atypical psychosexual dysfunction.

In one embodiment, the neurological disorder is excessive daytime sleepiness. In another embodiment, the neurological disorder is cognitive impairment. In another embodiment, the neurological disorder is mood disorders. In another embodiment, the neurological disorder is movement disorders. In another embodiment, the neurological disorder is schizophrenia. In another embodiment, the neurological disorder is attention disorders. In another embodiment, the neurological disorder is anxiety disorder. In another embodiment, the neurological disorder is seizure. In another embodiment, the neurological disorder is epilepsy. In another embodiment, the neurological disorder is vertigo. In another embodiment, the neurological disorder is pain. In another embodiment, the neurological disorder is neuropathic pain. In another embodiment, the neuropathic pain is diabetic neuropathy. In another embodiment, the neurological disorder is sleeping disorder. In another embodiment, the neurological disorder is insomnia. In another embodiment, the neurological disorder is substance abuse.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the disorder is obesity, and the therapeutically effective amount of compound to supply to a patient is sufficient so that said patient feels satiated. In another embodiment, the disorder is diabetes. In another embodiment, the disorder is metabolic diseases. In another embodiment, the disorder is a disease effecting the enteric system.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein.

5. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

5.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy,* 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

5.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.3 Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

5.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage fauns encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

6. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

A. Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., *J. Org. Chem.,* 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, elemental microanalysis, and melting point. Proton magnetic resonance ($^1$H-NMR) spectra were determined using a NMR spectrometer operating at a certain field strength. Chemical shifts are reported in parts per million (ppm, δ) downfield from an internal standard, such as TMS. Alternatively, $^1$H-NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

1. Compound 1: (3-cyclobutyl-9-(4-(aminomethyl) phenyl)-2,3,4,5-tetrahydro-1H-[1,4]diazepino[1,7-a] benzimidazole)

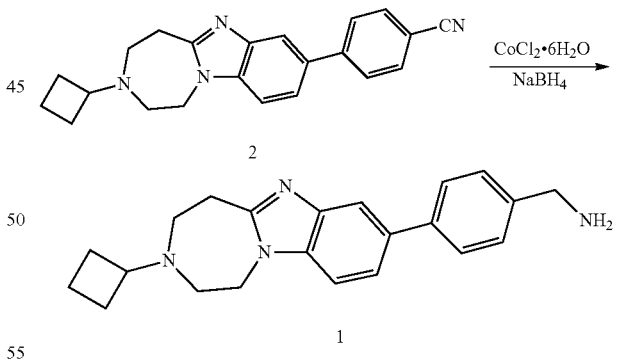

A solution of $CoCl_2.6H_2O$ (48 mg, 0.2 mmol), compound 2 (68 mg, 0.2 mmol) in a mixture of THF and $H_2O$ (10 mL and 5 mL) was stirred at 0° C. and two drops of acetic acid were added. The reaction mixture was stirred for 10 minutes and solid $NaBH_4$ (24 mg, 0.6 mmol) was added. The reaction mixture was stirred for 2 hours and an aqueous solution of ammonia (2 mL) was added. The reaction mixture was filtered and the filtrate was extracted with dichloromethane, the combined organic layers were dried over sodium sulfate, the solids were removed by filtration and the filtrate was concentrated. The crude reaction mixture was purified by preparative HPLC to give compound 1 as a white solid (15 mg, 22%). $^1$H-NMR (500 MHz, CD$_3$OD), δ 7.77 (m, 1H), 7.62~7.63 (m, 2H), 7.48~7.54 (m, 2H), 7.42~7.43 (m, 2H), 4.35 (t, 2H, J=5.0 Hz), 3.87 (s, 2H), 3.20~3.23 (m, 2H), 2.95~3.01 (m, 1H), 2.62~2.69 (m, 4H), 2.14~2.16 (m, 2H), 1.92~1.96 (m, 2H), 1.70~7.74 (m, 2H). MS (ESI): m/z 347 (M+H$^+$).

2. Compound 2: (4-(3-cyclobutyl-2,3,4,5-tetrahydro-1H-[1,4]diazepino[1,7-a]benzimidazol-9-yl)benzonitrile)

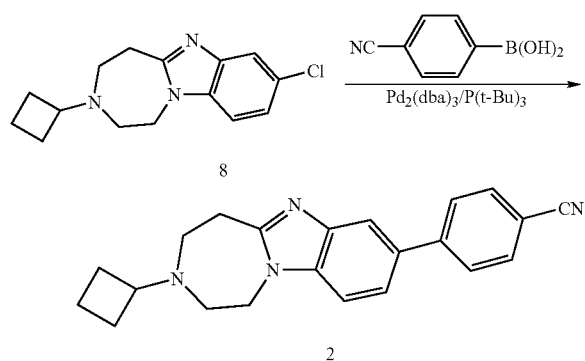

A flask was charged with a hexane solution of tri-t-butylphosphine (610 mg, 0.3 mmol) and evacuated to remove hexane. The flask was refilled with argon and 8 (275 mg, 1.0 mmol), 4-cyanophenylboronic acid (221 mg, 1.5 mmol), Pd$_2$(dba)$_3$ (970 mg, 0.1 mmol) and anhydrous KF (203 mg, 3.5 mmol) were added. 1,4-dioxane (5 mL, freshly distilled from sodium) was added and the reaction flask was filled with argon (repeated 2x). The reaction mixture was refluxed for 16 hours and diluted with ethyl acetate. The organic layer was collected, solids were removed by filtration and filtrate was purified by preparative TLC or preparative HPLC giving 2 as a white solid (55 mg, 16%). $^1$H-NMR (400 MHz, Acetone-d$_6$): δ 8.04 (s, 1H), 7.71~7.85 (m, 6H), 4.96 (t, 2H, J=4.4 Hz), 3.50~3.82 (m, 7H), 2.48~2.54 (m, 2H), 2.24~2.30 (m, 2H), 1.59~1.74 (m, 2H). MS (ESI): m/z 343 (M+H$^+$).

3. Compound 3: (N-(4-(3-(1-cyclopropylethyl)-2,3,4,5-tetrahydro-1H-[1,4]diazepino[1,7-a]benzimidazol-9-yl)phenyl)acetamide)

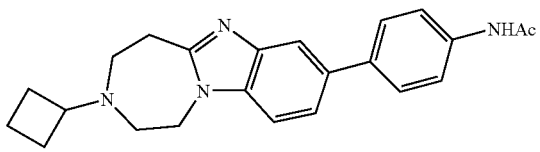

This compound was prepared in 7% yield as described for compound 2 but using 4-acetamidophenylboronic acid as the starting material. $^1$H-NMR (500 MHz, CDCl$_3$), δ 7.87 (s, 1H), 7.56~7.60 (m, 4H), 7.46~7.48 (m, 1H), 7.26~7.34 (m, 2H), 4.27 (m, 2H), 3.28 (m, 2H), 2.93~2.96 (m, 1H), 2.63~2.64 (m, 4H), 2.21 (s, 3H), 2.11~2.16 (m, 2H), 1.91~1.94 (m, 2H), 1.64~1.70 (m, 2H). MS (ESI): m/z 375 (M+H$^+$).

4. Compound 4: (3-cyclobutyl-9-(1H-indol-5-yl)-2,3,4,5-tetrahydro-1H-[1,4]diazepino[1,7-a]benzimidazole)

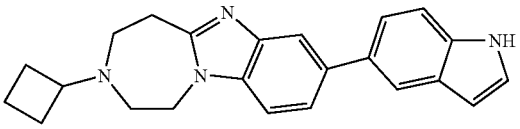

This compound was prepared in 16% yield as described for compound 2 but using 1H-indol-5-ylboronic as the starting material. $^1$H-NMR (400 MHz, DMSO-d$_6$): δ 11.11 (s, 1H), 7.76 (d, 21-1, J=21.2 Hz), 7.45~7.54 (m, 3H), 7.36~7.41 (m, 2H), 6.48 (d, 1H, J=2.0 Hz), 4.31 (t, 2H, J=4.4 Hz), 3.13 (m, 2H), 2.94 (m, 1H), 2.50~2.58 (m, 4H), 2.06~2.07 (m, 2H), 1.80~1.85 (m, 2H), 1.61~1.64 (m, 2H). MS (ESI): m/z 357 (M+H$^+$).

5. Compound 5: (3-(1-cyclopropylethyl)-9-(4-(aminomethyl)phenyl)-2,3,4,5-tetrahydro-1H-[1,4]diazepino[1,7-a]benzimidazole)

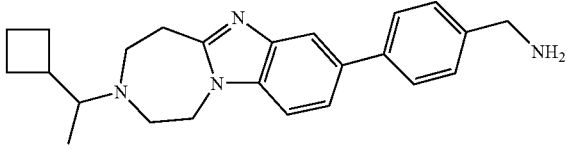

This compound was prepared in 10% yield as described for compound 1 but using compound 6 as the starting material. $^1$H-NMR (500 MHZ, CD$_3$OD), δ 7.78 (d, 1H, J=1.5 Hz), 7.63~7.65 (d, 21-1, J=8.0 Hz), 7.53~7.55 (dd, 1H, J$_1$=1.0 Hz, J$_2$=8.0 Hz), 7.49~7.50 (d, 1H, J=8.0 Hz), 7.43~7.45 (d, 2H, J=8.0 Hz), 4.25~4.34 (m, 2H), 3.89 (s, 2H), 3.16~3.21 (m, 2H), 2.75~2.86 (m, 5H), 2.43~2.48 (m, 1H), 1.72~2.05 (m, 6H), 0.89 (d, 3H). MS (ESI): m/z 375 (M+H$^+$).

6. Compound 6: (4-(3-(1-cyclopropylethyl)-2,3,4,5-tetrahydro-1H-[1,4]diazepino[1,7-a]benzimidazol-9-yl)benzonitrile)

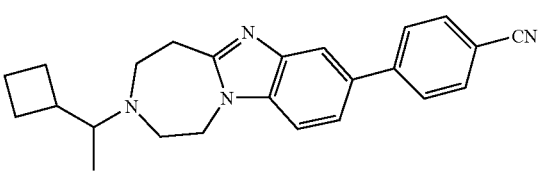

This compound was prepared in 65% yield as described for compound 2 but using compound 11 and 4-cyanophenylboronic acid as the starting materials. $^1$H-NMR (400 MHz, Acetone-d$_6$), δ 8.09 (s, 1H), 7.75~7.85 (m, 6H), 5.00 (t, 2H, J=4.4 Hz), 3.58~3.88 (m, 7H), 2.75~2.77 (m, 1H), 1.62~2.03 (m, 6H), 1.30 (d, 3H). MS (ESI): m/z 371 (M+H$^+$).

7. Compound 7: (N-(4-(3-(1-cyclopropylethyl)-2,3,4,5-tetrahydro-1H-[1,4]diazepino[1,7-a]benzimidazol-9-yl)phenyl)acetamide)

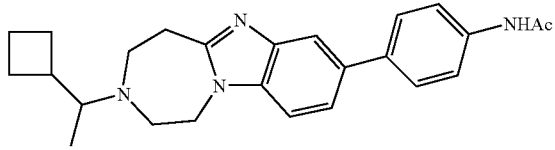

This compound was prepared in 12% yield as described for compound 2 but using compound 11 and 4-acetamidophenylboronic acid as the starting materials. $^1$H-NMR (500 MHz, CDCl$_3$), δ 7.85 (d, 1H, J=1.2 Hz), 7.54~7.58 (m, 5H), 7.26~7.29 (m, 1H), 7.45~7.54 (m, 1H), 4.18~4.22 (m, 2H), 3.20~3.23 (m, 2H), 2.70~2.87 (m, 5H), 2.37~2.39 (m, 1H), 2.21 (s, 3H), 1.63~2.01 (m, 6H), 0.88 (d, 3H). MS (ESI): m/z 403 (M+H$^+$).

8. Compound 8: (3-cyclobutyl-9-chloro-2,3,4,5-tetrahydro-1H-[1,4]diazepino[1,7-a]benzimidazole)

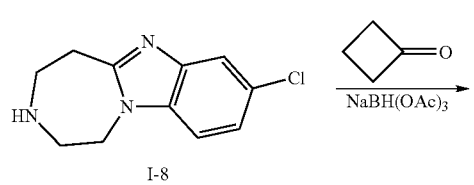

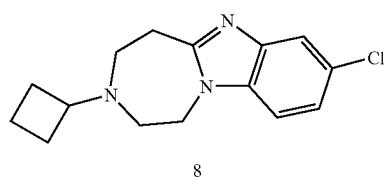

To a solution of intermediate I-8 (1.1 g, 5.0 mmol) in dichloromethane (30 mL) was added acetic acid (0.45 g, 7.5 mmol, 1.5 eq.) and the reaction mixture was stirred at room temperature for 5 minutes. Cyclobutanone (0.53 g, 7.5 mmol, 1.5 eq.) was added and the reaction mixture was stirred for 20 minutes. Solid NaBH(OAc)$_3$ (1.6 g, 7.5 mmol, 1.5 eq.) was added and the reaction mixture was stirred for 2 hours. Aqueous saturated solution of NaHCO$_3$ was added and the reaction mixture was extracted with dichloromethane, the combined organic layers were dried over Na$_2$SO$_4$, solids were removed by filtration and the filtrate was concentrated. The crude reaction mixture was purified by flash chromatography to give compound 8 as a pale yellow solid (1.3 g, 95%). $^1$H-NMR (400 MHz, CDCl$_3$): δ 7.66 (d, 1H, J=1.6 Hz), 7.21 (dd, 1H, J1=1.6 Hz, J2=8.8 Hz), 7.15 (d, 1H, J=8.4 Hz), 4.21 (t, 2H, J=4.8 Hz), 3.24 (t, 2H, J=4.8 Hz), 2.93 (m, 1H), 2.59~2.65 (m, 4H), 2.09~2.13 (m, 2H), 1.89~1.91 (m, 2H), 1.65~1.76 (m, 2H). MS (ESI): m/z 276 (M+H$^+$).

9. Compound 9: (N-(4-(3-(1-methylpiperidin-4-yl)-2,3,4,5-tetrahydro-1H-[1,4]diazepino[1,7-a]benzimidazol-9-yl)phenyl)acetamide)

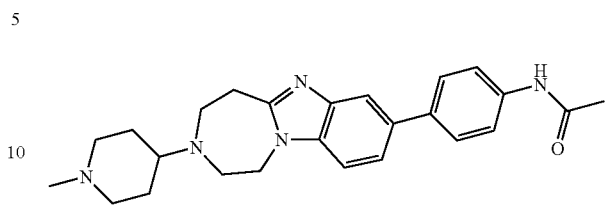

This compound was prepared in 9% yield as described for compound 2 but using compound 14 and 4-acetamidophenylboronic acid as the starting materials. $^1$H-NMR (500 MHz, CDCl$_3$), δ 7.85 (d, 1H, J=0.8 Hz), 7.58~7.60 (m, 4H), 7.42~7.47 (m, 2H), 7.27~7.30 (m, 1H), 4.23 (t, 2H, J=3.6 Hz), 3.24~3.26 (m, 2H), 2.98~3.01 (m, 2H), 2.89~2.93 (m, 4H), 2.61~2.63 (m, 1H), 2.33 (s, 3H), 2.21 (s, 3H), 2.01~2.07 (m, 3H), 1.73~7.76 (m, 3H). MS (ESI): m/z 418 (M+H$^+$).

10. Compound 10: (3-(1-cyclopropylethyl)-9-(1H-indol-5-yl)-2,3,4,5-tetrahydro-1H-[1,4]diazepino[1,7-a]benzimidazole)

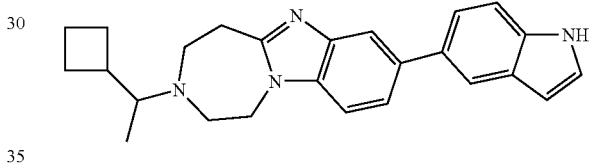

This compound was prepared in 18% yield as described for compound 2 but using compound 11 and 1H-indol-5-ylboronic acid as the starting materials and tricyclohexylphosphine as the ligand. $^1$H-NMR (400 MHz, CDCl$_3$), δ 8.26 (s, 1H), 7.9 (d, 2H, J=20.8 Hz), 7.46~7.57 (m, 2H), 7.24~7.31 (m, 2H), 6.62 (t, 1H, J=2.0 Hz), 4.22 (t, 2H, J=4.4 Hz), 3.23 (t, 2H, J=7.2 Hz), 2.70~2.89 (m, 5H), 2.37~2.40 (m, 1H), 1.55~1.91 (m, 6H), 0.9 (d, 3H). MS (ESI): m/z 385 (M+H$^+$).

11. Compound 11: (3-(1-cyclopropylethyl)-9-chloro-2,3,4,5-tetrahydro-1H-[1,4]diazepino[1,7-a]benzimidazole)

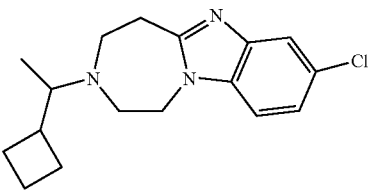

This compound was prepared in 64% yield as described for compound 8 but using 1-cyclopropylethanone as the starting material. $^1$H-NMR (400 MHz, CDCl$_3$): δ 7.65 (d, 1H, J=2.0 Hz), 7.20 (dd, 1H, J$_1$=2.0, Hz J$_2$=9.2 Hz), 7.14 (d, 1H, J=8.8 Hz), 4.14 (t, 2H, J=7.2 Hz), 3.17 (t, 2H, J=7.2 Hz), 2.68~2.85 (m, 5H), 2.35 (m, 1H), 1.67~2.00 (m, 6H), 0.9 (s, 3H). MS (ESI): m/z 304 (M+H$^+$).

12. Compound 12: (4-(3-(1-methylpiperidin-4-yl)-2,3,4,5-tetrahydro-1H-[1,4]diazepino[1,7-a]benzimidazol-9-yl)benzonitrile)

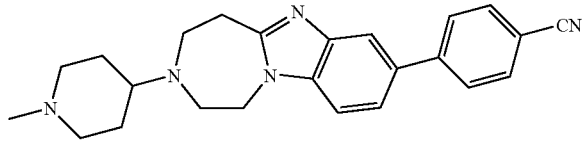

This compound was prepared in 26% yield as described for compound 2 but using compound 14 and 4-cyanophenylboronic acid as the starting materials. $^1$H-NMR (400 MHz, CDCl$_3$), δ 7.90 (d, 1H, J=1.6 Hz), 7.73 (s, 4H), 7.49 (dd, 1H, J=8.4 Hz, J2=1.6 Hz), 7.35 (d, 1H, J=8.4 Hz), 4.25 (t, 2H, J=4.4 Hz), 3.26 (m, 2H), 2.90~2.97 (m, 6I-1), 2.30 (s, 3H), 1.99 (t, 2I-1, J=9.6 Hz), 1.67~1.77 (m, 4H). MS (ESI): m/z 386 (M+H$^+$).

13. Compound 13: (3-(1-methylpiperidin-4-yl)-9-(1H-indol-5-yl)-2,3,4,5-tetrahydro-1H-[1,4]diazepino[1,7-a]benzimidazole)

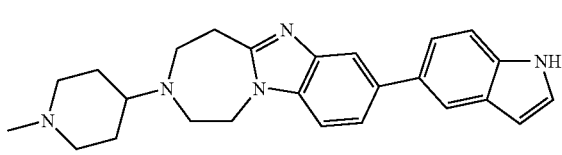

This compound was prepared in 13% yield as described for compound 2 but using compound 14 and 1H-indol-5-ylboronic acid as the starting materials. $^1$H-NMR (400 MHz, CDCl$_3$), δ 8.32 (s, 1H), 7.90 (d, 2H, J=20.8 Hz), 7.45~7.57 (m, 3H), 7.24~7.32 (m, 2H), 6.62 (s, 1H), 4.24 (t, 2I1, J=4.4), 3.26 (t, 2H, J=4.8 Hz), 2.90~2.94 (m, 6H), 2.57~2.60 (m, 1H), 2.29 (s, 3H), 1.99 (t, 2H, J=8.8 Hz), 1.67~1.77 (m, 4H). MS (ESI): m/z 400 (M+H$^+$).

14. Compound 14: (3-(1-methylpiperidin-4-yl)-9-chloro-2,3,4,5-tetrahydro-1H-[1,4]diazepino[1,7-a]benzimidazole)

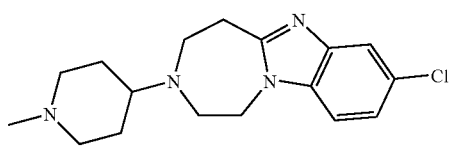

This compound was prepared in 79% yield as described for compound 8 but using 1-methylpiperidin-4-one as the starting material. $^1$H-NMR (400 MHz, CDCl$_3$): δ 7.65 (s, 1H), 7.14~7.21 (m, 2H), 4.18 (t, 2H, J=4.0 Hz), 3.22 (t, 2I-1, J=4.8 Hz), 2.96~2.99 (m, 2H), 2.88~2.92 (m, 4H), 2.57~2.62 (m, 1H), 2.30 (s, 3H), 1.99~2.04 (m, 2H), 1.69~1.74 (m, 4H). MS (ESI): m/z 319 (M+H$^+$).

15. Compound 15: (3-(1H-imidazol-5-yl)methyl)-9-chloro-2,3,4,5-tetrahydro-1H-[1,4]diazepino[1,7-a]benzimidazole)

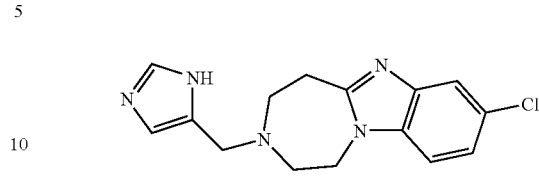

This compound was prepared in 40% yield as described for compound 8 but using 1H-imidazole-5-carbaldehyde as the starting material. $^1$H-NMR (400 MHz, DMSO-d$_6$), δ 11.97 (s, 1H), 7.53~7.57 (m, 3H), 7.21 (dd, 1H, J$_1$=2.0 Hz, J$_2$=8.8 Hz), 6.93 (s, 1H), 4.31 (t, 2H, J=4.4 Hz), 3.67 (s, 2H), 3.13 (t, 2H, J=4.8 Hz), 2.68~2.76 (m, 4H). MS (ESI): m/z 302 (M+H$^+$).

16. Compound 16: (3-(1-methylpiperidin-4-yl)-9-(4-(aminomethyl)phenyl)-2,3,4,5-tetrahydro-1H-[1,4]diazepino[1,7-a]benzimidazole)

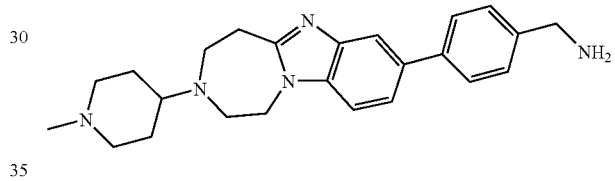

This compound was prepared in 19% yield as described for compound 1 but using compound 12 as the starting material. $^1$H-NMR (400 MHz, CD$_3$OD) δ 7.87 (s, 1H), 7.74~7.81 (m, 2H), 7.64 (d, 2I1, J=8.0), 7.45 (d, 2H, J=8.4 Hz), 4.67 (t, 2I1, J=4.0 Hz), 4.05 (s, 2H), 3.49~3.55 (m, 4H), 3.27~3.36 (m, 5H), 3.15~3.17 (m, 2H), 2.74 (s, 3H), 1.94~2.10 (m, 4H). MS (ESI): m/z 390 (M+H$^+$).

17. Compound 17: (3-(1H-imidazol-5-yl)-9-(4-(aminomethyl)phenyl)-2,3,4,5-tetrahydro-1H-[1,4]diazepino[1,7-a]benzimidazole)

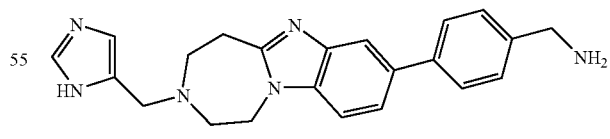

This compound was prepared in 18% yield as described for compound 1 but using compound 18 as the starting material. $^1$H-NMR (400 MHz, CD$_3$OD) δ 7.79 (s, 1H), 7.68~7.72 (m, 3I-1), 7.50~7.57 (m, 4H), 7.05 (d, 1H, J=3.2 Hz), 4.40 (t, 2I-1, J=4.0 Hz), 4.08 (s, 2H), 3.80 (s, 2H), 3.25~3.28 (m, 1H), 2.84~2.91 (m, 4H). MS (ESI): m/z 373 (M+H$^+$).

18. Compound 18: (4-(3-(1H-imidazol-5-yl)-2,3,4,5-tetrahydro-1H-[1,4]diazepino[1,7-a]benzimidazol-9-yl)benzonitrile)

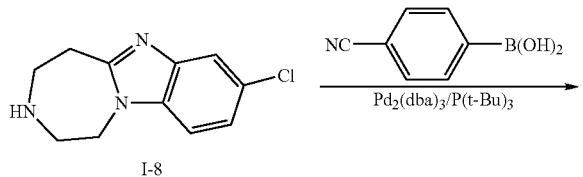

I-8

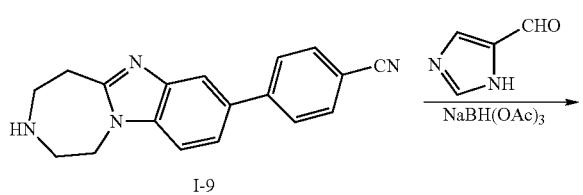

I-9

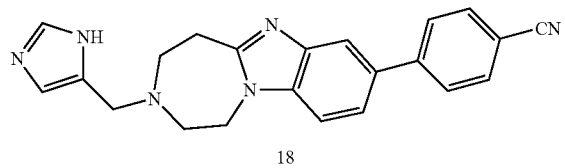

18

I-8 was converted to I-9 as described for compound 2 but using I-8 as the starting material. I-9 was converted to 18 as described for compound 8 but using I-9 and 1H-imidazole-5-carbaldehyde as the starting materials. Overall yield was 78%. $^1$H-NMR (400 MHz, DMSO-$d_6$): δ 11.9 (s, 1H), 7.87~7.95 (m, 5H), 7.56~7.64 (m, 3H), 4.34 (m, 2H), 3.64~3.70 (m, 2H), 3.12~3.19 (m, 2H), 2.69~2.76 (m, 4H). MS (ESI): m/z 369 (M+H$^+$).

19. Compound 19: (N-(4-(3-(1H-imidazol-5-yl)-2,3,4,5-tetrahydro-1H-[1,4]diazepino[1,7-a]benzimidazol-9-yl)phenyl)acetamide)

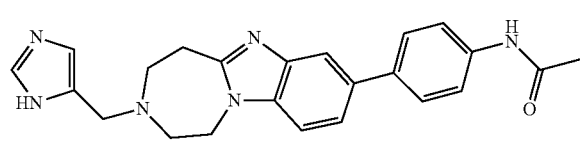

This compound was prepared in 15% yield as described for compound 18 but using 4-acetamidophenylboronic acid as the starting material. $^1$H-NMR (500 MHz, CD$_3$OD), δ 7.74 (s, 1H), 7.61~7.66 (m, 1H), 7.57~7.58 (m, 2H), 7.49~7.51 (m, 2H), 7.44~7.49 (m, 2H), 7.03 (s, 1H), 4.34 (t, 2H, J=4.0 Hz), 3.77 (s, 2H), 3.23 (t, 2H, J=4.5 Hz), 2.81~2.86 (m, 4H), 2.14 (s 3H). MS (ESI): m/z 401 (M+H$^+$).

20. Compound 20: (3-(1H-imidazol-5-yl)-9-(1H-indol-5-yl)-2,3,4,5-tetrahydro-1H-[1,4]diazepino[1,7-a]benzimidazole)

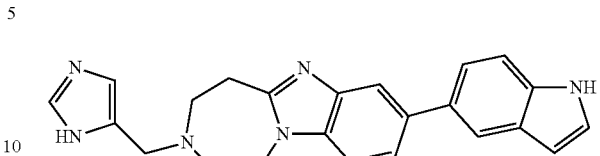

This compound was prepared in 22% yield as described for compound 18 but using 1H-indol-5-ylboronic acid as the starting material. $^1$H-NMR (500 MHz, CD$_3$OD) δ 7.67 (dd, 2H, J$_1$=1.5 Hz, J$_2$=4.5 Hz), 7.56 (s, 1H), 7.45 (dd, 1H, J$_1$=2.0 Hz, J$_2$=3.5 Hz), 7.34 (d, 2H, J=8.5 Hz), 7.29 (dd, 1H, J$_1$=1.5 Hz, J$_2$=8.5 Hz), 7.159 (d, 1H, J=3.0 Hz), 6.93 (s, 1H), 6.39 (s, 1H, J=2.5 Hz), 4.25 (t, 2H, J=4.5 Hz), 3.67 (s, 2H), 3.13~3.15 (m, 2H), 2.72~2.77 (m, 4H). MS (ESI): m/z 383 (M+H$^+$).

21. Compound 21: (3-cyclobutyl-9-bromo-2,3,4,5-tetrahydro-1H-[1,4]diazepino[1,7-a]benzimidazole)

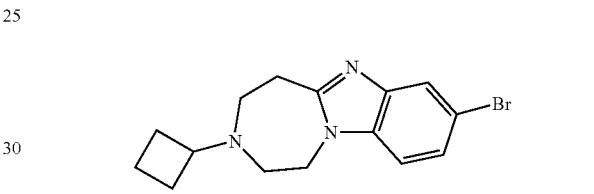

This compound was prepared in 93% yield (3.8 g) as described for compound 8 but using I-16 as the starting material. MS (ESI): m/z 321 (M+H$^+$).

22. Compound 22: (4-(3-cyclobutyl-2,3,4,5-tetrahydro-1H-[1,4]diazepino[1,7-a]benzimidazol-9-yl)-2-fluorobenzonitrile)

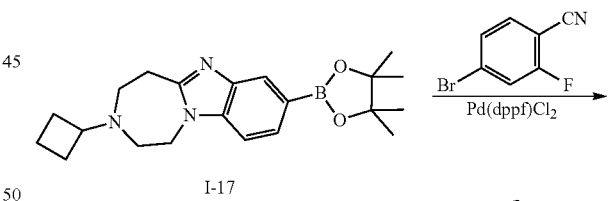

I-17

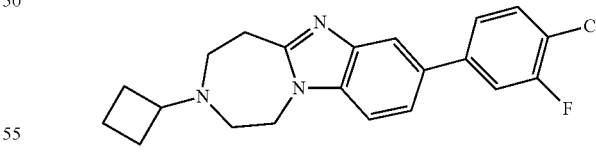

22

I-17 (100 mg), 4-bromo-2-fluorobenzonitrile (32 mg), Pd(dppf)Cl$_2$ (15 mg) and sodium hydroxide were dissolved in DMF (3 mL) in a microwave tube that was filled with argon. The reaction mixture was stirred at 100° C. for 30 minutes under microwave irradiation, diluted with ethyl acetate and filtered through a short plug of silica gel. The filtrate was washed with water, the combined organic layers were dried over Na$_2$SO$_4$, the solids were removed by filtration and the filtrate was concentrated. The crude reaction mixture was purified by preparative TLC to give 22 as a white powder (17 mg, 17%). $^1$H-NMR (400 MHz, CDCl$_3$): δ 7.89 (d, 1H, J=1.2 Hz), 7.66~7.65 (m, 1H), 7.51 (dd, 1H, J$_1$=1.6 Hz, J$_2$=8.0 Hz), 7.48~7.45 (m, 2H), 7.34 (d, 1H, J=8.4 Hz), 4.28 (t, 21-1, J=4.4 Hz), 3.28 (t, 2H, J=5.2 Hz), 2.96~2.92 (m, 111), 2.65 (td, 4H, J$_1$=4.4 Hz, J$_2$=16.0 Hz), 2.15~2.12 (m, 2H), 1.95~1.90 (m, 2H), 1.77~1.65 (m, 2H). MS (ESI): m/z 361 (M+H$^+$).

23. Compound 23: (3-cyclobutyl-9-(2-methoxypyrimidin-5-yl)-2,3,4,5-tetrahydro-1H-[1,4]diazepino[1,7-a]benzimidazole)

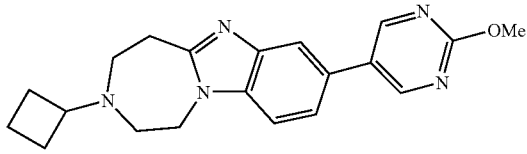

This compound was prepared in 30% yield as described for compound 22 but using 5-bromo-2-methoxypyrimidine as the starting material. $^1$H-NMR (400 MHz, CDCl$_3$): δ 8.68 (s, 2H), 7.74 (d, 1H, J=1.2 Hz), 7.32~7.26 (m, 2H), 4.20 (m, 2H), 3.99 (s, 3H), 3.20 (m, 2H), 2.87 (m, 1H), 2.61~2.54 (m, 4H), 2.07~2.03 (m, 2H), 1.87-1.82 (m, 2H), 1.68~1.57 (m, 2H). MS (ESI): m/z 350 (M+H$^+$).

24. Compound 24: (3-cyclobutyl-9-(pyrazin-2-yl)-2,3,4,5-tetrahydro-1H-[1,4]diazepino[1,7-a]benzimidazole)

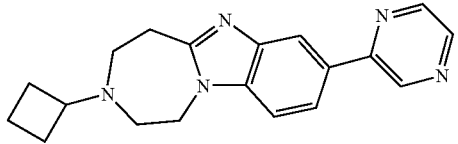

This compound was prepared in 28% yield as described for compound 22 but using 2-iodopyrazine as the starting material. $^1$H-NMR (400 MHz, CDCl$_3$): δ 9.08 (d, 1H, J=1.2 Hz), 8.62 (s, 1H), 8.47 (d, 1H, J=2.4 Hz), 8.31 (d, 1H, J=1.2 Hz), 7.98 (dd, 1H, J$_1$=1.6 Hz, J$_2$=8.8 Hz), 7.37 (d, 1H, J=8.8 Hz), 4.28 (m, 2H), 3.28 (m, 2H), 2.96~2.92 (m, 1H), 2.65 (m, 4H), 2.14-2.3 (m, 2H), 1.95~1.90 (m, 2H), 1.76~1.65 (m, 2H). MS (ESI): m/z 320 (M+H$^+$).

25. Compound 25: (5-(3-cyclobutyl-2,3,4,5-tetrahydro-1H-[1,4]diazepino[1,7-a]benzimidazol-9-yl)-nicotinonitrile)

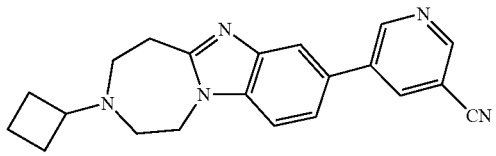

This compound was prepared in 18% yield as described for compound 22 but using 5-bromonicotinonitrile as the starting material. $^1$H-NMR (400 MHz, CDCl$_3$): δ 9.08 (d, 1H, J=2.4 Hz), 8.83 (d, 1H, J=2.0 Hz), 8.17 (t, 1H, J=1.6 Hz), 7.89 (d, 1H, J=2.0 Hz), 7.46~7.38 (m, 2H), 4.30 (m, 2H), 3.29 (m, 2H), 2.99~2.92 (m, 1H), 2.67 (m, 4H), 2.16~2.14 (m, 2H), 1.96~4.91 (m, 2H), 1.77~1.67 (m, 2H). MS (ESI): m/z 344 (M+H$^+$).

26. Compound 26: (3-cyclobutyl-9-(1,3,5-trimethyl-1H-pyrazol-4-yl)-2,3,4,5-tetrahydro-1H-[1,4]diazepino[1,7-a]benzimidazole)

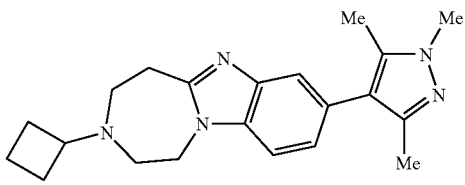

This compound was prepared in 28% yield as described for compound 22 but using 4-bromo-1,3,5-trimethyl-1H-pyrazole as the starting material. $^1$H-NMR (400 MHz, CDCl$_3$): δ 7.76 (s, 1H), 7.30 (s, 1H), 7.14 (dd, 1H, J$_1$=1.2 Hz, J$_2$=8.4 Hz), 4.28 (m, 2H), 3.80 (s, 3H), 3.29 (m, 2H), 2.99~2.90 (m, 1H), 2.68 (m, 4H), 2.25 (s, 3H), 2.24 (s, 3H), 2.15~2.11 (m, 2H), 2.00~1.93 (m, 2H), 1.77~1.66 (m, 2H). MS (ESI): m/z 350 (M+H$^+$).

27. Compound 27: (5-(3-cyclobutyl-2,3,4,5-tetrahydro-1H-[1,4]diazepino[1,7-a]benzimidazol-9-yl)-picolinonitrile)

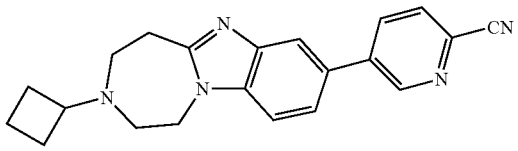

This compound was prepared in 20% yield as described for compound 22 but using 5-bromopicolinonitrile as the starting material. $^1$H-NMR (400 MHz, CDCl$_3$): δ 8.99 (d, 1H, J=1.2 Hz), 8.04 (dd, 1H, J$_1$=2.0 Hz, J$_2$=8.0 Hz), 7.92 (d, 1H, J=2.0 Hz), 7.76 (d, 1H, J=8.0 Hz), 7.49 (dd, 1H, J$_1$=1.2 Hz, J$_2$=8.0 Hz), 7.38 (d, 1H, J=8.8 Hz), 4.29 (m, 2H), 3.29 (m, 2H), 2.98~2.90 (m, 1H), 2.66 (m, 4H), 2.15~2.13 (m, 2H), 1.95~1.90 (m, 2H), 1.79~1.75 (m, 2H). MS (ESI): m/z 344 (M+H$^+$).

28. Compound 28: (3-cyclobutyl-9-(imidazo[1,2-a]pyridin-6-yl)-2,3,4,5-tetrahydro-1H-[1,4]diazepino[1,7-a]benzimidazole)

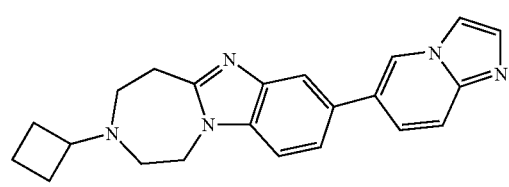

This compound was prepared in 40% yield as described for compound 22 but using 6-bromoimidazo[1,2-a]pyridine as the starting material. $^1$H-NMR (400 MHz, CDCl$_3$): δ 8.31 (m, 1H), 7.85 (d, 1H, J=1.6 Hz), 7.69~7.64 (m, 3H), 7.49~7.42 (m, 2H), 7.33 (dd, 1H, J$_1$=0.4 Hz, J$_2$=8.0 Hz), 4.27 (m, 2H), 3.27 (m, 2H), 2.99~2.90 (m, 1H), 2.65 (m, 4H), 2.14~2.12 (m, 2H), 1.94~1.90 (m, 2H), 1.76~1.66 (m, 2H). MS (ESI): m/z 359 (M+H$^+$).

29. Compound 29: (3-cyclobutyl-9-(midazo[1,2-a]pyridin-8-yl)-2,3,4,5-tetrahydro-1H-[1,4]diazepino[1,7-a]benzimidazole)

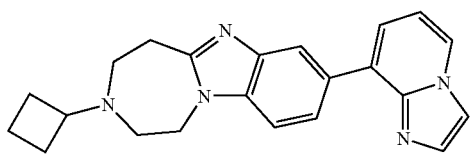

This compound was prepared in 20% yield as described for compound 22 but using 8-bromoimidazo[1,2-a]pyridine as the starting material. $^1$H-NMR (400 MHz, CDCl$_3$): δ 8.13~8.07 (m, 3H), 7.66 (dd, 2H, J$_1$=1.2 Hz, J$_2$=7.2 Hz), 7.36 (d, 1H, J=8.4 Hz), 7.30 (dd, 1H, J$_1$=1.2 Hz, J$_2$=6.8 Hz), 6.88 (m, 1H), 4.27 (m, 2H), 3.27 (m, 2H), 2.96~2.91 (m, 1H), 2.66~2.60 (m, 4H), 2.14~2.10 (m, 2H) 1.95-1.90 (m, 2H), 1.76~1.65 (m, 2H). MS (ESI): m/z 359 (M+H$^+$).

30. Compound 30: (3-cyclobutyl-9-(1H-pyrazol-4-yl)-2,3,4,5-tetrahydro-1H-[1,4]diazepino[1,7-a]benzimidazole)

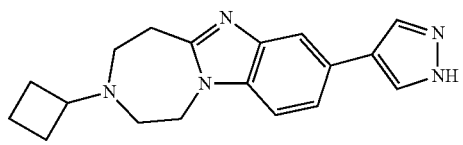

This compound was prepared in 20% yield as described for compound 22 but using 4-bromo-1-tosyl-1H-pyrazole as the starting material. $^1$H-NMR (400 MHz, CDCl$_3$): δ 7.89~7.82 (m, 2H), 7.43 (d, 1H, J=7.6 Hz), 7.26~7.24 (m, 3H), 4.26 (m, 2H), 3.28 (m, 2H), 2.97~2.94 (m, 1H), 2.70~2.65 (m, 4H), 2.17~2.11 (m, 2H), 1.97~1.91 (m, 2H), 1.78~1.66 (m, 2H). MS (ESI): m/z 308 (M+H$^+$).

31. Compound 31: (3-cyclobutyl-9-(1H-pyrrolo[2,3-b]pyridin-3-yl)-2,3,4,5-tetrahydro-1H-[1,4]diazepino[1,7-a]benzimidazole)

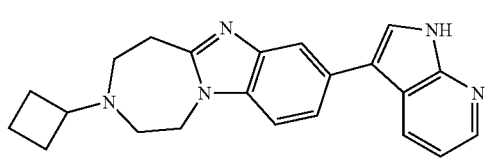

This compound was prepared in 20% yield as described for compound 22 but using 3-bromo-1H-pyrrolo[2,3-b]pyridine as the starting material. $^1$H-NMR (400 MHz, D$_2$O): δ 8.75 (d, 1H, J=4.0 Hz), 8.29 (d, 1H, J=2.8 Hz), 7.94 (s, 1H), 7.85~7.80 (m, 3H), 7.51~7.48 (m, 1H), 3.86~3.81 (m, 1H), 3.72~3.55 (m, 6I-1), 2.35~2.22 (m, 4H), 1.82~1.69 (m, 2H). MS (ESI): m/z 358 (M+H$^+$). $^1$H-NMR was collected on the 3×HCl salt and signals for two protons overlapped with the H$_2$O peak.

32. Compound 32: (4-(3-isopropyl-2,3,4,5-tetrahydro-1H-[1,4]diazepino[1,7-a]benzimidazol-9-yl)benzonitrile)

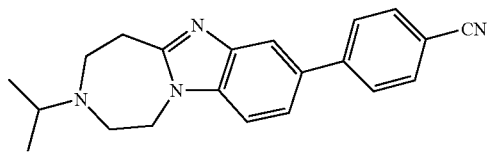

This compound was prepared in 91% yield (60 mg) as described for compound 18 but using acetone as the starting material. $^1$H-NMR (400 MHz, D$_2$O): δ 8.02 (s, 1H), 7.95 (m, 2H), 7.79~7.85 (m, 4H), 5.11 (m, 2H), 3.93~3.97 (m, 7H), 1.47 (d, 6H, J=6.8 Hz). MS (ESI): m/z 331 (M+H$^+$). $^1$H-NMR was collected on the 2×HCl salt of compound 32.

33. Compound 33: (4-(3-cyclopentyl-2,3,4,5-tetrahydro-1H-[1,4]diazepino[1,7-a]benzimidazol-9-yl)benzonitrile)

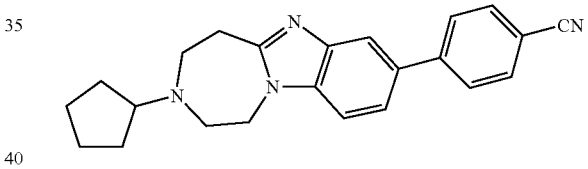

This compound was prepared in 96% yield as described for compound 18 but using cyclopentanone as the starting material. $^1$H-NMR (400 MHz, CDCl$_3$): δ 7.91 (s, 1H), 7.72 (m, 4H), 7.50 (dd, 1H, J$_1$=2.0 Hz, J$_2$=8.4 Hz), 7.34 (d, 1H, J=8.4 Hz), 4.29 (m, 2H), 3.30 (m, 2H), 3.04 (m, 1H), 3.02 (m, 2H), 2.94 (m, 2H), 1.90~1.92 (m, 2H), 1.73 (m, 2H), 1.58~1.61 (m, 4H). MS (ESI): m/z 357 (M+H$^+$).

34. Compound 34: (rac-cis/trans-4-(3-(3-methylcyclopentyl)-2,3,4,5-tetrahydro-1H-[1,4]diazepino[1,7-a]benzimidazol-9-yl)benzonitrile)

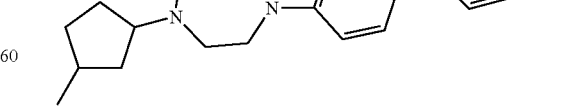

This compound was prepared in 92% yield as described for compound 18 but using (rac)-3-methylcyclopentanone as the starting material. $^1$H-NMR (400 MHz, CDCl$_3$): δ 7.91 (s, 1H), 7.72 (d, 4H, J=8.4 Hz), 7.48 (d, 1H, J=8.0 Hz), 7.34 (d, 1H, J=8.4 Hz), 4.28 (m, 2H), 3.29 (m, 2H), 3.03~3.18 (m, 1H), 2.85~2.93 (m, 4H), 1.50~2.04 (m, 6H), 1.13 (m, 1H), 1.00~4.04 (m, 3H). MS (ESI): m/z 371 (M+H⁺).

35. Compound 35: (rac-cis/trans-4-(3-(2-methylcyclopentyl)-2,3,4,5-tetrahydro-1H-[1,4]diazepino[1,7-a]benzimidazol-9-yl)benzonitrile)

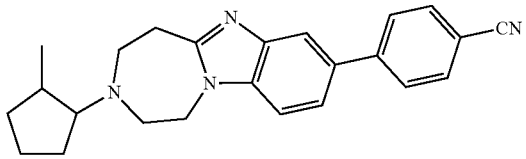

This compound was prepared in 78% yield as described for compound 18 but using (rac)-2-methylcyclopentanoneas the starting material. ¹H-NMR (400 MHz, CDCl₃): δ 7.90 (d, 1H, J=1.6 Hz), 7.72 (m, 4H), 7.48 (dd, 1H, J₁=1.6 Hz, J₂=8.4 Hz), 7.34 (d, 1H, J=8.4 Hz), 4.29 (m, 2H), 3.30 (m, 2H), 2.78~2.94 (m, 5H), 2.25 (m, 1H), 1.47~1.92 (m, 6H), 0.92 (d, 3H, J=7.2 Hz). MS (ESI): m/z 371 (M+H⁺).

36. Compound 36: (4-(3-cyclohexyl-2,3,4,5-tetrahydro-1H-[1,4]diazepino[1,7-a]benzimidazol-9-yl)benzonitrile)

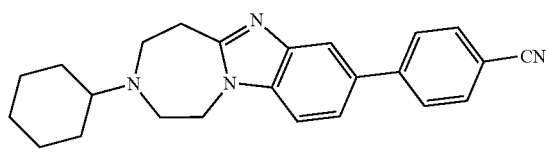

This compound was prepared in 93% yield as described for compound 18 but using cyclohexanone as the starting material. ¹H-NMR (400 MHz, CDCl₃): δ 7.90 (s, 1H), 7.70 (s, 4H), 7.48 (dd, 1H, J₁=1.2 Hz, J₂=8.8 Hz), 7.34 (d, 1H, J=8.4 Hz), 4.25 (m, 2H), 3.26 (m, 2H), 2.94 (m, 2H), 2.90 (m, 2H), 2.59 (m, 1H), 1.81~1.85 (m, 4H), 1.64~1.67 (m, 1H), 1.22~1.32 (m, 4H), 1.07~1.13 (m, 1H). MS (ESI): m/z 371 (M+H⁺).

37. Compound 37: (cis/trans-4-(3-(4-methylcyclohexyl)-2,3,4,5-tetrahydro-1H-[1,4]diazepino[1,7-a]benzimidazol-9-yl)benzonitrile)

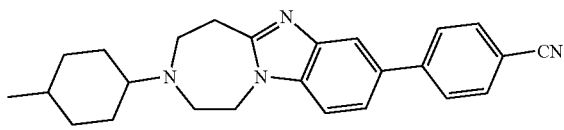

This compound was prepared in 78% yield as described for compound 18 but using 4-methylcyclohexanone as the starting material. ¹H-NMR (400 MHz, CDCl₃): δ 7.91 (t, 1H, J=0.8 Hz), 7.72 (s, 4H), 7.47 (dd, 1H, J₁=0.8 Hz, J₂=8.4 Hz), 7.34 (d, 1H, J=8.4 Hz), 4.24 (m, 2H), 3.26~3.28 (m, 2H), 2.92~3.00 (m, 4H), 2.58 (m, 1H), 1.78~1.88 (m, 3H), 1.53~1.58 (m, 5H), 1.30~1.34 (m, 1H), 0.88~0.99 (d, 3H, J=6.4 Hz). MS (ESI): m/z 385 (M+H⁺).

38. Compound 38: (4-(3-(tetrahydro-2H-pyran-4-yl)-2,3,4,5-tetrahydro-1H-[1,4]diazepino[1,7-a]benzimidazol-9-yl)benzonitrile)

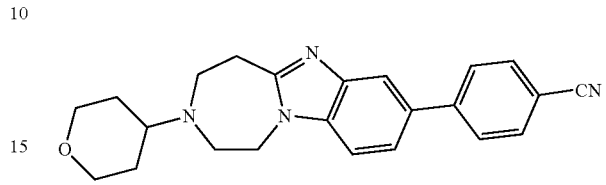

This compound was prepared in 95% yield as described for compound 18 but using dihydro-2H-pyran-4(3H)-one as the starting material. ¹H-NMR (400 MHz, CDCl₃): δ 7.91 (s, 1H), 7.72 (s, 4H), 7.48 (d, 1H, J=8.0 Hz), 7.35 (d, 1H, J=8.4 Hz), 4.27 (m, 2H), 4.06 (m, 2H), 3.37~3.43 (m, 2H), 3.28 (m, 2H), 2.92~2.98 (m, 4H), 2.82~2.85 (m, 1H), 1.62~1.72 (m, 4H). MS (ESI): m/z 373 (M+H⁺).

39. Compound 39: (4-(3-(cyclopropylmethyl)-2,3,4,5-tetrahydro-1H-[1,4]diazepino[1,7-a]benzimidazol-9-yl)benzonitrile)

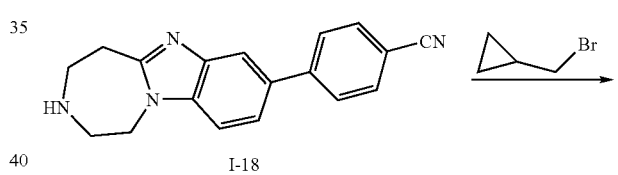

I-18

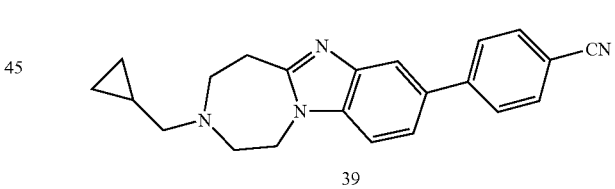

39

I-18 (78 mg, 0.27 mmol) and (bromomethyl)cyclopropane (73 mg, 0.54 mmol, 2.0 eq.) was dissolved in DIPEA (3 mL) and stirred at 100° C. for 90 minutes. The reaction mixture was diluted with dichloromethane and washed with water. The combined organic layers were dried over sodium sulfate, the solids were removed by filtration and the filtrate was concentrated. The crude reaction mixture was purified by preparative TLC to give compound 39 as a pale yellow solid (25 mg, 27%). ¹H-NMR (400 MHz, CDCl₃): δ 7.92 (d, 1H, J=0.8 Hz), 7.72 (s, 4H), 7.49 (dd, 1H, J₁=1.2 Hz, J₂=8.4 Hz), 7.34 (d, 1H, J=8.8 Hz), 4.32 (m, 2H), 3.32 (m, 2H), 2.99 (m, 2H), 2.94 (m, 2H), 2.56 (m, 2H), 0.93~0.95 (m, 1H), 0.56~0.61 (m, 2H), 0.14~0.17 (m, 2H). MS (ESI): m/z 343 (M+H⁺).

40. Compound 40: (3-cyclobutyl-8-bromo-2,3,4,5-tetrahydro-1H-[1,4]diazepino[1,7-a]benzimidazole)

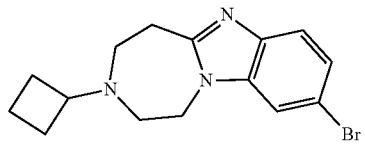

This compound was prepared in 93% yield (5.2 g) as described for compound 8 but intermediate I-26 as the starting material. $^1$H-NMR (400 MHz, CDCl$_3$): δ 7.54 (d, 1H, J=8.4 Hz), 7.40 (d, 1H, J=1.6 Hz), 7.31 (dd, 1H, J$_1$=1.6 Hz, J$_2$=8.4 Hz), 4.18 (m, 2H), 3.22 (m, 2H), 2.90~2.94 (m, 1H), 2.59-164 (m, 4H), 2.09~2.13 (m, 2H), 1.88~1.93 (m, 2H), 1.65~1.75 (m, 2H). MS (ESI): m/z 321 (M+H$^+$).

41. Compound 41: (4-(3-cyclobutyl-2,3,4,5-tetrahydro-1H-[1,4]diazepino[1,7-a]benzimidazol-8-yl)benzonitrile)

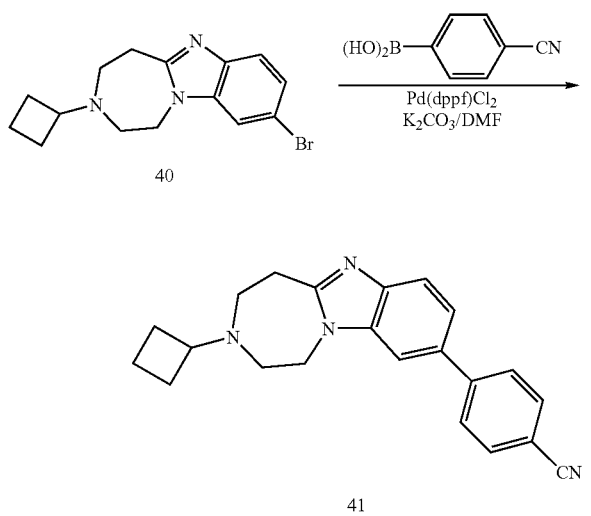

Compound 40 (160 mg, 0.5 mmol), 4-cyanophenylboronic acid (93 mg, 0.65 mmol, 1.3 eq), Pd(dppf)Cl$_2$ (37 mg, 0.05 mmol, 10 mol %) and K$_2$CO$_3$ were dissolved in DMF (3 mL) in a microwave tube that was filled with argon. The mixture was stirred at 100° C. for 30 minutes under microwave irradiation. The reaction mixture was diluted with ethyl acetate, filtered through a short plug of silica gel and the filtrate was washed with water. The combined organic layers were dried over magnesium sulfate, the solids were removed by filtration and the filtrate was concentrated. The crude reaction mixture was purified by preparative TLC to give compound 41 as a white powder (68 mg, 40%). $^1$H-NMR (400 MHz, CDCl$_3$): δ 7.73~7.78 (m, 5H), 7.45~7.47 (m, 2H), 4.30 (m, 2H), 3.28 (m, 2H), 2.95 (m, 1H), 2.64~2.69 (m, 4H), 2.13~2.15 (m, 2H), 1.88~1.95 (m, 2H), 1.66~1.83 (m, 2H). MS (ESI): m/z 343 (M+H$^+$).

42. Compound 42: (N-(4-(3-(1-cyclopropylethyl)-2,3,4,5-tetrahydro-1H-[1,4]diazepino[1,7-a]benzimidazol-8-yl)phenyl)acetamide)

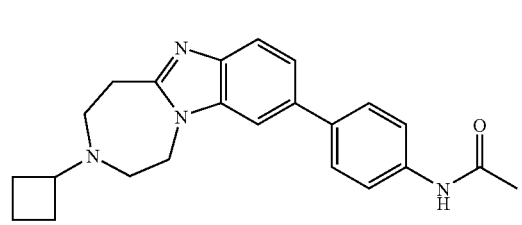

This compound was prepared in 32% yield as described for compound 41 but using 4-acetamidophenylboronic acid as the starting material. $^1$H-NMR (400 MHz, CDCl$_3$): δ 7.70 (d, 1H, J=8.4 Hz), 7.56~7.60 (m, 5H), 7.43 (dd, 1H, J$_1$=1.2 Hz, J$_2$=8.4 Hz), 7.38 (s, 1H), 4.27 (m, 2H), 3.26 (m, 2H,), 2.92~2.95 (m, 1H), 2.66 (m, 2H), 2.62 (m, 2H), 2.20 (s, 3H) 2.10~2.16 (m, 2H), 1.90~1.97 (m, 2H), 1.65~1.76 (m, 2H). MS (ESI): m/z 375 (M+H$^+$).

43. Compound 43: (3-cyclobutyl-8-(1H-indol-5-yl)-2,3,4,5-tetrahydro-1H-[1,4]diazepino[1,7-a]benzimidazole)

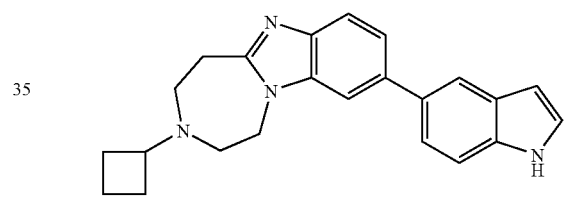

This compound was prepared in 11% yield as described for compound 41 but using 1H-indol-5-ylboronic acid as the starting material. $^1$H-NMR (400 MHz, CDCl$_3$): δ 8.48 (s, 1H), 7.88 (s, 1H), 7.73 (d, 1H, J=8.8 Hz), 7.54 (dd, 1H, J$_1$=2.0 Hz, J$_2$=8.4 Hz), 7.44~7.50 (m, 3H), 7.24~7.26 (m, 1H), 6.60~6.61 (m, 1H), 4.29 (m, 2H), 3.26 (m, 2H), 2.93 (m, 1H), 2.67 (m, 2H), 2.62 (m, 2H), 2.10~2.14 (m, 2H), 1.90~1.95 (m, 2H), 1.65~1.76 (m, 2H). MS (ESI): m/z 357 (M+H$^+$).

44. Compound 44: (3-cyclobutyl-8-(4-(aminomethyl)phenyl)-2,3,4,5-tetrahydro-1H-[1,4]diazepino[1,7-a]benzimidazole)

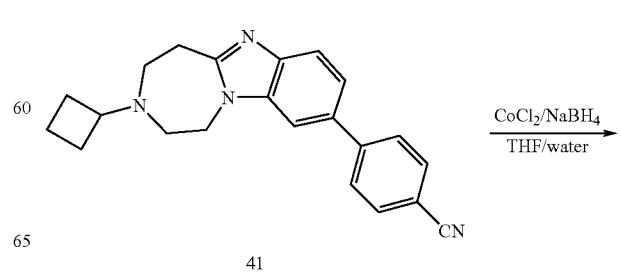

-continued

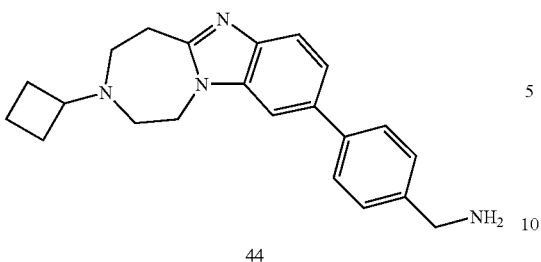

44

To a solution of CoCl$_2$.6H$_2$O (48 mg, 0.2 mmol) and compound 41 (54 mg, 0.16 mmol) in a 2:1 mixture of THF and water (15 mL) was added solid NaBH$_4$ (3.0 eq.) and the reaction mixture was stirred for 1 hour. The crude reaction mixture was filtered through a short plug of Celite, the filtrate was extracted with dichloromethane, the combined organic layers were dried over sodium sulfate, the solids were removed by filtration and the filtrate was concentrated. The crude reaction mixture was purified by preparative TLC to give compound 44 as a white solid (30 mg, 55%). $^1$H-NMR (400 MHz, CDCl$_3$): δ 7.73 (d, 1H, J=8.0 Hz), 7.60 (d, 2H, J=8.4 Hz), 7.46 (dd, 1H, J$_1$=2.0 Hz, J$_2$=8.0 Hz), 7.38~7.42 (m, 3H), 4.27 (m, 2H), 3.92 (s, 2H), 3.26 (m, 2H), 2.91~2.95 (m, 1H), 2.66 (m, 2H), 2.62 (m, 2H), 2.10~2.14 (m, 2H), 1.89~1.94 (m, 2H), 1.63~1.76 (m, 2H). MS (ESI): m/z 347 (M+H$^+$).

45. Compound 45: (4-(3-cyclobutyl-2,3,4,5-tetrahydro-1H-[1,4]diazepino[1,7-a]benzimidazol-8-yl)-2-fluorobenzonitrile)

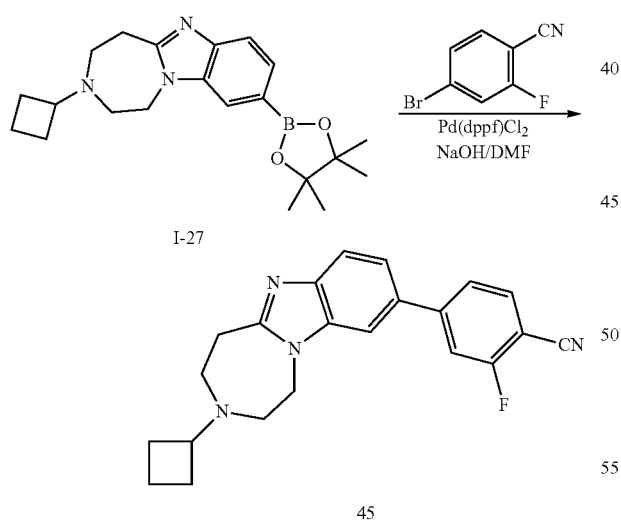

45

This compound was prepared in 44% yield (35 mg) as described for compound 22 but using intermediate I-27 as the starting material. $^1$H-NMR (400 MHz, CDCl$_3$): δ 7.76~7.28 (m, 1H), 7.68 (m, 1H), 7.52 (dd, 1H, J$_1$=1.6 Hz, J$_2$=8.0 Hz), 7.48 (d, 1H, J=1.6 Hz), 7.46 (m, 1H), 7.43 (s, 1H), 4.30 (m, 2H), 3.28 (m, 2H), 2.96~2.92 (m, 1H), 2.68 (m, 2H), 2.64 (m, 2H), 2.15~2.11 (m, 2H), 1.95~1.89 (m, 2H), 1.76~1.66 (m, 2H). MS (ESI): m/z 361 (M+H$^+$).

46. Compound 46: (5-(3-cyclobutyl-2,3,4,5-tetrahydro-1H-[1,4]diazepino[1,7-a]benzimidazol-8-yl)-nicotinonitrile)

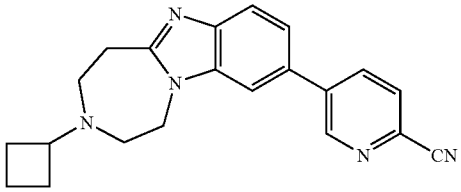

This compound was prepared in 31% yield as described for compound 45 but using 5-bromopicolinonitrile as the starting material. $^1$H-NMR (400 MHz, CDCl$_3$): δ 8.99 (d, 1H, J=3.2 Hz), 8.05 (dd, 1H, J$_1$=2.0 Hz, J$_2$=8.0 Hz), 7.81 (d, 1H, J=9.2 Hz), 7.77 (d, 1H, J=8.0 Hz), 7.74 (m, 2H), 4.31 (m, 2H), 3.29 (m, 2H), 2.97-2.93 (m, 1H), 2.69 (m, 2H), 2.64 (m, 2H), 2.15~2.11 (m, 2H), 1.77~1.66 (m, 2H). MS (ESI): m/z 344 (M+H$^+$).

47. Compound 47: (3-cyclobutyl-8-(imidazo[1,2-a]pyridin-6-yl)-2,3,4,5-tetrahydro-1H-[1,4]diazepino[1,7-a]benzimidazole)

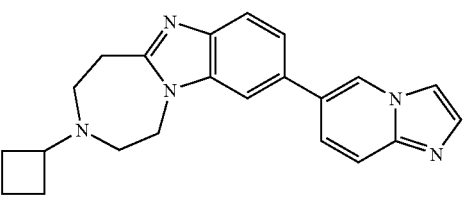

This compound was prepared in 31% yield as described for compound 45 but using 6-bromoimidazo[1,2-a]pyridine as the starting material. $^1$H-NMR (400 MHz, CDCl$_3$): δ 8.32 (s, 1H), 7.75 (m, 1H), 7.69~7.63 (m, 3H), 7.46 (d, 1H, J=9.2 Hz), 7.41~7.39 (m, 2H), 4.28 (m, 2H), 3.27 (m, 2H), 2.96~2.92 (m, 1H), 2.67 (m, 2H), 2.62 (m, 2H), 2.14~2.12 (m, 2H), 1.94~1.90 (m, 2H), 1.76~1.65 (m, 2H). MS (ESI): m/z 358 (M+H$^+$).

48. Compound 48: (3-cyclobutyl-8-(pyrazin-2-yl)-2,3,4,5-tetrahydro-1H-[1,4]diazepino[1,7-a]benzimidazole)

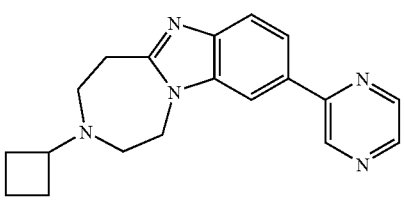

This compound was prepared in 20% yield as described for compound 45 but using 2-iodopyrazine as the starting material. ¹H-NMR (400 MHz, CDCl₃): δ 9.03 (s, 1H), 8.56~8.55 (m, 1H), 8.42 (d, 1H, J=2.4 Hz) 7.96 (d, 1H, J=1.2 Hz), 7.77~7.71 (m, 2H), 4.27 (m, 2H), 3.22 (m, 2H), 2.80~2.77 (m, 1H), 2.62~2.56 (m, 4H), 2.08~2.04 (m, 2H), 1.89~1.85 (m, 2H), 1.70~1.59 (m, 2H). MS (ESI): m/z 319 (M+H⁺).

49. Compound 49: (3-cyclobutyl-9-(1H-pyrazol-4-yl)-2,3,4,5-tetrahydro-1H-[1,4]diazepino[1,7-a]benzimidazole)

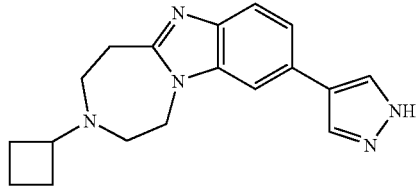

This compound was prepared in 30% yield as described for compound 45 but using 4-bromo-1-tosyl-1H-pyrazole as the starting material. ¹H-NMR (400 MHz, d₆-DMSO): δ 12.87 (s, 1H), 7.97~8.14 (m, 2H), 7.74 (d, 1H, J=0.8 Hz), 7.47 (d, 1H, J=8.4 Hz), 7.39 (dd, 1H, J₁=1.2 Hz, J₂=8.0 Hz), 4.30~4.32 (m, 2H), 3.09~3.11 (m, 2H), 2.93~2.97 (m, 1H), 2.50~2.59 (m, 4H), 2.05~2.07 (m, 2H), 1.80~1.85 (m, 2H), 1.61~1.66 (m, 2H). MS (ESI): m/z 308 (M+H⁺).

50. Compound 50: (6-(3-cyclobutyl-2,3,4,5-tetrahydro-1H-[1,4]diazepino[1,7-a]benzimidazol-9-yloxy)-N-methylnicotinamide)

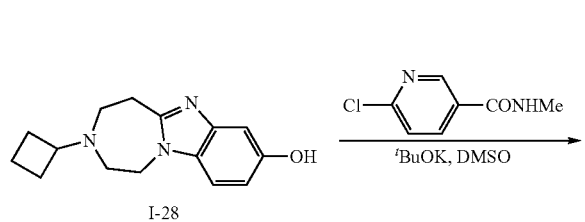

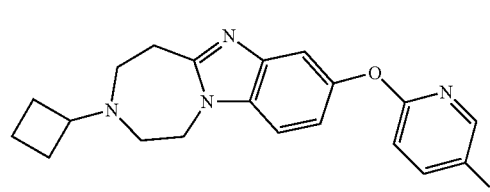

I-28 (60 mg), 6-chloro-N-methylnicotinamide (1.5 eq.) and ᵗBuOK (1.5 eq.) were dissolved in dry DMSO (1.0 mL) and stirred at 120° C. overnight. The mixture was purified by reverse phase preparative HPLC to give compound 50 (30 mg, 33%). ¹H-NMR (400 MHz, CDCl₃): δ 8.53 (d, 1H, J=2.0 Hz), 8.10 (dd, 1H, J₁=8.8 Hz, J₂=2.0 Hz), 7.42 (s, 1H), 7.26 (d, 1H, J=8.8 Hz), 7.03 (d, 1H, J=8.4 Hz), 6.89 (d, 1H, J=8.4 Hz), 6.6 (brs, 1H), 4.23 (m, 2H), 3.22 (m, 2H), 2.98 (s, 3H), 2.93~2.97 (m, 1H), 2.65 (m, 2H), 2.60 (m, 2H), 2.12~2.14 (m, 2H), 1.89~1.94 (m, 2H), 1.68~1.76 (m, 2H). MS (ESI): m/z 392 (M+H⁺).

51. Compound 51: (3-cyclobutyl-9-(pyrazin-2-yloxy)-2,3,4,5-tetrahydro-1H-[1,4]diazepino[1,7-a]benzimidazole)

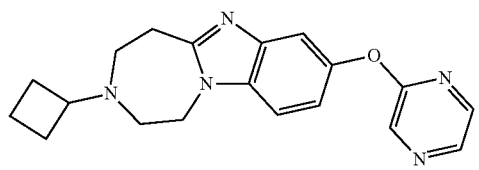

This compound was prepared in 26% yield as described for compound 50 but using 2-iodopyrazine as the starting material. ¹H-NMR (400 MHz, CDCl₃): δ 8.43 (d, 1H, J=1.2 Hz), 8.23 (d, 1H, J=2.8 Hz), 8.07 (dd, 1H, J₁=1.6 Hz, J₂=2.8 Hz), 7.48 (d, 1H, J=2.0 Hz), 7.27 (d, 1H, J=8.8 Hz), 7.06 (dd, 1H, J₁=2.0 Hz, J₂=8.8 Hz), 4.25 (m, 2H), 3.26 (m, 2H), 2.92~2.96 (m, 1H), 2.67 (m, 2H), 2.62 (m, 2H), 2.12~2.14 (m, 2H), 1.91~1.95 (m, 2H), 1.66~1.77 (m, 2H). MS (ESI): m/z 336 (M+H⁺).

52. Compound 52: (6-(3-cyclobutyl-2,3,4,5-tetrahydro-1H-[1,4]diazepino[1,7-a]benzimidazol-9-yloxy)-nicotinonitrile)

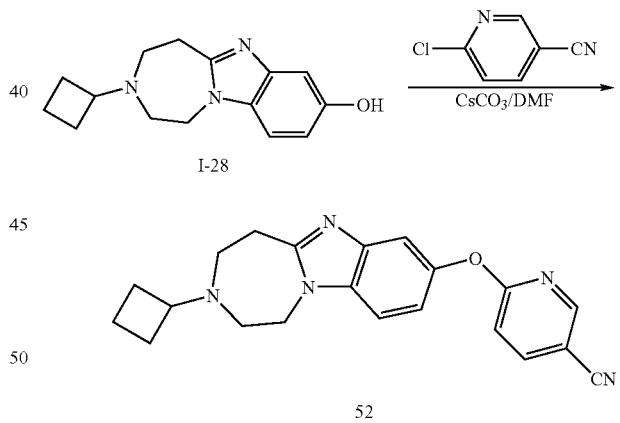

I-28 (23 mg, 0.089 mmol), 6-chloronicotinonitrile (25 mg, 0.178 mmol) and cesium carbonate (58 mg, 0.0178 mmol) were dissolved in DMF (5 mL) and stirred at room temperature for 60 minutes. The crude reaction mixture was purified by reverse phase chromatography to yield compound 52 as a pale yellow solid (20 mg, 62%). ¹H-NMR (400 MHz, CDCl₃): δ 8.45 (d, 1H, J=3.2 Hz), 7.90 (dd, 1H, J₁=2.4 Hz, J₂=9.2 Hz), 7.45 (d, 1H, J=2.4 Hz), 7.29 (d, 1H, J=8.4 Hz), 7.01~7.05 (m, 2H), 4.25 (m, 2H), 3.26 (m, 2H), 2.92~2.96 (m, 1H), 2.66 (m, 2H), 2.62 (m, 2H), 2.11~2.15 (m, 2H), 1.89~1.94 (m, 2H), 1.64~1.76 (m, 2H). MS (ESI): m/z 360 (M+H⁺).

53. Compound 53: (4-((3-cyclobutyl-2,3,4,5-tetrahydro-1H-[1,4]diazepino[1,7-a]benzimidazol-9-yloxy)methyl)benzonitrile)

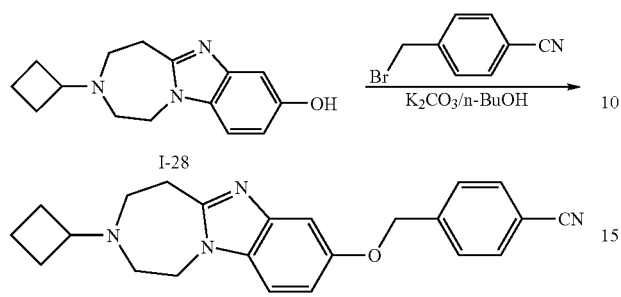

I-28 (70 mg), 4-(bromomethyl)benzonitrile (100 mg) and potassium carbonate (14 mg) were dissolved in butanol (5.0 mL) and stirred at room temperature for 60 minutes. The reaction mixture was concentrated and the residue was dissolved in ethyl acetate and washed with water. The combined organic layers were dried over sodium sulfate, solids were removed by filtration and the filtrate was concentrated. The crude reaction mixture was purified by preparative TLC to give compound 53 as a pale yellow solid (12 mg, 11%). $^1$H-NMR (400 MHz, CDCl$_3$): δ 7.55~7.57 (m, 2H), 7.46~7.48 (m, 2H), 7.08 (d, 1H, J=2.4 Hz), 7.04 (d, 1H, J=8.8 Hz), 6.85 (dd, 1H, J$_1$=2.4 Hz, J$_2$=8.8 Hz), 5.07 (s, 2H), 4.10 (m, 2H), 3.12 (m, 2H), 2.79~2.87 (m, 1H), 2.54 (m, 2H), 2.50 (m, 2H), 2.01~2.04 (m, 2H), 1.80~1.84 (m, 2H), 1.55~1.66 (m, 2H). MS (ESI): m/z 373 (M+H$^+$).

54. Compound 54: (3-cyclobutyl-2,3,4,5-tetrahydro-1H-[1,4]diazepino[1,7-a]benzimidazol-9-carbonitrile)

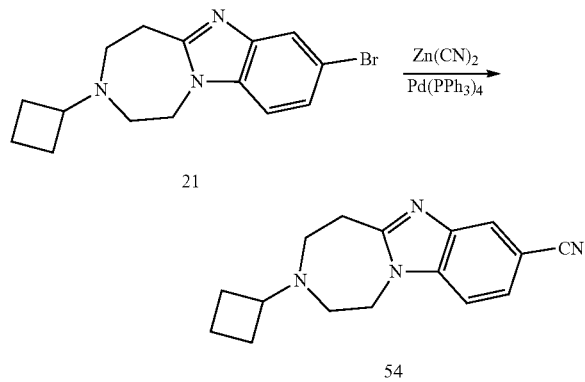

Compound 21 (1.0 g), Zn(CN)$_2$ (1.1 eq.) and Pd(PPh$_3$)$_4$ (catalytic, 10 mol %) were dissolved in DMF (8 mL) in a microwave tube that was filled with argon. The mixture was stirred at 120° C. for 90 minutes under microwave irradiation. The reaction mixture was diluted with ethyl acetate and filtered through a short plug of silica gel. The filtrate was washed with water, the combined organic layers were dried over sodium sulfate, the solids were filtered and the filtrate was concentrated. The crude reaction mixture was purified by chromatography to give compound 54 (670 mg, 85%). $^1$H-NMR (400 MHz, CDCl$_3$): δ 8.02 (d, 1H, J=1.2 Hz), 7.52 (dd, 1H, J$_1$=1.6 Hz, J$_2$=8.0 Hz), 7.32 (d, 1H, J=8.8 Hz), 4.28 (m, 2H), 3.28~3.30 (m, 2H), 2.95 (m, 1H), 2.64~2.69 (m, 4H), 2.13~2.15 (m, 2H), 1.92~1.93 (m, 2H), 1.66~1.75 (m, 2H). MS (ESI): m/z 267 (M+H$^+$).

55. Compound 55: (3-cyclobutyl-9-(4-phenylpiperidin-1-yl)-2,3,4,5-tetrahydro-1H-[1,4]diazepino[1,7-a]benzimidazole)

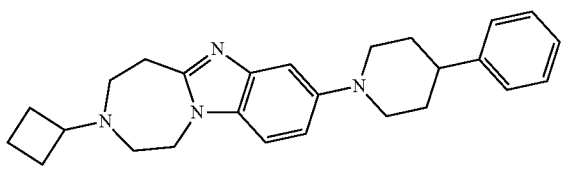

This compound was prepared in 12% yield as described for I-38 but using 4-phenylpiperidine as the starting material. $^1$H-NMR (400 MHz, CDCl$_3$): δ 7.30 (m, 51-1), 7.22 (t, 1H, J=7.1 Hz), 7.15 (d, 1H, J=8.8 Hz), 7.06 (dd, 1H, J$_1$=2.0 Hz, J$_2$=8.8 Hz), 4.19 (d, 2H, J=8.9 Hz), 3.71 (d, 2H, J=12.0 Hz), 3.21 (d, 2H, J=10.4 Hz), 2.92 (m, 1H), 2.82 (m, 2H), 2.58~2.64 (m, 5H), 2.12 (dd, 2H, J$_1$=9.3 Hz, J$_2$=16.6 Hz), 1.97~2.01 (m, 3H), 1.91 (t, 2H, J=9.5 Hz), 1.62~1.75 (m, 3H). MS (ESI): m/z 401 (M+H$^+$).

56. Compound 56: ((3-cyclobutyl-2,3,4,5-tetrahydro-1H-[1,4]diazepino[1,7-a]benzimidazol-9-yl)(morpholino)-methanone)

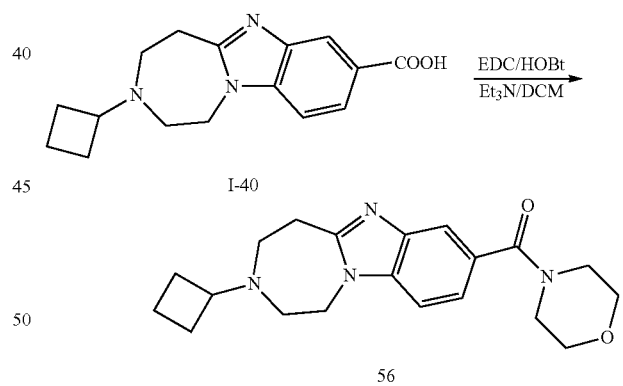

To a mixture of I-40 (100 mg), HOBt (1.5 eq.), EDC (1.5 eq.) in dichloromethane was added triethylamine. The reaction mixture was stirred at room temperature overnight, diluted with dichloromethane and washed with water. The combined organic layers were dried over sodium sulfate, solids were filtered and the filtrate was concentrated. The crude reaction mixture was purified by preparative TLC to give compound 56 (10 mg, 8%). $^1$H-NMR (400 MHz, CDCl$_3$): δ 7.72 (s, 1H), 7.37 (dd, 111, J$_1$=2.0 Hz, J$_2$=8.4 Hz), 7.30 (s, 1H), 4.26 (m, 2H), 3.69~3.71 (m, 8H), 3.25~3.28 (m, 2H), 2.94 (m, 1H), 2.66 (m, 2H), 2.63 (m, 2H), 2.12~2.14 (m, 2H), 1.89~1.95 (m, 2H), 1.68 (m, 2H). MS (ESI): m/z 355 (M+H$^+$).

57. Compound 57: (3-cyclobutyl-N,N-dimethyl-2,3,4,5-tetrahydro-1H-[1,4]diazepino[1,7-a]benzimidazole-9-carboxamide)

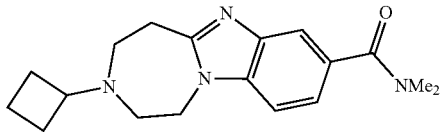

This compound was prepared in 21% yield as described for compound 56 but using dimethylamine as the starting material. $^1$H-NMR (400 MHz, CDCl$_3$): δ 7.74 (d, 1H, J=1.2 Hz), 7.38 (dd, 1H, J$_1$=1.6 Hz, J$_2$=8.4 Hz), 7.28 (s, 1H), 4.26 (m, 2H), 3.26 (m, 2H), 3.13 (m, 3H), 3.03 (m, 3H), 2.87~2.95 (m, 1H), 2.66 (m, 2H), 2.62 (m, 2H), 2.10~2.14 (m, 2H), 1.89~1.95 (m, 2H), 1.65~1.76 (m, 2H). MS (ESI): m/z 313 (M+H$^+$).

58. Compound 58: ((3-cyclobutyl-2,3,4,5-tetrahydro-1H-[1,4]diazepino[1,7-a]benzimidazol-9-yl)(4-methylpiperazin-1-yl)methanone)

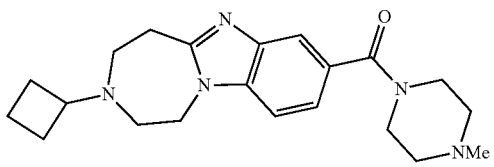

This compound was prepared in 8% yield as described for compound 56 but using N-methylpiperazine as the starting material. $^1$H-NMR (400 MHz, CDCl$_3$): δ 7.73 (d, 1H, J=0.8 Hz), 7.37 (dd, 1H, J$_1$=1.6 Hz, J$_2$=8.8 Hz), 7.29 (s, 1H), 4.25 (m, 2H), 3.5~3.8 (m, 4H), 3.26 (m, 2H), 2.92~2.95 (m, 1H), 2.66 (m, 2H), 2.62 (m, 2H), 2.44 (m, 4H), 2.32 (s, 3H), 2.12~2.14 (m, 2H), 1.89~1.92 (m, 2H), 1.76~1.80 (m, 2H). MS (ESI): m/z 368 (M+H$^+$).

59. Compound 59: 43-cyclobutyl-2,3,4,5-tetrahydro-1H-[1,4]diazepino[1,7-a]benzimidazol-9-yl)(piperidin-1-yl)methanone)

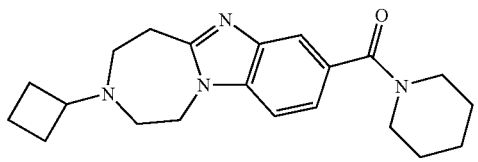

This compound was prepared in 23% yield as described for compound 56 but using piperidine as the starting material. $^1$H-NMR (400 MHz, CDCl$_3$): δ 7.71 (s, 1H), 7.35 (d, 1H, J=8.4 Hz), 7.28 (d, 1H), 4.25 (m, 2H), 3.4-3.7 (m, 4H), 3.26 (m, 2H), 2.93 (m, 1H), 2.65 (m, 2H), 2.62 (m, 2H), 2.12~2.14 (m, 2H), 1.89~1.94 (m, 2H), 1.58~1.76 (m, 8H). MS (ESI): m/z 353 (M+H$^+$).

60. Compound 60: 43-cyclobutyl-2,3,4,5-tetrahydro-1H-[1,4]diazepino[1,7-a]benzimidazol-9-yl)(pyrrolidin-1-yl)methanone)

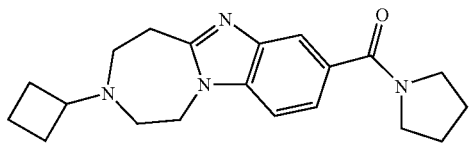

This compound was prepared in 16% yield as described for compound 56 but using pyrrolidine as the starting material. $^1$H-NMR (400 MHz, CDCl$_3$): δ 7.84 (d, 1H, J=0.8 Hz), 7.51 (dd, 1H, J$_1$=1.2 Hz, J$_2$=8.4 Hz), 7.26 (d, 1H, J=8.4 Hz), 4.25 (m, 2H), 3.68 (m, 2H), 3.49 (m, 2H), 3.26 (m, 2H), 2.92~2.96 (m, 1H), 2.66 (m, 2H), 2.62 (m, 2H), 2.12~2.14 (m, 2H), 1.68~1.97 (m, 8H). MS (ESI): m/z 339 (M+H$^+$).

61. Compound 61: (3-cyclobutyl-N-(4-cyanophenyl)-2,3,4,5-tetrahydro-1H-[1,4]diazepino[1,7-a]benzimidazole-9-carboxamide)

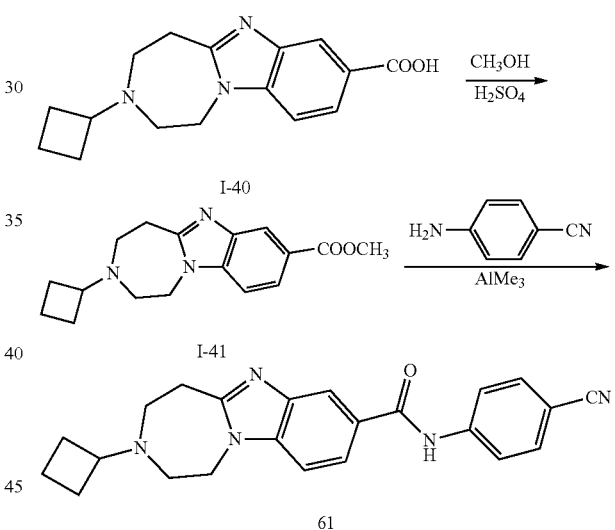

61

To a solution of I-40 (80 mg) in methanol was added sulfuric acid (2 mL) and the reaction mixture was refluxed for 5 hours. The reaction mixture was basified and concentrated. The residue was diluted with ethyl acetate and washed with water. The combined organic layers were dried over sodium sulfate, the solids were filtered and the filtrate was concentrated to yield I-41 (77 mg, 92%).

A solution of 4-aminobenzonitrile (33 mg, 1.0 eq) in dichloromethane was cooled to 0° C., a toluene solution of Al(CH$_3$)$_3$ was added and the reaction was stirred for 15 minutes. A solution of I-41 (77 mg) in dichloromethane was added and the reaction was stirred for 10 minutes. The reaction mixture was refluxed overnight. Aqueous solution of sodium hydroxide (0.3 mL) was added and the reaction mixture was diluted with water and extracted with dichloromethane. The combined organic layers were dried over magnesium sulfate, the solids were filtered and the filtrate was concentrated. The crude reaction mixture was purified by preparative TLC to give compound 61 (15 mg, 15%).

¹H-NMR (400 MHz, CDCl₃): δ 8.66 (s, 1H), 8.25 (s, 1H), 7.86~7.89 (m, 3H), 7.66 (d, 1H, J=8.4 Hz), 7.35 (d, 1H, J=8.4 Hz), 4.27 (m, 2H), 3.23 (m, 2H), 2.91~2.93 (m, 1H), 2.67 (m, 2H), 2.59 (m, 2H), 2.10~2.14 (m, 2H), 1.64~1.93 (m, 4H). MS (ESI): m/z 386 (M+H⁺).

62. Compound 62: (3-cyclobutyl-N-(4-fluorobenzyl)-2,3,4,5-tetrahydro-1H-[1,4]diazepino[1,7-a]benzimidazol-9-amine)

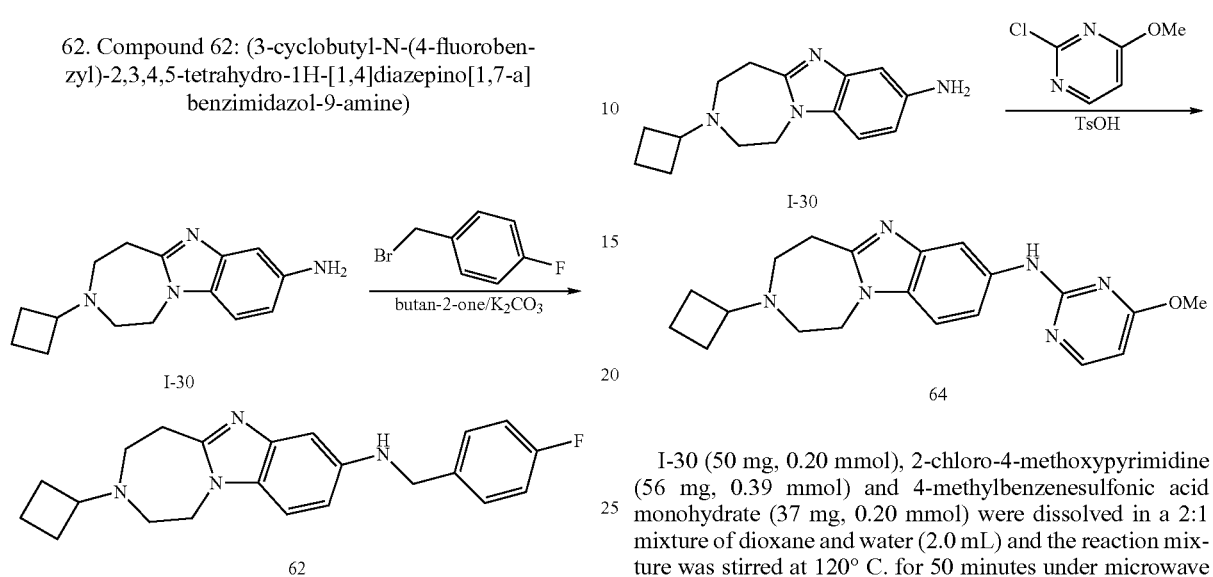

A mixture of K₂CO₃ (86 mg), I-30 (60 mg), and 1-(bromomethyl)-4-fluorobenzene (42 mg) in butan-2-one (2 mL) was stirred at room temperature for 2 hours. The reaction mixture was concentrated and diluted with ethyl acetate and washed with water. The combined organic layers were dried over sodium sulfate, the solids were removed by filtration and the filtrate was concentrated. The crude reaction mixture was purified by chromatography to give compound 62 (35 mg, 41%). ¹H-NMR (400 MHz, CDCl₃): δ 7.60 (d, 2H, J=8.0 Hz), 7.50 (d, 2H, J=8.4 Hz), 7.04 (d, 1H, J=8.4 Hz), 6.80 (d, 1H, J=2.4 Hz), 6.62 (dd, 1H, J₁=2.4 Hz, J₂=8.4 Hz), 4.46 (s, 2H), 4.14 (m, 2H), 3.17 (m, 2H), 2.88~2.92 (m, 1H), 2.61 (m, 2H), 2.57 (m, 2H), 2.08~2.12 (m, 2H), 1.87~1.92 (m, 2H), 1.64~1.74 (m, 2H). MS (ESI): m/z 365 (M+H⁺).

63. Compound 63: (4-((3-cyclobutyl-2,3,4,5-tetrahydro-1H-[1,4]diazepino[1,7-a]benzimidazol-9-ylamino)methyl)-benzonitrile)

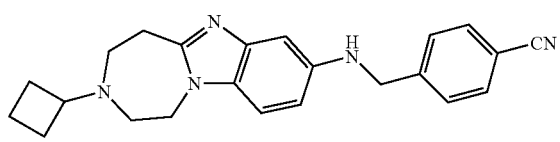

This compound was prepared in 34% yield as described for compound 62 but using 4-(bromomethyl)benzonitrile as the starting material. ¹H-NMR (400 MHz, CDCl₃): δ 7.34~7.38 (m, 2H), 6.98~7.04 (m, 3H), 6.90 (d, 1H, J=2.0 Hz), 6.64 (dd, 1H, J₁=2.0 Hz, J₂=8.8 Hz), 4.33 (s, 2H), 4.15 (m, 2H), 3.19 (m, 2H), 2.89~2.93 (m, 1H), 2.62 (m, 2H), 2.58 (m, 2H), 2.08~2.13 (m, 2H), 1.88~1.93 (m, 2H), 1.64~1.75 (m, 2H). MS (ESI): m/z 372 (M+H⁺).

64. Compound 64: (3-cyclobutyl-N-(4-methoxypyrimidin-2-yl)-2,3,4,5-tetrahydro-1H-[1,4]diazepino[1,7-a]benzimidazol-9-amine)

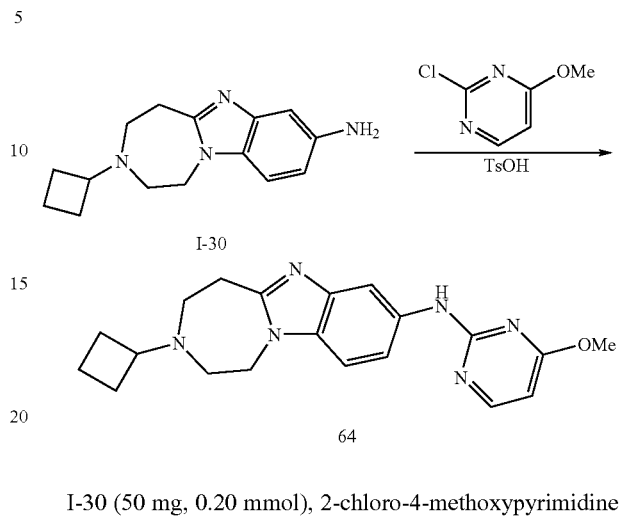

I-30 (50 mg, 0.20 mmol), 2-chloro-4-methoxypyrimidine (56 mg, 0.39 mmol) and 4-methylbenzenesulfonic acid monohydrate (37 mg, 0.20 mmol) were dissolved in a 2:1 mixture of dioxane and water (2.0 mL) and the reaction mixture was stirred at 120° C. for 50 minutes under microwave irradiation. The reaction mixture was concentrated and the residue was dissolved in dichloromethane and washed with aqueous saturated sodium bicarbonate. The combined organic layers were dried over sodium sulfate, the solids were filtered and the filtrate was concentrated. The crude reaction mixture was purified by preparative TLC to give compound 64 as a pale yellow solid (60 mg, 85%). ¹H-NMR (400 MHz, CDCl₃): δ 8.10 (d, 1H, J=5.6 Hz), 8.05 (d, 1H, J=2.0 Hz), 7.35 (dd, 1H, J₁=2.0 Hz, J₂=8.8 Hz), 7.30 (s, 1H), 7.18 (d, 1H, J=8.8 Hz), 6.16 (d, 1H, J=5.6 Hz), 4.22 (m, 2H), 3.97 (s, 3H), 3.24 (m, 2H), 2.93 (m, 1H), 2.64 (m, 2H), 2.60 (m, 2H), 2.11~2.14 (m, 2H), 1.88~1.91 (m, 2H), 1.65~1.76 (m, 2H). MS (ESI): m/z 365 (M+H⁺).

65. Compound 65: (3-cyclobutyl-N-(pyrazin-2-yl)-2,3,4,5-tetrahydro-1H-[1,4]diazepino[1,7-a]benzimidazol-9-amine)

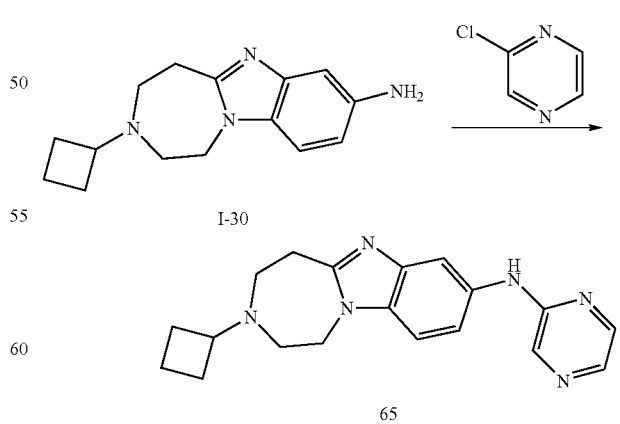

I-30 (50 mg) and 2-chloro-pyrazine was dissolved in DMF (3 mL) and the reaction mixture was stirred at 150° C. for 1 hour under microwave irradiation. The crude reaction mixture was purified by chromatography to give compound 65 as a pale yellow solid (5 mg, 8%). $^1$H-NMR (400 MHz, CDCl$_3$): δ 8.15 (d, 1H, J=2.0 Hz), 8.06~8.07 (m, 1H), 7.94 (d, 1H, J=2.8 Hz), 7.70 (d, 1H, J=1.6 Hz), 7.28 (dd, 1H, J$_1$=2.0 Hz, J$_2$=8.4 Hz), 7.24 (d, 1H, J=8.4 Hz), 6.62 (s, 1H), 4.26 (m, 2H), 3.27 (m, 2H), 2.92~3.01 (m, 1H), 2.69 (m, 2H), 2.64 (m, 2H), 2.11~2.20 (m, 2H), 1.90~1.98 (m, 2H), 1.69~1.77 (m, 2H). MS (ESI): m/z 335 (M+H$^+$).

66. Compound 66: (3-cyclobutyl-9-(1H-imidazol-1-yl)-2,3,4,5-tetrahydro-1H-[1,4]diazepino[1,7-a]benzimidazole)

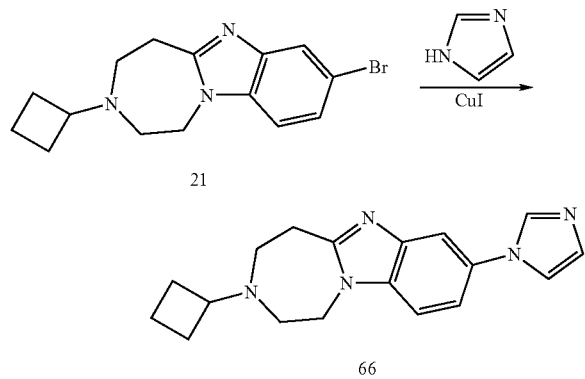

Compound 21 (100 mg), CuI (10 mol %), and Cs$_2$CO$_3$ (1.5 eq.) were dissolved in NMP (0.5 mL) and the reaction flask was flushed with argon. The reaction mixture was stirred at 150° C. overnight, diluted with dichloromethane and washed with water. The combined organic layers were dried over sodium sulfate, the solids were filtered and the filtrate was concentrated. The crude reaction mixture was purified by reverse phase preparative HPLC to give compound 66 (40 mg, 42%). $^1$H-NMR (400 MHz, CDCl$_3$): δ 7.84 (s, 1H), 7.68 (d, 1H, J=1.6 Hz), 7.26~7.33 (m, 3H), 7.21 (s, 1H), 4.27 (m, 2H), 3.27 (m, 2H), 2.94 (m, 1H), 2.68 (m, 2H), 2.63 (m, 2H), 2.13~2.15 (m, 2H), 1.92~1.93 (m, 2H), 1.66~1.74 (m, 2H). MS (ESI): m/z 308 (M+H$^+$).

67. Compound 67: (3-cyclobutyl-9-(1H-pyrazol-1-yl)-2,3,4,5-tetrahydro-1H-[1,4]diazepino[1,7-a]benzimidazole)

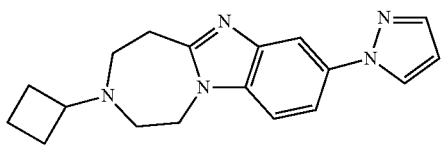

This compound was prepared in 42% yield as described for compound 66 but using 1H-pyrazole as the starting material. $^1$H-NMR (400 MHz, CDCl$_3$): δ 7.93 (d, 1H, J=2.4 Hz), 7.88 (d, 1H, J=2.0 Hz), 7.73 (d, 1H, J=1.2 Hz), 7.68 (dd, 1H, J$_1$=1.6, Hz J$_2$=8.4 Hz), 7.30 (d, 1H, J=8.4 Hz), 6.47~6.48 (m, 1H), 4.26 (m, 2H), 3.27 (m, 2H), 2.94 (m, 1H), 2.67 (m, 2H), 2.63 (m, 2H), 2.12~2.14 (m, 2H), 1.89~1.95 (m, 2H), 1.66~1.76 (m, 2H). MS (ESI): m/z 308 (M+H$^+$).

68. Compound 68: (3-cyclobutyl-9-(1H-benzimidazol-1-yl)-2,3,4,5-tetrahydro-1H-[1,4]diazepino[1,7-a]benzimidazole)

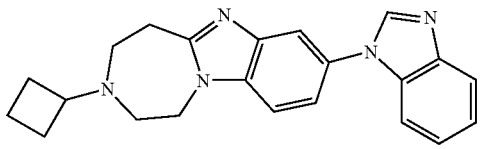

This compound was prepared in 23% yield as described for compound 66 but using 1H-benzo[d]imidazole as the starting material. $^1$H-NMR (400 MHz, CDCl$_3$): δ 8.14 (s, 1H), 7.88~7.90 (m, 1H), 7.81 (d, 1H, J=1.6 Hz), 7.50~7.56 (m, 1H), 7.31~7.42 (m, 4H), 4.31 (m, 2H), 3.30 (m, 2H), 2.92~2.96 (m, 1H), 2.71 (m, 2H), 2.65 (m, 2H), 2.14~2.16 (m, 2H), 1.93~1.96 (m, 2H), 1.70~7.75 (m, 2H). MS (ESI): m/z 358 (M+H$^+$).

69. Compound 69: (3-cyclobutyl-9-(1H-indazol-1-yl)-2,3,4,5-tetrahydro-1H-[1,4]diazepino[1,7-a]benzimidazole)

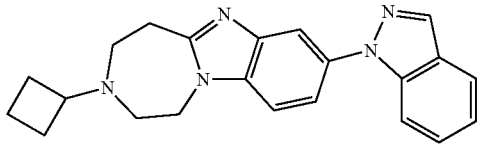

This compound was prepared in 14% yield as described for compound 66 but using 1H-indazole as the starting material. $^1$H-NMR (400 MHz, CDCl$_3$): δ 8.21 (d, 1H, J=0.8 Hz), 7.98 (d, 1H, J=1.6 Hz), 7.81 (dd, 1H, J=1.2 Hz, J=7.6 Hz), 7.73 (dd, 1H, J$_1$=0.8 Hz, J$_2$=8.4 Hz), 7.61 (dd, 1H, J$_1$=2.0 Hz, J$_2$=8.4 Hz), 7.37~7.41 (m, 2H), 7.22~7.24 (m, 1H), 4.30 (m, 2H), 3.29 (m, 2H), 2.92~2.96 (m, 1H), 2.70 (m, 2H), 2.65 (m, 2H), 2.13~2.15 (m, 2H), 1.92~1.93 (m, 2H), 1.6~1.8 (m, 2H). MS (ESI): m/z 358 (M+H$^+$).

70. Compound 70: (3-cyclobutyl-9-(1H-pyrrolo[2,3-b]pyridin-1-yl)-2,3,4,5-tetrahydro-1H-[1,4]diazepino[1,7-a]benzimidazole)

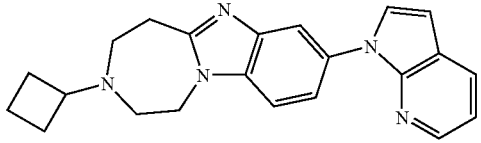

This compound was prepared in 17% yield as described for compound 66 but using 1H-pyrrolo[2,3-b]pyridine as the starting material. $^1$H-NMR (400 MHz, CDCl$_3$): δ 8.34 (dd, 1H, J$_1$=1.6 Hz, J$_2$=8.4 Hz), 7.98 (dd, 1H, J$_1$=2.0 Hz, J$_2$=8.0 Hz), 7.87 (d, 1H, J=1.6 Hz), 7.68 (dd, 1H, J$_1$=2.0 Hz, J$_2$=8.4 Hz), 7.52 (d, 1H, J=3.2 Hz), 7.37 (d, 1H, J=8.4 Hz), 7.10~7.13

(m, 1H), 6.63 (d, 1H, J=3.2 Hz), 4.28 (m, 2H), 3.27 (m, 2H), 2.93 (m, 1H), 2.66 (m, 2H), 2.62 (m, 2H), 2.13~2.15 (m, 2H), 1.92~1.93 (m, 2H), 1.6-1.8 (m, 2H). MS (ESI): m/z 358 (M+H$^+$).

71. Compound 71: (2-(3-cyclobutyl-2,3,4,5-tetrahydro-1H-[1,4]diazepino[1,7-a]benzimidazol-9-yl)pyridazin-3(2H)-one)

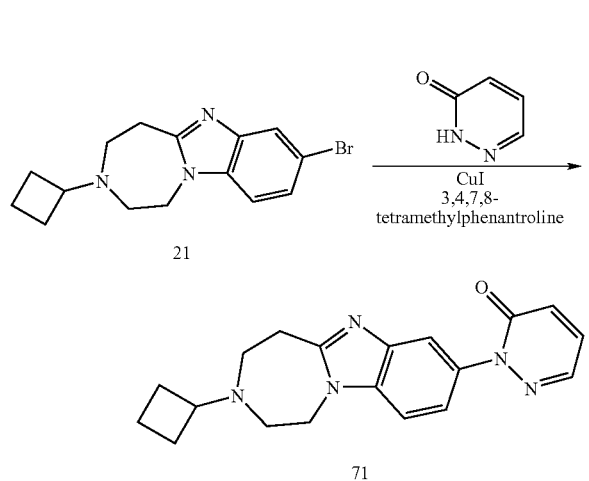

Compound 21 (100 g,), CuI (20 mol %), 3,4,7,8-tetramethylphenantroline (0.4 eq.) and K$_2$CO$_3$ (1.2 eq.) were dissolved in DMF (2.5 mL) in a microwave tube that was flushed with argon. The reaction mixture was stirred at 140° C. for 60 minutes, diluted with dichloromethane and filtered through a short plug of Celite. The filtrate was concentrated and the crude reaction mixture was purified by reverse phase chromatography to give compound 71 (20 mg, 19%). $^1$H-NMR (400 MHz, CDCl$_3$): δ 7.90 (dd, 1H, J$_1$=2.0 Hz, J$_2$=3.6 Hz), 7.84 (d, 1H, J=2.0 Hz), 7.44 (dd, 1H, J$_1$=2.4 Hz, J$_2$=8.8 Hz), 7.24~7.32 (m, 2H), 7.07 (dd, 1H, J$_1$=1.6 Hz, J$_2$=9.6 Hz), 4.26 (m, 2H), 3.26 (m, 2H), 2.93 (m, 1H), 2.64 (m, 2H), 2.61 (m, 2H), 2.10~2.14 (m, 2H), 1.89~1.94 (m, 2H), 1.55~1.73 (m, 2H). MS (ESI): m/z 336 (M+H$^+$).

72. Compound 72: (1-(3-cyclobutyl-2,3,4,5-tetrahydro-1H-[1,4]diazepino[1,7-a]benzimidazol-9-yl)-1H-benzo[d]imidazol-2(3H)-one)

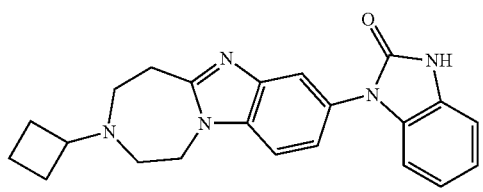

This compound was prepared in 19% yield as described for compound 71 but using 1H-benzo[d]imidazol-2(3H)-one as the starting material. $^1$H-NMR (400 MHz, CDCl$_3$): δ 9.83 (s, 1H), 7.83 (d, 1H, J=0.8 Hz), 7.41~7.42 (m, 2H), 7.13 (d, 1H, J=6.0 Hz), 7.08 (dt, 1H, J$_1$=0.8 Hz, J$_2$=6.0 Hz), 7.03 (dt, 1H, J$_1$=0.8 Hz, J$_2$=6.4 Hz), 6.99 (d, 1H, J=6.0 Hz), 4.30 (m, 2H), 3.30 (m, 2H), 2.95 (m, 1H), 2.68 (m, 2H), 2.64 (m, 2H), 2.14~2.15 (m, 2H), 1.91~1.95 (m, 2H), 1.67~1.79 (m, 2H). MS (ESI): m/z 374 (M+H$^+$).

73. Compound 73: (3-cyclobutyl-9-(4-methylpiperazin-1-yl)-2,3,4,5-tetrahydro-1H-[1,4]diazepino[1,7-a]benzimidazole)

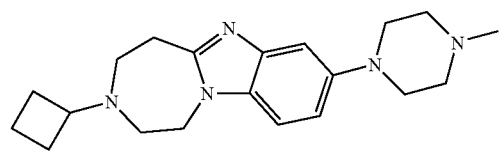

This compound was prepared in 56% yield as described for I-38 but using N-methylpiperazine as the starting material. $^1$H-NMR (400 MHz, CDCl$_3$): δ 7.24 (d, 1H, J=2.1 Hz), 7.13 (d, 1H, J=8.8 Hz), 7.00 (dd, 1H, J$_1$=2.0 Hz, J$_2$=8.8 Hz), 4.17 (m, 2H), 3.20 (m, 61-1), 2.90 (m, 1H), 2.62 (m, 4H), 2.58 (m, 2H), 2.36 (s, 3H), 2.10 (m, 2H), 1.90 (m, 2H), 1.71 (m, 4H). MS (ESI): m/z 340 (M+H$^+$).

74. Compound 74: (3-cyclobutyl-9-(morpholin-1-ylmethyl)-2,3,4,5-tetrahydro-1H-[1,4]diazepino[1,7-a]benzimidazole)

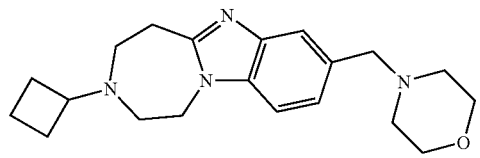

This compound was prepared in 42% yield (20 mg) as described for compound 8 but using intermediate I-31 and morpholine as the starting materials. $^1$H-NMR (400 MHz, CDCl$_3$): δ 7.61 (d, 1H, J=0.4 Hz), 7.25 (dd, 1H, J$_1$=1.2 Hz, J$_2$=8.4 Hz), 7.19 (d, 1H, J=8.4 Hz), 4.22 (m, 2H), 3.70 (m, 4H), 3.61 (s, 2H), 3.24 (m, 2H), 2.85~2.97 (m, 1H), 2.64 (m, 2H), 2.60 (m, 2H), 2.46 (m, 4H), 2.07~2.15 (m, 2H), 1.89~1.97 (m, 2H), 1.75~1.81 (m, 2H). MS (ESI): 341 (M+H$^+$).

75. Compound 75: (3-cyclobutyl-9-(pyrrolidin-1-ylmethyl)-2,3,4,5-tetrahydro-1H-[1,4]diazepino[1,7-a]benzimidazole)

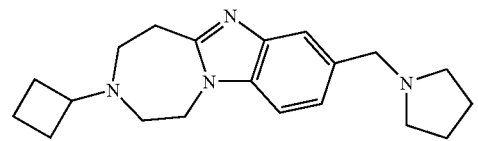

This compound was prepared in 54% yield as described for compound 8 but using intermediate I-31 and pyrrolidine as the starting materials. $^1$H-NMR (400 MHz, CDCl$_3$): δ 7.60 (s, 1H), 7.28 (dd, 1H, J$_1$=1.2 Hz, J$_2$=8.4 Hz), 7.19 (d, 1H, J=8.0 Hz), 4.22 (m, 2H), 3.73 (s, 2H), 3.23 (m, 2H), 2.90~2.94 (m, 1H), 2.64 (m, 2H), 2.60 (m, 2H), 2.52 (m, 4H), 2.09~2.15 (m, 2H), 1.88~1.93 (m, 2H), 1.62~1.79 (m, 6H). MS (ESI): m/z 325 (M+H⁺).

76. Compound 76: (6-(3-cyclobutyl-2,3,4,5-tetrahydro-1H-[1,4]diazepino[1,7-a]benzimidazol-8-yloxy)-N-methyl-nicotinamide)

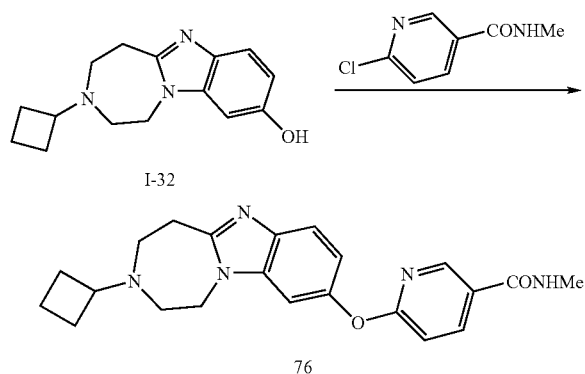

Intermediate I-32 (30 mg), 6-chloro-N-methylnicotinamide (1.5 eq.) and ᵗBuOK (1.5 eq.) were dissolved in dry DMSO (1.0 mL) in a microwave tube and the reaction mixture was stirred at 120° C. for 30 minutes under microwave irradiation. The mixture was purified by reverse phase chromatography to give compound 76 (29 mg, 64%). $^1$H-NMR (400 MHz, CDCl$_3$): δ 8.52 (d, 1H, J=2.0 Hz), 8.13 (dd, 1H, J$_1$=8.8 Hz, J$_2$=2.0 Hz), 7.68 (d, 1H, J=8.8 Hz), 7.06 (d, 1H, J=2.0 Hz), 6.99 (dd, 1H, J$_1$=8.4 Hz, J$_2$=2.0 Hz), 6.94 (d, 1H, J=8.4 Hz), 6.25 (brs, 1H), 4.20 (m, 2H), 3.26 (m, 2H), 3.01 (d, 31-1, J=4.8 Hz), 2.65 (m, 4H), 2.10~2.18 (m, 2H), 1.88~1.98 (m, 2H), 1.65~1.79 (m, 2H). MS (ESI): m/z 392 (M+H⁺).

77. Compound 77: (3-cyclobutyl-8-(pyrazin-2-yloxy)-2,3,4,5-tetrahydro-1H-[1,4]diazepino[1,7-a]benzimidazole)

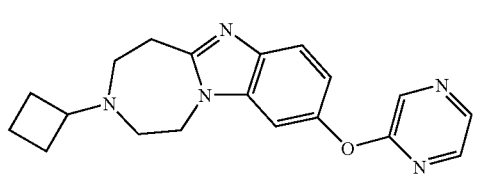

This compound was prepared in 92% yield as described for compound 76 but using 2-chloropyrazine as the starting material. $^1$H-NMR (400 MHz, CDCl$_3$): δ 8.43 (d, 1H, J=1.2 Hz), 8.23 (d, 1H, J=2.8 Hz), 8.07 (dd, 1H, J$_1$=1.6 Hz, J$_2$=2.8 Hz), 7.48 (d, 1H, J=2.0 Hz), 7.27 (d, 1H, J=8.8 Hz), 7.06 (dd, 1H, J$_1$=2.0 Hz, J$_2$=8.8 Hz), 4.25 (m, 2H), 3.26 (m, 2H), 2.92~2.96 (m, 1H), 2.67 (m, 2H), 2.62 (m, 2H), 2.12~2.14 (m, 2H), 1.91~1.95 (m, 2H), 1.66~1.77 (m, 2H). MS (ESI): m/z 336 (M+H⁺).

78. Compound 78: (3-cyclobutyl-8-(4-methoxypyrimidin-2-yloxy)-2,3,4,5-tetrahydro-1H-[1,4]diazepino[1,7-a]benzimidazole)

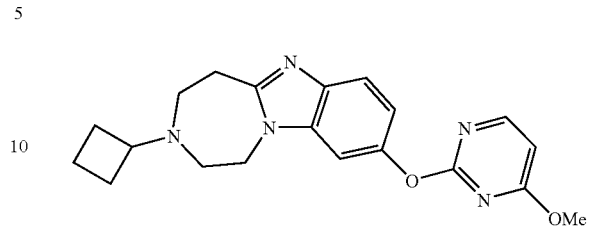

This compound was prepared in 47% yield as described for compound 76 but using 2-chloro-4-methoxypyrimidine as the starting material. $^1$H-NMR (400 MHz, CDCl$_3$): δ 8.17 (d, 1H, J=5.6 Hz), 7.68 (d, 1H, J=8.8 Hz), 7.10 (m, 2H), 6.45 (d, 1H, J=5.6 Hz), 4.20 (m, 2H), 3.97 (s, 3H), 3.26 (m, 2H), 2.94 (m, 1H), 2.62~2.68 (m, 4H), 2.12~2.14 (m, 2H), 1.91~1.96 (m, 2H), 1.63~1.78 (m, 2H). MS (ESI): m/z 366 (M+H⁺).

79. Compound 79: (4-((3-cyclobutyl-2,3,4,5-tetrahydro-1H-[1,4]diazepino[1,7-a]benzimidazol-8-yloxy)methyl)-benzonitrile)

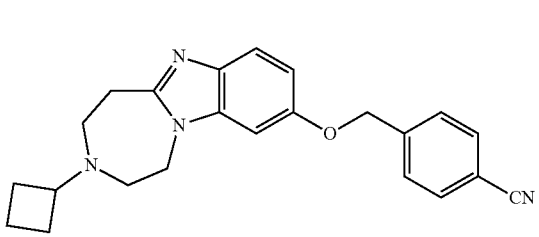

This compound was prepared in 42% yield (18 mg) as described for compound 52 but using intermediate I-32 and 4-(bromomethyl)benzonitrile as the starting materials. $^1$H-NMR (400 MHz, CDCl$_3$): δ 7.55~7.57 (m, 2H), 7.46~7.48 (m, 2H), 7.08 (d, 1H, J=2.4 Hz), 7.04 (d, 1H, J=8.8 Hz), 6.85 (dd, 1H, J$_1$=2.4 Hz, J$_2$=8.8 Hz), 5.07 (s, 2H), 4.10 (m, 2H), 3.12 (m, 2H), 2.79~2.87 (m, 1H), 2.54 (m, 2H), 2.50 (m, 2H), 2.01~2.04 (m, 2H), 1.80~1.84 (m, 2H), 1.55~1.66 (m, 2H). MS (ESI): m/z 373 (M+H⁺).

80. Compound 80: (3-cyclobutyl-N-(4-methoxypyrimidin-2-yl)-2,3,4,5-tetrahydro-1H-[1,4]diazepino[1,7-a]benzimidazol-8-amine)

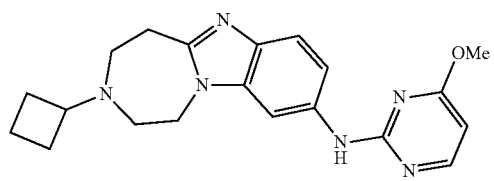

This compound was prepared in 79% yield (45 mg) as described for compound 64 but using intermediate I-34 as the starting material. $^1$H-NMR (400 MHz, CDCl$_3$): δ 8.14 (d, 1H, J=5.6 Hz), 7.97 (d, 1H, J=1.6 Hz), 7.59 (d, 1H, J=8.4 Hz), 7.36 (s, 1H), 7.11 (dd, 1H, J$_1$=3.0 Hz, J$_2$=8.4 Hz), 6.19 (d, 1H, J=5.6 Hz), 4.21 (m, 2H), 3.96 (s, 3H), 3.22 (m, 2H), 2.90~2.94 (m, 1H), 2.64 (m, 2H), 2.60 (m, 2H), 2.09~2.15 (m, 2H), 1.88~1.93 (m, 2H), 1.65~1.75 (m, 2H). MS (ESI): m/z 365 (M+H⁺).

81. Compound 81: (4-((3-cyclobutyl-2,3,4,5-tetrahydro-1H-[1,4]diazepino[1,7-a]benzimidazol-8-ylamino)methyl)-benzonitrile)

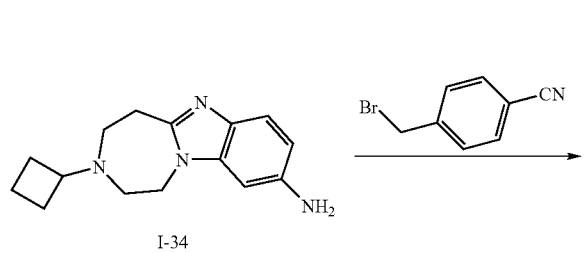

I-34

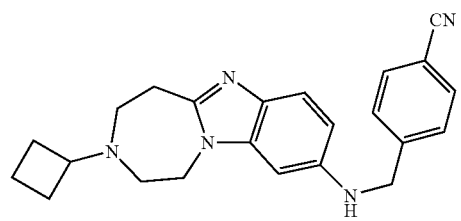

81

I-34 (50 mg, 0.20 mmol), 4-(bromomethyl)benzonitrile (38 mg, 0.20 mmol) and CsCO₃ (127 mg, 0.39 mmol) were dissolved in acetone (5 mL) and the reaction mixture was stirred overnight at room temperature. The reaction mixture was concentrated and the residue was diluted with ethyl acetate and washed with water. The combined organic layers were dried over sodium sulfate, solids were filtered and the filtrate was concentrated. The crude reaction mixture was purified by preparative TLC to give compound 81 (35 mg, 49%). ¹H-NMR (400 MHz, CDCl₃): δ 7.63 (m, 2H), 7.46~7.52 (m, 3H), 6.58 (m, 1H), 6.29 (s, 1H), 4.46 (s, 2H), 4.26 (m, 1H), 4.05 (m, 2H), 3.16 (m, 2H), 2.88~2.92 (m, 1H), 2.58 (m, 4H), 2.05~2.11 (m, 2H), 1.84~1.91 (m, 2H), 1.61~1.74 (m, 2H). MS (ESI): m/z 372 (M+H⁺).

82. Compound 82: (3-cyclobutyl-2,3,4,5-tetrahydro-1H-[1,4]diazepino[1,7-a]benzimidazol-8-carbonitrile)

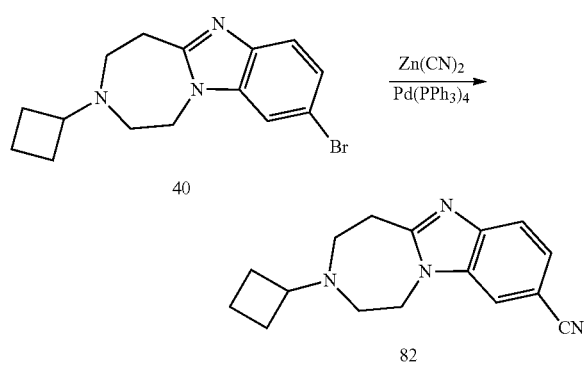

This compound was prepared in 86% yield (710 mg) as described for compound 54 but using compound 40 as the starting material. MS (ESI): m/z 267 (M+H⁺).

83. Compound 83: (6-((3-cyclobutyl-2,3,4,5-tetrahydro-1H-[1,4]diazepino[1,7-a]benzimidazol-9-yl)piperazin-1-yl)benzonitrile)

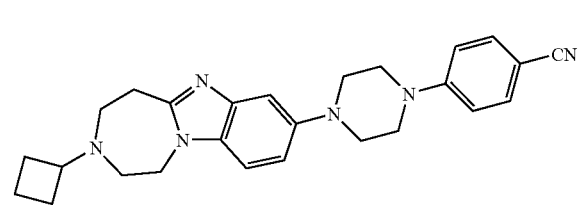

This compound was prepared in 12% yield as described for I-38 but using 4-(piperazin-1-yl)benzonitrile as the starting material. ¹H-NMR (400 MHz, CDCl₃): δ 7.52 (d, J=9.0 Hz, 2H), 7.27 (d, J=2.1 Hz, 1H), 7.17 (d, J=8.8 Hz, 1H), 7.02 (dd, J=2.2, 8.8 Hz, 1H), 6.92 (d, J=9.0 Hz, 2H), 4.19 (d, J=9.1 Hz, 2H), 3.50 (m, 4H), 3.27~3.30 (m, 3H), 3.21 (d, J=10.5 Hz, 2H), 2.92 (t, J=7.5 Hz, 1H), 2.58~2.64 (m, 3H), 2.11 (m, 2H), 1.90 (m, 2H), 1.68 (m, 4H). MS (ESI): m/z 427 (M+H⁺).

84. Compound 84: ((3-cyclobutyl-2,3,4,5-tetrahydro-1H-[1,4]diazepino[1,7-a]benzimidazol-8-yl)(morpholino)-methanone)

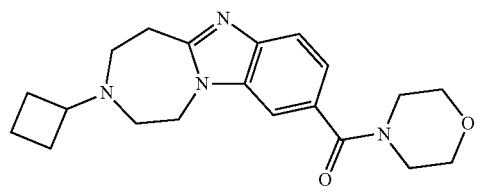

This compound was prepared in 57% yield (50 mg) as described for compound 56 but intermediate I-37 as the starting material. ¹H-NMR (400 MHz, CDCl₃): δ 7.67 (d, 1H, J=8.4 Hz), 7.45 (d, 1H, J=0.8 Hz), 7.23 (dd, 1H, J₁=1.2 Hz, J₂=8.4 Hz), 4.25 (m, 2H), 3.69 (m, 8H), 3.26 (m, 2H), 2.91~2.95 (m, 1H), 2.60~2.66 (m, 4H), 2.10~2.14 (m, 2H), 1.65~1.94 (m, 4H). MS (ESI): m/z 355 (M+H⁺).

85. Compound 85: (3-cyclobutyl-N,N-dimethyl-2,3,4,5-tetrahydro-1H-[1,4]diazepino[1,7-a]benzimidazole-8-carboxamide)

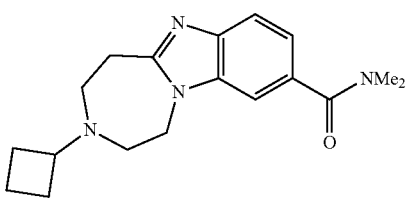

This compound was prepared in 30% yield as described for compound 84 but using dimethylamine as the starting material. ¹H-NMR (400 MHz, CDCl₃): δ 7.66 (d, 1H, J=8.4 Hz), 7.44 (s, 1H), 7.26 (d, 1H, J=8.4 Hz), 4.24 (m, 2H), 3.26 (m, 2H), 3.03~3.12 (m, 6H), 2.93 (m, 1H), 2.60~2.65 (m, 4H), 2.12~2.14 (m, 2H), 1.88~1.94 (m, 2H), 1.68~1.73 (m, 2H). MS (ESI): m/z 313 (M+H⁺).

86. Compound 86: ((3-cyclobutyl-2,3,4,5-tetrahydro-1H-[1,4]diazepino[1,7-a]benzimidazol-8-yl)(pyrrolidin-1-yl)methanone)

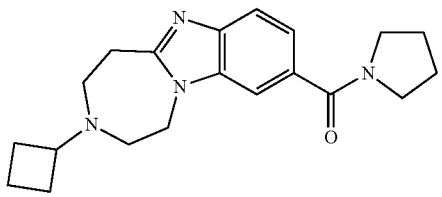

This compound was prepared in 60% yield as described for compound 84 but using pyrrolidine as the starting material. ¹H-NMR (400 MHz, CDCl₃): δ 7.66 (d, 1H, J=8.0 Hz), 7.56 (d, 1H, J=0.8 Hz), 7.38 (dd, 1H, J₁=1.6 Hz, J₂=8.4 Hz), 4.26 (m, 2H), 3.68 (m, 2H), 3.50 (m, 2H), 3.27 (m, 2H), 2.91~2.95 (m, 1H), 2.63 (m, 4H), 2.10~2.17 (m, 2H), 1.70~2.01 (m, 8H). MS (ESI): m/z 339 (M+H⁺).

87. Compound 87: (3-cyclobutyl-8-((dimethylamino)methyl)-2,3,4,5-tetrahydro-1H-[1,4]diazepino[1,7-a]benzimidazole)

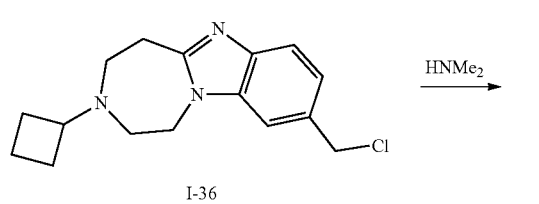

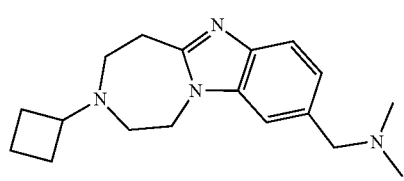

Aqueous dimethylamine solution was cooled to −60° C. to freeze water. The resulting dimethylamine oil was transferred into a solution of I-36 (21 mg) in dry THF at −60° C. The reaction mixture was stirred at −60° C. for 10 minutes and for 2 hours at room temperature, concentrated and the residue was purified by preparative HPLC to give compound 87 (15 mg, 70%). ¹H-NMR (400 MHz, CDCl₃): δ 7.59 (d, 1H, d, J=8.0 Hz), 7.25 (s, 11-1), 7.12 (dd, 1H, J₁=8.0, J₂=1.6 Hz,), 4.21~4.23 (m, 2H), 3.53 (s, 2H), 3.21-3.23 (m, 2H), 2.90 (m, 1H), 2.57~2.62 (m, 4H), 2.11 (s, 6H), 2.10~2.12 (m, 2H), 1.87~1.92 (m, 2H), 1.63~1.71 (m, 2H). MS (ESI): m/z 299 (M+H⁺).

88. Compound 88: (3-cyclobutyl-8-(morpholin-1-ylmethyl)-2,3,4,5-tetrahydro-1H-[1,4]diazepino[1,7-a]benzimidazole)

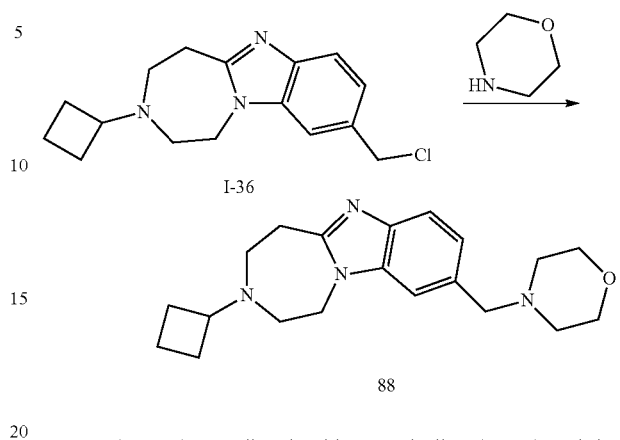

I-36 (21 mg) was dissolved in morpholine (5 mL) and the reaction was stirred at room temperature for 2 hours. The reaction mixture was concentrated and the crude product was purified by preparative HPLC to give compound 88 (13 mg, 91%). ¹H-NMR (400 MHz, CDCl₃): δ 7.54 (d, 1H, d, J=8.0 Hz), 7.19 (s, 1H), 7.10 (dd, 1H, J₁=8 MHz, J₂=1.2 Hz), 4.16 (m, 2H, m), 3.64 (m, 4H), 3.55 (s, 2H), 3.15 (m, 2H), 2.90 (m, 1H), 2.52~2.58 (m, 4H), 2.41 (m, 4H), 2.10 (m, 2H), 2.05 (m, 2H), δ 1.84 (m, 2H). MS (ESI): m/z 341 (M+H⁺).

89. Compound 89: (3-cyclobutyl-8-(pyrrolidin-1-ylmethyl)-2,3,4,5-tetrahydro-1H-[1,4]diazepino[1,7-a]benzimidazole)

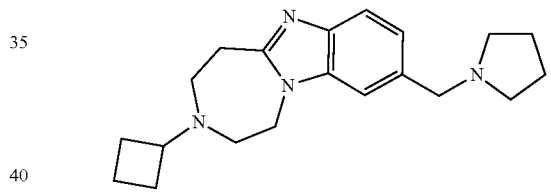

This compound was prepared in 85% yield as described for compound 88 but using pyrrolidine as the starting material. ¹H-NMR (400 MHz, CDCl₃): δ 7.59-7.61 (d, 1H, J=8.0 Hz), 7.32 (s, 1H), 7.15~7.17 (dd, 1H, J₁=8.0 Hz, J₂=1.6 Hz), 4.23-4.25 (m, 2H), 3.77 (s, 2H), 3.22~3.25 (m, 2H), 2.92 (m, 1H), 2.58~2.64 (m, 8H), 2.11~2.14 (m, 2H), 1.93~1.94 (m, 2H), 1.89 (m, 4H), 1.80~1.88 (m, 2H). MS (ESI): m/z 325 (M+H⁺).

90. Compound 90: (3-cyclobutyl-8-(furan-2-yl)-2,3,4,5-tetrahydro-1H-[1,4]diazepino[1,7-a]benzimidazole)

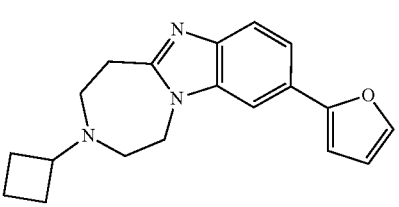

This compound was prepared in 26% yield as described for compound 41 but using furan-2-ylboronic acid as the starting material. The reaction was run at 85° C. $^1$H-NMR (400 MHz, d$_6$-Acetone), δ 7.67 (d, 1H, J=8.8 Hz), 7.53~7.58 (m, 2H), 7.47 (s, 1H), 6.63~6.64 (m, 1H), 6.48~6.49 (m, 1H), 4.27 (m, 2H), 3.25 (m, 2H), 2.90~2.97 (m, 1H), 2.66 (m, 2H), 2.62 (m, 2H), 2.12~2.17 (m, 2H), 1.88~1.97 (m, 2H), 1.68~1.76 (m, 2H). MS (ESI): m/z 308 (M+H$^+$).

91. Compound 91: (3-cyclobutyl-9-(5-(pyrrolidin-1-yl)pyrazin-2-yl)-2,3,4,5-tetrahydro-1H-[1,4]diazepino[1,7-a]benzimidazole)

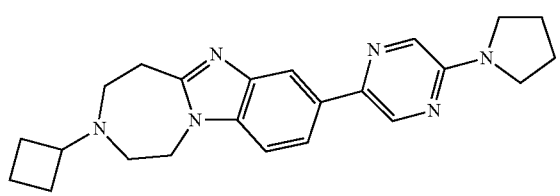

This compound was prepared in 25% yield as described for compound 22 but using 2-bromo-5-(pyrrolidin-1-yl)pyrazine as the starting material. $^1$H-NMR (400 MHz, CDCl$_3$): δ 8.55 (d, 1H, J=1.6 Hz), 8.12 (d, 1H, J=1.6 Hz), 7.96 (d, 1H, J=1.2 Hz), 7.84 (dd, 1H, J$_1$=1.6 Hz, J$_2$=8.4 Hz), 7.28 (d, 1H, J=8.4 Hz), 4.26~4.24 (m, 2H), 3.56~3.53 (m, 4H), 3.27~3.24 (m, 2H), 2.98~2.80 (m, 1H), 2.67~2.61 (m, 4H), 2.13~2.01 (m, 2H), 2.07-2.05 (m, 4H), 1.95~1.90 (m, 2H), 1.73~1.67 (m, 2H). MS (ESI): m/z 389 (M+H$^+$).

92. Compound 92: (3-cyclobutyl-9-(5-(4-methylpiperazin-1-yl)pyrazin-2-yl)-2,3,4,5-tetrahydro-1H-[1,4]diazepino[1,7-a]benzimidazole)

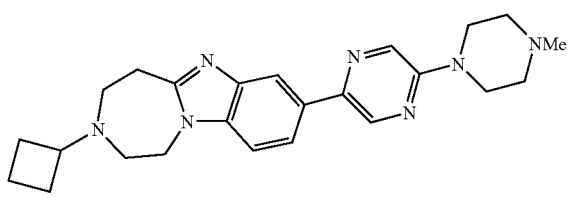

This compound was prepared in 30% yield as described for compound 22 but using 2-bromo-5-(4-methylpiperazin-1-yl)pyrazine as the starting material. $^1$H-NMR (400 MHz, CDCl$_3$): δ 8.58 (s, 1H), 8.22 (s, 1H), 8.14 (s, 1H), 7.85 (d, 1H, J=8.8 Hz), 7.31 (d, 1H, J=8.4 Hz), 4.27~4.25 (m, 2H), 3.68~3.66 (m, 4H), 3.28~3.25 (m, 2H), 2.98~2.90 (m, 114), 2.68~2.57 (m, 814), 2.38 (s, 3H), 2.17~2.11 (m, 2H), 1.98~1.87 (m, 2H), 1.80~1.65 (m, 2H). MS (ESI): m/z 418 (M+H$^+$).

93. Compound 93: (3-cyclobutyl-9-(5-methoxypyrazin-2-yl)-2,3,4,5-tetrahydro-1H-[1,4]diazepino[1,7-a]benzimidazole)

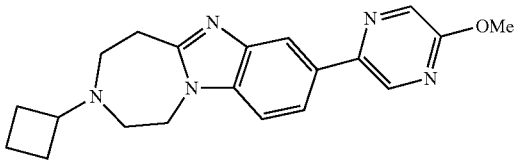

This compound was prepared in 30% yield as described for compound 22 but using 2-bromo-5-methoxypyrazine as the starting material. $^1$H-NMR (400 MHz, CDCl$_3$): δ 8.56 (s, 1H), 8.30 (s, 1H), 8.17 (s, 1H), 7.88 (d, 1H, J=8.4 Hz), 7.33 (d, 1H, J=8.4 Hz), 4.29~4.27 (m, 2H), 4.01 (s, 3H), 3.29~3.27 (m, 2H), 2.96~2.92 (m, 1H), 2.69~2.63 (m, 4H), 2.17~2.10 (m, 2H), 1.96~1.91 (m, 2H), 1.76~1.65 (m, 2H) MS (ESI): m/z 350 (M+H$^+$).

94. Compound 94: (3-cyclobutyl-9-(6-(pyrrolidin-1-yl)pyrazin-2-yl)-2,3,4,5-tetrahydro-1H-[1,4]diazepino[1,7-a]benzimidazole)

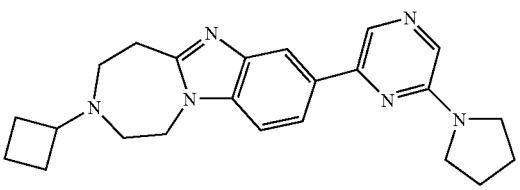

This compound was prepared in 28% yield as described for compound 22 but using 2-bromo-6-(pyrrolidin-1-yl)pyrazine as the starting material. $^1$H-NMR (400 MHz, CDCl$_3$): δ 8.39 (s, 1H), 8.31 (s, 1H), 7.95 (d, 1H, J=8.4 Hz), 7.77 (s, 1H), 7.30 (d, 1H, J=8.8 Hz), 4.25 (d, 2H, J=6.0 Hz), 3.58 (s, 4H), 3.27~3.25 (m, 2H), 2.95~2.91 (m, 1H), 2.67~2.62 (m, 4H), 2.13~2.09 (m, 2H), 2.04 (s, 4H), 1.94~1.87 (m, 2H), 1.75~1.65 (m, 2H). MS (ESI): m/z 389 (M+H$^+$).

95. Compound 95: (3-cyclobutyl-9-(6-(4-methylpiperazin-1-yl)pyrazin-2-yl)-2,3,4,5-tetrahydro-1H-[1,4]diazepino[1,7-a]benzimidazole)

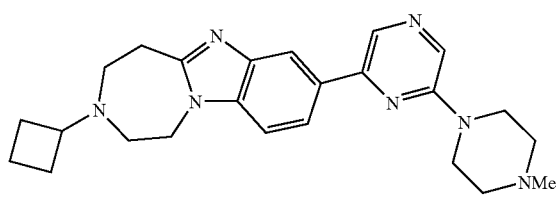

This compound was prepared in 50% yield as described for compound 22 but using 2-bromo-6-(4-methylpiperazin-1-yl)pyrazine as the starting material. $^1$H-NMR (400 MHz, CDCl₃): δ 8.78 (d, 2H, J=7.2 Hz), 8.04 (s, 1H), 7.92 (d, 1H, J=8.8 Hz), 7.30 (d, 1H, J=8.4 Hz), 4.27~4.25 (m, 2H), 3.75~3.73 (m, 4H), 3.27~3.25 (m, 2H), 2.95~2.91 (m, 1H), 2.67~2.61 (m, 4H), 2.58~2.56 (m, 4H), 2.37 (s, 3H), 2.14~2.12 (m, 2H), 1.94~1.89 (m, 2H), 1.76~1.65 (m, 2H). MS (ESI): m/z 418 (M+H⁺).

96. Compound 96: (3-cyclobutyl-9-(6-methoxy-pyrazin-2-yl)-2,3,4,5-tetrahydro-1H-[1,4]diazepino[1,7-a]benzimidazole)

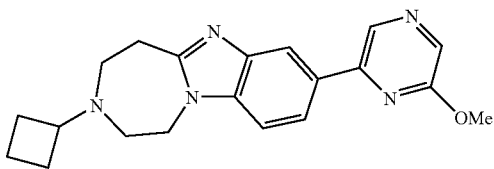

This compound was prepared in 49% yield as described for compound 22 but using 2-bromo-6-methoxypyrazine as the starting material. ¹H-NMR (400 MHz, CDCl₃): δ 8.63 (s, 1H), 8.40 (s, 1H), 8.11 (s, 1H), 7.95 (d, 1H, J=8.0 Hz), 7.32 (d, 1H, J=8.8 Hz), 4.26 (d, 2H, J=6.4 Hz), 4.07 (s, 3H), 3.29~3.26 (m, 2H), 2.95~2.91 (m, 1H), 2.67~2.61 (m, 4H), 2.13~2.11 (m, 2H), 1.94~1.89 (m, 2H), 1.75~1.65 (m, 2H). MS (ESI): m/z 350 (M+H⁺).

97. Compound 97: (3-cyclobutyl-9-(piperazin-1-yl)-2,3,4,5-tetrahydro-1H-[1,4]diazepino[1,7-a]benzimidazole)

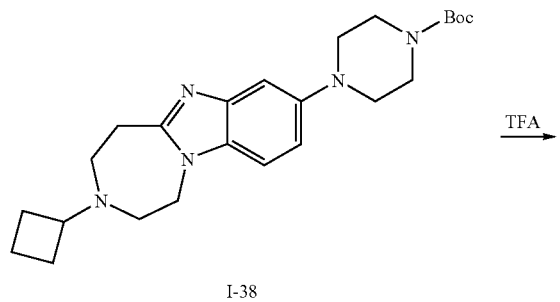

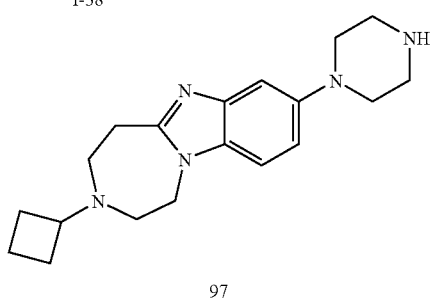

I-38 (0.50 g, 1.2 mmol) was dissolved in TFA (10 mL) and the reaction mixture was stirred at room temperature for 2 hours. The reaction mixture was concentrated and the residue was dissolved in ethyl acetate and saturated aqueous NaHCO₃ was added. The combined organic layers were washed with brine, dried over Na₂SO₄, the solids were filtered and the filtrate was concentrated. The crude reaction mixture was purified by preparative TLC. The purified compound 97 was acidified with methanolic solution of HCl and the HCl salt of 97 was obtained after crystallization from MeOH (0.50 g, 97%). ¹H-NMR (400 MHz, CD₃OD and D₂O) δ: 7.80 (d, 1H, J=9.2 Hz), 7.45 (dd, 1H, J₁=2.4 Hz, J₂=9.2 Hz), 7.32 (d, 1H, J=2.4 Hz), 3.93 (m, 1H), 3.83-3.80 (m, 2H), 3.69~3.61 (m, 4H), 3.54~3.51 (m, 4H), 3.41~3.39 (m, 4H), 3.27 (m, 2H), 2.44~2.40 (m, 4H), 1.91~1.77 (m, 2H). MS (ESI): m/z 326 (M+H⁺).

98. Compound 98: (Benzyl 4-(3-cyclobutyl-2,3,4,5-tetrahydro-1H-[1,4]diazepino[1,7-a]benzimidazol-9-yl)piperazine-1-carboxylate)

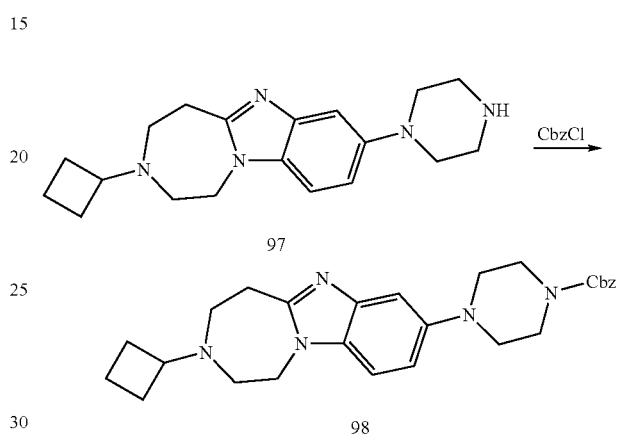

Compound 97 (50 mg, 0.15 mmol) and Et₃N (38 mg, 0.38 mmol) were dissolved in dichloromethane (2 mL), neat CbzCl (52 mg, 0.31 mmol) was added and the mixture was stirred at room temperature. After TLC analysis indicated complete disappearance of compound 97 the reaction mixture was washed with brine, the combined organic layers were dried with Na₂SO₄, the solids were removed by filtration and the filtrate was concentrated. The crude reaction mixture was purified by preparative TLC to give compound 98 (16 mg, 23%). ¹H-NMR (400 MHz, CDCl₃): δ 7.39-7.37 (m, 4H), 7.36-7.32 (m, 1H), 7.24 (d, 1H, J=2.0 Hz), 7.17 (d, 1H, J=8.8 Hz), 7.00 (dd, 1H, J₁=2.0 Hz, J₂=8.8 Hz), 5.17 (s, 2H), 4.20 (m, 2H), 3.72 (m, 4H), 3.23 (m, 2H), 3.11 (br, 4H), 2.96-2.88 (m, 1H), 2.64-2.58 (m, 4H), 2.13-2.11 (m, 2H), 1.79-1.73 (m, 2H), 1.68-1.63 (m, 2H). MS (ESI): m/z 460 (M+H⁺).

99. Compound 99: (3-cyclobutyl-9-(4-cyclobutylpiperazin-1-yl)-2,3,4,5-tetrahydro-1H-[1,4]diazepino[1,7-a]benzimidazole)

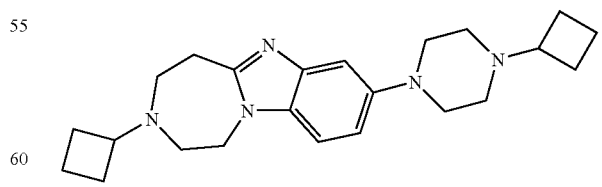

This compound was prepared in 25% yield (24 mg) as described for compound 21 but using compound 97 as the starting material. ¹H-NMR (400 MHz, CDCl₃): δ 7.26 (s, 1H), 7.15 (d, 1H, J=8.8 Hz), 7.01 (d, 1H, J=8.8 Hz), 4.19-4.17 (m, 2H), 3.22-3.19 (m, 6H), 2.93-2.80 (m, 2H), 2.63-2.56 (m, 8H), 2.13-2.07 (m, 4H), 1.97-1.88 (m, 4H), 1.76-1.62 (m, 4H). MS (ESI): m/z 380 (M+H⁺).

100. Compound 100: (3-cyclobutyl-9-(4-cyclopentylpiperazin-1-yl)-2,3,4,5-tetrahydro-1H-[1,4]diazepino[1,7-a]benzimidazole)

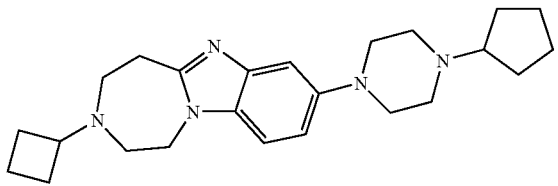

This compound was prepared in 32% yield as described for compound 99 but using cyclopentanone as the starting material. ¹H-NMR (400 MHz, CDCl₃): δ 7.26 (d, 1H, J=2.0 Hz), 7.15 (d, 1H, J=8.8 Hz), 7.02 (dd, 1H, J₁=2.0 Hz, J₂=8.8 Hz), 4.18 (m, 2H), 3.19 (m, 6H), 2.94-2.86 (m, 1H), 2.71 (m, 4H), 2.55 (m, 5H), 2.11-2.09 (m, 2H), 1.91-1.89 (m, 4H), 1.71 (m, 4H), 1.56 (m, 2H), 1.44 (m, 2H). MS (ESI): m/z 394 (M+H⁺).

101. Compound 101: (rac-3-cyclobutyl-9-(4-(tetrahydrofuran-3-yl)piperazin-1-yl)-2,3,4,5-tetrahydro-1H-[1,4]diazepino[1,7-a]benzimidazole)

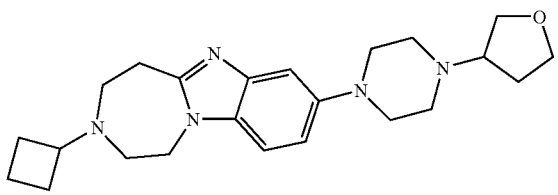

This compound was prepared in 18% yield as described for compound 99 but using dihydrofuran-3(2H)-one as the starting material. ¹H-NMR (400 MHz, CDCl₃): δ 7.23 (d, 1H, J=2.0 Hz), 7.14 (d, 1H, J=8.8 Hz), 6.99 (dd, 1H, J₁=2.0 Hz, J₂=8.8 Hz), 4.18 (m, 2H), 3.97-3.93 (m, 2H), 3.84 (q, 1H, J=8.0 Hz), 3.68 (t, 1H, J=8.0 Hz), 3.21-3.17 (m, 6H), 3.03-3.01 (m, 1H), 2.92-2.88 (m, 1H), 2.77-2.73 (m, 2H), 2.62-2.56 (m, 6H), 2.11-2.08 (m, 3H), 1.92-1.71 (m, 3H), 1.68-1.63 (m, 2H). MS (ESI): m/z 396 (M+H⁺).

102. Compound 102: (3-cyclobutyl-9-(4-cyclopentylpiperazin-1-yl)-2,3,4,5-tetrahydro-1H-[1,4]diazepino[1,7-a]benzimidazole)

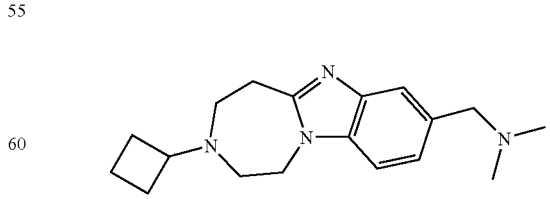

This compound was prepared in 13% yield as described for compound 99 but using cyclohexanone as the starting material. ¹H-NMR (400 MHz, CD₃OD): δ 7.37 (d, 1H, J=8.8 Hz), 7.13 (s, 1H, J=8.8 Hz), 7.08 (d, 1H, J=8.8 Hz), 4.30 (m, 2H), 3.20 (m, 6H), 2.95 (m, 5H), 2.65 (m, 2H), 2.58 (m, 3H), 2.14 (m, 2H), 2.04 (m, 2H), 1.91-1.86 (m, 5H), 1.70 (m, 3H), 1.35-1.28 (m, 4H). MS (ESI): m/z 408 (M+H⁺).

103. Compound 103: (3-cyclobutyl-9-(4-(tetrahydro-2H-pyran-4-yl)piperazin-1-yl)-2,3,4,5-tetrahydro-1H-[1,4]diazepino[1,7-a]benzimidazole)

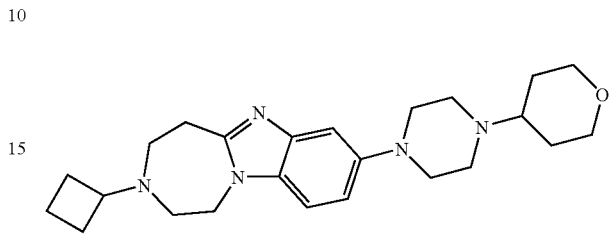

This compound was prepared in 25% yield as described for compound 99 but using dihydro-2H-pyran-4(3H)-one as the starting material. ¹H-NMR (400 MHz, CDCl₃): δ 7.26 (s, 1H), 7.17 (d, 1H, J=8.8 Hz), 7.01 (d, 1H, J=8.8 Hz), 4.22 (m, 2H), 4.08-4.06 (m, 2H), 3.44 (t, 2H, J=7.2 Hz), 3.27 (br, 6H), 2.92 (br, 5H), 2.65 (br, 5H), 2.13-2.11 (m, 2H), 1.95-1.87 (m, 4H), 1.75-1.67 (m, 4H). MS (ESI): m/z 410 (M+H⁺).

104. Compound 104: (3-cyclobutyl-9-(4-(cyclopropylmethyl)piperazin-1-yl)-2,3,4,5-tetrahydro-1H-[1,4]diazepino[1,7-a]benzimidazole)

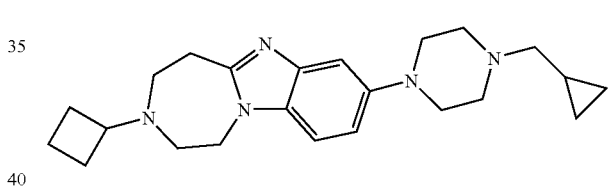

This compound was prepared in 29% yield as described for compound 99 but using 1-cyclopropylethanone as the starting material. ¹H-NMR (400 MHz, CDCl₃): δ 7.24 (s, 1H), 7.12 (d, 1H, J=8.8 Hz), 6.99 (d, 1H, J=8.8 Hz), 4.16 (m, 2H), 3.20-3.17 (m, 6H), 2.90-2.86 (m, 1H), 2.75 (br, 4H), 2.60-2.54 (m, 4H), 2.35 (d, 2H, J=6.4 Hz), 2.10-2.06 (m, 2H), 1.90-1.85 (m, 2H), 1.72-1.61 (m, 2H), 0.92-0.90 (m, 1H), 0.54 (d, 2H, J=7.6 Hz), 0.14 (d, 2H, J=4.8 Hz). MS (ESI): m/z 380 (M+H⁺).

105. Compound 105: (3-cyclobutyl-9-((dimethylamino)methyl)-2,3,4,5-tetrahydro-1H-[1,4]diazepino[1,7-a]benzimidazole)

This compound was prepared in 16% yield as described for compound 74 but using dimethylamine as the starting material. ¹H-NMR (400 MHz, CDCl₃): 7.59 (s, 1H), 7.29~7.31 (m, 1H), 7.22~7.25 (m, 1H), 4.24~4.26 (m, 2H), 3.61 (s, 2H), 3.25~3.28 (m, 2H), 2.95 (m, 1H), 2.62~2.68 (m, 4H), 2.30 (s, 6H), 2.14~2.16 (m, 2H), 1.91~1.96 (m, 2H), 1.63~1.78 (m, 2H). MS (ESI): m/z 299 (M+H$^+$).

106. Compound 106: (2-(3-cyclobutyl-2,3,4,5-tetrahydro-1H-[1,4]diazepino[1,7-a]benzimidazol-9-yl)methanol)

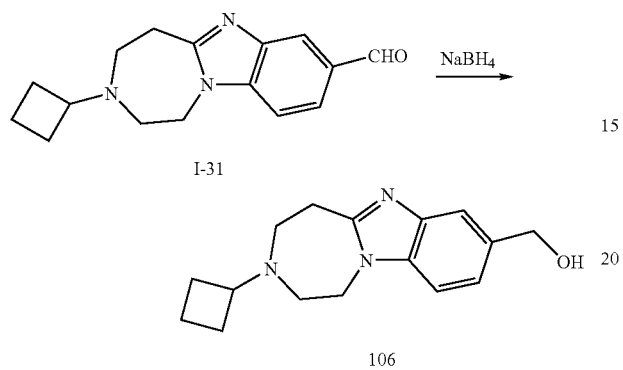

To a solution of I-31 (186 mg) in methanol (7 mL) was added solid NaBH$_4$ (105 mg, 4.0 eq.) in one portion at 0° C. and the reaction mixture was stirred at 0° C. for 30 minutes. Water (2 mL) was added and the reaction mixture was stirred at room temperature for 10 minutes. The reaction mixture was concentrated and the residue was dissolved in dichloromethane and washed with water. The combined organic layers were dried over sodium sulfate, solids were removed by filtration and the filtrate was concentrated to give compound 106 as a white solid (178 mg, 95%). $^1$H-NMR (400 MHz, CDCl$_3$): δ 7.66 (s, 1H), 7.22~7.30 (m, 2H), 4.78 (s, 2H), 4.22~4.24 (m, 2H), 3.23~3.25 (m, 2H), 2.90~2.94 (m, 1H), 2.59~2.65 (m, 4H), 2.09~2.16 (m, 2H), 1.89~1.94 (m, 2H), 1.65~1.76 (m, 2H). MS (ESI): m/z 272 (M+H$^+$).

107. Compound 107: (3-cyclobutyl-9-((4-methoxypyrimidin-2-yloxy)methyl)-2,3,4,5-tetrahydro-1H-[1,4]diazepino[1,7-a]benzimidazole)

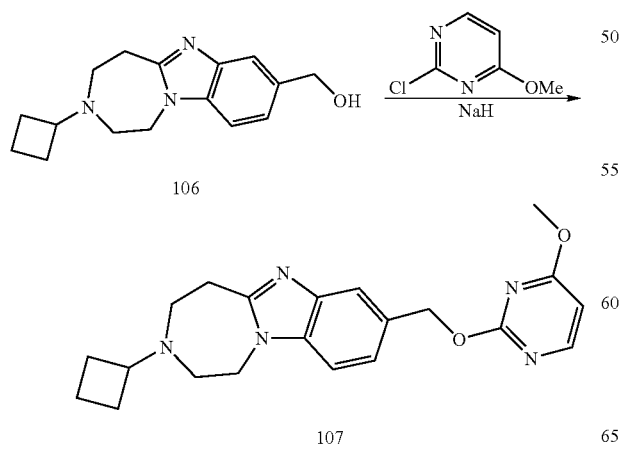

To a solution of 106 (33 mg) in DMF was added sodium hydride (2.0 eq.) and the reaction mixture was stirred at room temperature for 30 minutes. Solid 2-chloro-4-methoxypyrimidine (1.5 eq.) was added and the reaction mixture was stirred at 50° C. overnight. Saturated aqueous solution of sodium bicarbonate was added and the reaction mixture was extracted with ethyl acetate. The combined organic layers were washed with brine, dried over Na$_2$SO$_4$, solids were removed by filtration and the filtrate was concentrated. The crude reaction mixture was purified by preparative TLC to give compound 107 (26 mg, 57%). $^1$H-NMR (400 MHz, CDCl$_3$): δ 8.18 (d, 1H, J=4.8 Hz), 7.80 (s, 1H), 7.41 (d, 1H, J=6.8 Hz), 7.23 (d, 1H, J=6.8 Hz), 6.35 (d, 1H, J=4.4 Hz), 5.53 (s, 2H), 4.22~4.23 (m, 2H), 3.96 (s, 3H), 3.23~3.25 (m, 2H), 2.90~2.93 (m, 1H), 2.59~2.64 (m, 4H), 2.10~2.14 (m, 2H), 1.89~1.93 (m, 2H), 1.65~1.75 (m, 2H). MS (ESI): m/z 380 (M+H$^+$).

108. Compound 108: (6-((3-cyclobutyl-2,3,4,5-tetrahydro-1H-[1,4]diazepino[1,7-a]benzimidazol-9-yl)methoxy)nicotino-nitrile)

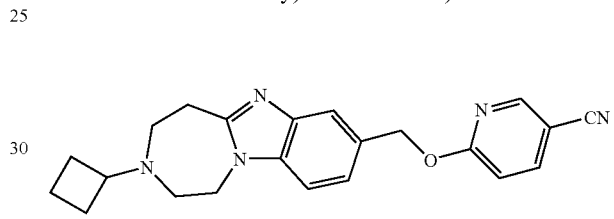

This compound was prepared in 88% yield as described for compound 107 but using 6-chloronicotinonitrile as the starting material. The reaction was run at room temperature. $^1$H-NMR (400 MHz, CDCl$_3$): δ 8.51 (d, 1H, J=1.2 Hz), 7.75~7.78 (m, 2H), 7.34 (d, 1H, J=6.8 Hz), 7.26 (d, 1H, J=6.8 Hz), 6.84 (d, 1H, J=7.2 Hz), 5.54 (s, 2H), 4.23~4.25 (m, 2H), 3.23~3.26 (m, 2H), 2.90~2.93 (m, HA), 2.59~2.64 (m, 4H), 2.10~2.15 (m, 2H), 1.89~1.93 (m, 2H), 1.65~1.75 (m, 2H). MS (ESI): m/z 374 (M+H$^+$).

109. Compound 109: (3-cyclobutyl-9-((pyrazin-2-yloxy)methyl)-2,3,4,5-tetrahydro-1H-[1,4]diazepino[1,7-a]benzimidazole)

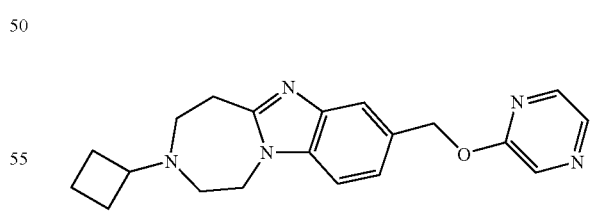

This compound was prepared in 91% yield as described for compound 107 but using 2-chloropyrazine as the starting material. $^1$H-NMR (400 MHz, CDCl$_3$): δ 8.25 (s, 1H), 8.10~8.12 (m, 2H), 7.80 (s, 1H), 7.36 (d, 1H, J=6.8 Hz), 7.26 (d, 1H, J=7.2 Hz), 5.50 (s, 2H), 4.23~4.25 (m, 2H), 3.24~3.26 (m, 2H), 2.89~2.93 (m, 1H), 2.59~2.64 (m, 4H), 2.10~2.15 (m, 2H), 1.87~1.95 (m, 2H), 1.63~1.77 (m, 2H). MS (ESI): m/z 350 (M+H$^+$).

110. Compound 110: (2-(3-cyclobutyl-2,3,4,5-tetrahydro-1H-[1,4]diazepino[1,7-a]benzimidazol-8-yl)methanol)

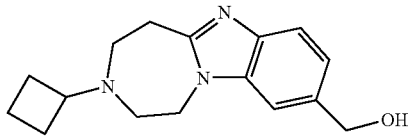

This compound was prepared in 96% yield (130 mg) as described for compound 106 but intermediate I-39 as the starting material. $^1$H-NMR (400 MHz, CD$_3$OD): δ 7.42 (d, 1H, J=8.0 Hz), 7.35 (d, 1H, J=0.8 Hz), 7.13 (dd, 1H, J$_1$=1.2 Hz, J$_2$=8.0 Hz), 4.62 (s, 2H), 4.24~4.26 (m, 2H), 3.09~3.12 (m, 2H), 2.87~2.91 (m, 1H), 2.51~2.59 (m, 4H), 2.02~2.09 (m, 2H), 1.83~1.87 (m, 2H), 1.58~1.67 (m, 2H). MS (ESI): m/z 272 (M+H$^+$).

111. Compound III: (3-cyclobutyl-8-((4-methoxypyrimidin-2-yloxy)methyl)-2,3,4,5-tetrahydro-1H-[1,4]diazepino[1,7-a]benzimidazole)

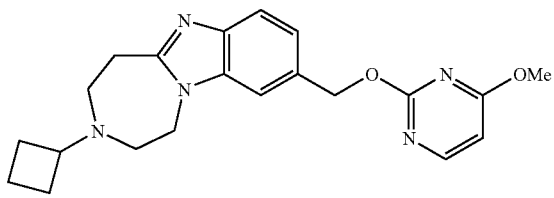

This compound was prepared in 74% yield as described for compound 107 but using compound 110 as the starting material. $^1$H-NMR (400 MHz, CDCl$_3$): δ 8.20 (d, 1H, J=5.6 Hz), 7.66 (d, 1H, J=8.0 Hz), 7.44 (d, 1H, J=0.8 Hz), 7.32 (dd, 1H, J$_1$=1.2 Hz, J$_2$=8.0 Hz), 6.38 (d, 1H, J=5.6 Hz), 5.54 (s, 2H), 4.23~4.25 (m, 2H), 3.97 (s, 3H), 3.23~3.25 (m, 2H), 2.92 (m, 1H), 2.59~2.64 (m, 4H), 2.10~2.18 (m, 2H), 1.88~1.93 (m, 2H), 1.65~1.73 (m, 2H). MS (ESI): m/z 380 (M+H$^+$).

112. Compound 112: (6-((3-cyclobutyl-2,3,4,5-tetrahydro-1H-[1,4]diazepino[1,7-a]benzimidazol-8-yl)methoxy)nicotino-nitrile)

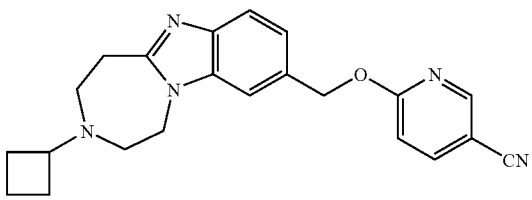

This compound was prepared in 94% yield as described for compound 107 but using compound 110 and 2-chloro-5-cyanopyridine as starting materials. The reaction was run at room temperature. $^1$H-NMR (400 MHz, CDCl$_3$): δ 8.52 (s, 1H), 7.78 (dd, 1H, J$_1$=2.0 Hz, J$_2$=8.4 Hz), 7.69 (d, 1H, J=8.0 Hz), 7.36 (s, 1H), 7.31 (d, 1H, J=8.8 Hz), 6.86 (d, 1H, J=8.4 Hz), 5.55 (s, 2H), 4.23~4.26 (m, 2H), 3.24~3.26 (m, 2H), 2.88~2.95 (m, 1H), 2.60~2.66 (m, 4H), 2.10~2.16 (m, 2H), 1.86~1.94 (m, 2H), 1.63~1.76 (m, 2H). MS (ESI): m/z 374 (M+H$^+$).

113. Compound 113: (3-cyclobutyl-9-((pyrazin-2-yloxy)methyl)-2,3,4,5-tetrahydro-1H-[1,4]diazepino[1,7-a]benzimidazole)

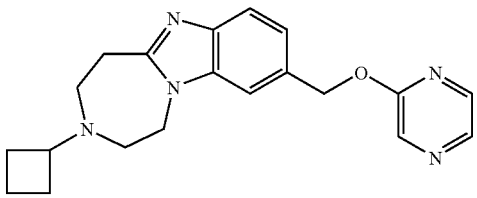

This compound was prepared in 89% yield as described for compound 107 but using compound 110 and 2-chloropyrazine as starting materials. $^1$H-NMR (400 MHz, CDCl$_3$): δ 8.28 (d, 1H, J=1.2 Hz), 8.11~8.15 (m, 2H), 7.69 (d, 1H, J=8.4 Hz), 7.38 (s, 1H), 7.32 (dd, 1H, J$_1$=1.2 Hz, J$_2$=8.4 Hz), 5.50 (s, 2H), 4.24~4.26 (m, 2H), 3.24~3.27 (m, 2H), 2.90~2.94 (m, 1H), 2.59~2.66 (m, 4H), 2.09~2.14 (m, 2H), 1.88~1.93 (m, 2H), 1.65~1.76 (m, 2H). MS (ESI): m/z 350 (M+H$^+$).

114. Compound 114: (3-cyclobutyl-9-(pyridin-2-yl)-2,3,4,5-tetrahydro-1H-[1,4]diazepino[1,7-a]benzimidazole)

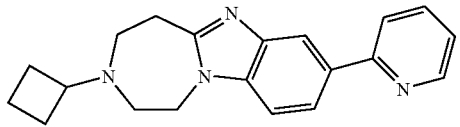

This compound was prepared in 38% yield as described for compound 22 but using 2-bromopyridine as the starting material. $^1$H-NMR (400 MHz, CDCl$_3$): δ 1.65-1.75 (m, 2H), 1.85-1.95 (m, 2H), 2.10-2.15 (m, 2H), 2.62-2.68 (m, 4H), 2.91-2.95 (m, 1H), 3.28 (m, 2H), 4.27 (m, 2H), 7.18-7.22 (m, 1H), 7.34 (d, 1H), 7.74-7.79 (m, 2H), 8.02 (dd, 1H), 8.23 (s, H), 8.68 (d, 1H). MS (ESI): m/z 319.0 (M+H$^+$).

115. Compound 115: (3-cyclobutyl-9-(pyridin-3-yl)-2,3,4,5-tetrahydro-1H-[1,4]diazepino[1,7-a]benzimidazole)

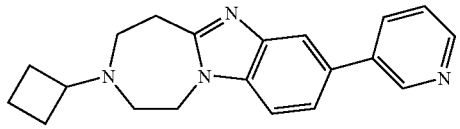

This compound was prepared in 17% yield as described for compound 22 but using 2-bromopyridine as the starting material. $^1$H-NMR (400 MHz, CDCl$_3$) δ: 1.65-1.80 (m, 2H), 1.85-1.95 (m, 2H), 2.11-2.16 (m, 2H), 2.62-2.68 (m, 4H), 2.92-2.96 (m, 1H), 3.28 (m, 2H), 4.28 (m, 2H), 7.33-7.38 (m, 2H), 7.47 (dd, 1H), 7.89-7.92 (m, 2H), 8.56 (d, 1H), 8.89 (s, 1H). MS (ESI): m/z 319.0 (M+H⁺).

116. Compound 116: (3-cyclobutyl-9-(pyridin-4-yl)-2,3,4,5-tetrahydro-1H-[1,4]diazepino[1,7-a]benzimidazole)

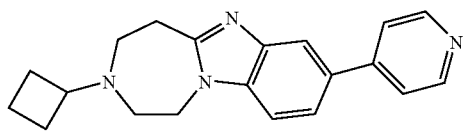

This compound was prepared in 14% yield as described for compound 22 but using 2-bromopyridine as the starting material. ¹H-NMR (400 MHz, CDCl₃) δ: 1.65-1.75 (m, 2H), 1.85-1.95 (m, 2H), 2.11-2.16 (m, 2H), 2.61-2.67 (m, 4H), 2.91-2.95 (m, 1H), 3.27 (m, 2H), 4.27 (m, 2H), 7.34 (d, 1H), 7.52-7.56 (m, 3H), 7.97 (s, 1H), 8.64 (d, 2H). MS (ESI): m/z 319.0 (M+H⁺).

117. Compound 117: (N-((3-cyclobutyl-2,3,4,5-tetrahydro-1H-[1,4]diazepino[1,7-a]benzimidazol-9-yl)methyl)pyridin-3-amine)

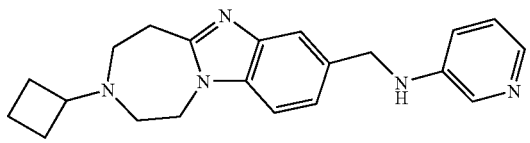

This compound was prepared in 14% yield as described for compound 74 but using pyridin-3-amine as the starting material. ¹H-NMR (400 MHz, CDCl₃): δ 8.08 (d, 1H, J=2.8 Hz), 7.95 (d, 1H, J=4.4 Hz), 7.67 (s, 1H), 7.21~7.25 (m, 2H), 7.03~7.07 (m, 1H), 6.90~6.91 (m, 1H), 4.44 (s, 2H), 4.22~4.24 (m, 2H), 4.16 (brs, 1H), 3.23~3.25 (m, 2H), 2.92 (m, 1H), 2.59~2.65 (m, 4H), 2.11~2.14 (m, 2H), 1.89~1.94 (m, 2H), 1.68~1.76 (m, 2H). MS (ESI): m/z 348 (M+H⁺).

118. Compound 118: (3-cyclobutyl-9-(4-isopropylpiperazin-1-yl)-2,3,4,5-tetrahydro-1H-[1,4]diazepino[1,7-a]benzimidazole)

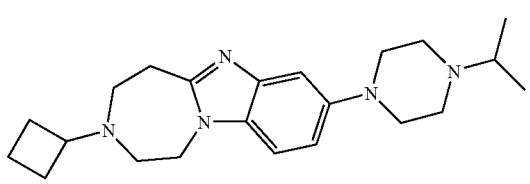

This compound was prepared in 23% yield as described for compound 99 but using acetone as the starting material. ¹H-NMR (400 MHz, CD₃OD): δ 7.50 (d, 1H, J=8.8 Hz), 7.23 (s, 1H), 7.18 (d, 1H, J=8.8 Hz), 4.55 (br, 2H), 3.61~3.57 (m, 2H), 3.46 (br, 10H), 3.14~3.08 (m, 4H), 2.27~2.22 (m, 4H), 1.85~1.74 (m, 2H), 1.44 (d, 6H, J=6.8 Hz). MS (ESI): m/z 368 (M+H⁺).

119. Compound 119: (mixture of 4-(3-(tert-butyl)-2,3,4,5-tetrahydro-1H-benzo[4,5]imidazo[1,2-d][1,4]diazepin-8-yl)benzonitrile and 4-(3-(tert-butyl)-2,3,4,5-tetrahydro-1H-benzo[4,5]imidazo[1,2-d][1,4]diazepin-9-yl)benzonitrile)

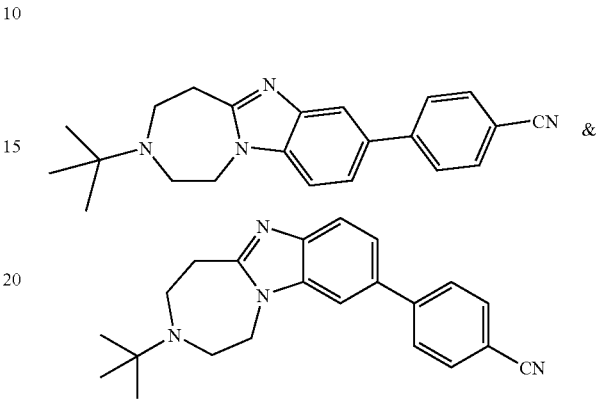

This compound was prepared in 30% yield (19 mg) as described for compound 41 but using intermediate I-44 as the starting material. ¹H-NMR (400 MHz, CDCl₃) δ: 7.91-7.33 (m, 7H), 4.26 (t, 2H, J=8.4 Hz), 3.26 (t, 2H, J=4.8 Hz), 2.96 (t, 2H, J=8.4 Hz), 2.90 (t, 2H, J=4.8 Hz), 1.16 (s, 9H). MS (ESI): m/z 345.1 (M+H⁺).

120. Compound 120: (3-cyclobutyl-2,3,4,5-tetrahydro-1H-benzo[4,5]imidazo[1,2-d][1,4]diazepin-8-yl)(pyrazin-2-yl)methanol)

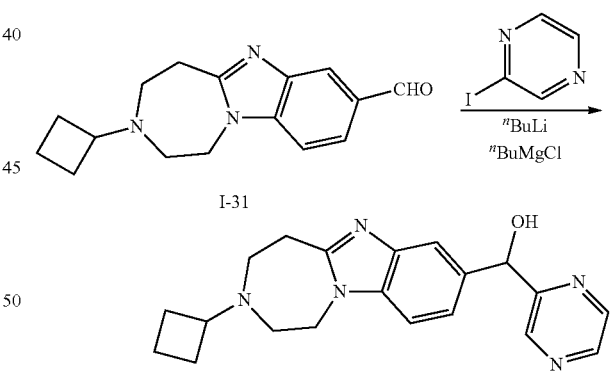

To a solution of ⁿBuMgCl (0.17 mmol, 0.33 eq) in dry THF (4 mL) was added ⁿBuLi (0.55 mmol, 1.1 eq) at −20° C. and the reaction mixture was stirred at −20° C. for 30 minutes. 2-Iodopyrazine (103 mg, 0.50 mmol, 1.0 eq) was added at −20° C. and the reaction mixture was stirred at −10° C. for 2 hours. The reaction mixture was cooled to −20° C. and a solution of intermediate I-31 (135 mg, 0.50 mmol, 1.0 eq) in THF (1 mL) was added. The reaction mixture was stirred at −20° C. for 1 hour and then at room temperature until TLC analysis indicated complete disappearance of the starting material. The reaction mixture was quenched by adding saturated aqueous solution of ammonium chloride and extracted with dichloromethane. The combined organic layers were dried over anhydrous Na₂SO₄, the solids were removed by filtration and the filtrate was concentrated by evaporation. The crude reaction product was purified by preparative TLC to give compound 120 (130 mg, 74%). $^1$H-NMR (400 MHZ, CDCl₃): δ 8.63 (d, 1H, J=0.8 Hz), 8.49 (dd, 1H, $J_1$=0.8 Hz, $J_2$=2.8 Hz), 8.44 (d, 1H, J=2.8 Hz), 7.68 (s, 1H), 7.25 (dd, 1H, $J_1$=1.2 Hz, $J_2$=8.8 Hz), 7.20 (d, 1H, J=8.8 Hz), 5.98 (s, 1H), 5.30 (s, 1H), 4.18~4.20 (m, 2H), 3.18~3.21 (m, 2H), 2.88~2.91 (m, 1H), 2.54~2.61 (m, 4H), 2.08~2.14 (m, 2H), 1.86~1.91 (m, 2H), 1.61~1.74 (m, 2H). MS (ESI): m/z 350 (M+H⁺).

121. Compound 121: 43-cyclobutyl-2,3,4,5-tetrahydro-1H-benzo[4,5]imidazo[1,2-d][1,4]diazepin-8-yl)(pyrazin-2-yl)methanone)

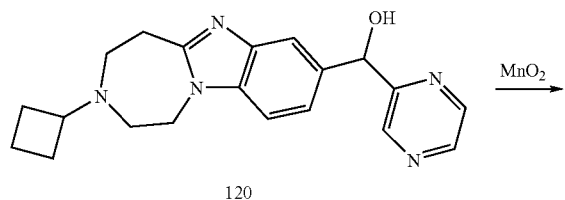

To a solution of compound 120 (3.6 mg, 0.010 mmol, 1.0 eq) in dichloromethane (5 mL) was added MnO₂ (2.0 mg, 0.021 mmol, 2.0 eq) and the reaction mixture was stirred at room temperature for 60 minutes. The solids were removed by filtration through a short plug of silica gel and the filtrate was concentrated by evaporation to give compound 121 (3.5 mg, 98%). $^1$H-NMR (400 MHz, CD₃OD): δ 9.04 (d, 1H, J=1.6 Hz), 8.73 (d, 1H, J=2.4 Hz), 8.65 (dd, 1H, $J_1$=1.6 Hz, $J_2$=2.4 Hz), 8.27 (d, 1H, J=1.2 Hz), 7.96 (dd, 1H, $J_1$=2.0 Hz, $J_2$=8.4 Hz), 7.50 (d, 1H, J=8.4 Hz), 4.31~4.34 (m, 2H), 3.15~3.17 (m, 2H), 2.90~2.93 (m, 1H), 2.55~2.63 (m, 4H), 2.03-2.1 (m, 2H), 1.80~1.90 (m, 2H), 1.57~1.67 (m, 2H). MS (ESI): m/z 348 (M+H⁺).

122. Compound 122: (3-cyclobutyl-8-(pyrazin-2-ylmethyl)-2,3,4,5-tetrahydro-1H-benzo[4,5]imidazo[1,2-d][1,4]diazepine)

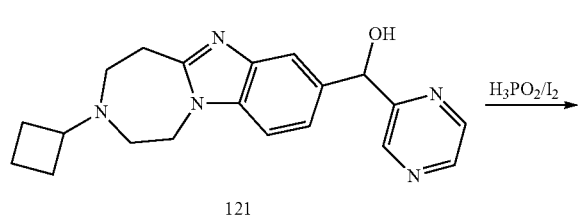

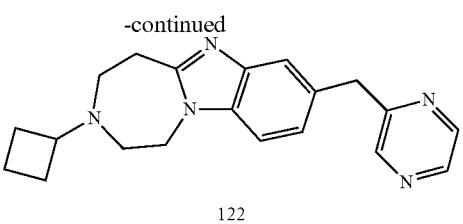

To a solution of compound 121 (54 mg, 0.15 mmol, 1.0 eq) in acetic acid (8 mL) was added solid I₂ (38 mg) and H₃PO₂ (50% solution in water, 100 mg, 0.75 mmol, 5.0 eq) and the reaction mixture was stirred at 60° C. for 16 hours. The reaction mixture was concentrated by evaporation; the residue was dissolved in an aqueous sodium bicarbonate solution and extracted with ethyl acetate. The combined organic layers were dried over anhydrous Na₂SO₄, the solids were removed by filtration and the filtrate was concentrated by evaporation. The crude reaction product was purified by preparative TLC to give compound 122 (25 mg, 51%) as a pale yellow solid. $^1$H-NMR (400 MHz, CDCl₃): δ 8.50 (dd, 1H, $J_1$=2.4 Hz, $J_2$=1.6 Hz), 8.46 (d, 1H, J=1.2 Hz), 8.38 (d, 1H, J=2.8 Hz), 7.58 (s, 1H), 7.15~7.21 (m, 2H), 4.29 (s, 2H), 4.20~4.22 (m, 2H), 3.21~3.24 (m, 2H), 2.90~2.93 (m, 1H), 2.58~2.64 (m, 4H), 2.08~2.15 (m, 2H), 1.87~1.93 (m, 2H), 1.65~1.75 (m, 2H). MS (ESI): m/z 334 (M+H⁺).

123. Compound 123: (3-cyclobutyl-8-(pyrimidin-2-yl)-2,3,4,5-tetrahydro-1H-benzo[4,5]imidazo[1,2-d][1,4]diazepine)

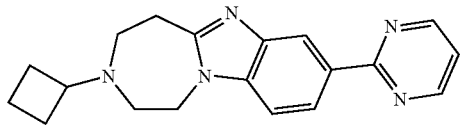

This compound was prepared in 38% yield (20 mg) as described for compound 22 but using 2-chloropyrimidine as the starting material. $^1$H-NMR (400 MHz, CDCl₃) δ: 8.78-8.81 (m, 3H), 8.40 (dd, 1H, $J_1$=8.4 Hz, $J_2$=1.2 Hz), 7.28-7.33 (m, 1H), 7.13 (m, 1H), 4.24-4.27 (m, 2H), 3.25-3.28 (m, 2H), 2.89-2.92 (m, 1H), 2.60-2.67 (m, 4H), 2.09-2.13 (m, 2H), 1.88-1.93 (m, 2H), 1.64-1.74 (m, 2H). MS (ESI): m/z 320.0 (M+H⁺).

124. Compound 124: (3-cyclobutyl-8-(pyrimidin-4-yl)-2,3,4,5-tetrahydro-1H-benzo[4,5]imidazo[1,2-d][1,4]diazepine)

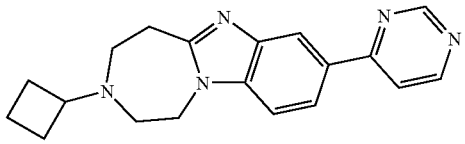

This compound was prepared in 36% yield (19 mg) as described for compound 22 but using 4-chloropyrimidine as the starting material. $^1$H-NMR (400 MHz, CDCl₃) δ: 9.25 (d, J=0.8 Hz, 1H), 8.73 (d, J=5.6 Hz, 1H), 8.37 (d, J=1.6 Hz, 1H), 8.12 (dd, J=8.4, 1.6 Hz, 1H), 7.77 (dd, $J_1$=5.2 Hz, $J_1$=1.2 Hz, 1H), 7.37 (d, J=8.4 Hz, 1H), 4.27-4.30 (m, 2H), 3.27-3.30 (m, 2H), 2.92-2.96 (m, 1H), 2.62-2.69 (m, 4H), 2.11-2.17 (m, 2H), 1.89-1.94 (m, 2H), 1.65-1.76 (m, 2H). MS (ESI): m/z 320.0 (M+H+).

125. Compound 125: (3-cyclobutyl-8-(pyridazin-3-yl)-2,3,4,5-tetrahydro-1H-benzo[4,5]imidazo[1,2-d][1,4]diazepine)

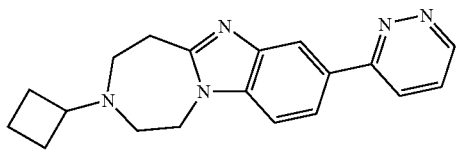

This compound was prepared in 47% yield (25 mg) as described for compound 22 but using 3-chloropyridazine as the starting material. $^1$H-NMR (400 MHz, CDCl$_3$) δ: 9.12 (dd, J$_1$=4.8 Hz, J$_1$=1.6 Hz, 1H), 8.26 (d, J=1.2 Hz, 1H), 8.19 (dd, J$_1$=8.4 Hz, J$_2$=1.6 Hz, 1H), 7.90 (dd, J$_1$=8.4 Hz, J$_2$=1.2 Hz, 1H), 7.51-7.55 (m, 1H), 7.40 (d, J=8.4 Hz, 1H), 4.28-4.30 (m, 2H), 3.27-3.29 (m, 2H), 2.92-2.96 (m, 1H), 2.62-2.69 (m, 4H), 2.10-2.16 (m, 2H), 1.89-1.94 (m, 2H), 1.65-1.76 (m, 2H). MS (ESI): m/z 320.0 (M+H+).

126. Compound 126: (3-cyclobutyl-8-(pyrimidin-5-yl)-2,3,4,5-tetrahydro-1H-benzo[4,5]imidazo[1,2-d][1,4]diazepine)

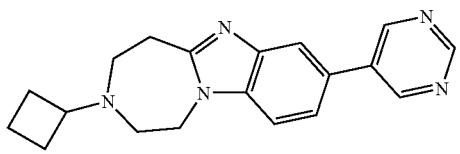

This compound was prepared in 15% yield (8 mg) as described for compound 22 but using 5-bromopyrimidine as the starting material. $^1$H-NMR (400 MHz, CDCl$_3$) δ: 9.19 (s, 1H), 8.99 (s, 2H), 7.90 (s, 1H), 7.46 (dd, J$_1$=8.4 Hz, J$_2$=1.2 Hz, 1H), 7.39 (d, J=8.4 Hz, 1H), 4.28-4.30 (m, 2H), 3.27-3.30 (m, 2H), 2.90-2.98 (m, 1H), 2.63-2.69 (m, 4H), 2.11-2.17 (m, 2H), 1.88-1.98 (m, 2H), 1.61-1.79 (m, 2H). MS (ESI): m/z 320.0 (M+H+).

127. Compound 127: (3-cyclobutyl-8-(pyridazin-4-yl)-2,3,4,5-tetrahydro-1H-benzo[4,5]imidazo[1,2-d][1,4]diazepine)

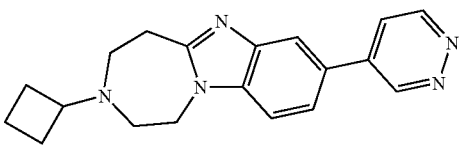

This compound was prepared in 23% yield (12 mg) as described for compound 22 but using 4-bromopyridazine as the starting material. $^1$H-NMR (400 MHz, CDCl$_3$) δ: 9.52 (s, 1H), 9.19 (d, J=5.2 Hz, 1H), 8.01 (s, 1H), 7.68 (dd, J$_1$=5.6 Hz, J$_2$=2.4 Hz, 1H), 7.56 (dd, J$_1$=8.0 Hz, J$_2$=2.4 Hz, 1H), 7.40 (d, J=8.0 Hz, 1H), 4.28-4.30 (m, 2H), 3.27-3.30 (m, 2H), 2.91-2.98 (m, 1H), 2.63-2.69 (m, 4H), 2.11-2.17 (m, 2H), 1.87-1.97 (m, 2H), 1.61-1.79 (m, 2H). MS (ESI): m/z 320.0 (M+H+).

128. Compound 128: (3-cyclobutyl-8-(1-cyclobutylpiperidin-3-yl)-2,3,4,5-tetrahydro-1H-benzo[4,5]imidazo[1,2-d][1,4]diazepine)

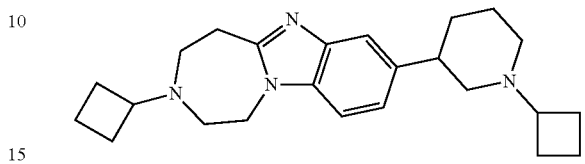

This compound was prepared in 30% yield (15 mg) as described for compound 8 but using intermediate I-45 as the starting material. $^1$H-NMR (400 MHz, CD$_3$OD) δ: 7.31 (s, 1H), 7.26 (d, J=6.8 Hz, 1H), 7.06-7.08 (m, 1H), 4.19-4.21 (m, 2H), 3.20-3.21 (m, 2H), 2.86-2.96 (m, 3H), 2.84-2.86 (m, 1H), 2.73-2.78 (m, 1H), 2.48-2.54 (m, 4H), 2.01-2.06 (m, 2H), 1.98-2.01 (m, 1H), 1.96-1.98 (m, 1H), 1.88-1.92 (m, 5H), 1.67-1.84 (m, 3H), 1.59-1.64 (m, 5H), 1.41-1.50 (m, 1H). MS (ESI): m/z 379 (M+H+).

129. Compound 129: (3-cyclobutyl-8-(1-(pyrazin-2-yl)piperidin-3-yl)-2,3,4,5-tetrahydro-1H-benzo[4,5]imidazo[1,2-d][1,4]diazepine)

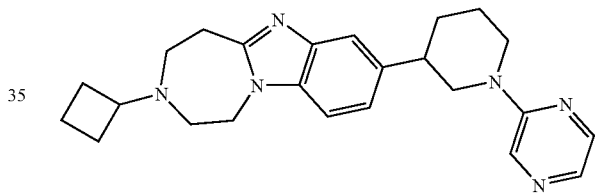

This compound was prepared in 16% yield (6 mg) as described for compound 65 but using intermediate I-45 as the starting material. $^1$H-NMR (400 MHz, CD$_3$OD) δ: 8.13 (d, J=1.2 Hz, 1H), 8.00-8.02 (m, 1H), 7.65 (d, J=2.8 Hz, 1H), 7.44 (s, 1H), 7.34 (d, J=8.4 Hz, 1H), 7.18 (dd, J$_1$=8.4 Hz, J$_2$=1.2 Hz, 1H), 4.41-4.84 (m, 2H), 4.25-4.27 (m, 2H), 3.12-3.15 (m, 2H), 2.90-2.95 (m, 3H), 2.78-2.84 (m, 1H), 2.54-2.61 (m, 4H), 2.00-2.12 (m, 3H), 1.82-1.90 (m, 4H), 1.62-1.70 (m, 3H). MS (ESI): m/z 403 (M+H+).

130. Compound 130: (3-cyclobutyl-8-(1-(pyrimidin-2-yl)piperidin-3-yl)-2,3,4,5-tetrahydro-1H-benzo[4,5]imidazo[1,2-d][1,4]diazepine)

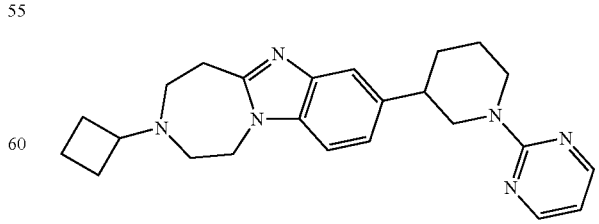

This compound was prepared in 10% yield (6 mg) as described for compound 65 but using intermediate I-45 and 2-chloropyrimidine as the starting materials. $^1$H-NMR (400

MHz, CD$_3$OD) δ: 8.21 (d, J=4.0 Hz, 2H), 7.41 (s, 1H), 7.73 (d, J=6.4 Hz, 1H), 7.16 (d, J=8.0 Hz, 1H), 6.44~6.47 (m, 1H), 4.68~4.75 (m, 2H), 4.23-4.25 (m, 2H), 3.11~3.13 (m, 2H), 2.87~2.91 (m, 3H), 2.76~2.75 (m, 1H), 2.53~2.59 (m, 4H), 1.98~2.09 (m, 3H), 1.77~1.90 (m, 4H), 1.51~1.70 (m, 3H). MS (ESI): m/z 403 (M+H$^+$).

131. Compound 131: (3-cyclobutyl-8-(2-(pyrrolidin-1-yl)pyrimidin-4-yl)-2,3,4,5-tetrahydro-1H-benzo[4,5]imidazo[1,2-d][1,4]diazepine)

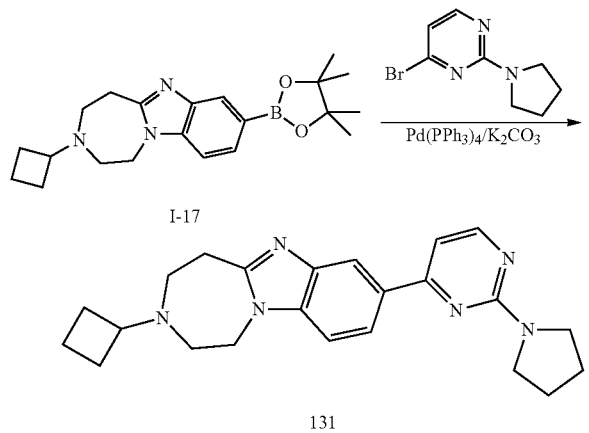

Intermediate I-17 (50 mg, 0.14 mmol, 1.0 eq), 4-bromo-2-(pyrrolidin-1-yl)pyrimidine (46 mg, 0.20 mmol 1.5 eq), Pd(PPh$_3$)$_4$ (16 mg, 0.014 mmol, 0.1 eq) and potassium carbonate (113 mg, 0.82 mmol, 6.0 eq) were dissolved in a mixture of dioxane (1.5 mL) and water (0.5 mL) and degassed by bubbling argon. The reaction mixture was stirred at 120° C. under microwave irradiation for 60 minutes, diluted with water and extracted with ethyl acetate. The combined organic layers were dried over anhydrous Na$_2$SO$_4$, the solids were removed by filtration and the filtrate was concentrated by evaporation. The crude reaction product was purified by preparative TLC to give compound 131 (30 mg, 58%) as pale yellow solid. $^1$H-NMR (400 MHz, CDCl$_3$) δ: 8.83 (d, 1H, J=1.2 Hz), 8.38 (dd, 1H, J$_1$=1.2 Hz, J$_2$=8.8 Hz), 8.26 (d, 1H, J=6.0 Hz), 7.26 (m, 1H), 6.16 (d, 1H, J=6.0 Hz), 4.24~4.26 (m, 2H), 3.35~3.76 (brm, 4H), 3.25~3.27 (m, 2H), 2.92 (m, 1H), 2.61~2.66 (m, 4H), 2.10~2.13 (m, 2H), 2.03 (m, 4H), 1.89~1.93 (m, 2H), 1.64~1.75 (m, 2H). MS (ESI): m/z 389 (M+H$^+$).

132. Compound 132: (3-cyclobutyl-8-(2-methoxypyrimidin-4-yl)-2,3,4,5-tetrahydro-1H-benzo[4,5]imidazo[1,2-d][1,4]diazepine)

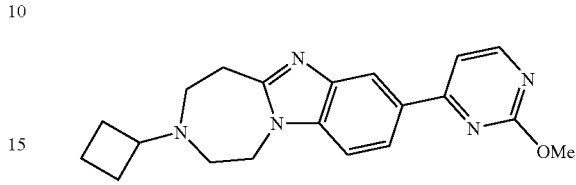

This compound was prepared in 27% yield (13 mg) as described for compound 22 but using 4-bromo-2-methoxypyrimidine as the starting material. $^1$H-NMR (400 MHz, CDCl$_3$) δ 8.77 (d, J=1.2 Hz, 1H). 8.42 (d, J=6.0 Hz, 1H), 8.33 (dd, J$_1$=1.6 Hz, J$_2$=8.8 Hz, 1H), 7.23 (d, J=8.8 Hz, 1H), 6.52 (d, J=6.0 Hz, 1H), 4.20 (m, 2H), 4.03 (s, 3H), 3.20 (m, 2H), 2.87 (m, 1H), 2.58 (m, 4H), 2.06 (m, 2H), 1.85 (m, 2H), 1.64 (m, 2H). MS (ESI): m/z 350 (M+H$^+$).

133. Compound 133: (3-cyclobutyl-8-(6-(pyrrolidin-1-yl)pyridazin-3-yl)-2,3,4,5-tetrahydro-1H-benzo[4,5]imidazo[1,2-d][1,4]diazepine)

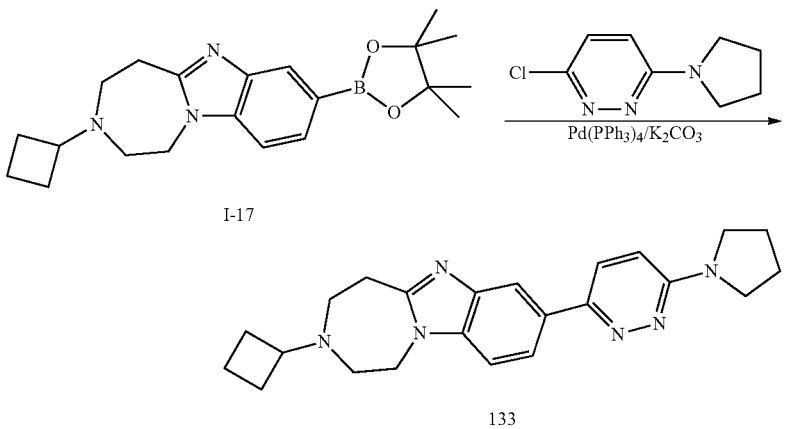

Intermediate I-17 (50 mg, 0.14 mol, 1.0 eq), 3-chloro-6-(pyrrolidin-1-yl)pyridazine (37 mg, 0.20 mmol, 1.5 eq), Pd(PPh$_3$)$_4$ (16 mg, 0.014 mmol, 0.1 eq) and potassium carbonate (56 mg, 0.41 mmol, 3.0 eq) were dissolved in a mixture of DME (1.0 mL) and water (0.5 mL) and degassed by bubbling argon. The reaction mixture was stirred at 85° C. under microwave irradiation for 70 minutes, diluted with water and extracted with ethyl acetate. The combined organic layers were dried over anhydrous Na$_2$SO$_4$, the solids were removed by filtration and the filtrate was concentrated by evaporation. The crude reaction product was purified by preparative TLC to give compound 133 (12 mg, 23%) as pale yellow solid. $^1$H-NMR (400 MHz, CDCl$_3$) δ: 8.12~8.14 (m, 2H), 7.68 (d, 1H, J=9.2 Hz), 7.33 (d, 1H, J=9.2 Hz), 6.73 (d, 1H, J=9.6 Hz), 4.25~4.27 (m, 2H), 3.59~3.62 (m, 4H), 3.25~3.28 (m, 2H), 2.91~2.95 (m, 1H), 2.61~2.67 (m, 4H), 2.11~2.14 (m, 2H), 2.04~2.09 (m, 4H), 1.89~1.94 (m, 2H), 1.50~1.76 (m, 2H). MS (ESI): m/z 389 (M+H⁺).

134. Compound 134: (3-cyclobutyl-8-(6-methoxypyridazin-3-yl)-2,3,4,5-tetrahydro-1H-benzo[4,5]imidazo[1,2-d][1,4]diazepine)

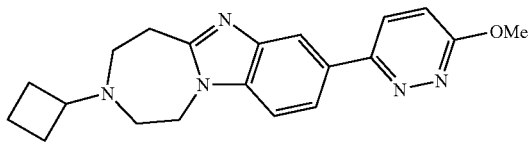

This compound was prepared in 13% yield (6 mg) as described for compound 133 but using 3-bromo-6-methoxypyridazine as the starting material. ¹H-NMR (400 MHz, CDCl₃) δ: 8.19 (d, J=1.6 Hz, 1H). 8.11 (dd, J₁=1.6 Hz, J_z=8.4 Hz, 1H), 7.85 (d, J=9.2 Hz, 1H), 7.36 (d, J=8.4 Hz, 1H), 7.06 (d, J=9.2 Hz, 1H), 4.28 (m, 2H), 4.19 (s, 3H), 3.28 (m, 2H), 2.94 (m, 1H), 2.65 (m, 4H), 2.15 (m, 2H), 1.91 (m, 2H), 1.71 (m, 2H). MS (ESI): m/z 350 (M+H⁺).

135. Compound 135: (3-cyclobutyl-8-(6-(pyrrolidin-1-yl)pyridin-2-yl)-2,3,4,5-tetrahydro-1H-benzo[4,5]imidazo[1,2-d][1,4]diazepine)

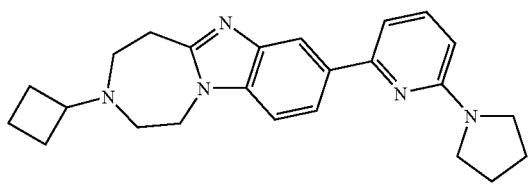

This compound was prepared in 15% yield (8 mg) as described for compound 22 but using 2-bromo-6-(pyrrolidin-1-yl)pyridine as the starting material. ¹H-NMR (400 MHz, CDCl₃) δ: 8.33 (m, 1H), 7.96 (d, 1H, J=8.8 Hz), 7.41~7.45 (m, 1H), 7.21 (m, 1H), 6.99 (d, 1H, J=7.6 Hz), 6.22 (d, 1H, J=8.0 Hz), 4.21~4.22 (m, 2H), 3.49 (m, 4H), 3.23 (m, 2H), 2.89 (m, 1H), 2.60 (m, 4H), 2.04~2.08 (m, 2H), 1.88~1.95 (m, 6H), 1.56~1.62 (m, 2H). MS (ESI): m/z 388 (M+H⁺).

136. Compound 136: (3-cyclobutyl-8-(6-(4-methylpiperazin-1-yl)pyridin-2-yl)-2,3,4,5-tetrahydro-1H-benzo[4,5]imidazo[1,2-d][1,4]diazepine)

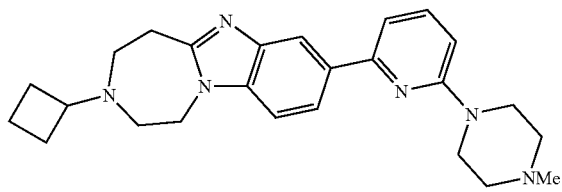

This compound was prepared in 26% yield (15 mg) as described for compound 22 but using 1-(6-bromopyridin-2-yl)-4-methylpiperazine as the starting material. ¹H-NMR (400 MHz CDCl₃) δ: 8.37 (d, 1H, J=1.2 Hz), 7.97 (dd, 1H, J₁=1.6 Hz, J₂=8.4 Hz), 7.53~7.57 (m, 1H), 7.27 (d, 1H, J=8.8 Hz), 7.16 (d, 1H, J=7.2 Hz), 6.57 (d, 1H, J=8.0 Hz), 4.24~4.26 (m, 2H), 3.68~3.70 (m, 4H), 3.24~3.27 (m, 2H), 2.91~2.93 (m, 1H), 2.61~2.67 (m, 4H), 2.55~2.58 (m, 4H), 2.37 (s, 3H), 2.10~2.14 (m, 2H), 1.89~1.94 (m, 2H), 1.65~1.76 (m, 2H). MS (ESI): m/z 417 (M+H⁺).

137. Compound 137: (3-cyclobutyl-8-(6-methoxypyridin-2-yl)-2,3,4,5-tetrahydro-1H-benzo[4,5]imidazo[1,2-d][1,4]diazepine)

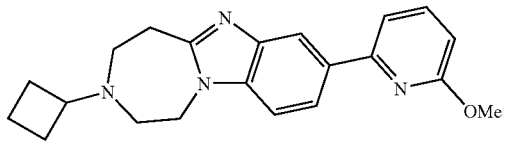

This compound was prepared in 20% yield (10 mg) as described for compound 22 but using 2-bromo-6-methoxypyridine as the starting material. ¹H-NMR (400 MHz, CDCl₃) δ: 8.19 (d, J=1.2 Hz, 1H), 8.01 (dd, J₁=1.6 Hz, J₂=8.4 Hz, 1H), 7.63 (m, 1H), 7.38 (d, J=7.6 Hz, 1H), 7.30 (d, J=8.8 Hz, 1H), 6.65 (d, J=7.6 Hz, 1H), 4.29 (m, 2H), 4.05 (s, 3H), 3.29 (m, 2H), 2.95 (m, 1H), 2.66 (m, 4H), 2.13 (m, 2H), 1.97 (m, 2H), 1.73 (m, 2H). MS (ESI): m/z 349 (M+H⁺).

138. Compound 138: (2-(3-cyclobutyl-2,3,4,5-tetrahydro-1H-benzo[4,5]imidazo[1,2-d][1,4]diazepin-8-yl)ethanamine)

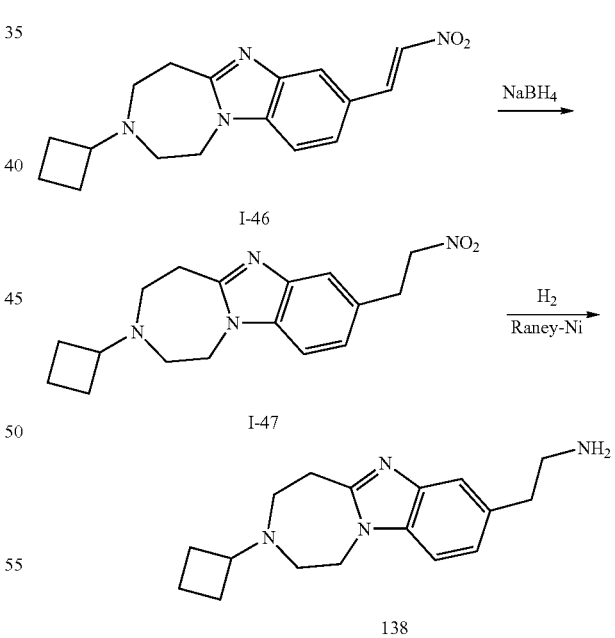

To a solution of intermediate I-46 (312 mg, 1.0 mmol, 1.0 eq) in MeOH (10 mL) was added NaBH₄ (120 mg, 3.0 mmol, 3.0 eq) and the reaction mixture was stirred at room temperature for 2 hours. The solids were removed by filtration through a short plug of Celite to give a solution of intermediate I-47 (MS (ESI): m/z 315.0 (M+H⁺)) to which an aqueous suspension of Raney Ni (300 mg) was added and the reaction mixture was stirred at room temperature under H₂ atmosphere (1 atm) for 2 hours. The solids were removed by filtration through a short plug of Celite, the filtrate was concentrated by evaporation and the crude reaction product was purified by reverse phase column chromatography to give compound 138 (140 mg, 50%) as white solid. $^1$H-NMR (400 MHz, CD$_3$OD) δ: 7.45 (t, J=8.8 Hz, 2H), 7.20 (dd, J=8.8 Hz, 1H), 4.36 (t, J=4.4 Hz, 2H), 3.23 (t, J=4.8 Hz, 2H), 2.97-3.11 (m, 5H), 2.63-2.70 (dt, J=4.8 Hz, 4H), 2.18 (m, 2H), 1.97 (m, 2H), 1.71-1.76 (m, 2H). MS (ESI): m/z 285.0 (M+H$^+$).

139. Compound 139: (2-(3-cyclobutyl-2,3,4,5-tetrahydro-1H-benzo[4,5]imidazo[1,2-d][1,4]diazepin-8-yl)-N,N-dimethylethanamine)

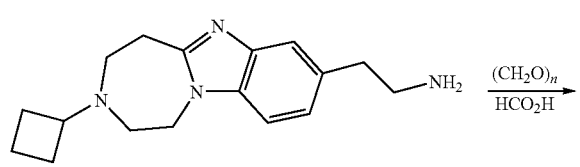

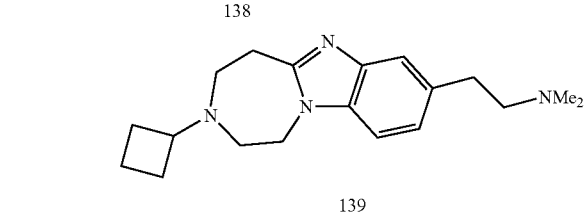

138

139

To a solution of compound 138 (20 mg, 0.07 mmol) in formic acid (3 mL) was added solid paraformaldehyde (50 mg, 1.6 mmol, 22 eq) and the reaction mixture was stirred at 50° C. for 16 hours. Excess solvent was removed by evaporation and the crude reaction product was purified by preparative TLC to give compound 139 (6 mg, 30%). $^1$H-NMR (400 MHz, CD$_3$OD) δ: 7.45 (t, J=8.8 Hz 2H), 7.20 (dd, J=8.8 Hz, 1H), 4.36 (t, J=4.4 Hz, 2H), 3.23 (t, J=4.8 Hz, 2H), 2.97-3.02 (m, 3H), 2.83 (m, 2H), 2.64-2.71 (dt, J=4.8 Hz, 4H), 2.50 (s, 6H), 2.18 (m, 2H), 1.97 (m, 2H), 1.71-1.76 (m, 2H). MS (ESI): m/z 313.0 (M+H$^+$).

140. Compound 140: ((3-cyclobutyl-2,3,4,5-tetrahydro-1H-benzo[4,5]imidazo[1,2-d][1,4]diazepin-8-yl)methanamine)

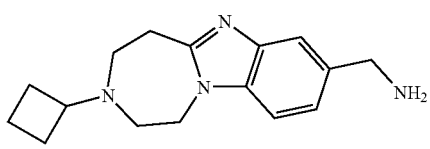

This compound was prepared in 90% yield (1.1 g) as described for compound 1 but using compound 54 as the starting material. $^1$H-NMR (400 MHz, CD$_3$OD) δ: 7.59 (s, 1H), 7.46 (d, J=8.8 Hz, 1H), 7.30 (dd, J=8.0 Hz, 1H), 4.35 (t, J=4.8 Hz, 2H), 3.99 (s, 2H), 3.21 (t, J=4.8 Hz, 2H), 3.00 (q, J=7.6 Hz, 1H), 2.62-2.69 (m, 4H), 2.12-2.18 (m, 2H), 1.92-1.97 (m, 2H), 1.69-1.77 (m, 2H). MS (ESI): m/z 271 (M+H$^+$).

141. Compound 141: (benzyl((3-cyclobutyl-2,3,4,5-tetrahydro-1H-benzo[4,5]imidazo[1,2-d][1,4]diazepin-8-yl)methyl)carbamate)

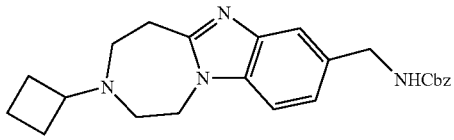

This compound was prepared in 40% yield (89 mg) as described for compound 98 but using compound 140 as the starting material. $^1$H-NMR (400 MHz, CDCl$_3$) δ: 7.59 (s, 1H), 7.30~7.37 (m, 5H), 7.21 (s, 1H), 5.12 (s, 2H), 4.49 (d, J=6.0 Hz, 2H), 4.27 (s, 2H), 3.28 (t, J=4.4 Hz, 2H), 2.97 (q, J=7.6 Hz, 11-1), 2.65 (m, 4H), 2.11-2.18 (m, 2H), 1.95~2.00 (m, 2H), 1.66~1.78 (m, 2H). MS (ESI): m/z 405 (M+H$^+$).

142. Compound 142: (benzyl((3-cyclobutyl-2,3,4,5-tetrahydro-1H-benzo[4,5]imidazo[1,2-d][1,4]diazepin-8-yl)methyl)(methyl)carbamate)

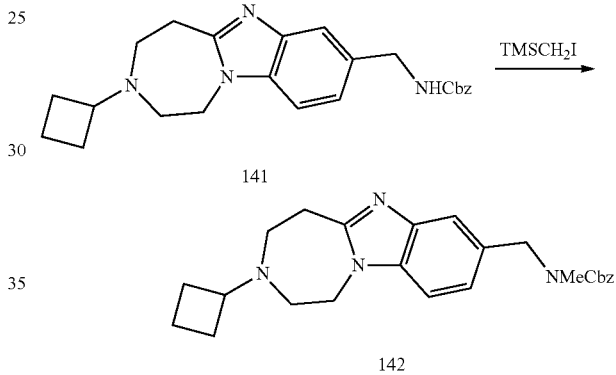

141

142

To a solution of compound 141 (122 mg, 0.30 mmol, 1.0 eq) in THF (5 mL) was added NaH (13 mg, 60% dispersion in mineral oil, 0.33 mmol, 1.1 eq) and the reaction was stirred at room temperature for 30 minutes. Neat TMSCH$_2$I (96 mg, 0.14 mmol, 4.6 eq) was added and the reaction mixture was refluxed for additional 18 hours and concentrated by evaporation. The crude reaction product was purified by C$_{18}$ reverse phase column chromatography to give compound 142 (90 mg, 71%). $^1$H-NMR (400 MHz, CDCl$_3$) δ: 7.43 (br, 1H), 7.17~7.24 (m, 5H), 7.09 (s, 1H), 5.06 (s, 2H), 4.46 (s, 2H), 4.10 (t, J=4.4 Hz, 2H), 3.11 (t, J=4.4 Hz, 2H), 2.72~2.81 (m, 4H), 2.49 (m, 4H), 1.97~2.00 (m, 2H), 1.76~1.81 (m, 2H), 1.52~1.62 (m, 2H). MS (ESI): m/z 419 (M+H$^+$).

143. Compound 143: (2-benzyl-8-cyclobutyl-7,8,9,10-tetrahydro-[1,4]diazepino[1',7':1,2]imidazo[4,5-f]isoindole-1,3(2H,6H)-dione)

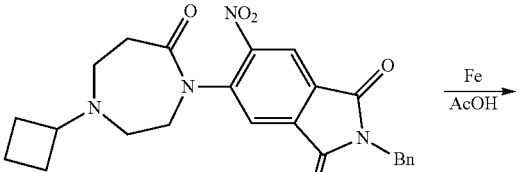

I-58

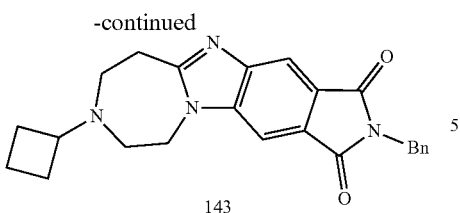

143

To a solution of intermediate I-58 (0.50 g, 1.1 mmol, 1.0 eq) in acetic acid (10 mL) was added elemental iron (0.25 g, 4.4 mmol, 4.0 eq) and the reaction mixture was stirred at 80° C. for 3 hours. The solids were removed by filtration through a short plug of Celite and the filtrate was concentrated by evaporation. The residue was dissolved with dichloromethane and pH was adjusted to neutral by adding an aqueous solution of $Na_2CO_3$ and the crude reaction mixture was extracted with dichloromethane. The combined organic layers were dried over anhydrous $MgSO_4$, the solids were removed by filtration and the filtrate was concentrated by evaporation. The crude reaction product was purified by silica gel column chromatography to give compound 143 (200 mg, 48%). $^1$H-NMR (400 MHz, $CDCl_3$) δ: 8.10 (s, 1H), 7.73 (s, 1H), 7.45 (d, J=7.6 Hz, 2H), 7.32 (t, J=7.2 Hz, 3H), 4.87 (s, 2H), 4.32 (s, 2H), 3.30 (s, 2H), 2.94 (t, J=4.4 Hz, 1H), 2.65 (m, 4H), 2.13~2.18 (m, 2H), 1.89~1.93 (m, 2H), 1.66~1.77 (m, 2H). MS (ESI): m/z 401.0 (M+H$^+$).

144. Compound 144: (2-benzyl-8-cyclobutyl-1,2,3,6,7,8,9,10-octahydro-[1,4]diazepino[1',7':1,2]imidazo[4,5-f]isoindole)

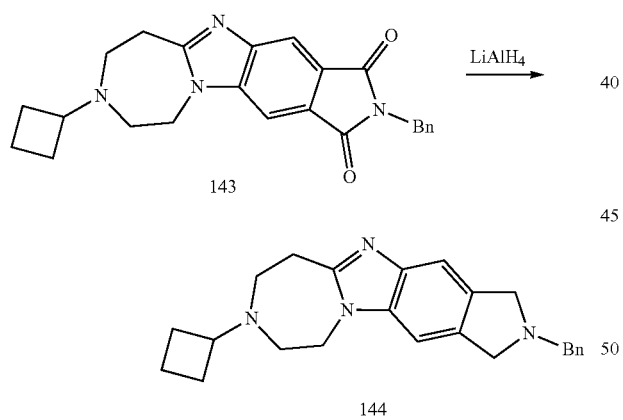

To a solution of compound 143 (1.3 g, 3.2 mmol, 1.0 eq) in THF (10 mL) was added drop wise a suspension of LiAlH$_4$ (350 mg, 9.6 mmol, 3.0 eq) in dry THF (20 mL) and the reaction mixture was refluxed for 3 hours. The reaction was quenched by adding a saturated aqueous solution of $Na_2SO_4$. The crude reaction mixture was extracted with dichloromethane, the combined organic layers were dried over anhydrous $MgSO_4$, the solids were removed by filtration and the filtrate was concentrated by evaporation to give compound 144 (850 mg, 70%). $^1$H-NMR (400 MHz, $CDCl_3$) δ: 7.44 (d, J=9.2 Hz, 3H), 7.36 (t, J=7.6 Hz, 2H), 7.30 (d, J=7.6 Hz, 1H), 7.02 (s, 1H), 4.18 (t, J=4.8 Hz, 2H), 4.02 (s, 4H), 3.95 (s, 2H), 3.21 (t, J=4.8 Hz, 2H), 2.94 (q, J=4.0 Hz, 1H), 2.58~2.63 (m, 4H), 2.09~2.17 (m, 2H), 1.88~1.93 (m, 2H), 1.64~1.75 (m, 2H). MS (ESI): m/z 373 (M+H$^+$).

145. Compound 145: (8-cyclobutyl-1,2,3,6,7,8,9,10-octahydro-[1,4]diazepino[1',7':1,2]imidazo[4,5-f]isoindole)

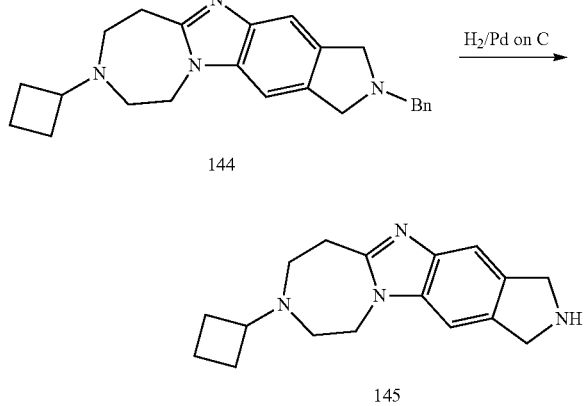

To a solution of compound 144 (400 mg, 1.1 mmol, 1.0 eq) in acetic acid (10 mL) was added palladium on carbon (0.30 g, 0.08 eq) and the reaction mixture was stirred at room temperature under H$_2$ atmosphere (1 atm) for 16 hours. The solids were removed by filtration through a short plug of Celite and the filtrate was concentrated by evaporation. The crude reaction product was purified reverse phase column chromatography to give compound 145 (150 mg, 50%). $^1$H-NMR (400 MHz, $CD_3OD$) δ: 7.59 (s, 1H), 7.54 (s, 1H), 4.66 (s, 4H), 4.38 (t, J=4.4 Hz, 2H), 3.24 (s, 2H), 3.01 (q, J=4.4 Hz, 11-1), 2.66~2.71 (m, 4H), 2.14~2.20 (m, 2H), 1.94~2.05 (m, 2H), 1.70~1.78 (m, 2H). MS (ESI): m/z 284 (M+H$^+$).

146. Compound 146: (8-cyclobutyl-2-methyl-1,2,3,6,7,8,9,10-octahydro-[1,4]diazepino[1',7':1,2]imidazo[4,5-f]isoindole)

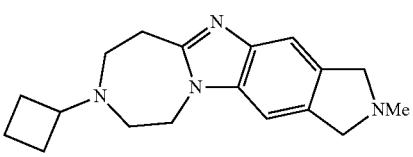

This compound was prepared in 33% yield (7 mg) as described for compound 139 but using compound 145 as the starting material. $^1$H-NMR (400 MHz, $CDCl_3$) δ: 7.49 (s, 1H), 7.08 (s, 1H), 4.20 (t, J=4.4 Hz, 2H), 4.15 (s, 4H), 3.22 (t, J=4.4 Hz, 2H), 2.92 (q, J=4.4 Hz, 1H), 2.72 (s, 3H), 2.58-2.63 (m, 4H), 2.10-2.13 (m, 2H), 1.88-1.94 (m, 2H), 1.65-1.73 (m, 2H). MS (ESI): m/z 297.0 (M+H$^+$).

147. Compound 147: (8-cyclobutyl-2-(cyclopropyl-methyl)-1,2,3,6,7,8,9,10-octahydro-[1,4]diazepino[1',7':1,2]imidazo[4,5-f]isoindole)

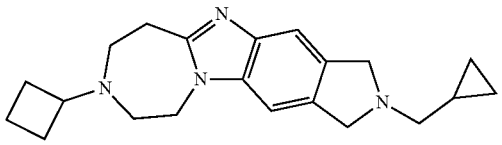

This compound was prepared in 30% yield (6 mg) as described for compound 8 but using compound 145 and cyclopropanecarbaldehyde as the starting materials. $^1$H-NMR (400 MHz, CDCl$_3$) δ: 7.50 (s, 1H), 7.08 (s, 1H), 4.19 (s, 6H), 3.23 (t, J=4.4 Hz, 2H), 2.92 (q, J=4.4 Hz, 1H), 2.73 (d, J=6.4 Hz, 2H), 2.59-2.64 (m, 4H), 2.09-2.15 (m, 2H), 1.86-1.98 (m, 2H), 1.62-1.78 (m, 2H), 1.08-1.11 (m, 1H), 0.60 (m, 2H), 0.28 (m, 2H). MS (ESI): m/z 337.1 (M+H$^+$).

148. Compound 148: (8-cyclobutyl-2-(pyrimidin-2-yl)-1,2,3,6,7,8,9,10-octahydro-[1,4]diazepino[1',7':1,2]imidazo[4,5-f]isoindole)

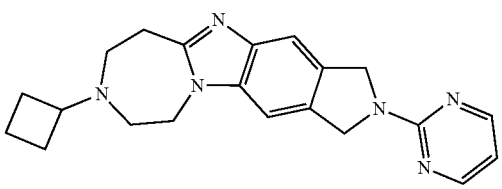

This compound was prepared in 27% yield (10 mg) as described for compound 65 but using compound 145 and 2-bromopyrimidine as the starting materials. $^1$H-NMR (400 MHz, CDCl$_3$) δ: 8.41 (s, 1H), 8.40 (s, 1H), 7.60 (s, 1H), 7.18 (s, 1H), 6.57 (t, J=4.8 Hz, 1H), 5.01 (s, 4H), 4.25 (t, J=4.4 Hz, 2H), 3.26 (t, J=4.4 Hz, 2H), 2.94 (q, J=4.4 Hz, 1H), 2.61-2.67 (m, 4H), 2.10-2.17 (m, 2H), 1.88-1.96 (m, 2H), 1.72-1.79 (m, 2H). MS (ESI): m/z 361.1 (M+H$^+$).

149. Compound 149: (8-cyclobutyl-2-(pyrazin-2-yl)-1,2,3,6,7,8,9,10-octahydro-[1,4]diazepino[1',7':1,2]imidazo[4,5-f]isoindole)

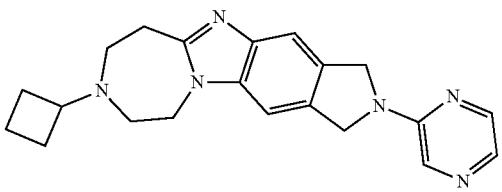

This compound was prepared in 25% yield (10 mg) as described for compound 65 but using compound 145 and 2-iodopyrazine as the starting materials. $^1$H-NMR (400 MHz, CDCl$_3$) δ: 8.13 (s, 1H), 8.05 (s, 1H), 7.88 (d, J=2.4 Hz, 1H), 7.63 (s, 1H), 7.20 (s, 1H), 4.95 (s, 4H), 4.25 (t, J=4.4 Hz, 2H), 3.26 (t, J=4.4 Hz, 2H), 2.94 (q, J=4.4 Hz, 1H), 2.62~2.68 (m, 4H), 2.11~2.17 (m, 2H), 1.89~1.96 (m, 2H), 1.66~1.77 (m, 2H). MS (ESI): m/z 361.1 (M+H$^+$).

150. Compound 150: (3-cyclobutyl-8-(1H-1,2,3-triazol-1-yl)-2,3,4,5-tetrahydro-1H-benzo[4,5]imidazo[1,2-d][1,4]diazepine)

151. Compound 151: (3-cyclobutyl-8-(2H-1,2,3-triazol-2-yl)-2,3,4,5-tetrahydro-1H-benzo[4,5]imidazo[1,2-d][1,4]diazepine)

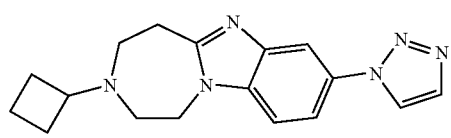

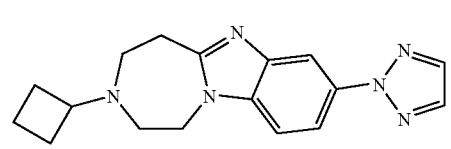

Compound 150 was prepared in 40% yield (150 mg) and compound 151 was prepared in 10% yield (38 mg) by reverse phase preparative HPLC separation of a mixture of regioisomers prepared as described for compound 66 but using 1,2,3-triazole as the starting material.

Compound 150: $^1$H-NMR (400 MHz, CD$_3$OD) δ: 8.57 (d, 1H, J=0.8 Hz), 8.03 (d, 1H, J=2.4 Hz), 7.94 (d, 1H, J=1.2 Hz), 7.80 (m, 1H), 7.70 (d, 1H, J=8.8 Hz), 4.45 (m, 2H), 3.30 (m, 2H), 3.05 (m, 1H), 2.71 (m, 4H), 2.21 (m, 2H), 1.99 (m, 2H), 1.78 (m, 2H). MS (ESI): m/z 309.2 (M+H$^+$).

Compound 151: $^1$H-NMR (400 MHz, CD$_3$OD) δ: 8.22 (d, 1H, J=2.0 Hz), 8.03 (m, 1H), 7.91 (s, 2H), 7.60 (m, 1H), 4.40 (m, 2H), 3.25 (m, 2H), 3.02 (m, 1H), 2.71 (m, 4H), 2.16 (m, 2H), 1.98 (m, 2H), 1.72 (m, 2H). MS (ESI): m/z 309.2 (M+H$^+$).

152. Compound 152: (3-cyclobutyl-8-(1H-1,2,4-triazol-1-yl)-2,3,4,5-tetrahydro-1H-benzo[4,5]imidazo[1,2-d][1,4]diazepine)

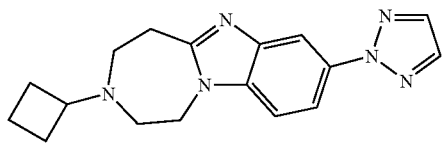

This compound was prepared in 40% yield (77 mg) as described for compound 66 but using 1,2,4-triazole as the starting material. $^1$H-NMR (400 MHz, CD$_3$OD) δ: 9.08 (s, 1H), 8.17 (s, 1H), 7.98 (d, 1H, J=2.0 Hz), 7.74 (m, 1H), 7.65 (d, 1H, J=8.8 Hz), 4.42 (m, 2H), 3.25 (m, 2H), 3.02 (m, 1H), 2.70 (m, 4H), 2.16 (m, 2H), 1.96 (m, 2H), 1.72 (m, 2H). MS (ESI): m/z 309.2 (M+H$^+$).

153. Compound 153: (3-cyclobutyl-8-(2-methyl-1H-imidazol-1-yl)-2,3,4,5-tetrahydro-1H-benzo[4,5]imidazo[1,2-d][1,4]diazepine)

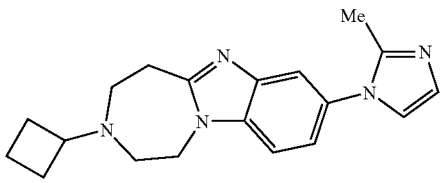

This compound was prepared in 30% yield (60 mg) as described for compound 66 but using 2-methyl-1H-imidazole as the starting material. $^1$H-NMR (400 MHz, CDCl$_3$) δ: 7.60 (d, 1H, J=1.6 Hz), 7.31 (m, 1H), 7.16 (m, 1H), 7.03 (s, 2H), 4.29 (m, 2H), 3.28 (m, 2H), 2.95 (m, 1H), 2.65 (m, 4H), 2.34 (s, 3H), 2.13 (m, 2H), 1.92 (m, 2H), 1.74 (m, 2H). MS (ESI): m/z 322.2 (M+H$^+$).

154. Compound 154: (3-cyclobutyl-8-(1H-tetrazol-1-yl)-2,3,4,5-tetrahydro-1H-benzo[4,5]imidazo[1,2-d][1,4]diazepine)

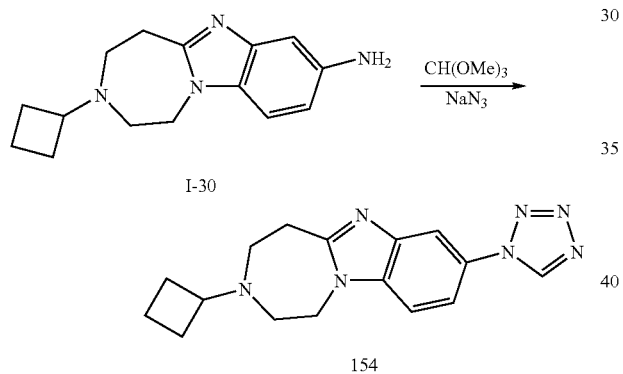

To a solution of intermediate I-30 (100 mg, 0.39 mmol, 1.0 eq) and trimethoxymethane (62 mg, 0.59 mmol, 1.5 eq) in acetic acid (5 mL) was added NaN$_3$ (40 mg, 0.59 mmole, 1.5 eq) and the reaction mixture was stirred at 100° C. for 16 hours. An aqueous saturated solution of NaHCO$_3$ was added and the pH was adjusted to ~8. The crude reaction mixture was extracted with dichloromethane, the combined organic layers were dried over anhydrous MgSO$_4$, the solids were removed by filtration and the filtrate was concentrated by evaporation. The crude reaction product was purified by silica gel column chromatography to give compound 154 (72 mg, 60%). $^1$H-NMR (400 MHz, DMSO-d$_6$) δ: 10.07 (s, 1H), 8.07 (d, 1H, J=2.0 Hz), 7.73 (m, 2H), 4.39 (m, 2H), 3.19 (m, 2H), 2.95 (m, 1H), 2.58 (m, 4H), 2.06 (m, 2H), 1.82 (m, 2H), 1.61 (m, 2H). MS (ESI): m/z 310.1 (M+H$^+$).

155. Compound 155: (mixture of 3-cyclobutyl-8-(5-methyl-1H-imidazol-1-yl)-2,3,4,5-tetrahydro-1H-benzo[4,5]imidazo[1,2-d][1,4]diazepine and 3-cyclobutyl-8-(4-methyl-1H-imidazol-1-yl)-2,3,4,5-tetrahydro-1H-benzo[4,5]imidazo[1,2-d][1,4]diazepine)

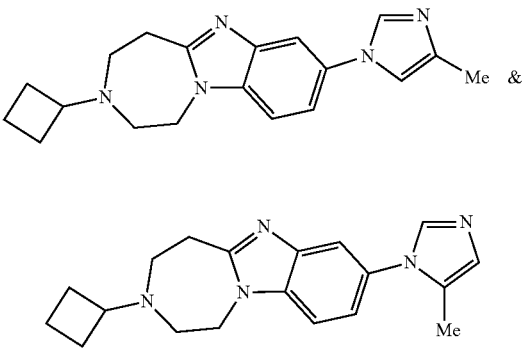

This compound was prepared in 40% yield (40 mg) as described for compound 66 but using 4-methyl-1H-imidazole as the starting material. $^1$H-NMR (400 MHz, CD$_3$OD) δ: 8.11 (s, 1H), 7.69 (d, 1H, J=2.4 Hz), 7.59 (d, 1H, J=9.2 Hz), 7.45 (m, 1H), 7.33 (s, 1H), 4.43 (m, 2H), 3.26 (m, 2H), 3.05 (m, 1H), 2.75 (m, 4H), 2.28 (s, 3H), 2.17 (m, 2H), 1.99 (m, 2H), 1.78 (m, 2H). MS (ESI): m/z 322.2 (M+H$^+$).

156. Compound 156: (3-cyclobutyl-8-(5-methyl-1H-tetrazol-1-yl)-2,3,4,5-tetrahydro-1H-benzo[4,5]imidazo[1,2-d][1,4]diazepine)

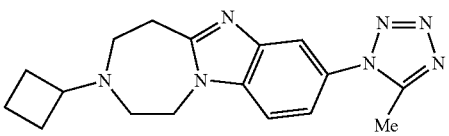

This compound was prepared in 50% yield (60 mg) as described for compound 154 but using 1,1,1-trimethoxyethane as the starting material. $^1$H-NMR (400 MHz, CD$_3$OD) δ: 7.71 (d, 1H, J=2.0 Hz), 7.42 (d, 1H, J=8.4 Hz), 7.33 (m, 1H), 4.36 (m, 2H), 3.33 (m, 2H), 2.98 (m, 1H), 2.73 (m, 4H), 2.59 (s, 3H), 2.15 (m, 2H), 1.97 (m, 2H), 1.70 (m, 2H). MS (ESI): m/z 324.2 (M+H$^+$).

157. Compound 157: (3-cyclobutyl-8-(3-methyl-4H-1,2,4-triazol-4-yl)-2,3,4,5-tetrahydro-1H-benzo[4,5]imidazo[1,2-d][1,4]diazepine)

AcNHNH$_2$ + (MeO)$_2$CHNMe$_2$

↓

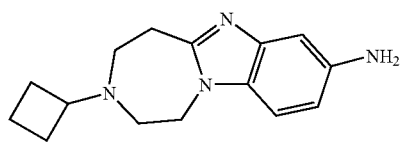 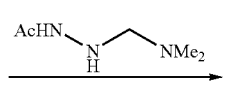 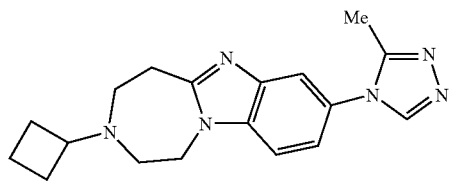

I-30 → 157

To a solution of (MeO)₂CHNMe₂ (70 mg, 0.59 mmol, 1.5 eq) in acetonitrile (5 mL) was added AcNHNH₂ (44 mg, 0.59 mmol, 1.0 eq) and the reaction mixture was stirred at 50° C. for 30 minutes. Acetic acid (100 mg, 1.6 mmol, 4.0 eq) and intermediate 1-30 (100 mg, 0.39 mmol, 1.0 eq) were added and the reaction mixture was stirred at 120° C. for additional 2 hours. The crude reaction mixture was concentrated by evaporation and the crude reaction product was purified by silica gel column chromatography to give compound 157 (69 mg, 55%). $^1$H-NMR (400 MHz, CD₃OD) δ: 8.63 (s, 1H), 7.69 (m, 2H), 7.34 (m, 1H), 4.44 (m, 2H), 3.29 (m, 2H), 3.03 (m, 1H), 2.69 (m, 4H), 2.40 (s, 3H), 2.18 (m, 2H), 1.97 (m, 2H), 1.76 (m, 2H). MS (ESI): m/z 323.2 (M+H⁺).

158. Compound 158: (mixture of 3-cyclobutyl-8-(2,4-dimethyl-1H-imidazol-1-yl)-2,3,4,5-tetrahydro-1H-benzo[4,5]imidazo[1,2-d][1,4]diazepine and 3-cyclobutyl-8-(2,5-dimethyl-1H-imidazol-1-yl)-2,3,4,5-tetrahydro-1H-benzo[4,5]imidazo[1,2-d][1,4]diazepine)

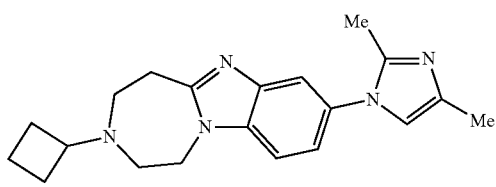

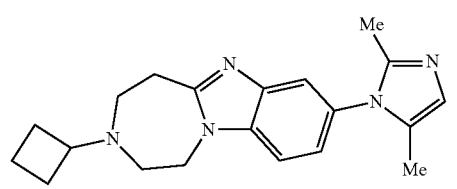

This compound was prepared in 30% yield (63 mg) as described for compound 66 but using 2,4-dimethyl-1H-imidazole as the starting material. $^1$H-NMR (400 MHz, CD₃OD) δ: 7.60 (m, 1H), 7.55 (m, 1H), 7.27 (m, 1H), 6.94 (s, 1H), 4.43 (m, 2H), 3.25 (m, 2H), 3.02 (m, 1H), 2.70 (m, 4H), 2.27 (s, 3H), 2.22 (s, 3H), 2.16 (m, 2H), 1.96 (m, 2H), 1.72 (m, 2H). MS (ESI): m/z 336.2 (M+H⁺).

159. Compound 159: (3-cyclobutyl-8-((4-fluoropiperidin-1-yl)methyl)-2,3,4,5-tetrahydro-1H-benzo[4,5]imidazo[1,2-d][1,4]diazepine)

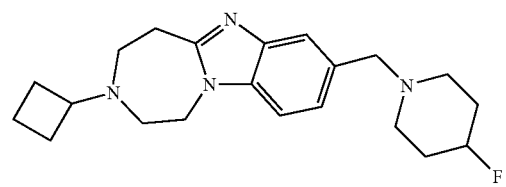

This compound was prepared in 40% yield (27 mg) as described for compound 74 but using 4-fluoropiperidine as the starting material. $^1$H-NMR (400 MHz, CD₃OD): δ 7.54 (s, 1H), 7.42 (d, 1H, J=8.4 Hz), 7.27 (dd, 1H, J₁=8.4 Hz, J₂=1.6 Hz), 4.65 (m, 1H), 4.34 (m, 2H), 3.655 (s, 2H), 3.30 (m, 2H), 3.00 (m, 1H), 2.65 (m, 6H), 2.45 (m, 2H), 2.15 (m, 2H), 1.60 (m, 8H). MS (ESI): m/z 357.2 (M+H⁺).

160. Compound 160: (3-cyclobutyl-8-((4,4-difluoropiperidin-1-yl)methyl)-2,3,4,5-tetrahydro-1H-benzo[4,5]imidazo[1,2-d][1,4]diazepine)

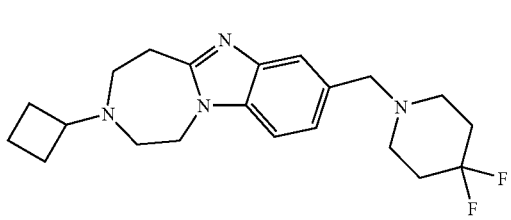

This compound was prepared in 43% yield (39 mg) as described for compound 74 but using 4,4-difluoropiperidine as the starting material. $^1$H-NMR (400 MHz, CDCl₃) δ: 7.53 (s, 1H), 7.14 (m, 2H), 4.15 (m, 2H), 3.59 (s, 2H), 3.16 (m, 2H), 2.85 (m, 1H), 2.55 (m, 8H), 2.05 (m, 2H), 1.88 (m, 6H), 1.65 (m, 2H). MS (ESI): m/z 375.2 (M+H⁺).

161. Compound 161: (3-cyclobutyl-8-((3-fluoropiperidin-1-yl)methyl)-2,3,4,5-tetrahydro-1H-benzo[4,5]imidazo[1,2-d][1,4]diazepine)

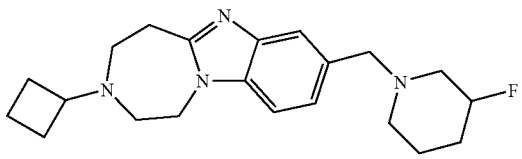

This compound was prepared in 34% yield (27 mg) as described for compound 74 but using 3-fluoropiperidine as the starting material. ¹HNMR (400 MHz, CDCl₃) δ: 7.58 (s, 1H), 7.20 (m, 2H), 4.60 (m, 1H), 4.22 (m, 2H), 3.69 (s, 2H), 3.24 (m, 2H), 2.92 (m, 1H), 2.80 (m, 1H,), 2.63 (m, 4H), 2.50 (m, 1H), 2.30 (m, 2H), 2.13 (m, 2H), 1.50-1.95 (m, 8H). MS (ESI): m/z 357.2 (MAT).

162. Compound 162: (3-cyclobutyl-8-((3,3-difluoropiperidin-1-yl)methyl)-2,3,4,5-tetrahydro-1H-benzo[4,5]imidazo[1,2-d][1,4]diazepine)

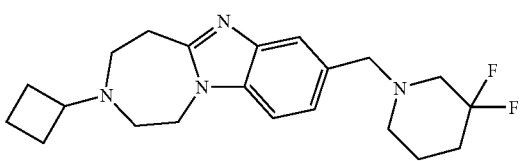

This compound was prepared in 59% yield (53 mg) as described for compound 74 but using 3,3-difluoropiperidine as the starting material. ¹H-NMR (400 MHz, CDCl₃) δ: 7.53 (s, 1H), 7.39 (d, 1H, J=8.4 Hz), 7.24 (dd, 1H, J₁=8.4 Hz, J₂=1.6 Hz), 4.30 (m, 2H), 3.66 (s, 2H), 3.30 (m, 2H), 3.00 (m, 1H), 2.65 (m, 6H), 2.45 (m, 2H), 2.15 (m, 2H). MS (ESI): m/z 375.2 (M+H⁺).

163. Compound 163: (3-cyclobutyl-8-((3,4-dihydroisoquinolin-2(1H)-yl)methyl)-2,3,4,5-tetrahydro-1H-benzo[4,5]imidazo[1,2-d][1,4]diazepine)

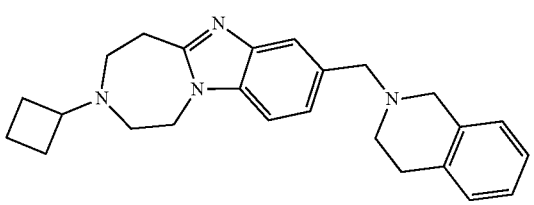

This compound was prepared in 43% yield (40 mg) as described for compound 74 but using 1,2,3,4-tetrahydroisoquinoline as the starting material. ¹HNMR (400 MHz, CD₃OD) δ: 7.61 (d, 1H, J=1.2 Hz), 7.44 (d, 1H, J=8.4 Hz), 7.33 (dd, 1H, J₁=8.0 Hz, J₂=1.2 Hz), 7.07 (m, 3H), 6.94 (d, 1H, J=6.8 Hz), 4.33 (m, 2H), 3.81 (s, 2H), 3.63 (s, 2H), 3.31 (m, 2H), 2.97 (m, 1H), 2.87 (m, 2H), 2.76 (m, 2H), 2.61 (m, 4H), 2.14 (m, 2H), 1.94 (m, 2H), 1.72 (m, 2H). MS (ESI): m/z 387.3 (M+H⁺).

164. Compound 164: (3-cyclobutyl-8-((6-fluoro-3,4-dihydroisoquinolin-2(1H)-yl)methyl)-2,3,4,5-tetrahydro-1H-benzo[4,5]imidazo[1,2-d][1,4]diazepine)

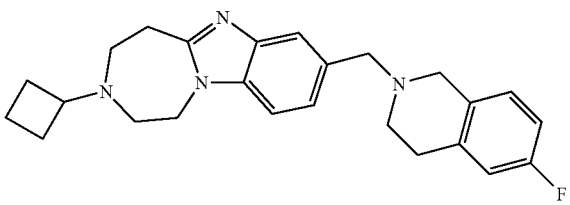

This compound was prepared in 54% yield (52 mg) as described for compound 74 but using 6-fluoro-1,2,3,4-tetrahydroisoquinoline as the starting material. ¹H-NMR (400 Hz, CD₃OD): δ 7.61 (s, 1H), 7.43 (d, 1H, J=8.0 Hz), 7.27 (dd, 1H, J₁=8.4 Hz, J₂=1.6 Hz), 6.95 (m, 1H), 6.81 (m, 2H), 4.33 (m, 2H), 3.79 (s, 2H), 3.57 (s, 2H), 3.20 (m, 2H), 2.95 (m, 1H), 2.87 (m, 2H), 2.74 (m, 2H), 2.61 (m, 4H), 2.13 (m, 2H), 1.93 (m, 2H), 1.75 (m, 2H). MS (ESI): m/z 405.2 (M+H⁺).

165. Compound 165: (3-cyclobutyl-8-((3-fluoropyrrolidin-1-yl)methyl)-2,3,4,5-tetrahydro-1H-benzo[4,5]imidazo[1,2-d][1,4]diazepine)

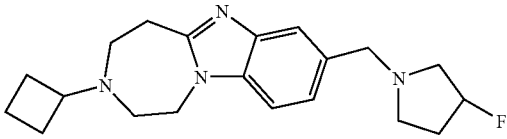

This compound was prepared in 61% yield (51 mg) as described for compound 74 but using 3-fluoropyrrolidine as the starting material. ¹H-NMR (400 MHz, CD₃OD) δ: 7.55 (d, 1H, J=1.2 Hz), 7.41 (d, 1H, J=8.4 Hz), 7.29 (dd, 1H, J₁=8.4 Hz, J₂=1.2 Hz), 5.18 (m, 1H), 4.34 (m, 2H), 3.77 (dd, 2H, J₁=36 Hz, J₂=12.4 Hz), 3.20 (m, 2H), 2.90 (m, 3H), 2.65 (m, 5I-1), 2.48 (m, 1H), 2.10 (m, 6H), 1.70 (m, 2H). MS (ESI): m/z 343.2 (M+H⁺).

166. Compound 166: (3-cyclobutyl-8-((3,3-difluoropyrrolidin-1-yl)methyl)-2,3,4,5-tetrahydro-1H-benzo[4,5]imidazo[1,2-d][1,4]diazepine)

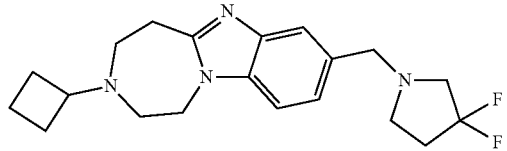

This compound was prepared in 26% yield (23 mg) as described for compound 74 but using 3,3-difluoropyrrolidine as the starting material. ¹H-NMR (400 MHz, D₂O): δ 7.95 (s, 1H), 7.89 (d, 1H, J=8.8 Hz), 7.71 (d, 1H, J=8.8 Hz), 4.85 (br, 2H), 4.67 (s, 2H), 3.88 (m, 4H), 3.70 (m, 7H), 2.66 (m, 2H), 2.30 (m, 4H), 1.80 (m, 2H). MS (ESI): m/z 361.3 (M+H⁺).

167. Compound 167: (1-(4-(3-cyclobutyl-2,3,4,5-tetrahydro-1H-benzo[4,5]imidazo[1,2-d][1,4]diazepin-8-yl)piperazin-1-yl)ethanone)

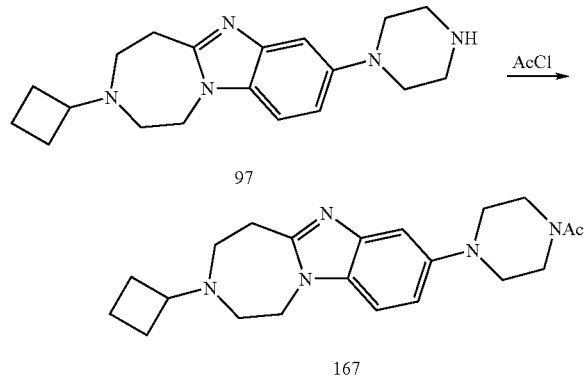

To a solution of compound 97 (100 mg, 0.31 mmol, 1.0 eq) in dichloromethane was added neat triethylamine (79 mg, 0.77 mmol, 2.5 eq) followed by drop wise addition of acetyl chloride (49 mg, 0.62 mmol, 2.0 eq) at 0° C. and the reaction mixture was stirred at room temperature for 2 hours. The reaction was quenched by adding methanol and the reaction mixture was concentrated by evaporation. The crude reaction product was purified by reverse phase silica gel column chromatography to give compound 167 (40 mg, 30%). ¹H-NMR (400 MHz, CDCl₃) δ: 7.23 (d, 1H, J=1.6 Hz), 7.16 (d, 1H, J=8.8 Hz), 7.00 (m, 1H), 4.19 (m, 2H), 3.80 (m, 2H), 3.65 (m, 2H), 3.21 (m, 2H), 3.13 (m, 4H), 2.91 (m, 1H), 2.60 (m, 4H), 2.13 (m, 5H), 1.90 (m, 2H), 1.68 (m, 2H). MS (ESI): m/z 368.2 (M+H⁺).

168. Compound 168: (4-(4-(3-cyclobutyl-2,3,4,5-tetrahydro-1H-benzo[4,5]imidazo[1,2-d][1,4]diazepin-8-yl)piperazine-1-carbonyl)benzonitrile)

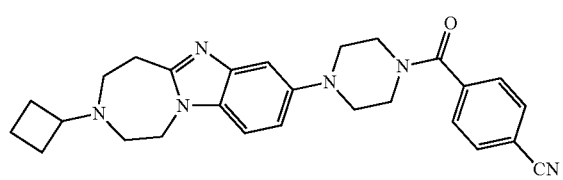

This compound was prepared in 70% yield (95 mg) as described for compound 167 but using 4-cyanobenzoyl chloride as the starting material. ¹H-NMR (400 MHz, CDCl₃) δ: 7.74 (m, 2H), 7.56 (m, 2H), 7.23 (d, 1H, J=2.4 Hz), 7.17 (d, 1H, J=8.8 Hz), 6.99 (m, 1H), 4.20 (m, 2H), 3.98 (m, 2H), 3.56 (m, 2H), 3.22 (m, 4H), 3.08 (m, 2H), 2.92 (m, 1H), 2.62 (m, 4H), 2.12 (m, 2H), 1.90 (m, 2H), 1.72 (m, 2H). MS (ESI): m/z 455.2 (M+H⁺).

169. Compound 169: 44-(3-cyclobutyl-2,3,4,5-tetrahydro-1H-benzo[4,5]imidazo[1,2-d][1,4]diazepin-8-yl)piperazin-1-yl)(pyrazin-2-yl)methanone)

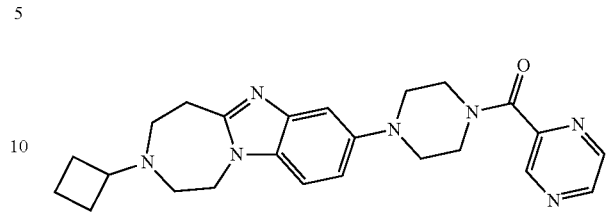

This compound was prepared in 30% yield (40 mg) as described for compound 167 but using pyrazine-2-carbonyl chloride as the starting material. ¹H-NMR (400 MHz, CDCl₃) δ: 9.00 (d, 1H, J=1.6 Hz), 8.66 (d, 1H, J=2.0 Hz), 8.58 (m, 1H), 7.26 (s, 1H), 7.17 (d, 1H, J=8.8 Hz), 7.02 (m, 1H), 4.21 (m, 2H), 4.02 (m, 2H), 3.84 (m, 2H), 3.26 (m, 4H), 3.17 (m, 2H), 2.93 (m, 1H), 2.64 (m, 4H), 2.12 (m, 2H), 1.93 (m, 2H), 1.73 (m, 2H). MS (ESI): m/z 432.2 (M+H⁺).

170. Compound 170: 44-(3-cyclobutyl-2,3,4,5-tetrahydro-1H-benzo[4,5]imidazo[1,2-d][1,4]diazepin-8-yl)piperazin-1-yl)(cyclopropyl)methanone)

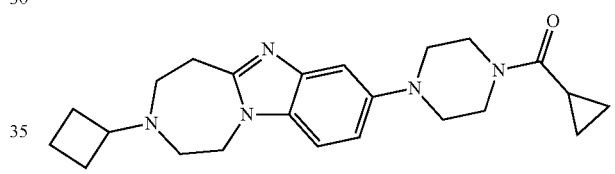

This compound was prepared in 50% yield (60 mg) as described for compound 167 but using cyclopropanecarbonyl chloride as the starting material. ¹H-NMR (400 MHz, CDCl₃) δ: 7.32 (m, 2H), 7.16 (d, 1H, J=8.2 Hz), 4.65 (m, 2H), 3.76 (m, 4H), 3.53 (m, 2H), 3.30 (m, 2H), 3.12 (m, 8H), 2.36 (m, 4H), 2.25 (m, 4H), 2.03 (m, 1H), 1.89 (m, 2H), 1.74 (m, 1H). MS (ESI): m/z 408.2 (M+H⁺).

171. Compound 171: (1-(3-(3-cyclobutyl-2,3,4,5-tetrahydro-1H-benzo[4,5]imidazo[1,2-d][1,4]diazepin-8-yl)piperidin-1-yl)ethanone)

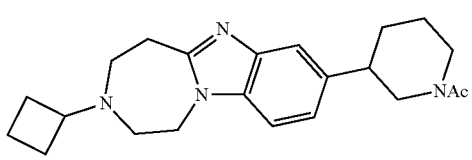

This compound was prepared in 80% yield (36 mg) as described for compound 167 but using compound I-45 as the starting material. ¹H-NMR (400 MHz, CDCl₃) δ: 7.54 (s, 1H), 7.10-7.23 (m, 2H), 4.77 (m, 1H), 4.21 (m, 2H), 3.87 (m, 1H), 3.24 (m, 2H), 3.10 (m, 1H), 2.91 (m, 1H), 2.79 (m, 1H), 2.60 (m, 5H), 2.11 (m, 6H), 1.57-1.93 (m, 7H). MS (ESI): m/z 367.2 (M+H⁺).

172. Compound 172: (4-(3-(3-cyclobutyl-2,3,4,5-tetrahydro-1H-benzo[4,5]imidazo[1,2-d][1,4]diazepin-8-yl)piperidine-1-carbonyl)benzonitrile)

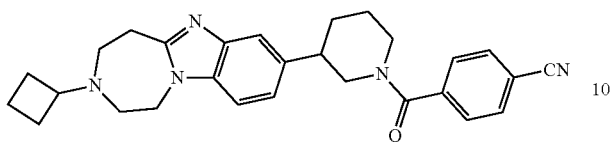

This compound was prepared in 70% yield (38 mg) as described for compound 168 but using compound I-45 as the starting material. $^1$H-NMR (400 MHz, CDCl$_3$) δ: 7.66-7.74 (m, 2H), 7.41-7.59 (m, 3H), 7.20 (m, 1H), 6.95-7.16 (m, 1H), 4.83 (m, 1H), 4.22 (m, 2H), 3.68 (m, 1H), 3.27 (m, 2H), 2.79-3.12 (m, 4H), 2.63 (m, 4H), 2.13 (m, 3H), 1.62-2.02 (m, 7H). MS (ESI): m/z 454.2 (M+H$^+$).

173. Compound 173: ((3-(3-cyclobutyl-2,3,4,5-tetrahydro-1H-benzo[4,5]imidazo[1,2-d][1,4]diazepin-8-yl)piperidin-1-yl)(pyrazin-2-yl)methanone)

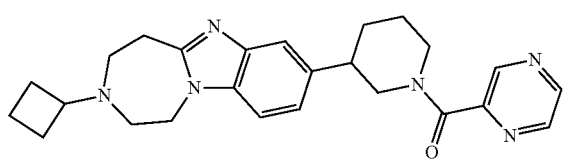

This compound was prepared in 50% yield (26 mg) as described for compound 169 but using compound I-45 as the starting material. $^1$H-NMR (400 MHz, CDCl$_3$) δ: 8.91 (d, 1H, J=11.6 Hz), 8.59 (m, 2H), 7.50-7.60 (m, 1H), 7.08-7.22 (m, 2H), 4.90 (m, 1H), 4.23 (m, 2H), 4.00 (m, 1H), 2.89-3.26 (m, 6H), 2.63 (m, 4H), 2.15 (m, 3H), 1.65-2.00 (m, 7H). MS (ESI): m/z 431.2 (M+H$^+$).

174. Compound 174: ((3-(3-cyclobutyl-2,3,4,5-tetrahydro-1H-benzo[4,5]imidazo[1,2-d][1,4]diazepin-8-yl)piperidin-1-yl)(pyrazin-2-yl)methanone)

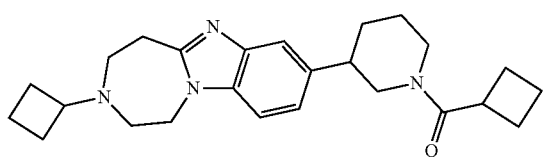

This compound was prepared in 55% yield (28 mg) as described for compound 167 but using compound I-45 and cyclobutanecarbonyl chloride as the starting materials. $^1$H-NMR (400 MHz, CDCl$_3$) δ: 7.50 (d, 1H, J=3.6 Hz), 7.07-7.21 (m, 2H), 4.75 (m, 1H), 4.22 (m, 2H), 3.76 (d, 1H, J=12.4 Hz), 3.25 (m, 3H), 2.95 (m, 2H), 2.65 (m, 6H), 2.38 (m, 2H), 2.19 (m, 5H), 1.55-2.00 (m, 9H). MS (ESI): m/z 407.2 (M+H$^+$).

175. Compound 175: (3-cyclobutyl-8-(piperidin-1-yl)-2,3,4,5-tetrahydro-1H-benzo[4,5]imidazo[1,2-d][1,4]diazepine)

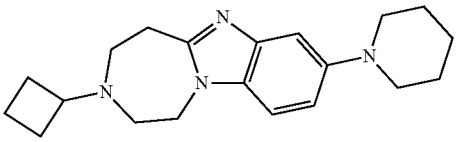

This compound was prepared in 45% yield (320 mg) as described for intermediate I-38 but using piperidine as the starting material. $^1$H-NMR (400 MHz, CDCl$_3$) δ: 7.24 (d, J=2.4 Hz, 1H), 7.13 (d, J=8.8 Hz, 1H), 7.01 (m, 1H), 4.17-4.20 (m, 2H), 3.21-3.23 (m, 2H), 3.08-3.11 (m, 4H), 2.92 (m, 1H), 2.58-2.64 (m, 4H), 2.11-2.13 (m, 2H), 1.89-1.94 (m, 2H), 1.55-1.79 (m, 8H). MS (ESI): m/z 325 (M+H$^+$).

176. Compound 176: (3-cyclobutyl-8-(3,4-dihydroisoquinolin-2(1H)-yl)-2,3,4,5-tetrahydro-1H-benzo[4,5]imidazo[1,2-d][1,4]diazepine)

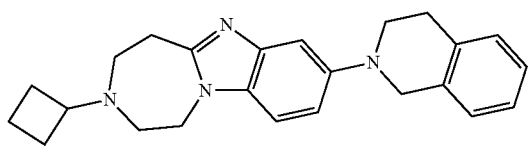

This compound was prepared in 23% yield (16 mg) as described for intermediate I-38 but using 1,2,3,4-tetrahydroisoquinoline as the starting material. $^1$H-NMR (400 MHz, CDCl$_3$) δ: 7.31 (d, J=2.0 Hz, 1H), 7.13-7.19 (m, 4H), 7.07 (m, 2H), 4.38 (s, 2H), 4.20-4.22 (m, 2H), 3.52-3.55 (m, 2H), 3.22-3.25 (m, 2H), 3.21-3.25 (m, 2H), 2.90-3.00 (m, 1H), 2.60-2.65 (m, 4H), 1.73-1.94 (m, 2H), 1.73-1.94 (m, 2H), 1.62-1.73 (m, 2H). MS (ESI): m/z 373 (M+H$^+$).

177. Compound 177: (3-cyclobutyl-8-(7-fluoro-3,4-dihydroisoquinolin-2(1H)-yl)-2,3,4,5-tetrahydro-1H-benzo[4,5]imidazo[1,2-d][1,4]diazepine)

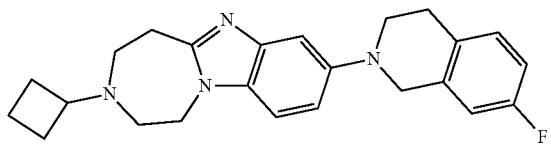

This compound was prepared in 13% yield (10 mg) as described for intermediate I-38 but using 7-fluoro-1,2,3,4-tetrahydroisoquinoline as the starting material. $^1$H-NMR (400 MHz, CDCl$_3$) δ: 7.29 (d, J=1.6 Hz, 1H), 7.15 (d, J=8.4 Hz, 1H), 7.05~7.12 (m, 2H), 6.83 (m, 2H), 4.32 (s, 2H), 4.19~4.21 (m, 2H), 3.50~3.52 (m, 2H), 3.21~3.24 (m, 2H), 2.97~3.00 (m, 2H), 2.90~2.94 (m, 1H), 2.58~2.65 (m, 4H), 2.09-2.15 (m, 2H), 1.89~1.96 (m, 2H), 1.64~1.75 (m, 2H). MS (ESI): m/z 391 (M+H$^+$).

178. Compound 178: (3-cyclobutyl-8-(4,4-difluoropiperidin-1-yl)-2,3,4,5-tetrahydro-1H-benzo[4,5]imidazo[1,2-d][1,4]diazepine)

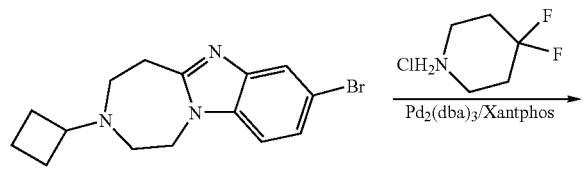

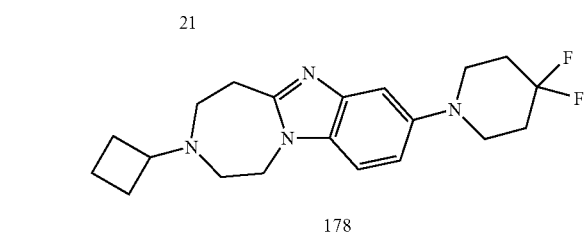

178

A solution of compound 21 (150 mg, 0.47 mmol, 1.0 eq), 4,4-difluoropiperidine hydrochloride (88 mg, 0.56 mmol, 1.2 eq), Pd$_2$(dba)$_3$ (22 mg, 0.024 mmol, 0.05 eq), Xantphos (41 mg, 0.071 mmol, 0.15 eq.) and $^t$BuONa (108 mg, 1.1 mmol, 2.4 eq) in toluene (4 mL) was degassed by bubbling argon and the mixture was stirred under microwave irradiation at 80° C. for 60 minutes. The crude reaction mixture was diluted with ethyl acetate, the solids were removed by filtration through a short plug of silica gel and the filtrate was concentrated by evaporation. The crude reaction product was purified by silica gel column chromatography to give compound 178 (15 mg, 9%) as pale yellow solid. $^1$H-NMR (400 MHz, CDCl$_3$) δ: 7.26 (m, 1H), 7.13 (d, J=8.8 Hz, 1H), 6.98 (m, 1H), 4.11-4.22 (m, 2H), 3.22-3.30 (m, 6H), 2.91-2.95 (m, 1H), 2.60-2.65 (m, 4H), 2.09-2.20 (m, 6H), 1.91-1.95 (m, 2H), 1.54-1.76 (m, 2H). MS (ESI): m/z 361 (M+H$^+$).

179. Compound 179: (3-cyclobutyl-8-(4-fluoropiperidin-1-yl)-2,3,4,5-tetrahydro-1H-benzo[4,5]imidazo[1,2-d][1,4]diazepine)

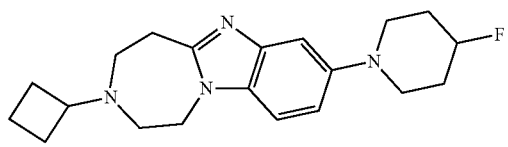

This compound was prepared in 6% yield (20 mg) as described for compound 178 but using 4-fluoropiperidine as the starting material. $^1$H-NMR (400 MHz, CDCl$_3$) δ: 7.25 (d, J=1.6 Hz, 1H), 7.12 (d, J=8.8 Hz, 11-1), 6.98 (dd, J$_1$=2.4 Hz, J$_2$=8.8 Hz, 1H), 4.85 (m, 1H), 4.17 (m, 2H), 3.32 (m, 2H), 3.16 (m, 2H), 3.10 (m, 2H), 2.91 (m, 1H), 2.59 (m, 4H), 2.01 (m, 6H), 1.90 (m, 2H), 1.69 (m, 2H). MS (ESI): m/z 343 (M+H$^+$).

180. Compound 180: (3-cyclobutyl-8-(3-fluoropiperidin-1-yl)-2,3,4,5-tetrahydro-1H-benzo[4,5]imidazo[1,2-d][1,4]diazepine)

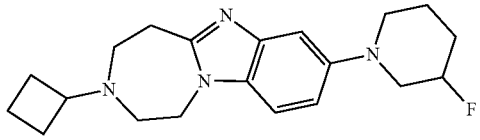

This compound was prepared in 13% yield (40 mg) as described for compound 178 but using 3-fluoropiperidine as the starting material. $^1$H-NMR (400 MHz, CDCl$_3$) δ: 7.24 (d, J=2.0 Hz, 1H), 7.14 (m, 1H), 7.00 (m, 1H), 4.85 (m, 1H), 4.17 (m, 2H), 3.43 (m, 1H), 3.16 (m, 4H), 3.03 (m, 1H), 2.93 (m, 1H), 2.59 (m, 4H), 2.11 (m, 2H), 1.97 (m, 4H), 1.79 (m, 4H). MS (ESI): m/z 343 (MAT).

181. Compound 181: (3-cyclobutyl-8-(3-fluoropyrrolidin-1-yl)-2,3,4,5-tetrahydro-1H-benzo[4,5]imidazo[1,2-d][1,4]diazepine)

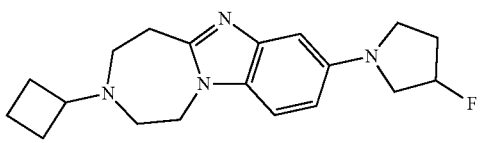

This compound was prepared in 6% yield (17 mg) as described for compound 178 but using 3-fluoropyrrolidine as the starting material. $^1$H-NMR (400 MHz, CDCl$_3$) δ: 7.10 (d, J=8.8 Hz, 1H), 6.87 (d, J=2.0 Hz, 1H), 6.62 (dd, J$_1$=2.0 Hz, J$_2$=8.8 Hz, 1H), 5.31 (m, 1H), 4.17 (m, 2H), 3.43 (m, 4H), 3.22 (m, 2H), 2.92 (m, 1H), 2.60 (m, 4H), 2.10 (m, 4H), 1.91 (m, 2H), 1.67 (m, 2H). MS (ESI): m/z 329 (M+H$^+$).

182. Compound 182: (3-cyclobutyl-8-(3,3-difluoropyrrolidin-1-yl)-2,3,4,5-tetrahydro-1H-benzo[4,5]imidazo[1,2-d][1,4]diazepine)

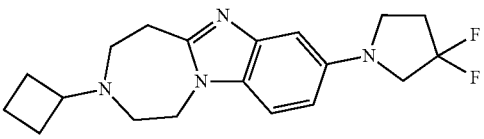

This compound was prepared in 4% yield (4 mg) as described for compound 178 but using 3,3-difluoropyrrolidine as the starting material. $^1$H-NMR (400 MHz, CDCl$_3$) δ: 7.11 (d, J=8.4 Hz, 1H), 6.86 (d, J=2.0 Hz, 1H), 6.59-6.62 (m, 1H), 4.17-4.20 (m, 2H), 3.71-3.75 (m, 2H), 3.51-3.54 (m, 2H), 3.21-3.23 (m, 2H), 2.90-2.94 (m, 1H), 2.45-2.64 (m, 4H), 2.13-2.15 (m, 2H), 1.85 (m, 6H). MS (ESI): m/z 347 (M+H$^+$).

183. Compound 183: (9-cyclobutyl-2,3,4,7,8,9,10,11-octahydro-1H-[1,4]diazepino[7',1':2,3]imidazo[4,5-g]isoquinoline)

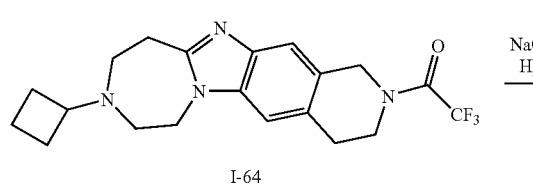

I-64

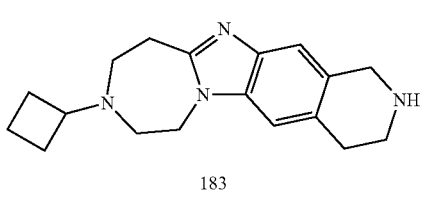

183

To a solution of intermediate I-64 (298 mg, 0.76 mmol, 1.0 eq) in methanol (10 mL) was added a solution of sodium hydroxide (61 mg, 1.5 mmol, 2.0 eq) in water (0.5 mL) and the reaction mixture was stirred at room temperature for 60 minutes. The crude reaction mixture was concentrated by evaporation and the residue was dissolved in dichloromethane and washed with water. The combined organic layers were dried over anhydrous $Na_2SO_4$, the solids were removed by filtration and the filtrate was concentrated by evaporation to give compound 183 (200 mg, 89%). $^1$H-NMR (400 MHz, $CD_3OD$) δ: 7.23 (s, 1H), 7.18 (s, 1H), 4.27~4.29 (m, 2H), 4.07 (s, 2H), 3.20~3.22 (m, 2H), 3.15~3.18 (m, 2H), 2.93~3.01 (m, 3H), 2.59~2.67 (m, 4H), 2.12~2.18 (m, 2H), 1.89~1.99 (m, 2H), 1.66~1.80 (m, 2H). MS (ESI): m/z 297 (M+H$^+$).

184. Compound 184: (10-cyclobutyl-2,3,4,8,9,10,11,12-octahydro-1H-[1,4]diazepino[1',7':1,2]imidazo[4,5-f]isoquinoline)

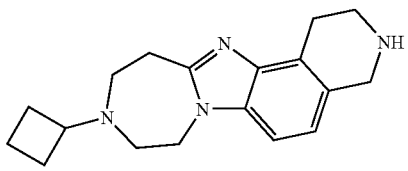

This compound was prepared in 89% yield (40 mg) as described for compound 183 but using intermediate I-65 as the starting material. $^1$H-NMR (400 MHz, $CD_3OD$) δ: 7.04 (d, 1H, J=8.4 Hz), 6.90 (d, 1H, J=8.4 Hz), 4.20~4.22 (m, 2H), 4.10 (s, 2H), 3.22~3.27 (m, 4H), 3.13~3.16 (m, 2H), 2.91 (m, 1H), 2.58~2.64 (m, 4H), 2.11~2.13 (m, 2H), 1.88~1.93 (m, 2H), 1.60~1.76 (m, 2H). MS (ESI): 297 (M+H$^+$).

185. Compound 185: (4-(9-cyclobutyl-2,3,4,7,8,9,10,11-octahydro-1H-[1,4]diazepino[7',1':2,3]imidazo[4,5-d]isoquinoline-2-carbonyl)benzonitrile)

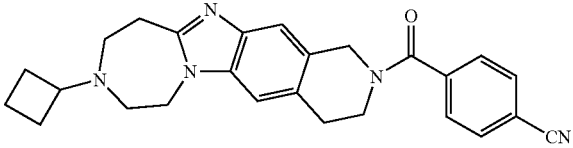

This compound was prepared in 81% yield (35 mg) as described for compound 172 but using compound 183 as the starting material. $^1$H-NMR (400 MHz, CDCl$_3$) δ: 7.75 (d, 2H, J=8.0 Hz), 7.54~7.59 (m, 2H), 7.28 (s, 1H), 7.10 (s, 1H), 5.00 (s, 1H), 4.61 (s, 1H), 4.20~4.22 (m, 2H), 3.98~4.00 (m, 2H), 3.59 (m, 1H), 3.23 (m, 2H), 3.13~3.16 (m, 1H), 2.90~3.01 (m, 1H), 2.60~2.64 (m, 4H), 2.10~2.18 (m, 2H), 1.86~1.96 (m, 2H), 1.63~1.78 (m, 2H). MS (ESI): m/z 426 (M+H$^+$).

186. Compound 186: (cyclobutyl(9-cyclobutyl-3,4,8,9,10,11-hexahydro-1H-[1,4]diazepino[7',1':2,3]imidazo[4,5-g]isoquinolin-2(7H)-yl)methanone)

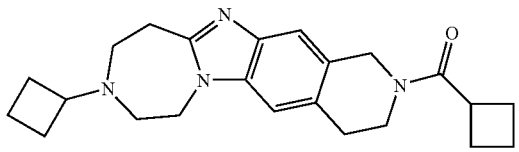

This compound was prepared in 79% yield (30 mg) as described for compound 174 but using compound 183 as the starting material. $^1$HNMR (400 MHZ, CDCl$_3$), δ 7.38 (s, 1H), 7.28 (s, 1-1), 4.64 (m, 2H), 4.30 (m, 2H), 3.72 (m, 1H), 3.62~3.64 (m, 1H), 3.49~3.56 (m, 1H), 3.16~3.18 (m, 2H), 2.94~3.02 (m, 3H), 2.59~2.65 (m, 4H), 1.68~2.30 (m, 12H). MS (ESI): m/z 379 (M+H$^+$).

187. Compound 187: (1-(9-cyclobutyl-3,4,8,9,10,11-hexahydro-1H-[1,4]diazepino[7',1':2,3]imidazo[4,5-g]isoquinolin-2(7H)-yl)ethanone)

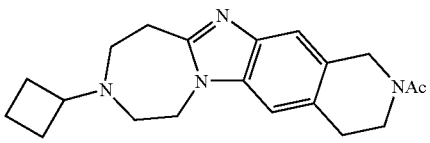

This compound was prepared in 50% yield (20 mg) as described for compound 171 but using compound 183 as the starting material. $^1$H-NMR (400 MHz, CDCl$_3$) δ: 7.49 (s, 1H), 7.05 (s, 1H), 4.72 (m, 2H), 4.20~4.21 (m, 2H), 3.81 (m, 1H), 3.68 (m, 1H), 3.21~3.24 (m, 2H), 3.04 (m, 1H), 2.99 (m, 1H), 2.90~2.92 (m, 1H), 2.58~2.63 (m, 4H), 2.22 (m, 3H), 2.10~2.13 (m, 2H), 1.88~1.93 (m, 2H), 1.65~1.75 (m, 2H). MS (ESI): m/z 339 (M+H$^+$).

188. Compound 188: (1-(10-cyclobutyl-9,10,11,12-tetrahydro-1H-[1,4]diazepino[1',7':1,2]imidazo[4,5-f]isoquinolin-3(2H,4H,8H)-yl)ethanone)

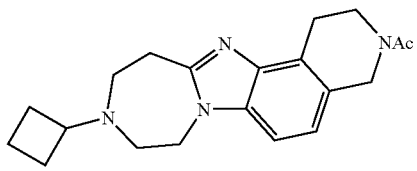

This compound was prepared in 100% yield (43 mg) as described for compound 187 but using compound 184 as the starting material. $^1$H-NMR (400 MHz, CDCl$_3$) δ: 7.13 (d, 1H, J=8.4 Hz), 7.00 (d, 1H, J=8.4 Hz), 4.72 (m, 2H), 4.40 (brs, 2H), 3.77~3.91 (m, 2H), 3.44 (brs, 2H), 3.25 (m, 2H), 3.05 (m, 1H), 2.78 (brs, 4H), 2.21 (m, 3H), 2.08~2.20 (m, 4H), 1.67~1.80 (m, 2H). MS (ESI): m/z 339 (M+H$^+$).

189. Compound 189: (9-cyclobutyl-2,3,4,7,8,9,10,11-octahydro-1H-[1,4]diazepino[1',7':1,2]imidazo[4,5-g]isoquinoline)

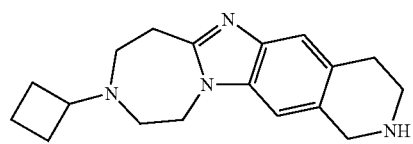

This compound was prepared in 43% yield (30 mg) as described for compound 143 but using intermediate I-73 as the starting material. $^1$H-NMR (400 MHz, CDCl$_3$) δ: 7.39 (s, 1H), 6.89 (s, 1H), 4.18 (m, 4H), 3.22 (m, 4H), 2.99 (m, 2H), 2.91 (m, 1H), 2.59 (m, 4H), 2.20 (m, 2H), 1.92 (m, 2H), 1.72 (m, 2H). MS (ESI): m/z 297.4 (M+H$^+$).

190. Compound 190: (9-cyclobutyl-2-(pyrazin-2-yl)-2,3,4,7,8,9,10,11-octahydro-1H-[1,4]diazepino[1',7':1,2]imidazo[4,5-g]isoquinoline)

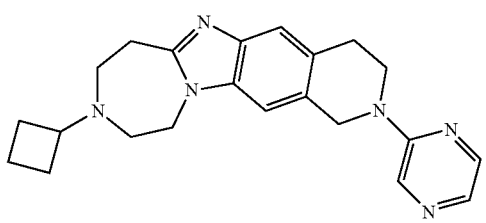

This compound was prepared in 67% yield (11 mg) as described for compound 149 but using compound 189 as the starting material. $^1$H-NMR (400 MHz, CDCl$_3$) δ: 8.10 (m, 2H), 7.83 (d, J=2.8 Hz, 1H), 7.51 (s, 11-1), 7.12 (s, 1H), 4.88 (s, 2H), 4.22 (m, 2H), 3.81 (m, 2H), 3.24 (m, 2H), 3.14 (m, 2H), 2.92 (m, 1H), 2.61 (m, 4H), 2.11 (m, 2H), 1.90 (m, 2H), 1.67 (m, 2H). MS (ESI): m/z 375.5 (M+H$^+$).

191. Compound 191: (cyclobutyl(9-cyclobutyl-3,4,8,9,10,11-hexahydro-1H-[1,4]diazepino[1',7':1,2]imidazo[4,5-g]isoquinolin-2(7H)-yl)methanone)

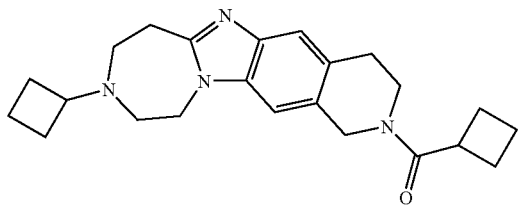

This compound was prepared in 16% yield (3.9 mg) as described for compound 174 but using compound 189 as the starting material. $^1$H-NMR (400 MHz, CDCl$_3$) δ: 7.45 (s, 1H), 7.00 (s, 1H), 4.82 (m, 2H), 4.20 (m, 2H), 3.70 (m, 2H), 3.38 (m, 1H), 3.24 (m, 2H), 3.00 (m, 2H), 2.92 (m, 1H), 2.62 (m, 4H), 2.40 (m, 2H), 2.20 (m, 4H), 2.00 (m, 2H), 1.95 (m, 2H), 1.72 (m, 2H). MS (ESI): m/z 378.5 (M+H$^+$).

192. Compound 192: (4-(9-cyclobutyl-2,3,4,7,8,9,10,11-octahydro-1H-[1,4]diazepino[1',7':1,2]imidazo[4,5-g]isoquinoline-2-carbonyl)benzonitrile)

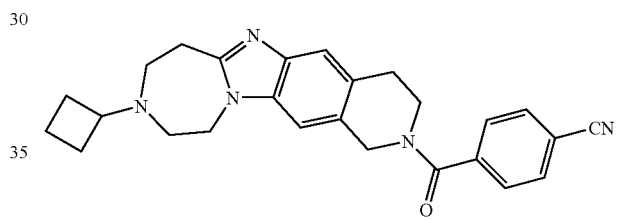

This compound was prepared in 36% yield (10 mg) as described for compound 168 but using compound 189 as the starting material. $^1$H-NMR (400 MHz, CDCl$_3$) δ: 7.76 (d, J=8.4 Hz, 2H), 7.57 (m, 2H), 7.48 (m, 1H), 7.00 (m, 1H), 4.86 (m, 2H), 4.15 (m, 2H), 3.61 (m, 2H), 3.244 (m, 2H), 3.14 (m, 2H), 2.94 (m, 1H), 2.64 (m, 4H), 2.12 (m, 2H), 1.94 (m, 2H), 1.66 (m, 2H). MS (ESI): m/z 426.5 (M+H$^+$).

193. Compound 193: (9-cyclobutyl-2-(pyrimidin-2-yl)-2,3,4,7,8,9,10,11-octahydro-1H-[1,4]diazepino[1',7':1,2]imidazo[4,5-g]isoquinoline)

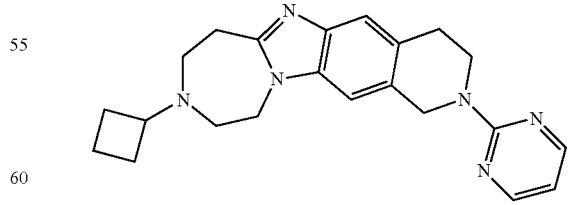

This compound was prepared in 55% yield (16 mg) as described for compound 148 but using compound 189 as the starting material. $^1$H-NMR (400 MHz, CDCl$_3$) δ: 8.36 (d, J=4.8 Hz, 2H), 7.50 (s, 1H), 7.10 (m, 1H), 6.50 (m, 1H), 5.02 (s, 2H), 4.21 (m, 2H), 4.01 (m, 2H), 3.23 (m, 2H), 3.10 (m, 2H), 2.92 (m, 1H), 2.62 (m, 4H), 2.11 (m, 2H), 1.93 (m, 2H), 1.67 (m, 2H). MS (ESI): m/z 375.5 (M+H⁺).

194. Compound 194: (1-(9-cyclobutyl-3,4,8,9,10,11-hexahydro-1H-[1,4]diazepino[1',7':1,2]imidazo[4,5-g]isoquinolin-2(7H)-yl)ethanone)

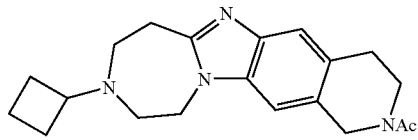

This compound was prepared in 17% yield (11 mg) as described for compound 167 but using compound 189 as the starting material. ¹H-NMR (400 MHz, CDCl₃) δ: 7.40 (s, 1H), 6.97 (s, 1H), 4.70 (m, 2H), 4.15 (m, 2H), 3.61 (m, 2H), 3.18 (m, 2H), 2.88~2.98 (m, 3H), 2.57 (m, 4H), 2.09 (m, 5H), 1.87 (m, 2H), 1.62 (m, 2H). MS (ESI): m/z 339.4 (M+Er).

195. Compound 195: (3-cyclobutyl-8-(2-methylimidazo[1,2-a]pyridin-6-yl)-2,3,4,5-tetrahydro-1H-benzo[4,5]imidazo[1,2-d][1,4]diazepine)

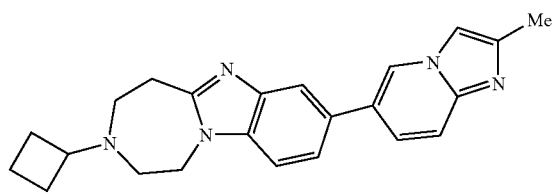

This compound was prepared in 30% yield (6 mg) as described for compound 22 but using intermediate I-75 as the starting material. ¹H-NMR (400 MHz, CD₃OD) δ: 8.52 (br, 1H), 7.72 (s, 1H), 7.42-7.56 (m, 5H), 4.29-4.31 (m, 2H), 3.15-3.18 (m, 2H), 2.93 (m, 1H), 2.56-2.64 (m, 4H), 2.35 (s, 3H), 2.08-2.10 (m, 2H), 1.86-1.88 (m, 2H), 1.64-1.67 (m, 2H). MS (ESI): m/z 372.2 (M+H⁺).

196. Compound 196: (3-cyclobutyl-8-(1H-pyrrolo[2,3-b]pyridin-6-yl)-2,3,4,5-tetrahydro-1H-benzo[4,5]imidazo[1,2-d][1,4]diazepine)

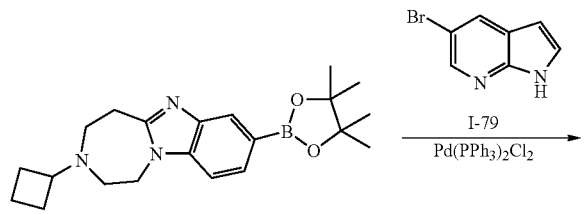

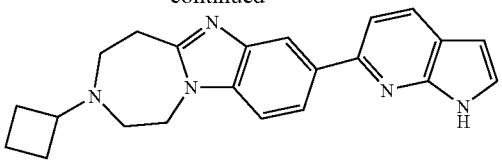

Intermediates I-17 (40 mg, 0.11 mmol, 1.0 eq) and I-79 (17 mg, 0.11 mmol, 1.0 eq), Pd(PPh₃)₂Cl₂ (5 mg, 0.007 mmol, 0.1 eq) and a solution of Na₂CO₃ in water (0.5 mL, 2.0 M, 1.0 mmol, 10 eq) were mixed in acetonitrile (0.5 mL) and the solution was purged by bubbling argon. The reaction mixture was stirred at 150° C. for 30 minutes under microwave irradiation, diluted with ethyl acetate, the solids were removed by filtration and the filtrate was concentrated by evaporation. The crude reaction product was purified by silica gel column chromatography to give compound 196 (9 mg, 23%) as a white solid. ¹H-NMR (400 MHz, CD₃OD) δ: 11.66 (s, 1H), 8.51 (m, 1H), 8.19 (m, 1H), 7.80 (m, 1H), 7.49~7.60 (m, 3H), 6.49~6.50 (m, 1H) 4.31~4.34 (m, 2H), 3.13-3.18 (m, 2H), 2.95 (m, 1H), 2.57~2.59 (m, 4H), 2.09 (m, 2H), 1.82 (m, 2H), 1.60 (m, 2H). MS (ESI): m/z 358.2 (M+H⁺).

197. Compound 197: (3-cyclobutyl-8-(1H-pyrrolo[3,2-b]pyridin-5-yl)-2,3,4,5-tetrahydro-1H-benzo[4,5]imidazo[1,2-d][1,4]diazepine)

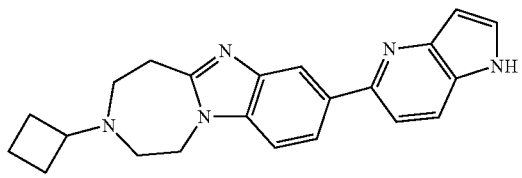

This compound was prepared in 4% yield (2 mg) as described for compound 196 but using 5-chloro-1H-pyrrolo[3,2-b]pyridine as the starting material. ¹H-NMR (400 MHz, CD₃OD) δ: 8.29 (br, 1H), 8.22~8.23 (m, 1H), 8.10~8.12 (m, 1H), 7.75~7.77 (m, 1H), 7.64~7.66 (m, 1H), 7.45~7.47 (m, 1H), 7.33~7.35 (m, 1H), 6.84~6.85 (m, 1H), 4.27-4.29 (m, 2H), 3.26~3.29 (m, 2H), 2.95 (m, 1H), 2.62~2.69 (m, 4H), 2.13~2.15 (m, 2H), 1.93 (m, 2H), 1.56~1.59 (m, 2H). MS (ESI): m/z 358.1 (M+H⁺).

198. Compound 198: (3-cyclobutyl-8-(imidazo[1,5-a]pyridin-6-yl)-2,3,4,5-tetrahydro-1H-benzo[4,5]imidazo[1,2-d][1,4]diazepine)

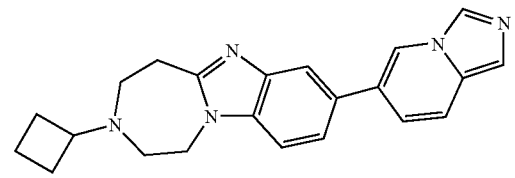

This compound was prepared in 17% yield (6 mg) as described for compound 22 but using intermediate I-81 as the starting material. ¹H-NMR (400 MHz, CD₃OD) δ: 8.51 (s, 1H), 8.38 (s, 1H), 7.83 (s, 1H), 7.57~7.64 (m, 31-1), 7.40 (s, 1H), 7.18-7.21 (m, 1H), 4.38~4.40 (m, 2H), 3.24~3.27 (m, 2H), 3.02 (m, 1H), 2.66~2.73 (m, 4H), 2.17~2.19 (m, 2H), 1.95~1.97 (m, 2H), 1.73~1.76 (m, 2H). MS (ESI): m/z 358.2 (M+H⁺).

199. Compound 199: (3-cyclobutyl-8-(5H-pyrrolo[2,3-b]pyrazin-2-yl)-2,3,4,5-tetrahydro-1H-benzo[4,5]imidazo[1,2-d][1,4]diazepine)

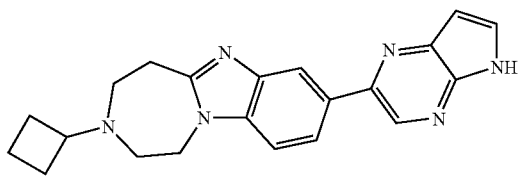

This compound was prepared in 8% yield (5 mg) as described for compound 196 but using intermediate I-85 as the starting material. ¹H-NMR (400 MHz, CD₃OD) δ: 9.04 (br, 1H), 8.77 (s, 1H), 8.29 (s, 1H), 8.03-8.05 (d, 1H, J=8.0 Hz), 7.62 (s, 1H), 7.37-7.39 (d, 1H, J=9.2 Hz), 6.81 (s, 1H), 4.30 (m, 2H), 3.28-3.29 (m, 2H), 2.95 (m, 1H), 2.65-2.70 (m, 4H), 2.11-2.15 (m, 2H), 1.91-1.96 (m, 2H), 1.64-1.67 (m, 2H). MS (ESI): m/z 359.1 (M+H⁺).

200. Compound 200: (3-cyclobutyl-8-(1H-pyrrolo[3,2-b]pyridin-6-yl)-2,3,4,5-tetrahydro-1H-benzo[4,5]imidazo[1,2-d][1,4]diazepine)

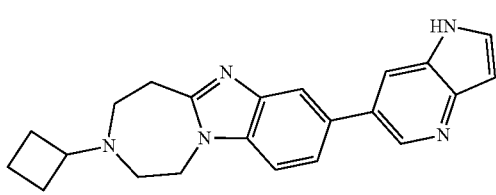

This compound was prepared in 15% yield (7 mg) as described for compound 196 but using 6-iodo-1H-pyrrolo[3,2-b]pyridine as the starting material. ¹H-NMR (400 MHz, CD₃OD) δ: 9.10 (br, 1H), 8.77 (d, J=4.0 Hz, 1H), 7.90~7.94 (m, 2H), 7.48~7.55 (m, 2H), 7.35~7.35 (m, 1H), 6.78~6.79 (m, 1H), 4.27~4.29 (m, 2H), 3.27-3.30 (m, 2H), 2.95 (m, 1H), 2.62~2.69 (m, 4H), 2.13~2.15 (m, 2H), 1.90~1.95 (m, 2H), 1.26~1.79 (m, 2H). MS (ESI): m/z 358.1 (M+H⁺).

201. Compound 201: (6-(3-cyclobutyl-2,3,4,5-tetrahydro-1H-benzo[4,5]imidazo[1,2-d][1,4]diazepin-8-yl)furo[3,2-b]pyridine)

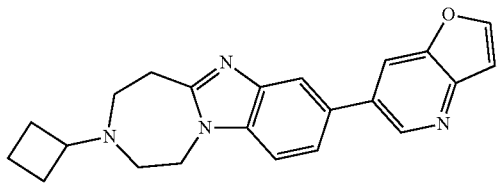

This compound was prepared in 10% yield (5 mg) as described for compound 196 but using 6-iodofuro[3,2-b]pyridine as the starting material. ¹H-NMR (400 MHz, CD₃OD) δ: 8.85 (d, J=2.0 Hz, 1H), 7.93~7.99 (m, 2H), 7.87 (d, J=2.4 Hz, 1H), 7.51~7.53 (m, 1H), 7.35~7.37 (m, 1H), 7.02~7.03 (m, 1H), 4.28~4.30 (m, 2H), 3.27-3.30 (m, 2H), 2.95 (m, 1H), 2.63~2.70 (m, 4H), 2.13~2.15 (m, 2H), 1.90~1.93 (m, 2H), 1.64-1.77 (m, 2H). MS (ESI): m/z 359.0 (M+H⁺).

202. Compound 202: (3-cyclobutyl-8-(3-methyl-3H-imidazo[4,5-b]pyridin-6-yl)-2,3,4,5-tetrahydro-1H-benzo[4,5]imidazo[1,2-d][1,4]diazepine)

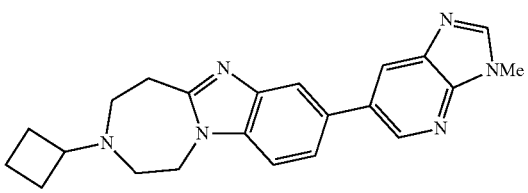

This compound was prepared in 11% yield (6 mg) as described for compound 196 but using 6-iodo-3-methyl-3H-imidazo[4,5-b]pyridine as the starting material. ¹H-NMR (400 MHz, CD₃OD) δ: 8.70~8.71 (d, J=2.0 Hz, 1H), 8.28 (d, J=2.0 Hz, 1H), 8.07 (s, 1H), 7.93 (d, J=1.2 Hz, 1H), 7.50~7.53 (m, 1H), 7.37~7.50 (m, 1H), 4.27-4.30 (m, 2H), 3.98 (s, 3H), 3.27~3.30 (m, 2H), 2.95 (m, 1H), 2.63~2.70 (m, 4H), 2.13-2.15 (m, 2H), 1.91~1.93 (m, 2H), 1.76 (m, 2H). MS (ESI): m/z 373.0 (M+H⁺).

203. Compound 203: (8-([1,2,4]triazolo[1,5-a]pyridin-6-yl)-3-cyclobutyl-2,3,4,5-tetrahydro-1H-benzo[4,5]imidazo[1,2-d][1,4]diazepine)

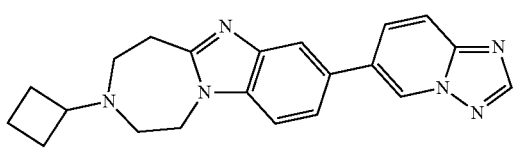

This compound was prepared in 4% yield (2 mg) as described for compound 22 but using 6-bromo-[1,2,4]triazolo[1,5-a]pyridine as the starting material. ¹H-NMR (400 MHz, CD₃OD) δ: 8.81 (s, 1H), 8.37 (s, 1H), 7.90 (m, 1H), 7.84 (s, 2H), 7.46-7.48 (m, 1H), 7.36~7.38 (m, 1H), 4.28~4.30 (m, 2H), 3.28~3.30 (m, 2H), 2.95 (m, 1H), 2.63-2.70 (m, 4H), 2.13~2.15 (m, 2H), 1.91~1.95 (m, 2H), 1.69 (m, 2H). MS (ESI): m/z 359.1 (M+H⁺).

204. Compound 204: (8-([1,2,4]triazolo[4,3-a]pyridin-6-yl)-3-cyclobutyl-2,3,4,5-tetrahydro-1H-benzo[4,5]imidazo[1,2-d][1,4]diazepine)

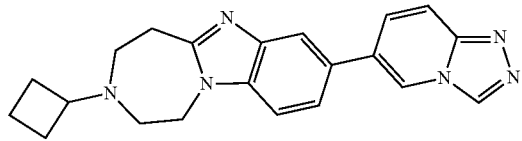

This compound was prepared in 26% yield (13 mg) as described for compound 22 but using 6-bromo-[1,2,4]triazolo[4,3-a]pyridine as the starting material. $^1$H-NMR (400 MHz, CD$_3$OD) δ: 8.87 (s, 1H), 8.28 (s, 1H), 7.83-7.86 (m, 2H), 7.58-7.61 (m, 1H), 7.41-7.44 (m, 1H), 7.34-7.37 (m, 1H), 4.27-4.30 (m, 2H), 3.27-3.30 (m, 2H), 2.95 (m, 1H), 2.63-2.70 (m, 4H), 2.13-2.15 (m, 2H), 1.93 (m, 2H), 1.68-1.72 (m, 2H). MS (ESI): m/z 359.1 (M+H$^+$).

205. Compound 205: (3-cyclobutyl-8-(1-methyl-1H-indazol-6-yl)-2,3,4,5-tetrahydro-1H-benzo[4,5]imidazo[1,2-d][1,4]diazepine)

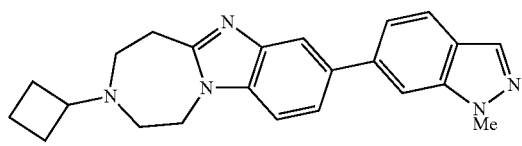

This compound was prepared in 11% yield (5 mg) as described for compound 22 but using 6-bromo-1-methyl-1H-indazole as the starting material. $^1$H-NMR (400 MHz, CD$_3$OD) δ: 7.98~8.00 (m, 2H), 7.77~7.80 (m, 1H), 7.56~7.59 (m, 2H), 7.45~7.47 (m, 1H), 7.33~7.35 (m, 1H), 4.28~4.30 (m, 2H), 4.12 (s, 3H), 3.28~3.30 (m, 2H), 2.95 (m, 1H), 2.63~2.70 (m, 4H), 2.15 (m, 2H), 1.94 (m, 2H), 1.75 (m, 2H). MS (ESI): m/z 372.2 (M+H$^+$).

206. Compound 206: (3-cyclobutyl-8-(2-methyl-2H-indazol-6-yl)-2,3,4,5-tetrahydro-1H-benzo[4,5]imidazo[1,2-d][1,4]diazepine)

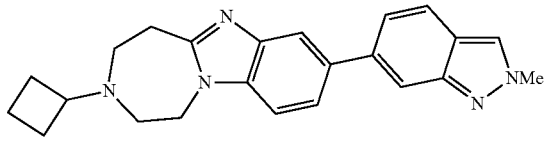

This compound was prepared in 11% yield (6 mg) as described for compound 22 but using 6-bromo-2-methyl-2H-indazole as the starting material. $^1$H-NMR (400 MHz, CD$_3$OD) δ: 7.90 (m, 1H), 7.98 (m, 2H), 7.70~7.72 (m, 1H), 7.57-7.59 (m, 1H), 7.42~7.44 (m, 1H), 7.27~7.33 (m, 1H), 4.24~4.28 (m, 2H), 4.21 (s, 3H), 3.26-3.29 (m, 2H), 2.94 (m, 1H), 2.62~2.68 (m, 4H), 2.12~2.17 (m, 2H), 1.87~1.95 (m, 2H), 1.68~1.74 (m, 2H). MS (ESI): m/z 372.2 (M+H$^+$).

207. Compound 207: (3-cyclobutyl-8-(2-methyl-1H-benzo[d]imidazol-1-yl)-2,3,4,5-tetrahydro-1H-benzo[4,5]imidazo[1,2-d][1,4]diazepine)

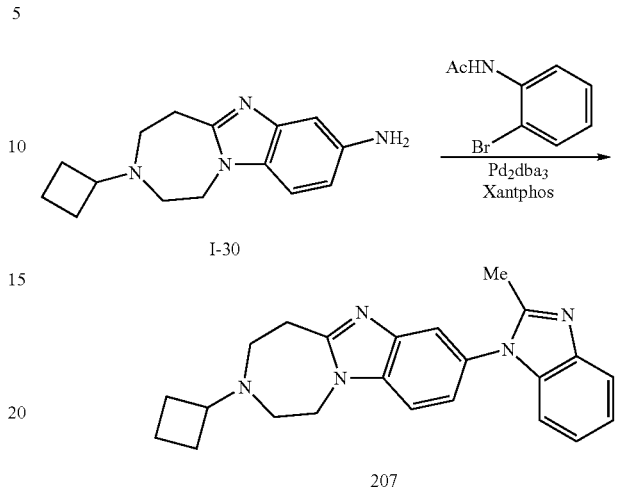

A mixture of intermediate I-30 (192 mg, 0.75 mmol, 1.5 eq), N-(2-bromophenyl)acetamide (106 mg, 0.50 mmol, 1.0 eq), Pd$_2$(dba)$_3$ (46 mg, 0.05 mmol, 0.1 eq), Xantphos (29 mg, 0.05 mmol, 0.1 eq), and K$_3$PO$_4$ (265 mg, 1.3 mmol, 2.5 eq) in $^t$BuOH (5 mL) was stirred at 110° C. for 60 minutes under microwave irradiation. The reaction mixture was concentrated by evaporation; the residue was diluted with dichloromethane and washed with water. The combined organic layers were dried over anhydrous Na$_2$SO$_4$, the solids were removed by filtration and the filtrate was concentrated by evaporation. The crude reaction product was purified by preparative TLC to give compound 207 (74 mg, 40%) as pale yellow solid. $^1$H-NMR (400 MHz, CDCl$_3$) δ: 7.74 (d, J=8.0 Hz, 1H), 7.68 (d, J=2.0 Hz, 1H), 7.39 (d, J=8.4 Hz, 1H), 7.17-7.28 (m, 3H), 7.07 (d, J=2.0 Hz, 1H), 4.31-4.34 (m, 2H), 3.29-3.32 (m, 2H), 2.93 (m, 1H), 2.65-2.71 (m, 4H), 2.50 (s, 3H), 2.14 (m, 2H), 1.99 (m, 2H), 1.66 (m, 2H). MS (CI): m/z 372 (M+H$^+$).

208. Compound 208: (3-cyclobutyl-8-(6-fluoro-2-methyl-1H-benzo[d]imidazol-1-yl)-2,3,4,5-tetrahydro-1H-benzo[4,5]imidazo[1,2-d][1,4]diazepine)

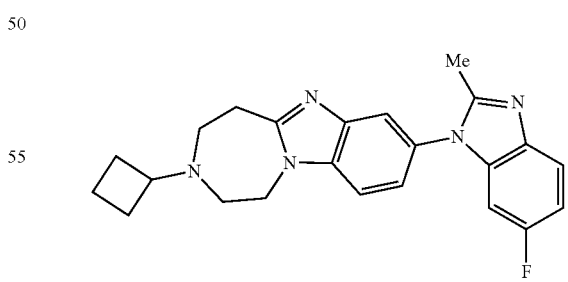

This compound was prepared in 30% yield (59 mg) as described for compound 207 but using N-(2-bromo-4-fluorophenyl)acetamide as the starting material. $^1$H-NMR (400 MHz, CDCl$_3$) δ: 7.63-7.67 (m, 2H), 7.40 (d, J=8.8 Hz, 1H), 7.18-7.21 (m, 1H), 6.96-7.02 (m, 1H), 6.75-6.78 (m, 1H), 4.32-4.34 (m, 2H), 3.30-3.33 (m, 2H), 2.97 (m, 1H), 2.65-

2.74 (m, 4H), 2.48 (s, 3H), 2.10-2.17 (m, 2H), 1.91-1.94 (m, 2H), 1.66-1.69 (m, 2H). MS (CI): m/z 390 (M+H⁺).

209. Compound 209 (3-cyclobutyl-8-(2,6-dimethyl-1H-benzo[d]imidazol-1-yl)-2,3,4,5-tetrahydro-1H-benzo[4,5]imidazo[1,2-d][1,4]diazepine)

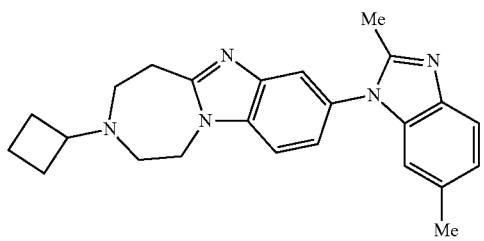

This compound was prepared in 35% yield (68 mg) as described for compound 207 but using N-(2-bromo-4-methylphenyl)acetamide as the starting material. ¹H-NMR (400 MHz, CDCl₃) δ: 7.67 (d, J=8.0 Hz, 1H), 7.60 (d, J=8.0 Hz, 1H), 7.40 (d, J=8.4 Hz, 1H), 7.22 (m, 1H), 7.11-7.13 (m, 1H), 6.88-6.89 (m, 1H), 4.31-4.34 (m, 2H), 3.30-3.32 (m, 2H), 3.01 (m, 1H), 2.71 (m, 4H), 2.48 (s, 3H), 2.38 (s, 3H), 2.17 (m, 2H), 1.88 (m, 2H), 1.65 (m, 2H). MS (CI): m/z 386 (M+H⁺).

210. Compound 210: (8-(benzo[d][1,3]dioxol-5-yl)-3-cyclobutyl-2,3,4,5-tetrahydro-1H-benzo[4,5]imidazo[1,2-d][1,4]diazepine)

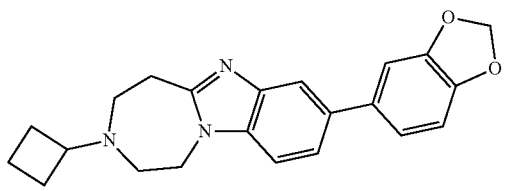

This compound was prepared in 59% yield (35 mg) as described for compound 41 but using compound 21 and benzo[d][1,3]dioxol-5-ylboronic acid as the starting materials. ¹H-NMR (400 MHz, CDCl₃) δ: 7.81 (s, 1H), 7.40 (d, 1H, J=8.4 Hz), 7.26 (m, 2H), 7.10 (m, 1H), 6.90 (d, 1H, J=8.4 Hz), 6.00 (s, 2H), 4.24 (m, 2H), 3.25 (m, 2H), 2.95 (m, 1H), 2.66-2.60 (m, 4H), 2.13 (m, 2H), 1.92 (m, 2H), 1.72 (m, 2H). MS (ESI): m/z 362 (M+H⁺).

211. Compound 211: (3-cyclobutyl-8-(3,4-dichlorophenyl)-2,3,4,5-tetrahydro-1H-benzo[4,5]imidazo[1,2-d][1,4]diazepine)

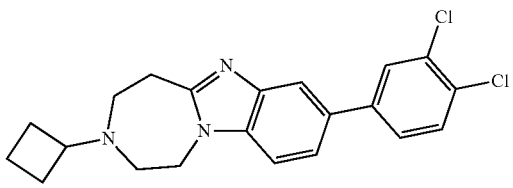

This compound was prepared in 53% yield (32 mg) as described for compound 41 but using compound 21 and 2-(3,4-dichlorophenyl)-4,4,5,5-tetramethyl-1,3,2-dioxaborolane as the starting materials. ¹H-NMR (400 MHz, CDCl₃) δ: 7.84 (s, 1H), 7.70 (d, 1H, J=2.0 Hz), 7.51 (d, 1H, J=8.4 Hz), 7.46 (d, 1H, J=2.0 Hz), 7.44 (d, 1H, J=8.4 Hz), 7.32 (d, 1H, J=8.8 Hz), 4.29 (m, 2H), 3.29 (m, 2H), 2.96 (m, 1H), 2.68-2.63 (m, 4H), 2.13 (m, 2H), 1.93 (m, 2H), 1.76 (m, 2H). MS (ESI): m/z 387 (M+H⁺).

212. Compound 212: (8-(4-(tert-butyl)phenyl)-3-cyclobutyl-2,3,4,5-tetrahydro-1H-benzo[4,5]imidazo[1,2-d][1,4]diazepine)

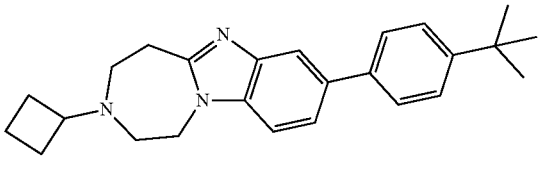

This compound was prepared in 38% yield (22 mg) as described for compound 41 but using compound 21 and 2-(4-(tert-butyl)phenyl)-4,4,5,5-tetramethyl-1,3,2-dioxaborolane as the starting materials. ¹H-NMR (400 MHz, CDCl₃) δ: 7.90 (d, 1H, J=1.6 Hz), 7.58 (d, 21-1, J=8.4 Hz), 7.51-7.47 (m, 3H), 7.29 (d, 1H, J=8.4 Hz), 4.27 (m, 2H), 3.27 (m, 2H), 2.94 (m, 1H), 2.68-2.63 (m, 4H), 2.14 (m, 2H), 1.93 (m, 2H), 1.73 (m, 2H), 1.37 (s, 9H). MS (ESI): m/z 374 (M+H⁺).

213. Compound 213: (3-cyclobutyl-8-(4-(trifluoromethyl)phenyl)-2,3,4,5-tetrahydro-1H-benzo[4,5]imidazo[1,2-d][1,4]diazepine)

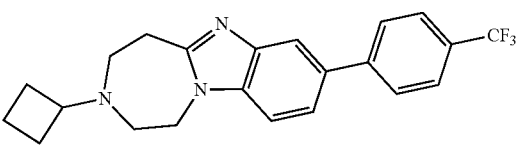

This compound was prepared in 8% yield (5 mg) as described for compound 41 but using compound 21 and 4,4,5,5-tetramethyl-2-(4-(trifluoromethyl)phenyl)-1,3,2-dioxaborolane as the starting materials. ¹H-NMR (400 MHz, CDCl₃) δ: 7.91 (s, 1H), 7.72 (m, 4H), 7.50 (d, 1H, J=8.4 Hz), 7.34 (d, 1H, J=8.4 Hz), 4.29 (m, 2H), 3.29 (m, 2H), 2.94 (m, 1H), 2.68-2.63 (m, 4H), 2.13 (m, 2H), 1.93 (m, 2H), 1.76 (m, 2H). MS (ESI): m/z 386 (M+H⁺).

214. Compound 214: (3-cyclobutyl-8-(naphthalen-2-yl)-2,3,4,5-tetrahydro-1H-benzo[4,5]imidazo[1,2-d][1,4]diazepine)

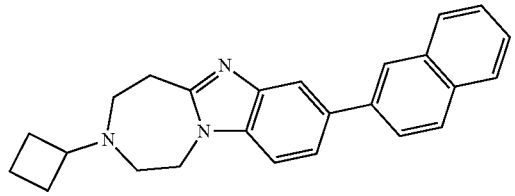

This compound was prepared in 33% yield (20 mg) as described for compound 22 but using 2-bromonaphthalene as the starting material. ¹H-NMR (400 MHz, CDCl₃) δ: 8.07 (s, 1H), 8.03 (s, 1H), 7.91 (t, 2H, J=8.0 Hz), 7.87 (d, 1H, J=8.0 Hz), 7.81 (d, 1H, J=8.0 Hz), 7.63 (d, 1H, J=8.4 Hz), 7.48 (m, 2H), 7.35 (d, 1H, J=8.4 Hz), 4.27 (m, 2H), 3.29 (m, 2H), 2.94

(m, 1H), 2.67 (m, 4H), 2.13 (m, 2H), 1.91 (m, 2H), 1.73 (m, 2H). MS (ESI): m/z 368 (M+H⁺).

215. Compound 215: (5-(3-cyclobutyl-2,3,4,5-tetrahydro-1,1-benzo[4,5]imidazo[1,2-d][1,4]diazepin-8-yl)benzo[d]oxazol-2(31-1)-one)

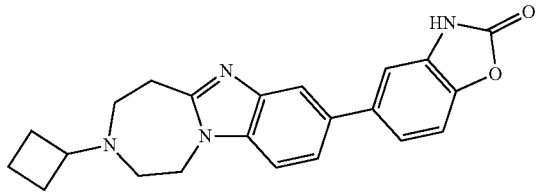

This compound was prepared in 11% yield (7 mg) as described for compound 22 but using 5-bromobenzo[d]oxazol-2(3H)-one as the starting material. ¹H-NMR (400 MHz, DMSO-d₆) δ: 7.70 (s, 1H), 7.53 (d, 1H, J=8.4 Hz), 7.44 (d, 1H, J=8.4 Hz), 7.16-7.11 (m, 3H), 4.31 (m, 2H), 3.22 (m, 2H), 3.12 (m, 1H), 2.58-2.50 (m, 4H), 2.06 (m, 2H), 1.84 (m, 2H), 1.64 (m, 2H). MS (ESI): m/z 375 (M+H⁺).

216. Compound 216: 6-(3-cyclobutyl-2,3,4,5-tetrahydro-1H-benzo[4,5]imidazo[1,2-d][1,4]diazepin-8-yl)-3,4-dihydroquinolin-2(1H)-one)

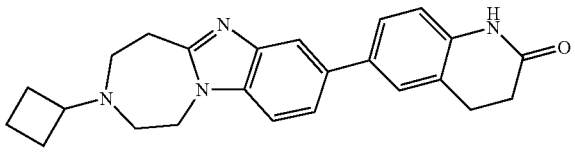

This compound was prepared in 11% yield (7 mg) as described for compound 22 but using 6-bromo-3,4-dihydroquinolin-2(1H)-one as the starting material. ¹H-NMR (400 MHz, CDCl₃) δ: 7.85 (d, 2H, J=10.4 Hz), 7.45 (m, 3H), 7.28 (d, 1H, J=8.4 Hz), 6.83 (d, 1H, J=8.8 Hz), 4.26 (m, 2H), 3.26 (m, 2H), 3.05 (m, 2H), 2.94 (m, 1H), 2.71-2.63 (m, 6H), 2.14 (m, 2H), 1.94 (m, 2H), 1.71 (m, 2H). MS (ESI): m/z 387 (M+H⁺).

217. Compound 217: (8-(1H-benzo[d]imidazol-5-yl)-3-cyclobutyl-2,3,4,5-tetrahydro-1H-benzo[4,5]imidazo[1,2-d][1,4]diazepine)

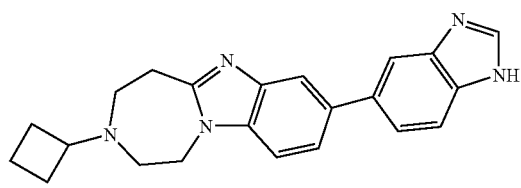

This compound was prepared in 16% yield (11 mg) as described for intermediate I-18 but using intermediate I-17 and 6-bromo-1H-benzo[d]imidazole as the starting materials. ¹H-NMR (400 MHz, CDCl₃) δ: 8.11 (s, 1H), 7.96 (s, 1H), 7.89 (br, 1H), 7.75 (br, 1H), 7.55 (d, 2H, J=8.4 Hz), 7.31 (d, 1H, J=8.4 Hz), 4.27 (m, 2H), 3.29 (m, 2H), 2.94 (m, 1H), 2.67 (m, 4H), 2.13 (m, 2H), 1.91 (m, 2H), 1.73 (m, 2H). MS (ESI): m/z 387 (M+H⁺).

218. Compound 218: (10-chloro-3-cyclobutyl-1,2,3,4,5,6-hexahydrobenzo[4,5]imidazo[1,2-a][1,5]diazocine)

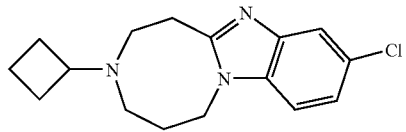

This compound was prepared in 70% yield (900 mg) as described for compound 143 but using intermediate I-94 as the starting material. ¹H-NMR (400 MHz, CDCl₃) δ: 7.67 (s, 1H), 7.19 (m, 2H), 4.39 (t, 2H, J=5.6 Hz), 3.13~3.09 (m, 3H), 2.78~2.76 (m, 2H), 2.07~2.00 (m, 4H), 1.77~1.57 (m, 6H). MS (ESI): m/z 290 (M+H⁺).

219. Compound 219: (4-(3-cyclobutyl-1,2,3,4,5,6-hexahydrobenzo[4,5]imidazo[1,2-a][1,5]diazocin-10-yl)benzonitrile)

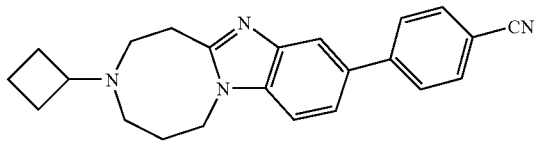

This compound was prepared in 20% yield (15 mg) as described for compound 2 but using compound 218 as the starting material. ¹H-NMR (400 MHz, CDCl₃): δ 8.05~8.03 (m, 1H), 7.77~7.71 (m, 4H), 7.61 (d, 1H, J=8.8 Hz), 7.55~7.45 (m, 11-1), 4.74 (s, 2H), 3.90=-3.00 (m, 7H), 2.55~2.50 (m, 3H), 2.27~2.23 (m, 3H), 1.96=-1.88 (m, 1H), 1.74~1.67 (m, 1H). MS (ESI): m/z 357 (M+H⁺).

220. Compound 220: (3-cyclobutyl-10-(imidazo[1,2-a]pyridin-6-yl)-1,2,3,4,5,6-hexahydrobenzo[4,5]imidazo[1,2-a][1,5]diazocine)

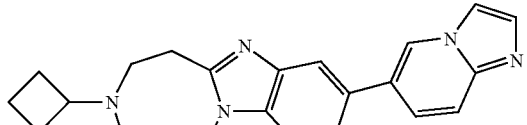

This compound was prepared in 61% yield (30 mg) as described for compound 41 but using intermediate I-95 and 6-bromoimidazo[1,2-a]pyridine as starting materials. ¹H-NMR (400 MHz, CDCl₃): δ 8.31 (s, 1H), 7.86 (d, 1H, J=0.8 Hz), 7.70~7.64 (m, 3H), 7.49 (dd, 1H, J₁=1.6 Hz, J₂=8.8 Hz), 7.44~7.37 (m, 2H), 4.45 (t, 2H, J=6.0 Hz), 3.16=-

3.13 (m, 3H), 2.78 (t, 2H, J=5.6 Hz), 2.13~2.10 (m, 2H), 2.07~2.00 (m, 2H), 1.84~4.79 (m, 4H), 1.69~1.59 (m, 2H), MS (ESI): m/z 372 (M+H⁺).

221. Compound 221: (4-((3-cyclobutyl-1,2,3,4,5,6-hexahydrobenzo[4,5]imidazo[1,2-a][1,5]diazocin-10-yl)methyl)morpholine)

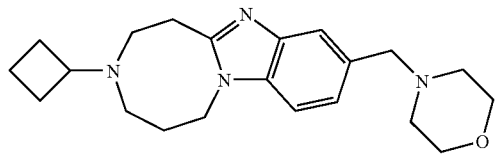

This compound was prepared in 63% yield (1.1 g) as described for compound 8 but using intermediate I-98 and morpholine as the starting materials. ¹H-NMR (400 MHz, CDCl₃): δ 7.62 (s, 1H), 7.21-7.26 (m, 2H), 4.39-4.42 (t, J=6.0 Hz), 3.69-3.72 (t, J=4.4 Hz, 4H), 3.62 (s, 2H), 3.09-3.12 (m, 3H), 2.75-2.78 (t, J=5.2 Hz, 2H), 2.47 (m, 4H), 1.98-2.08 (m, 4H), 1.58-1.83 (m, 6H). MS (ESI): m/z 355 (M+H⁺).

222. Compound 222: (3-cyclobutyl-10-((3,4-dihydroisoquinolin-2(1H)-yl)methyl)-1,2,3,4,5,6-hexahydrobenzo[4,5]imidazo[1,2-a][1,5]diazocine)

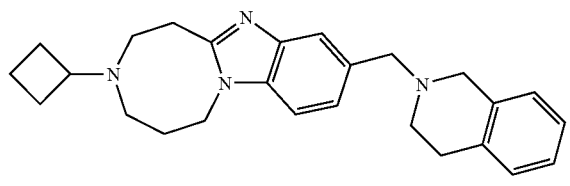

This compound was prepared in 56% yield (1.1 g) as described for compound 8 but using intermediate I-98 and 1,2,3,4-tetrahydroisoquinoline as the starting materials. ¹H-NMR (400 MHz, CDCl₃): δ 7.66 (s, 1H), 7.32-7.35 (m, 1H), 7.24-7.27 (m, 1H), 7.07-7.10 (m, 3H), 6.95-6.97 (m, 1H), 4.39-4.42 (t, J=6.0 Hz, 2H), 3.80 (s, 2H), 3.65 (s, 2H), 3.09-3.16 (m, 3H), 2.87-2.91 (t, J=6.0 Hz, 2H), 2.76-2.79 (t, J=6.0 Hz, 4H), 1.98-2.08 (m, 4H), 1.58-1.83 (m, 6H). MS (ESI): m/z 401 (M+H⁺).

223. Compound 223: (3-cyclobutyl-8-(1H-pyrazolo[3,4-b]pyridin-5-yl)-2,3,4,5-tetrahydro-1H-benzo[4,5]imidazo[1,2-d][1,4]diazepine)

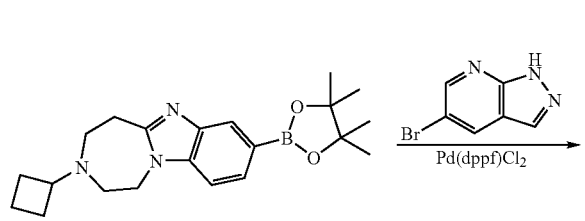

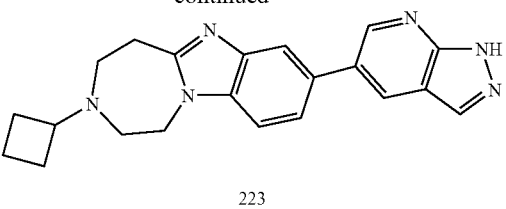

To a mixture of intermediate I-17 (100 mg, 0.27 mmol, 1.0 eq), 6-bromo-[1,2,4]triazolo-[4,3-a]pyridine (60 mg, 0.30 mmol, 1.1 eq) and Pd(dppf)Cl₂ (20 mg, 0.03 mmol, 0.1 eq) was added an emulsion of Na₂CO₃ in water (0.6 mL, 1.2 mmol, 4.5 eq, 2.0 M), toluene (1.5 mL) and ethanol (1.5 mL). The reaction flask was purged 3 times with argon and reaction mixture was stirred at 100° C. for 3 hours under microwave irradiation. The crude reaction mixture was diluted with ethyl acetate, the solids were removed by filtration and the filtrate was concentrated by evaporation. The crude reaction product was purified by silicagel flash chromatography to give compound 223 (10 mg, 10%) as a white solid. ¹H-NMR (400 MHz, CD₃OD): δ 10.91 (br, 1H), 8.87 (d, J=2.4 Hz, 1H), 8.28 (d, J=1.6 Hz, 1H), 8.16 (s, 1H), 7.92 (d, J=1.2 Hz, 1H), 7.49-7.52 (m, 1H), 7.36-7.38 (m, 1H), 4.29-4.31 (m, 2H), 3.29-3.31 (m, 2H), 2.92-2.99 (m, 1H), 2.64-2.71 (m, 4H), 2.14-2.16 (m, 2H), 1.91-1.96 (m, 2H), 1.67-1.77 (m, 2H). MS (ESI): m/z 359.1 (M+H⁺).

224. Compound 224: (8-(4-benzylpiperazin-1-yl)-3-cyclobutyl-2,3,4,5-tetrahydro-1H-benzo[4,5]imidazo[1,2-d][1,4]diazepine)

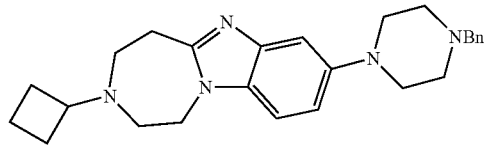

This compound was prepared in 23% yield (10 mg) as described for intermediate I-38 but using 1-benzylpiperazine as the starting material. ¹H-NMR (400 MHz, CDCl₃): δ 7.35 (m, 5I-1), 7.23 (d, J=2.0 Hz, 1H), 7.12 (d, J=8.8 Hz, 1H), 6.98 (dd, J₁=2.2 Hz, J₂=8.8 Hz, 1H), 4.17 (m, 2H), 3.59 (s, 1H), 3.18 (m, 6H), 2.90 (m, 1H), 2.61 (m, 7H), 2.11 (m, 2H), 1.89 (m, 2H), 1.66 (m, 3H). MS (ESI): m/z 416 (M+H⁺).

225. Compound 225: (4-(1-(3-cyclobutyl-2,3,4,5-tetrahydro-1,1-benzo[4,5]imidazo[1,2-d][1,4]diazepin-8-yl)piperidin-4-yl)morpholine)

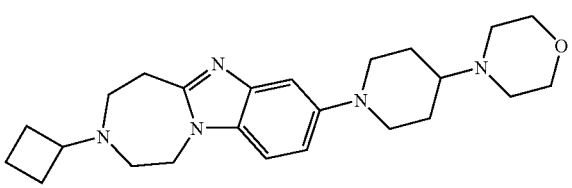

This compound was prepared in 6% yield as described for intermediate I-38 but using 4-(piperidin-4-yl)morpholine as the starting material. ¹H-NMR (400 MHz, CDCl₃): δ 7.24 (d, J=2.0 Hz, 1H), 7.12 (d, J=8.8 Hz, 1H), 7.00 (dd, J₁=2.2 Hz, J₂=8.8 Hz, 1H), 4.17 (m, 2H), 3.74 (m, 2H), 3.64 (m, 2H), 3.20 (m, 2H), 2.91 (m, 1H), 2.70 (m, 2H), 2.59 (m, 6H), 2.32 (m, 1H), 2.11 (m, 2H), 1.91 (m, 4H), 1.70 (m, 8H). MS (ESI): m/z 410 (M+H⁺).

226. Compound 226: (3-cyclobutyl-8-(pyrrolidin-1-yl)-2,3,4,5-tetrahydro-1H-benzo[4,5]imidazo[1,2-d][1,4]diazepine)

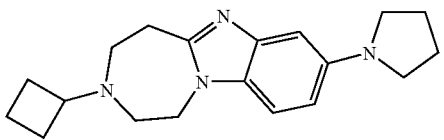

This compound was prepared in 9% yield (4.5 mg) as described for intermediate I-38 but using pyrrolidine as the starting material. ¹H-NMR (400 MHz, CDCl₃): δ 7.09 (m, 1H), 6.86 (m, 1H), 6.63 (dd, J₁=2.1 Hz, J₂=8.7 Hz, 1H), 4.18 (m, 2H), 3.30 (m, 3H), 3.19 (m, 2H), 2.91 (m, 1H), 2.60 (m, 4H), 2.11 (m, 2H), 2.01 (m, 3H), 1.90 (m, 3H), 1.69 (m, 3H). MS (ESI): m/z 311 (M+H⁺).

227. Compound 227: (3-cyclobutyl-8-(4-phenylpiperidin-1-yl)-2,3,4,5-tetrahydro-1H-benzo[4,5]imidazo[1,2-d][1,4]diazepine)

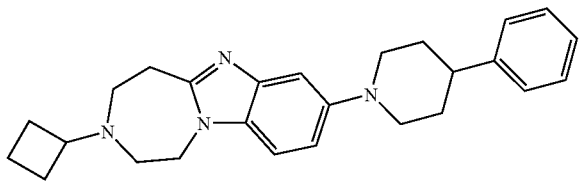

This compound was prepared in 12% yield as described for intermediate I-38 but using 4-phenylpiperidine as the starting material. ¹H-NMR (400 MHz, CDCl₃): δ 7.30 (m, 5H), 7.21 (m, 1H), 7.15 (d, J=8.8 Hz, 1H), 7.06 (dd, J₁=2.0 Hz, J₁=8.8 Hz, 1H), 4.19 (m, 2H), 3.71 (m, 2H), 3.21 (m, 2H), 2.92 (m, 1H), 2.82 (m, 2H), 2.61 (dt, J₁=4.8 Hz, J₂=15.4 Hz, 4H), 2.12 (m, 2H), 1.99 (m, 4H), 1.90 (m, 2H), 1.70 (m, 3H). MS (ESI): m/z 401 (MAT).

228. Compound 228: (4-(4-(3-cyclobutyl-2,3,4,5-tetrahydro-1H-benzo[4,5]imidazo[1,2-d][1,4]diazepin-8-yl)piperazin-1-yl)benzonitrile)

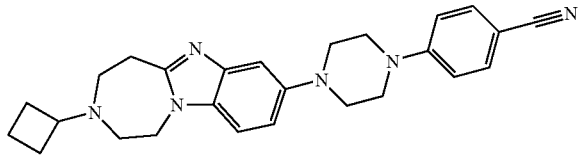

This compound was prepared in 17% yield as described for intermediate I-38 but using 4-(piperazin-1-yl)benzonitrile as the starting material. ¹H-NMR (400 MHz, CDCl₃): δ 7.52 (d, J=9.0 Hz, 2H), 7.27 (d, J=2.1 Hz, 1H), 7.17 (d, J=8.8 Hz, 1H), 7.02 (dd, J₁=2.2 Hz, J₂=8.8 Hz, 1H), 6.92 (d, J=9.0 Hz, 2H), 4.19 (m, 2H), 3.51 (m, 4H), 3.28 (m, 3H), 3.21 (m, 2H), 2.91 (m, 1H), 2.61 (dt, J₁=4.8 Hz, J₂=15.4 Hz, 4H), 2.12 (m, 2H), 1.90 (m, 2H), 1.70 (m, 3H). MS (ESI): m/z 427 (M+H⁺).

229. Compound 229: (3-cyclobutyl-8-(4-phenylpiperazin-1-yl)-2,3,4,5-tetrahydro-1H-benzo[4,5]imidazo[1,2-d][1,4]diazepine)

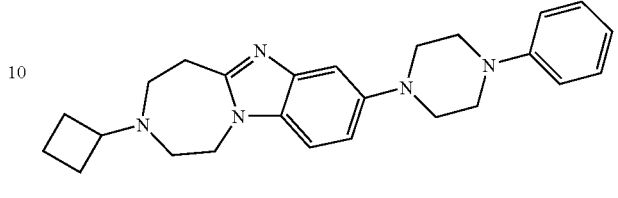

This compound was prepared in 42% yield (31 mg) as described for intermediate I-38 but using 1-phenylpiperazine as the starting material. ¹H-NMR (400 MHz, CDCl₃): δ 7.30 (m, 3H), 7.16 (d, J=8.8 Hz, 1H), 7.05 (dd, J₁=2.2 Hz, J₂=8.8 Hz, 1H), 7.00 (m, 2H), 6.89 (t, J=7.3 Hz, 1H), 4.19 (t, J=4.5 Hz, 2H), 3.35 (m, 7H), 3.21 (m, 2H), 2.92 (m, 1H), 2.61 (dt, J₁=4.9 Hz, J₂=14.8 Hz, 4H), 2.12 (m, 2H), 1.91 (m, 2H), 1.70 (m, 3H). MS (ESI): m/z 402 (M+H⁺).

230. Compound 230: (3-cyclobutyl-8-(4-(pyridin-2-yl)piperazin-1-yl)-2,3,4,5-tetrahydro-1H-benzo[4,5]imidazo[1,2-d][1,4]diazepine)

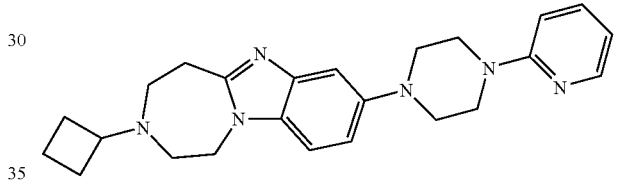

This compound was prepared in 32% yield (25 mg) as described for intermediate I-38 but using 1-(pyridin-2-yl)piperazine as the starting material. ¹H-NMR (400 MHz, CDCl₃): δ 8.22 (dd, J₁=1.3 Hz, J₂=4.9 Hz, 1H), 7.50 (m, 1H), 7.29 (d, J=2.1 Hz, 1H), 7.16 (d, J=8.8 Hz, 1H), 7.05 (dd, J₁=2.2 Hz, J₂=8.8 Hz, 1H), 6.71 (d, J=8.6 Hz, 1H), 6.64 (m, 1H), 4.19 (t, J=4.5 Hz, 2H), 3.74 (m, 4H), 3.26 (m, 3H), 3.21 (m, 2H), 2.91 (m, 1H), 2.61 (dt, J₁=4.8 Hz, J₂=15.3 Hz, 4H), 2.10 (m, 2H), 1.90 (m, 2H), 1.69 (m, 3H). MS (ESI): m/z 403 (M+H⁺).

231. Compound 231: (3-cyclobutyl-8-(4-(4-fluorophenyl)piperazin-1-yl)-2,3,4,5-tetrahydro-1H-benzo[4,5]imidazo[1,2-d][1,4]diazepine)

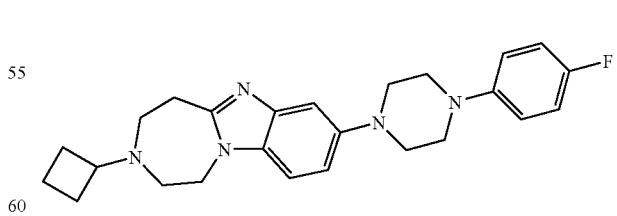

This compound was prepared in 27% yield (18 mg) as described for intermediate I-38 but using 1-(4-fluorphenyl)-piperazine as the starting material. ¹H-NMR (400 MHz, CDCl₃): δ 7.29 (d, J=2.1 Hz, 1H), 7.16 (d, J=8.8 Hz, 1H), 7.04 (dd, J₁=2.2 Hz, J₂=8.8 Hz, 1H), 6.93 (m, 4H), 4.19 (m, 2H), 3.49 (m, 2H), 3.30 (m, 5H), 3.21 (m, 2H), 2.91 (m, 1H), 2.61

(dt, $J_1$=4.8, $J_2$=15.0 Hz, 41-1), 2.12 (m, 2H), 1.90 (m, 2H), 1.68 (m, 3H). MS (ESI): m/z 420 (M+H$^+$).

232. Compound 232: (2-(4-(3-cyclobutyl-2,3,4,5-tetrahydro-1H-benzo[4,5]imidazo[1,2-d][1,4]diazepin-8-yl)piperazin-1-yl)thiazole)

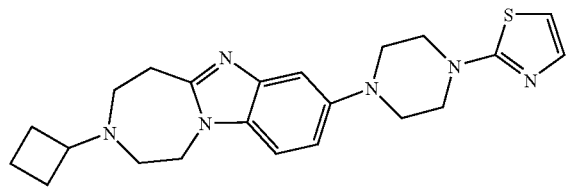

This compound was prepared in 30% yield (12 mg) as described for intermediate I-38 but using 2-(piperazin-1-yl)thiazole as the starting material. $^1$H-NMR (400 MHz, CDCl$_3$): δ 7.27 (d, J=2.1 Hz, 1H), 7.22 (d, J=3.6 Hz, 1H), 7.16 (d, J=8.8 Hz, 1H), 7.02 (dd, $J_1$=2.2, $J_2$=8.8 Hz, 1H), 6.60 (d, J=3.6 Hz, 1H), 4.20 (m, 2H), 3.69 (m, 4H), 3.26 (m, 3H), 3.22 (m, 2H), 2.92 (m, 1H), 2.61 (m, 4H), 2.11 (m, 2H), 1.91 (m, 2H), 1.70 (m, 3H). MS (ESI): m/z 409 (M+H$^+$).

233. Compound 233: (3-cyclobutyl-8-(4-(pyrazin-2-yl)piperazin-1-yl)-2,3,4,5-tetrahydro-1H-benzo[4,5]imidazo[1,2-d][1,4]diazepine)

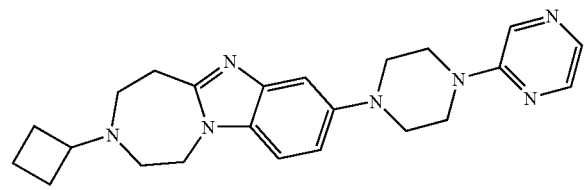

This compound was prepared in 10% yield as described for intermediate I-38 but using 2-(piperazin-1-yl)pyrazine as the starting material. $^1$H-NMR (400 MHz, CDCl$_3$): δ 8.20 (d, J=1.4 Hz, 1H), 8.09 (dd, $J_1$=1.5 Hz, $J_1$=2.6 Hz, 1H), 7.87 (d, J=2.6 Hz, 1H), 7.28 (d, J=2.1 Hz, 1H), 7.17 (d, J=8.8 Hz, 1H), 7.03 (dd, $J_1$=2.2, $J_1$=8.8 Hz, 1H), 4.19 (t, J=4.5 Hz, 2H), 3.79 (t, J=5.1 Hz, 4H), 3.26 (t, J=5.1 Hz, 311), 3.21 (m, 2H), 2.91 (m, 1H), 2.61 (dt, $J_1$=4.8, $J_2$=15.4 Hz, 4H), 2.11 (m, 2H), 1.90 (m, 2H), 1.67 (m, 31-1). MS (ESI): m/z 404 (M+H$^+$).

234. Compound 234: (3-cyclobutyl-9-(4-(pyridin-2-yl)piperazin-1-yl)-2,3,4,5-tetrahydro-1H-benzo[4,5]imidazo[1,2-d][1,4]diazepine)

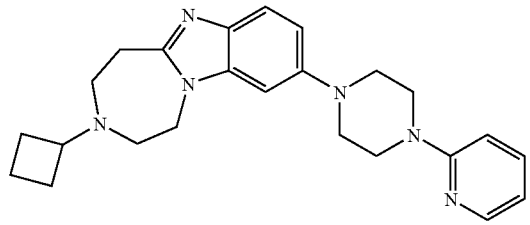

This compound was prepared in 18% yield as described for intermediate I-38 but using compound 40 and 1-(pyridin-2-yl)piperazine as the starting materials. $^1$H-NMR (400 MHz, CDCl$_3$): δ 8.22 (dd, $J_1$=1.2 Hz, $J_2$=4.9 Hz, 1H), 7.58 (d, J=8.7 Hz, 1H), 7.51 (m, 1H), 6.99 (dd, $J_1$=2.2, $J_2$=8.8 Hz, 1H), 6.78 (d, J=2.0 Hz, 1H), 6.72 (d, J=8.6 Hz, 1H), 6.66 (m, 1H), 4.19 (t, J=4.5 Hz, 2H), 3.73 (t, J=5.1 Hz, 4H), 3.29 (t, J=5.1 Hz, 3H), 3.20 (m, 2H), 2.92 (m, 1H), 2.62 (dt, $J_1$=4.8, $J_2$=18.6 Hz, 4H), 2.12 (m, 2H), 1.90 (m, 2H), 1.69 (m, 3H). MS (ESI): m/z 403 (M+H$^+$).

235. Compound 235: (7-Aza-3-cyclobutyl-9-bromo-2,3,4,5-tetrahydro-1H-[1,4]diazepino[1,7-a]benzimidazole)

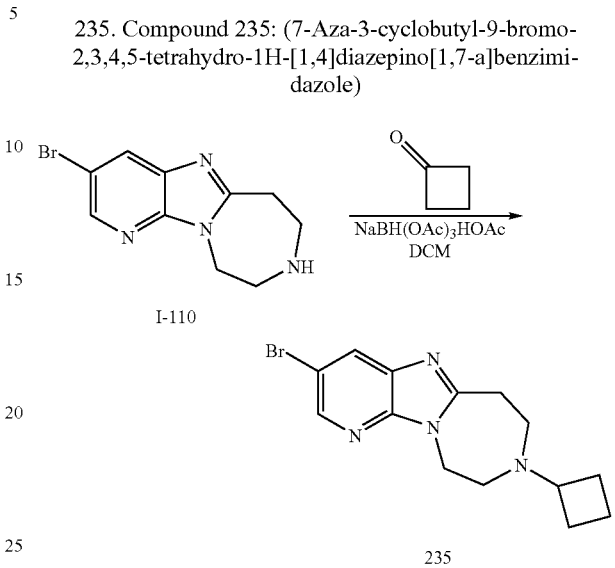

I-110 (0.29 g, 1.1 mmol) and acetic acid (0.072 g, 1.2 mmol) were dissolved in dichloromethane (2 mL) and the reaction mixture was stirred on ice bath for 30 minutes. Cyclobutanone (0.12 g, 1.6 mmol) was added and the mixture was stirred for 2 hours at room temperature. Solid NaBH(OAc)$_3$ (0.92 g, 4.4 mmol) was added and the reaction mixture was stirred for 16 hours at room temperature. The reaction mixture was concentrated, the residue was dissolved in ethyl acetate and aqueous saturated solution of NaHCO$_3$ was added. The reaction mixture was stirred for 20 minutes at room temperature, the organic layer was collected and washed with brine, the combined organic layers were dried over Na$_2$SO$_4$, the solids were filtered and the filtrate was concentrated. The crude reaction mixture was purified by preparative TLC to give compound 235 (0.20 g, 57%). $^1$H NMR (400 MHz, CDCl$_3$): δ 8.34 (1H, d, J=2.0 Hz), 8.06 (1H, d, J=2.0 Hz), 4.43 (m, 2H), 3.25 (m, 2H), 2.92 (m, 1H), 2.63 (m, 4H,), 2.10-2.14 (m, 2H), 1.92 (m, 2H), 1.65-1.73 (m, 2H). MS (ESI): m/z 322 (M+1)$^+$.

236. Compound 236: (7-Aza-3-cyclobutyl-9-(pyrazin-2-yl)-2,3,4,5-tetrahydro-1H-[1,4]diazepino[1,7-a]benzimidazole)

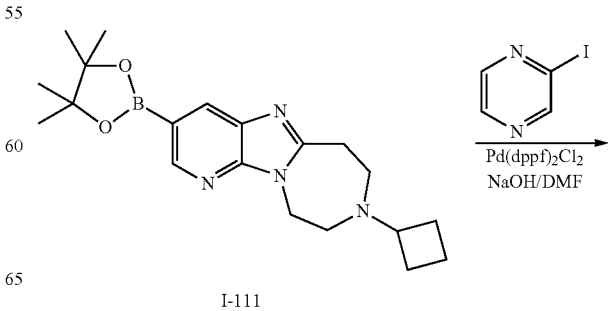

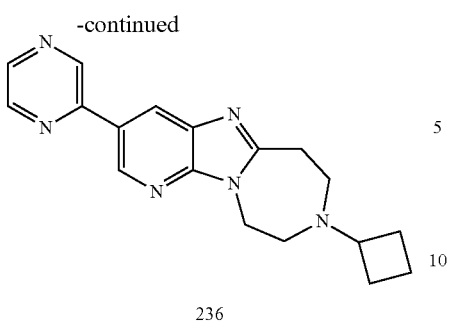

236

I-111 (0.10 g, 0.31 mmol), Pd(dppf)$_2$Cl$_2$ (23 mg, 0.03 mmol), NaOH (38 mg, 0.94 mmol) and 2-iodopyrazine (64 mg, 0.31 mmol) were dissolved in DMF (1 mL) in a microwave tube that was filled with argon. The reaction mixture was stirred at 100° C. for 1 h under microwave irradiation. The reaction mixture was diluted with ethyl acetate and filtered through a short plug of Celite. The filtrate was washed with brine and the combined organic layers were dried over Na$_2$SO$_4$, the solids were filtered and the filtrate was concentrated. The crude reaction mixture was purified by preparative TLC to give compound 236 (0.018 g, 21%). $^1$H NMR (400 MHz, CDCl$_3$): δ 9.08 (d, 2H). 8.98 (d, 1H, J=2.0 Hz), 8.67 (m, 1H), 8.540 (m, 2H), 4.53 (m, 2H), 3.30 (m, 2H), 2.85-2.94 (m, 1H), 2.68 (m, 4H), 2.12-2.16 (m, 2H), 1.86-1.98 (m, 2H), 1.62-1.78 (m, 2H). MS (ESI): m/z 321 (M+1)$^+$.

237. Compound 237: (4-(7-aza-3-cyclobutyl-2,3,4,5-tetrahydro-1H-[1,4]diazepino[1,7-a]benzimidazol-9-yl)benzonitrile)

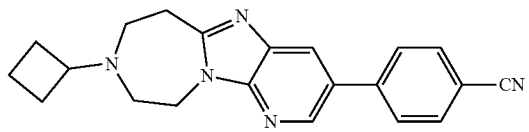

This compound was prepared in 53% yield as described for compound 236 but using compound 235 and 4-cyanophenylboronic acid as the starting material. $^1$H NMR (400 MHz, CDCl$_3$): δ 8.54 (d, 1H, J=2.0 Hz). 8.14 (d, 1H, J=2.0 Hz), 7.76 (d, 2H, J=6.8 Hz), 7.69 (d, 2H, J=8.8 Hz), 4.49 (m, 2H), 3.31 (m, 2H), 3.31 (m, 1H, m), 2.64-2.68 (m, 4H), 2.14 (m, 2H), 1.93 (m, 2H), 1.68-1.77 (m, 2H). MS (ESI): m/z 344 (M+1)$^+$.

238. Compound 238: (7-aza-3-cyclobutyl-8-(furan-2-yl)-2,3,4,5-tetrahydro-1H-[1,4]diazepino[1,7-a]benzimidazole)

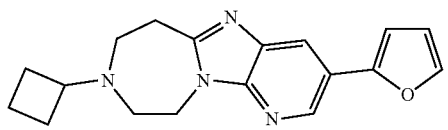

This compound was prepared in 56% yield as described for compound 236 but using compound 235 and furan-2-ylboronic acid as the starting material. $^1$H NMR (400 MHz, CDCl$_3$): δ 8.66 (d, 1H, J=2.0 Hz), 8.17 (d, 1H, J=2.0 Hz), 7.52 (dd, 1H, J$_1$=0.8 Hz, J$_2$=1.6 Hz), 6.68 (dd, 1H, J$_1$=0.8 Hz, J$_2$=3.2 Hz), 6.50 (dd, 1H, J$_1$=3.2 Hz, J$_2$=1.6 Hz), 4.46 (m, 2H), 3.26 (m, 2H), 2.85-2.97 (m, 1H), 2.652 (m, 4H), 2.12 (m, 2H), 1.89-1.94 (m, 2H), 1.67-1.76 (m, 2H). MS (ESI): m/z 309 (M+1)$^+$.

239. Compound 239: (3-cyclobutyl-9-(4-(aminomethyl)phenyl)-2,3,4,5-tetrahydro-1H-[1,4]diazepino[1,7-a]benzimidazole)

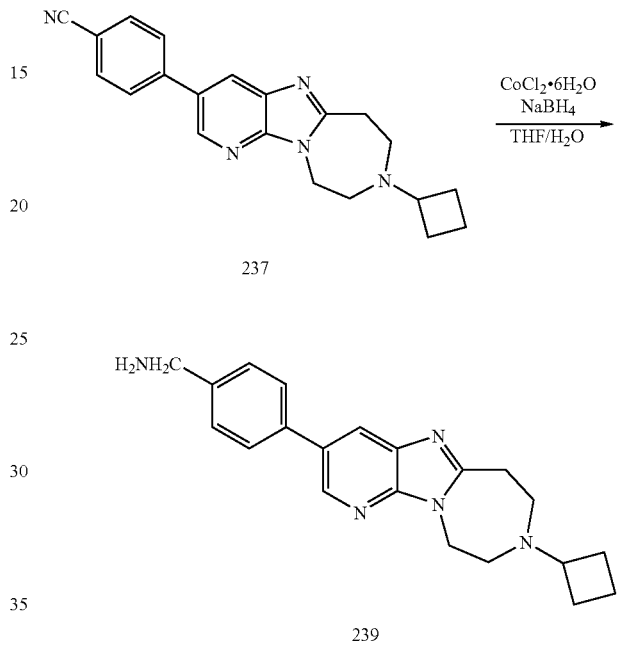

Compound 237 (70 mg, 0.20 mmol) and CoCl$_2$.6H$_2$O (49 mg, 0.20 mmol) were dissolved in a 2:1 mixture of THF and H$_2$O and the reaction mixture was stirred for 30 minutes at room temperature. Solid NaBH$_4$ (38 mg, 1.0 mmol) was added the reaction mixture was stirred for 2 hours at room temperature. The reaction mixture was concentrated and the residue was diluted with ethyl acetate and washed with brine. The combined organic layers were dried over Na$_2$SO$_4$, the solids were filtered and the filtrate was concentrated. The crude reaction mixture was purified with preparative TLC to give 239 (0.014 g, 20%). $^1$H NMR (400 MHz, CDCl$_3$): δ 8.52 (d, 1H, J=2.0 Hz). 8.09 (d, 1H, J=2.0 Hz), 7.57 (d, 2H, J=8.0 Hz), 7.42 (d, 2H, J=8.0 Hz), 4.48 (m, 2H), 3.94 (s, 2H), 3.26 (m, 2H), 2.93 (m, 1H), 2.64 (m, 4H), 2.11 (m, 2H), 1.88-1.96 (m, 2H), 1.65-1.76 (m, 2H). MS (ESI): m/z 348 (M+1)$^+$.

240. Intermediate I-2: ((2-(4-chloro-2-nitrophenylamino)ethanol)

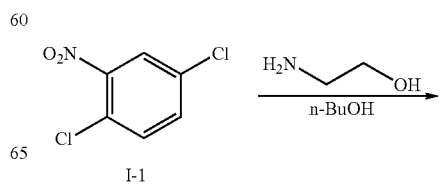

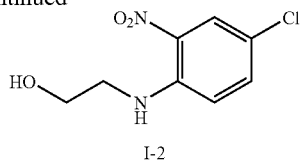

I-2

A mixture of 1,4-dichloro-2-nitrobenzene (I-1, Aldrich, Wis.; 38.4 g, 0.2 mol) and 2-aminoethanol (24.4 g, 0.4 mol, 2 eq.) in n-butanol (100 mL) was refluxed overnight. The solvent was evaporated and the residue was dispersed in petrol ether (600 mL) and stirred overnight. The solids were filtered to give intermediate I-2 as a yellow powder (37 g, 86%). $^1$H-NMR (400 MHz, CDCl$_3$): δ 8.24 (s, 1H), 8.19~8.20 (d, 1H, J=2.4 Hz), 7.39~7.42 (dd, 1H, J$_1$=2.4 Hz, J$_2$=9.2 Hz), 6.87~6.90 (d, 1H, J=9.6 Hz), 3.95~3.98 (t, 2H, J=5.2 Hz), 3.49~3.53 (dd, 2H, J$_1$=4.8 Hz, J$_2$=10.4 Hz). MS (ESI): m/z 217 (M+H$^+$).

241. Intermediate I-3: (2-(2-amino-4-chlorophenylamino)ethanol)

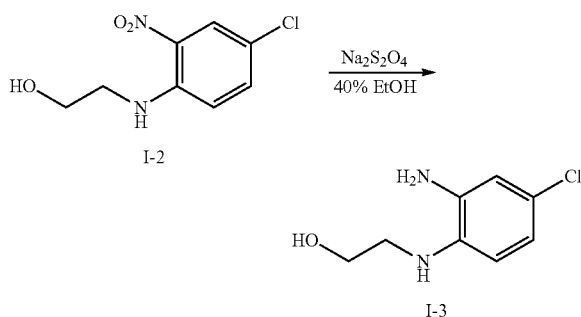

A slurry of Na$_2$S$_2$O$_4$ (13.7 g, 78.8 mmol) in H$_2$O (20 mL) was added over 5 minutes to a stirred solution of intermediate I-2 (4.26 g, 19.7 mmol, 4.0 eq.) in 40% aqueous ethanol (90 mL). The reaction mixture was refluxed for 1 hour and concentrated. The solid was collected by filtration and dried under vacuum to give intermediate I-3 as a pale yellow solid. The aqueous residue was basified with saturated aqueous NaHCO$_3$, extracted with ethyl acetate, the combined organic layers were dried over Na$_2$SO$_4$, the solids were removed by filtration and the filtrate was concentrated to give additional yellow solid. Both solids were combined to give I-3 (3.1 g, 84%). $^1$H-NMR (400 MHz, DMSO-d$_6$): δ 6.54~6.55 (d, 1H, J=2.4 Hz), 6.44~6.47 (dd, 1H, J$_1$=2.4 Hz, J$_2$=6.4 Hz), 6.35~3.37 (d, 1H, J=6.4 Hz), 4.80 (s, 2H), 4.68 (t, 1H, J=5.6 Hz), 4.46 (t, 1H, J=5.6 Hz), 3.55~3.66 (dd, 2H, J$_1$=6.0 Hz, J$_2$=12.0 Hz), 3.03~3.08 (dd, 2H, J$_1$=5.6 Hz, J$_2$=11.6 Hz). MS (ESI): m/z 187 (M+H$^+$).

242. Intermediate I-5: (tert-butyl 2-(5-chloro-1-(2-hydroxyethyl)-1H-benzo[d]imidazol-2-yl)ethylcarbamate)

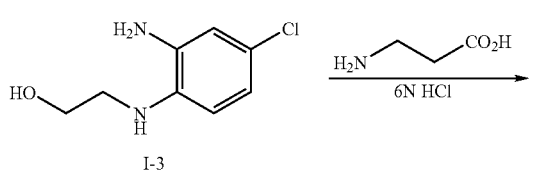

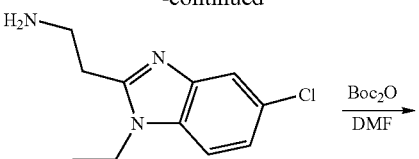

I-4

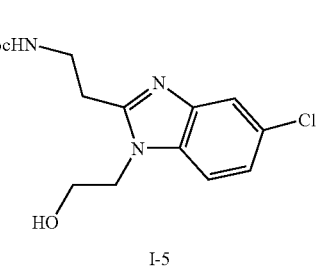

I-5

I-3 (6.1 g, 32.7 mmol) was added to a solution of 3-aminopropanonoc acid (4.7 g, 52.3 mmol, 1.6 eq.) in aqueous 6N HCl (70 mL) and refluxed for 24 h. The reaction mixture was basified with 20% aqueous NaOH and extracted with dichloromethane. The combined organic layers were dried over Na$_2$SO$_4$, the solids were removed by filtration and the filtrate was concentrated to obtain the crude intermediate I-4 (6.7 g, 86%). This intermediate was used in the next step without further purification. A sample for NMR analysis was purified by flash chromatography. $^1$H-NMR (400 MHz, DMSO-d$_6$): δ 7.58~7.59 (d, 1H, J=1.2), 7.51~7.53 (d, 1H, J=8.4), 7.17~7.19 (dd, 1H, J$_1$=8.4, J$_2$=2.0), 4.25 (t, 2H, J=9.6), 3.68 (t, 2H, J=5.6), 2.92~3.01 (m, 4H). MS (ESI): m/z 240 (M+1)$^+$.

A solution of intermediate I-4 (6.7 g, 28 mmol) in DMF (80 mL) was added to a solution of Boc$_2$O in DMF (20 mL) dropwise at room temperature and stirred for 1 hour. The reaction mixture was diluted with water and extracted with dichloromethane. The combined organic layers were dried over Na$_2$SO$_4$, the solids were removed by filtration and the filtrate was concentrated. The crude reaction mixture was purified by flash chromatography to give the intermediate I-5 as a light yellow solid (8.0 g, 84% overall yield from I-3 to I-5). $^1$H-NMR (400 MHz, DMSO-d$_6$): δ 7.59~7.60 (d, 1H, J=2.0 Hz), 7.53~7.55 (d, 1H, J=8.4 Hz), 7.18~7.21 (dd, 1H, J$_1$=2.0 Hz, J$_2$=8.8 Hz), 6.91 (t, 1H, J=5.2 Hz), 4.95 (t, 1H, J=5.2 Hz), 4.23 (t, 2H, J=5.6 Hz), 3.66 (dd, 2H, J$_1$=5.2 Hz, J$_2$=10.4 Hz), 3.39 (dd, 2H, J$_1$=7.2 Hz, J$_2$=10.8 Hz), 3.01 (t, 2H, J=7.2 Hz), 1.3 (s, 9H). MS (ESI): m/z 340 (M+H$^+$).

243. Intermediate I-6: (2-(2-(2-(tert-butoxycarbonylamino)ethyl)-5-chloro-1H-benzo[d]imidazol-1-yl)ethyl 4-methylbenzene-sulfonate)

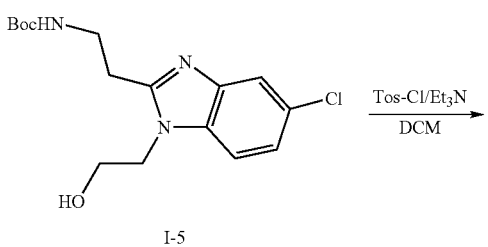

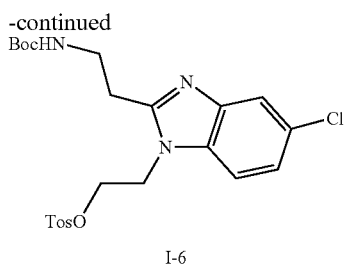

To a solution of intermediate I-5 (7.5 g, 22.2 mmol) in dichloromethane (100 mL) was added 4-methylbenzene-1-sulfonyl chloride (8.4 g, 44.4 mmol, 2.0 eq.) in dichloromethane (30 mL) dropwise at room temperature followed by neat triethylamine (6.7 g, 66.6 mmol, 3.0 eq.) and the reaction was stirred overnight. The precipitated solid was removed by filtration and dispersed in a mixture of dichloromethane and water. The product was extracted with dichloromethane and the organic layer was evaporated to give I-6 as a white powder. The filtrate was evaporated to dryness, dichloromethane (20 mL) was added, the solid was dispersed by irradiation with ultrasound and the solid was collected by filtration. This procedure was repeated until all triethylamine hydrochloride was removed. Intermediate I-6 was obtained as a white powder (9.2 g, 84%). (Note: Any residual 4-methylbenzene-1-sulfonyl chloride can be removed by washing with petrol ether). $^1$H-NMR (400 MHz, DMSO-$d_6$): δ 7.54 (d, 1H, J=1.6 Hz), 7.31~7.36 (m, 3H), 7.09~7.11 (m, 3H), 6.90 (m, 1H), 4.43~4.46 (m, 2H), 4.27~4.30 (m, 2H), 3.33-3.39 (m, 2H), 2.89~2.92 (m, 2H), 2.29 (s, 3H), 1.36 (s, 9H). MS (ESI): m/z 494 (M+H$^+$).

244. Intermediate I-8: (9-Chloro-2,3,4,5-tetrahydro-1H-[1,4]diazepino[1,7-a]benzimidazole)

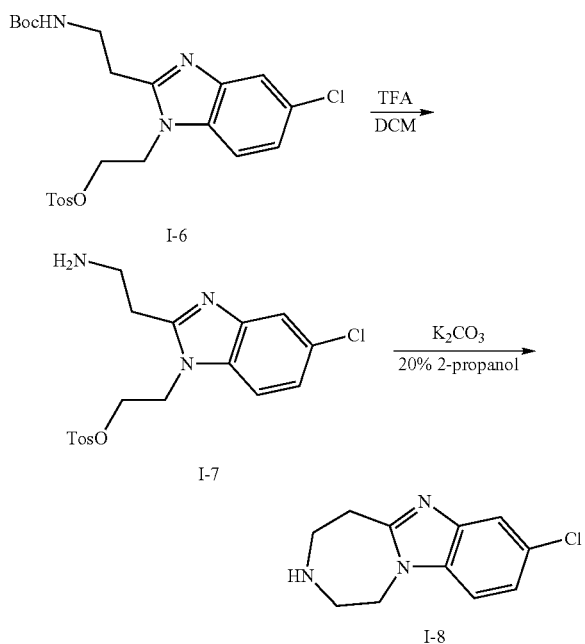

To a solution of intermediate I-6 (7.2 g, 14.6 mmol) in dichloromethane (50 mL) was added 2,2,2-trifluoroacetic acid (49 g, 30 eq.) over several minutes and the reaction mixture was stirred at room temperature for 1 hour. Reaction progress was monitored by LC-MS. The reaction mixture was concentrated to give intermediate I-7 as a light pink solid.

Intermediate I-7 was dissolved in 20% aqueous solution of 2-propanol (300 mL) containing solid K$_2$CO$_3$ (16.1 g, 8.0 eq.) and the reaction mixture was refluxed for 2 hours. The reaction mixture was concentrated and the aqueous residue was extracted with dichloromethane, the combined organic layers were dried over sodium sulfate, the solids were removed by filtration and the filtrate was evaporated to give intermediate I-8 as a pale yellow solid (3.4 g, 91%). $^1$H-NMR (400 MHz, CDCl$_3$): δ 7.66~7.67 (d, 1H, J=2.0 Hz), 7.20~7.23 (dd, 1H, J$_1$=2.0 Hz, J$_2$=8.8 Hz), 7.14~7.16 (d, 1H, J=8.4 Hz), 4.20 (t, 2H, J=4.8 Hz), 3.23~3.25 (m, 2H), 3.08~3.15 (m, 4H). MS (ESI): m/z 222 (M+H$^+$).

245. Intermediate I-10:
(2-(4-bromo-2-nitrophenylamino)ethanol)

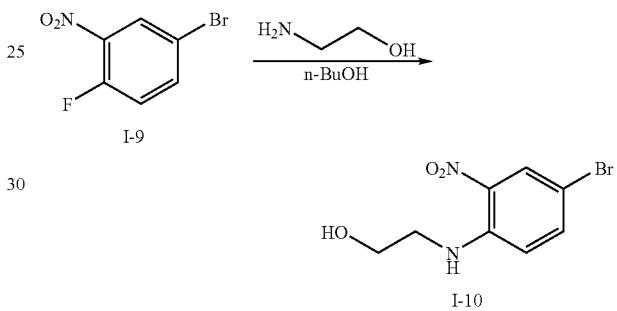

A mixture of 4-bromo-1-fluoro-2-nitrobenzene (I-9, Aldrich, Wis.; 25 g, 0.11 mol) and 2-aminoethanol (13.9 g, 0.23 mol, 2.0 eq.) in n-butanol (300 mL) was heated under reflux for 1 hour. The reaction mixture was concentrated and the residue was dispersed in petrol ether (600 mL) and stirred overnight. The solids were iltered to give I-10 as a yellow powder (29 g, 98%). MS (ESI): m/z 262 (M+H$^+$).

246. Intermediate I-11:
(2-(2-amino-4-bromophenylamino)ethanol)

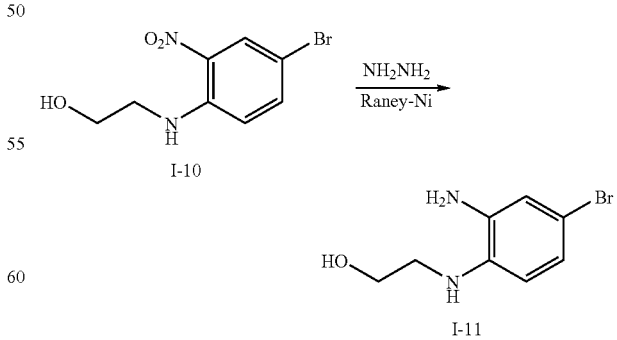

Raney-Ni was added dropwise to a solution of I-10 (20 g, 76.9 mmol) and hydrazine (15 g) in methanol (300 mL) at 0° C. and the resulting suspension was stirred for 1 hour. The solids were removed by filtration and the filtrate was concentrated to give the crude product I-11 (17 g, 96%). MS (ESI): m/z 232 (M+H$^+$).

247. Intermediate I-12: (tert-butyl 3-(5-bromo-2-(2-hydroxyethylamino)phenylamino)-3-oxopropylcarbamate)

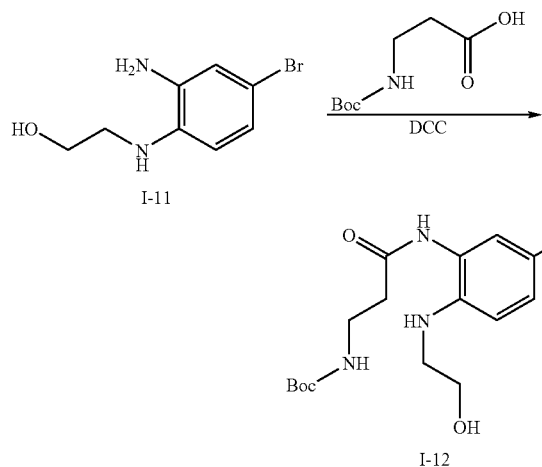

To a solution of I-11 (10 g, 43.4 mmol) in dichloromethane (250 mL) was added DCC (11.5 g, 55.8 mmol) and N-Boc-3-aminopropanoic acid (9.3 g, 49.2 mmol). The reaction mixture was stirred at 0° C. for 1 hour and at room temperature overnight. The reaction mixture was concentrated and the residue was diluted with ethyl acetate and washed with water. The combined organic layers were dried over sodium sulfate, the solids were filtered and the filtrate was concentrated. The crude reaction mixture was purified by flash chromatography to give I-12 (10 g, 57%). MS (ESI): m/z 403 (M+H$^+$).

248. Intermediate I-13: (tert-butyl 2-(5-bromo-1-(2-hydroxyethyl)-1H-benzo[d]imidazol-2-yl)ethylcarbamate)

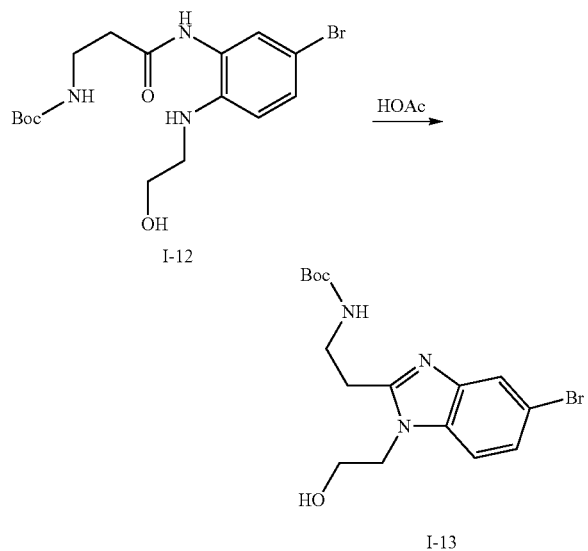

I-12 (10 g, 24.9 mmol) was dissolved in acetic acid and stirred at 65° C. for 2 hours. Reaction progress was followed by LC/MS to prevent esterification of the hydroxyl group upon prolonged heating. The reaction mixture was concentrated to give I-13 (8 g, 84%). MS (ESI): m/z 385 (M+H$^+$).

249. Intermediate I-14: (2-(5-bromo-2-(2-(tert-butoxycarbonylamino) ethyl)-1H-benzo[d]imidazol-1-yl)ethyl 4-methylbenzene-sulfonate)

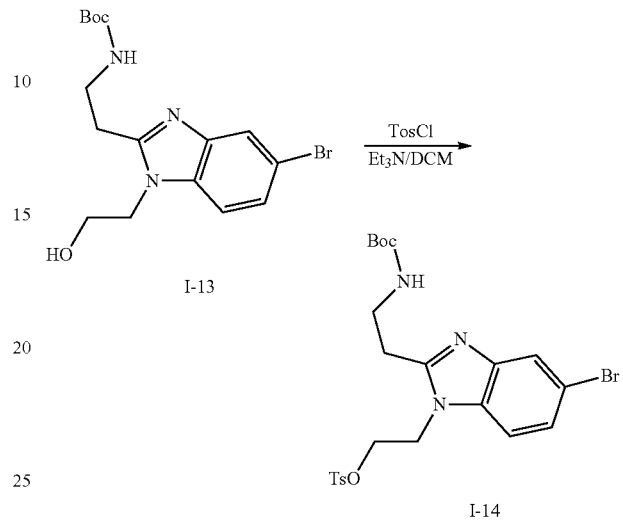

A solution of I-13 (8 g, 20.9 mmol) in dichloromethane (200 mL) was added to a solution of 4-methylbenzene-1-sulfonyl chloride (7.9 g, 41.7 mmol, 2.0 eq.) and triethylamine (4.0 g, 42 mmol, 2.0 eq.) in dichloromethane (50 mL) dropwise at 0° C. and the reaction mixture was stirred overnight. The crude reaction mixture was washed with water, the combined organic layers were dried over sodium sulfate, the solids were filtered and the filtrate was concentrated to give crude product I-14. The crude product was washed with petrol ether to give I-14 (10 g, 90%). MS (ESI): m/z 539 (M+H$^+$).

250. Intermediate I-15: (2-(2-(2-aminoethyl)-5-bromo-1H-benzo[d]imidazol-1-yl)ethyl 4-methylbenzenesulfonate)

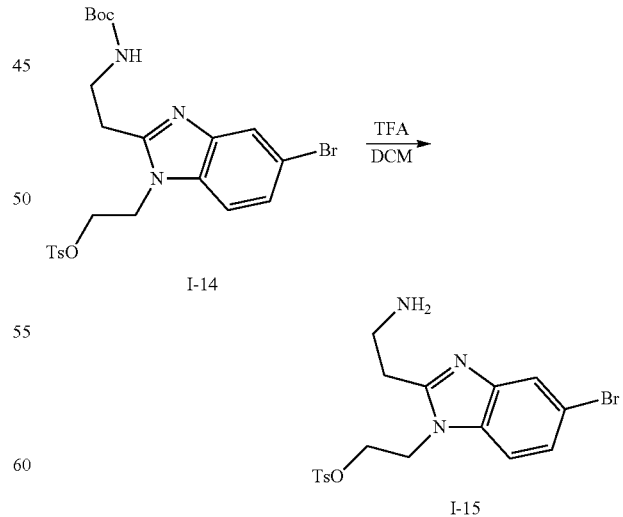

To a solution of I-14 (10 g, 18.6 mmol) in dichloromethane (50 mL) was added neat trifluoroacetic acid (50 mL) dropwise over the course of several minutes and the reaction mixture was stirred at room temperature for 1 hour. The reaction mixture was concentrated to give the crude product I-15. The crude product was washed with petrol ether to give I-15 (7.9 g, 98%). MS (ESI): m/z 439 (M+H⁺).

251. Intermediate I-16: (9-Bromo-2,3,4,5-tetrahydro-1H-[1,4]diazepino[1,7-a]benzimidazole)

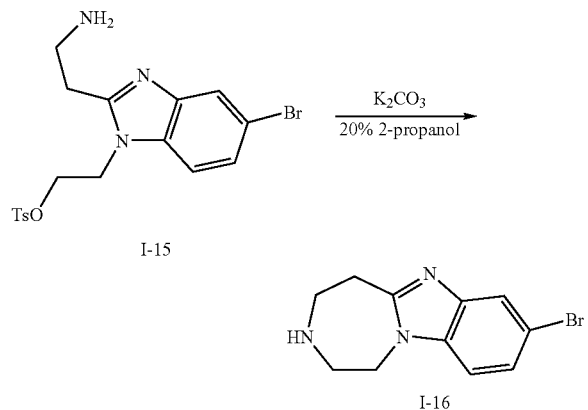

I-15 (6.5 g, 14.8 mmol) was dissolved in an aqueous solution containing 20% 2-propanol (200 mL) and solid K₂CO₃ (6.1 g, 3 eq). The reaction mixture was refluxed for 2 hours and the reaction mixture was concentrated. The residue was dissolved in water, extracted with dichloromethane, the combined organic layers were dried over sodium sulfate, the solids were removed by filtration and the filtrated was concentrated to give I-16 as a pale yellow solid (3.7 g, 95%). MS (ESI): m/z 267 (M+H⁺).

252. Intermediate I-17: (3-cyclobutyl-9-(4,4,5,5-tetramethyl-1,3,2-dioxaborolan-2-yl) 2,3,4,5-tetrahydro-1H-[1,4]diazepino[1,7-a]benzimidazole)

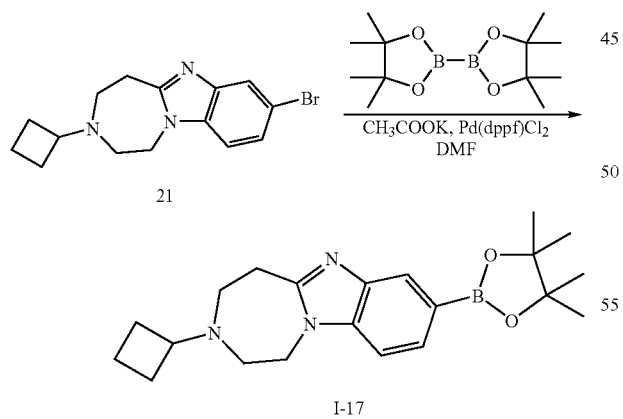

Compound 21 (2.0 g, 6.25 mmol), 4,4,4',4',5,5,5',5'-octamethyl-2,2'-bi(1,3,2-dioxaborolane) (1.86 g), Pd(dppf)Cl₂ (0.2 g) and potassium acetate (1.8 g) were dissolved in DMF (10 mL) in a microwave tube that was filled with argon. The reaction mixture was stirred at 100° C. for 1 hour under microwave irradiation, diluted with ethyl acetate and filtered through a short plug of silica gel and the filtrate was evaporated to dryness. The crude product was purified by flash chromatography to give I-17 (1.1 g, 50%). MS (ESI): m/z 368 (M+H⁺).

253. Intermediate I-18: (4-(2,3,4,5-tetrahydro-1H-[1,4]diazepino[1,7-a]benzimidazol-9-yl)benzonitrile)

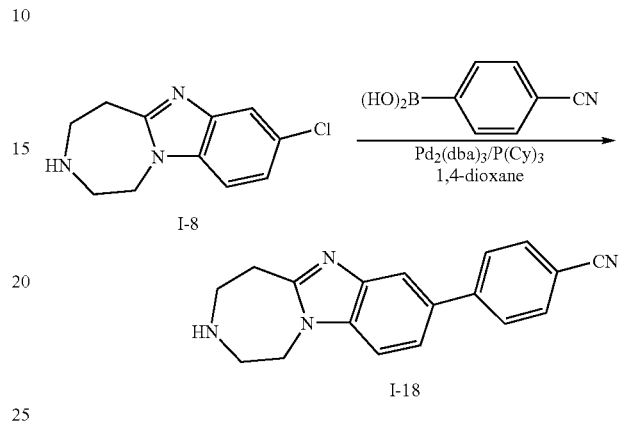

I-8 (508 mg, 2.3 mmol), 4-cyanophenylboronic acid (406 mg, 2.76 mmol, 1.2 eq), Pd₂(dba)₃ (106 mg, 0.115 mmol, 5 mol %), P(Cy)₃ (97 mg, 0.345 mmol, 15 mol %) and KF were dissolved in dry dioxane (10 mL) in a microwave tube that was filled with argon. The mixture was stirred at 100° C. under microwave irradiation and diluted with ethyl acetate. The crude reaction mixture was filtered through a short plug of silica gel and the organic filtrate was washed with water. The combined organic layers were concentrated and the crude reaction mixture was purified by preparative HPLC giving I-18 as a white powder (395 mg, 60%). MS (ESI): m/z 289 (M+H⁺).

254. Intermediate I-20: (2-(5-bromo-2-nitrophenylamino)ethanol)

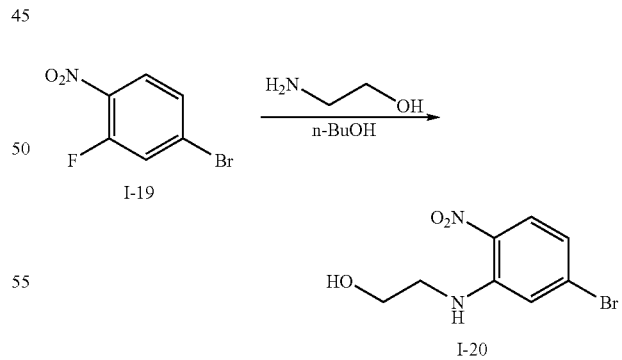

A mixture of 4-bromo-2-fluoro-1-nitrobenzene (I-19, Aldrich, Wis.; 25 g, 0.11 mol) and 2-aminoethanol (13.9 g, 0.23 mol, 2.0 eq.) in n-butanol (300 mL) was refluxed for 1 hour. The reaction mixture was concentrated and the residue was dispersed in petrol ether (600 mL) and stirred overnight. The solids were removed by filtration to give I-20 as a yellow powder (29 g, 98%). MS (ESI): m/z 262 (M+H⁺).

255. Intermediate I-21: (2-(2-amino-5-bromophenylamino)ethanol)

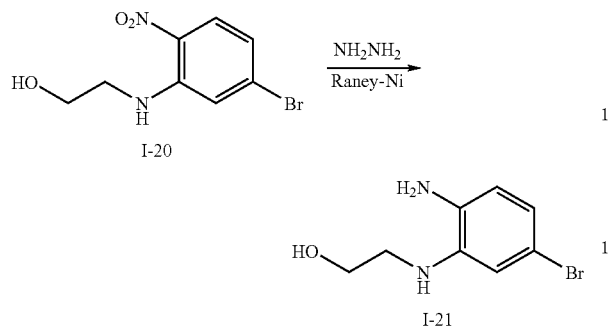

A suspension of Raney-Ni (1 g) was added to a solution of I-20 (22.8 g, 87.4 mmol) and hydrazine (17 g) in methanol (300 mL) at 0° C. and the reaction mixture was stirred for 1 hour. The solids were removed by filtration to give I-21 (9.5 g, 97%). MS (ESI): m/z 232 (M+H$^+$).

256. Intermediate I-22: (tert-butyl 3-(4-bromo-2-(2-hydroxyethylamino)phenylamino)-3-oxopropylcarbamate)

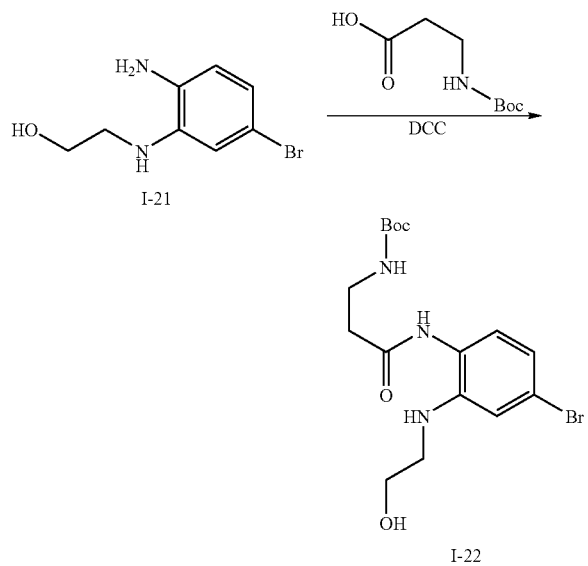

To a solution of I-21 (26 g, 112.6 mmol) in dichloromethane (500 mL) was added DCC (30.2 g, 146.4 mmol) and N-Boc-3-aminopropanoic acid (24.5 g, 129.5 mmol), and the reaction was stirred at 0° C. for 1 hour and at room temperature overnight. The reaction mixture was concentrated and the residue was diluted with ethyl acetate and washed with water. The combined organic layers were dried over sodium sulfate, the solids were removed by filtration and the filtrate was concentrated. The crude reaction mixture was purified by flash chromatography to give I-22 (28 g, 62%). MS (ESI): m/z 403 (M+H$^+$).

257. Intermediate I-23: tert-butyl 2-(6-bromo-1-(2-hydroxyethyl)-1H-benzo[d]imidazol-2-yl)ethylcarbamate)

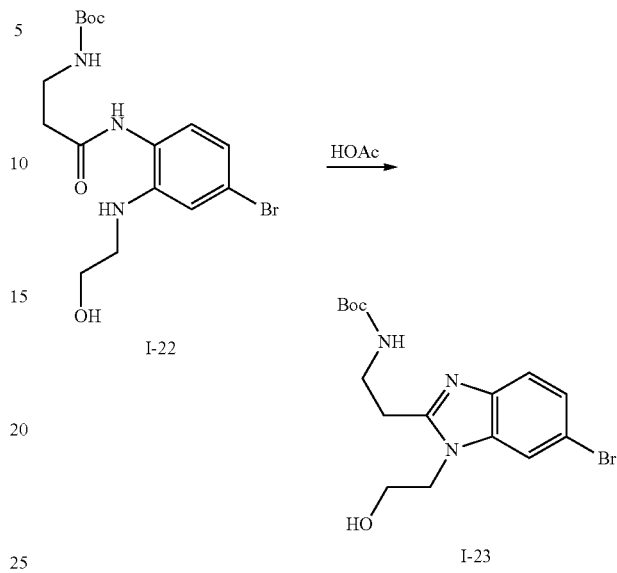

I-22 (20 g, 49.7 mmol) was dissolved in acetic acid and stirred at 65° C. for 2 hours. Reaction progress was followed by LC/MS to prevent esterification of the hydroxyl group upon prolonged heating. The reaction mixture was concentrated to give 1-23 (16 g, 83%). MS (ESI): m/z 385 (M+H$^+$).

258. Intermediate I-24: 2-(6-bromo-2-(2-(tert-butoxycarbonylamino) ethyl)-1H-benzo[d]imidazol-1-yl)ethyl 4-methylbenzene-sulfonate)

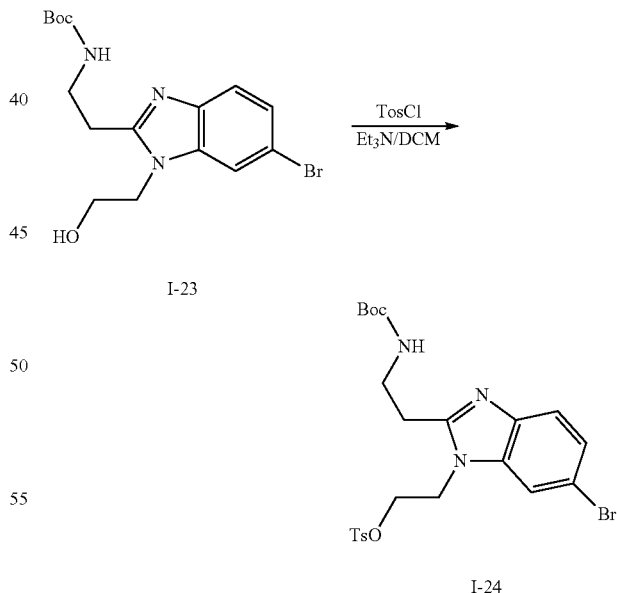

A solution of I-23 (16 g, 29.7 mmol) in dichloromethane (200 mL) was added to a solution of 4-methylbenzene-1-sulfonyl chloride (9.6 g, 35.7 mmol, 1.2 eq.) and triethylamine (8.0 g, 84 mmol, 2 eq.) in dichloromethane (50 mL) at 0° C. and the reaction mixture was stirred overnight. The reaction mixture was washed with water, the combined organic layers were dried over sodium sulfate, the solids were

259. Intermediate I-25: 2-(2-(2-aminoethyl)-6-bromo-1H-benzo[d]imidazol-1-yl)ethyl 4-methylbenzenesulfonate)

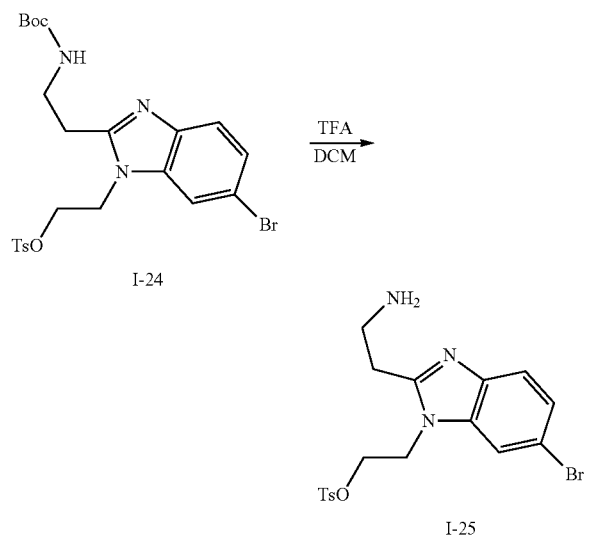

To a solution of I-24 (15 g, 27.9 mmol) in dichloromethane (50 mL) was added trifluoroacetic acid (40 g) dropwise over the course of several minutes and the reaction mixture was stirred for 1 hour at room temperature. The reaction mixture was concentrated to give a residue that was washed with ethyl ether to give I-25 (12 g, 98%). MS (ESI): m/z 439 (M+H$^+$).

260. Intermediate I-26: (8-Bromo-2,3,4,5-tetrahydro-1H-[1,4]diazepino[1,7-a]benzimidazole)

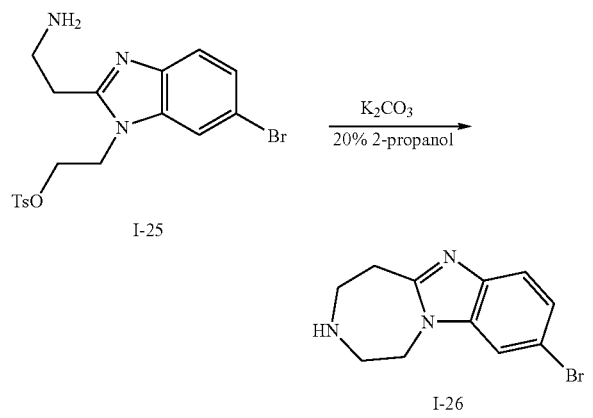

I-25 (12 g, 27.3 mmol) was dissolved in an aqueous solution of 20% 2-propanol (300 mL) containing solid K$_2$CO$_3$ (30.2 g, 8.0 eq.). The reaction mixture was refluxed for 2 hours and concentrated. The residue was extracted with dichloromethane, the combined organic layers were dried over sodium sulfate, the solids were removed by filtration and the filtrate was concentrated to give I-26 as a pale yellow solid (7 g, 95%). MS (ESI): m/z 267 (M+H$^+$).

261. Intermediate I-27: (3-cyclobutyl-8-(4,4,5,5-tetramethyl-1,3,2-dioxaborolan-2-yl) 2,3,4,5-tetrahydro-1H-[1,4]diazepino[1,7-a]benzimidazole)

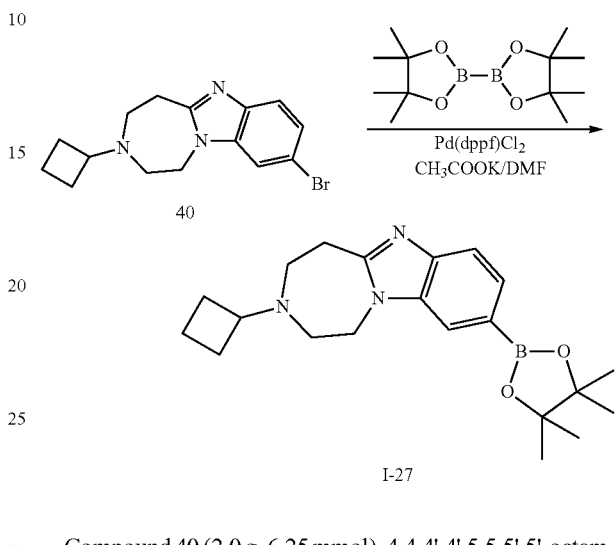

Compound 40 (2.0 g, 6.25 mmol), 4,4,4',4',5,5,5',5'-octamethyl-2,2'-bi(1,3,2-dioxaborolane) (1.86 g), Pd(dppf)Cl$_2$ (0.2 g) and potassium acetate (1.8 g) were dissolved in DMF (13 mL) in a microwave tube that was filled with argon. The mixture was stirred at 100° C. for 1 hour under microwave irradiation. The reaction mixture was diluted with ethyl acetate, filtered through a short plug of silica gel and the filtrate was washed with water. The combined organic layers were evaporated to dryness and the crude reaction mixture was purified by flash chromatography to give I-27 (1.1 g, 50%). MS (ESI): m/z 368 (M+H$^+$).

262. Intermediate I-28: (3-cyclobutyl-2,3,4,5-tetrahydro-1H-[1,4]diazepino[1,7-a]benzimidazol-9-ol)

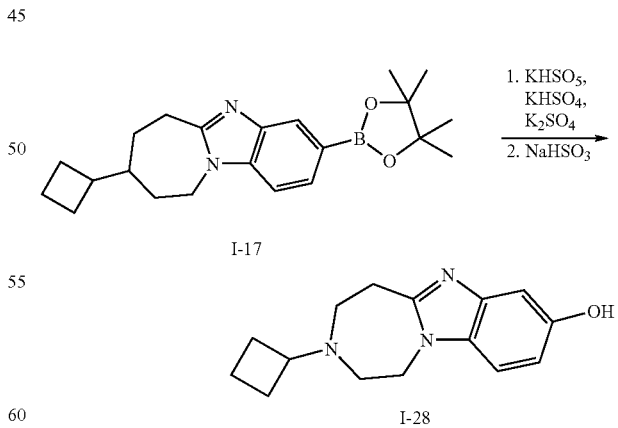

To an ice-cold solution of I-17 (100 mg) in a mixture of acetone and aqueous saturated NaHCO$_3$ solution (1 mL) was added 2KHSO$_5$.KHSO$_4$.K$_2$SO$_4$ (230 mg). After 5 min, solid NaHSO$_3$ (1 g) was added and the reaction mixture was concentrated. The residue was dispersed in methanol and solids were filtered. The filtrate was purified by reverse phase chromatography to give I-28 (23 mg, 33%). MS (ESI): m/z 258 (M+H⁺).

263. Intermediate I-30: (3-cyclobutyl-2,3,4,5-tetrahydro-1H-[1,4]diazepino[1,7-a]benzimidazol-9-amine)

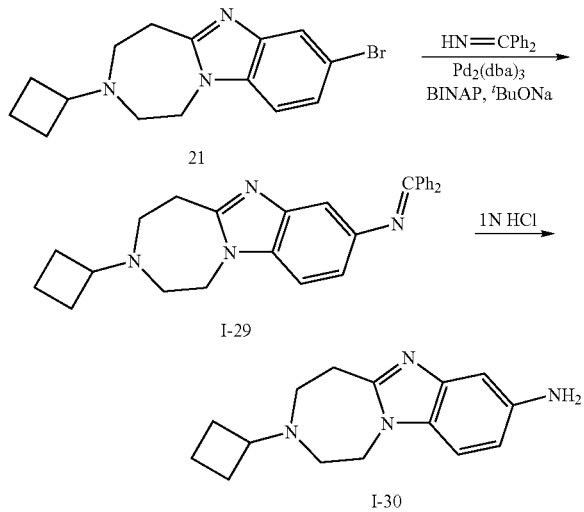

Compound 21 (2.0 g, 6.25 mmol), diphenylmethanimine (2.83 g, 15.6 mmol, 2.5 eq.), Pd$_2$(dba)$_3$ (0.286 g, 0.313 mmol, 5 mol %), BINAP (390 mg, 0.626 mmol, 10 mol %) and $^t$BuONa (0.84 g, 8.75 mmol) were dissolved in dry toluene (60 mL) and the flask was flushed with argon. The mixture was stirred at 110° C. for 15 hours. After LC/MS and TLC analysis indicated complete consumption of 21 the reaction mixture was filtered through a short plug of silica gel. The filtrate was washed with water, the combined organic layers were dried over sodium sulfate, the solids were filtered and the filtrate was concentrated. The crude reaction mixture was dissolved in a 1:1 mixture of 1N HCl and THF and the reaction mixture was stirred for 1 hour. The reaction mixture was concentrated and the residue was dissolved in water and extracted with ethyl acetate. The combined aqueous layers were basified by adding aqueous solution of sodium hydroxide and extracted with ethyl acetate. The combined organic layers were dried over sodium sulfate, solids were filtered and the filtrate was concentrated. The crude reaction mixture was purified by chromatography to give I-30 (0.85 g, 53%). MS (ESI): m/z 257 (M+H⁺).

264. Intermediate I-31: (3-cyclobutyl-2,3,4,5-tetrahydro-1H-[1,4]diazepino[1,7-a]benzimidazol-9-carbaldehyde)

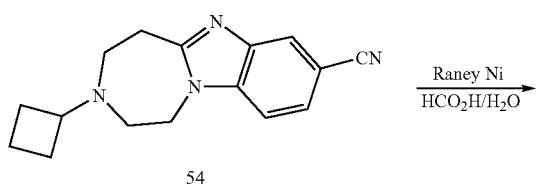

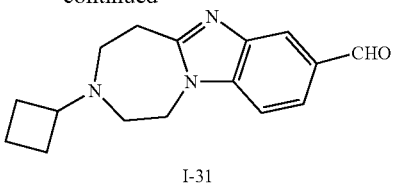

Compound 54 (108 mg) was dissolved in a 4:1 mixture of formic acid and water (15 mL) and 4 drops of a suspension of Raney-Ni were added. The mixture was stirred for 1 hour at room temperature, the solids were filtered and the filtrate was concentrated by evaporation. The residue was basified to pH ~8 and extracted with dichloromethane. The combined organic layers were dried over sodium sulfate, the solids were filtered and the filtrate was evaporated. The resulting residue was dissolved in dichloromethane and solid MnO$_2$ was added. The reaction mixture was stirred for 30 minutes at room temperature and the solid was filtered. The filtrate was concentrated and purified by preparative TLC to give I-31 (40 mg, 36%). MS (ESI): m/z 270 (M+H⁺).

265. Intermediate I-32: (3-cyclobutyl-2,3,4,5-tetrahydro-1H-[1,4]diazepino[1,7-a]benzimidazol-8-ol)

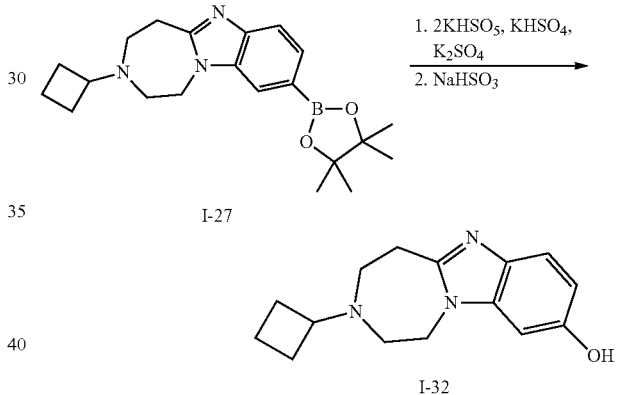

To an ice-cold solution of I-27 (432 mg) in acetone containing an aqueous saturated solution of NaHCO$_3$ (4.3 mL) was added 2 KHSO$_5$.KHSO$_4$.K$_2$SO$_4$ (900 mg) and the reaction mixture was stirred at 0° C. for 5 min. Solid NaHSO$_3$ (5 g) was added and the reaction mixture was concentrated. The residue was dispersed in methanol and the solids were filtered. The filtrate was concentrated and purified by reverse phase chromatography to give I-32 (150 mg, 50%). MS (ESI): m/z 258 (M+H⁺)

266. Intermediate I-34: (3-cyclobutyl-2,3,4,5-tetrahydro-1H-[1,4]diazepino[1,7-a]benzimidazol-8-amine)

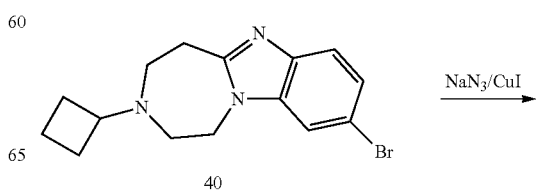

-continued

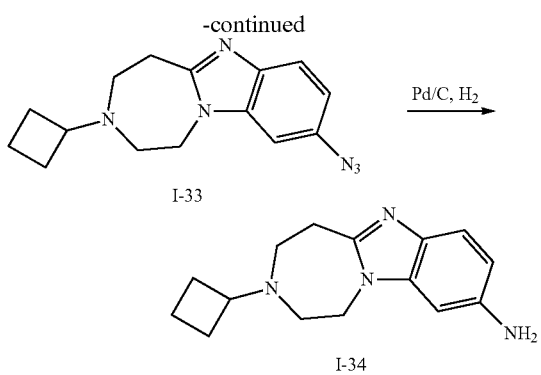

Compound 40 (0.64 g, 2 mmol), L-proline (0.3 eq.), CuI (0.2 eq.), NaN₃ (3.0 eq.), and sodium hydroxide (1.0 eq.) were dissolved in a 21:9 mixture of ethanol and water (30 mL) and the flask was flushed with argon. The reaction mixture was refluxed overnight and the solids were filtered through a short plug of silica gel. The filtrate was washed with water, the combined organic layers were dried over sodium sulfate, the solid was filtered and the organic filtrate was concentrated. Crude I-33 was dissolved in methanol and palladium on carbon was added. The flask with filled with hydrogen gas and the reaction progress was monitored until all I-34 was consumed. The solids were filtered through a short plug of silica gel and the filtrate was concentrated. The crude reaction mixture was purified by chromatography to give I-34 (0.15 g, 30%). MS (ESI): m/z 257 (M+H⁺).

267. Intermediate I-35: (2-(3-cyclobutyl-2,3,4,5-tetrahydro-1H-[1,4]diazepino[1,7-a]benzimidazol-8-yl)methanol)

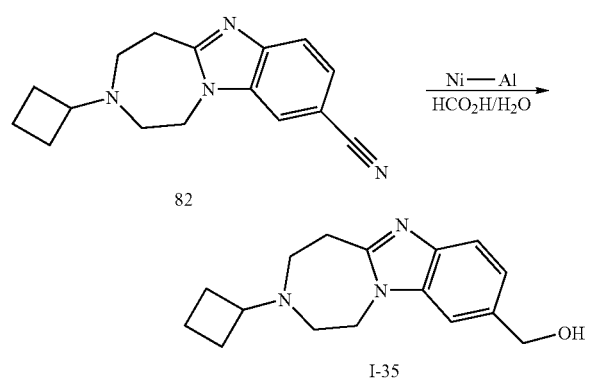

Compound 82 (100 mg), a suspension of Ni—Al (20 drops) and HCO₂H (2 mL) were dissolved in H₂O (120 mL) and stirred for 4 hours at room temperature. The solids were filtered and the pH of the filtrate was adjusted to pH ~12 by adding an aqueous solution of NaOH at 0° C. The aqueous solution was extracted with ethyl acetate, the combined organic layers were dried with Na₂SO₄, the solid was filtered and the filtrated was concentrated. The crude reaction mixture was purified by preparative HPLC to give I-35 (37 mg, 36%). MS (ESI): m/z 272 (M+1)⁺.

268. Intermediate I-36: (3-cyclobutyl-8-chloromethyl-2,3,4,5-tetrahydro-1H-[1,4]diazepino[1,7-a]benzimidazole)

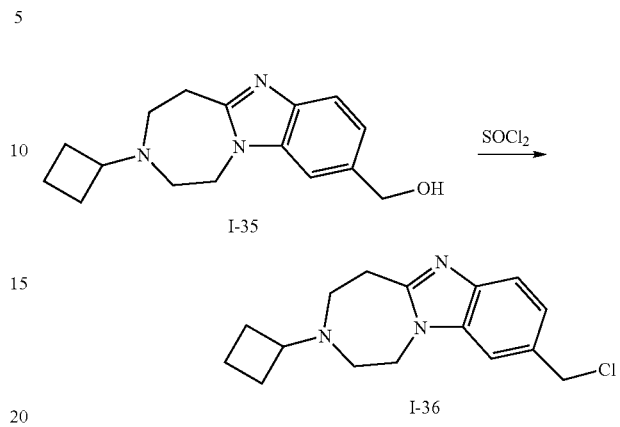

To a solution of I-35 (20 mg) in CH₂Cl₂ (5 mL) was added neat SOCl₂ (0.5 mL) dropwise at 0° C., the reaction mixture was warmed to room temperature and stirred for 90 minutes. The reaction mixture was concentrated to give I-36 as a yellow solid that was used directly in the following step.

269. Intermediate I-37: (3-cyclobutyl-2,3,4,5-tetrahydro-1H-[1,4]diazepino[1,7-a]benzimidazol-8-carboxylic acid)

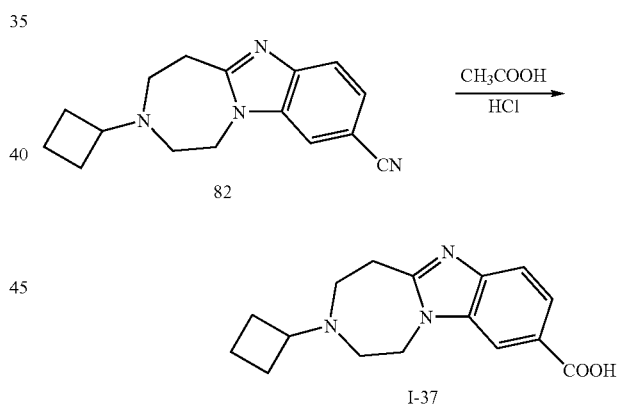

Compound 82 (610 mg) was dissolved in a 1:1 mixture of acetic acid and concentrated aqueous HCl and the reaction mixture was stirred at 80° C. for 3 hours. The reaction mixture was concentrated and the resulting residue was dissolved in water and basified to pH 5~6. The reaction mixture was concentrated and the residue was dispersed in methanol and the solids were filtered. The filtrate was concentrated and the crude reaction mixture was purified by reverse phase chromatography to give I-37 (300 mg, 46%). ¹H-NMR (400 MHz, CD₃OD), δ 8.18 (d, 1H, J=0.8 Hz), 7.94 (dd, 1H, $J_1$=1.2 Hz, $J_2$=8.4 Hz), 7.61 (d, 1H, J=8.4 Hz), 4.44 (m, 2H), 3.18 (m, 2H), 3.09 (m, 1H), 2.79 (m, 2H), 2.73 (m, 2H), 2.17~2.19 (m, 2H), 1.97~2.02 (m, 2H), 1.73~1.76 (m, 2H). MS (ESI): m/z 286 (M+H⁺).

270. Intermediate I-38: (tert-butyl 4-(3-cyclobutyl-2,3,4,5-tetrahydro-1H-[1,4]diazepino[1,7-a]benzimidazol-9-yl)piperazine-1-carboxylate)

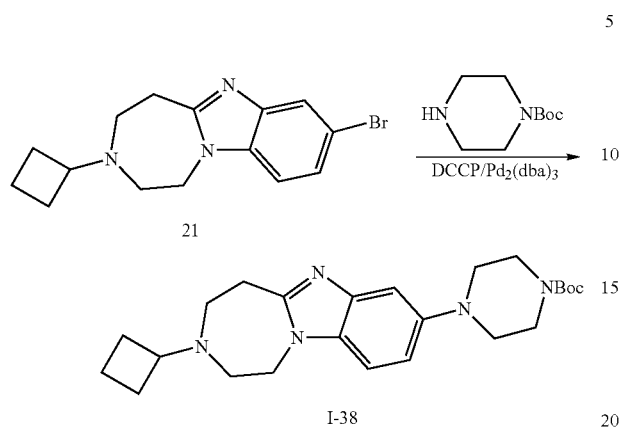

Compound 21 (0.52 g, 1.63 mmol), DCCP (0.12 g, 0.24 mmol), NaO'Bu (0.22 g, 2.22 mmol), Pd$_2$(dba)$_3$ (75 mg, 0.08 mmol) and N-Boc-piperazine (0.36 g, 1.96 mmol) were dissolved in toluene (8 mL) and the reaction mixture was heated at 100° C. for 14 h. The reaction mixture was diluted with ethyl acetate and filtered through a short plug of Celite. The filtrate was concentrated and the residue was purified with flash chromatography to give I-38 (0.75 g, 75%). MS (ESI): m/z 426 (M+1)$^+$.

271. Intermediate I-39: (3-cyclobutyl-2,3,4,5-tetrahydro-1H-[1,4]diazepino[1,7-a]benzimidazol-8-carbaldehyde)

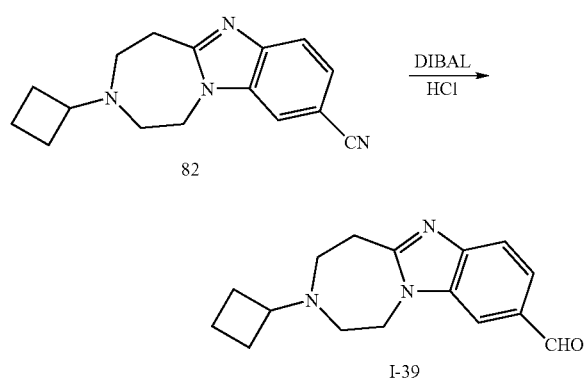

To a solution of compound 82 (60 mg) in dichloromethane at −78° C. was added a toluene solution of DIBAL (4.0 eq.) dropwise. The reaction was stirred at −78° C. for 1 hour and a saturated aqueous solution of NH$_4$Cl was added. The reaction mixture was stirred at room temperature for 3 hours and washed with water. The combined organic layers were dried over Na$_2$SO$_4$, the solids were removed by filtration and the filtrate was evaporated. The crude reaction mixture was purified by flash chromatography to give intermediate I-39 as a white solid (300 mg, 50%). MS (ESI): m/z 270 (M+1)$^+$.

272. Intermediate I-40: (3-cyclobutyl-2,3,4,5-tetrahydro-1H-[1,4]diazepino[1,7-a]benzimidazol-9-carboxylic acid)

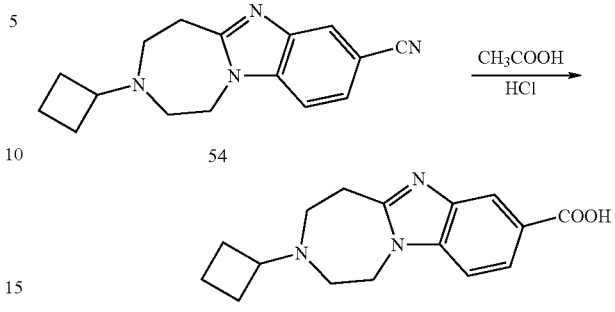

A solution of compound 54 (500 mg) in a 1:1 mixture of acetic acid/conc. HCl was stirred at 80° C. for 3 hours. The reaction mixture was concentrated and the residue was dissolved in water and basified to pH 5~6. The reaction mixture was concentrated and the crude reaction mixture was purified by reverse phase chromatography to give I-40 (160 mg, 30%). MS (ESI): m/z 286 (M+1)$^+$.

273. Intermediate I-42: (methyl 3-(tert-butylamino)propanoate)

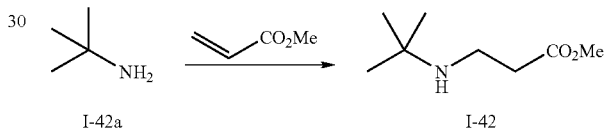

To a mixture of intermediate I-42a (3.7 g, 50 mmol, 1.0 eq) and methyl acrylate (5.2 g, 60 mmol, 1.2 eq) in DMSO (5 mL) was added 3 drops of H$_2$O and the reaction mixture was stirred at room temperature for 60 minutes. The reaction mixture was diluted with EtOAc (50 mL) and washed with H$_2$O and brine. The combined organic layers were dried over anhydrous Na$_2$SO$_4$, the solids were removed by filtration and the filtrate was concentrated by evaporation to give intermediate I-42 (3.9 g, 49%) as pale yellow oil. $^1$H-NMR (400 MHz, CDCl$_3$) δ: 3.68 (s, 3H), 2.83 (t, 2H, J=6.4 Hz), 2.51 (t, 2H, J=6.4 Hz), 1.11 (s, 9H). MS (ESI): m/z 160.1 (M+H$^+$).

274. Intermediate I-43: (N-(2-(5-bromo-1H-benzo[d]imidazol-2-yl)ethyl)-2-methylpropan-2-amine)

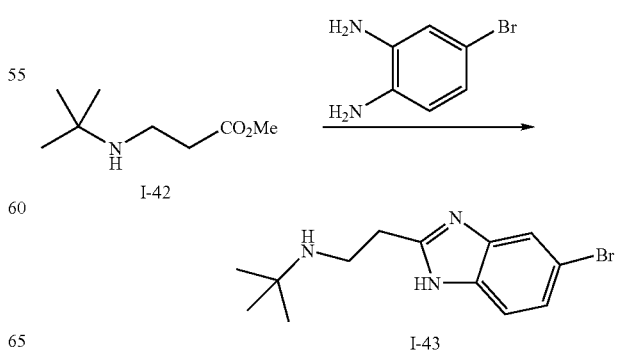

Intermediate I-42 (2.1 g, 13 mmol, 1.0 eq) and 4-bromobenzene-1,2-diamine (2.5 g, 13 mmol, 1.0 eq) was dissolved in aqueous HCl (4.0 M in water, 20 mL) and the reaction mixture was stirred at 100° C. for 16 hours. The reaction mixture was diluted with water (50 mL) and the pH was adjusted to 7-8 using an aqueous solution of ammonia. The crude reaction mixture was extracted with CH$_2$Cl$_2$, the combined organic layers were dried over anhydrous Na$_2$SO$_4$, the solids were removed by filtration and the filtrate was concentrated by evaporation. The crude reaction product was purified by silica gel column chromatography to give intermediate I-43 (580 mg, 15%) as yellow-brown solid. $^1$H-NMR (400 MHz, DMSO-d$_6$) δ: 7.67 (d, 1H, J=1.6 Hz), 7.43 (d, 1H, J=8.4 Hz), 7.25 (dd, 1H, J$_1$=1.6 Hz, J$_2$=8.4 Hz), 2.92 (m, 4H), 1.05 (s, 9H). MS (ESI): m/z 296.1, 298.1 (M+H$^+$).

275. Intermediate I-44: (1:1 mixture of 8-bromo and 9-bromo-3-(tert-butyl)-2,3,4,5-tetrahydro-1H-benzo[4,5]imidazo[1,2-d][1,4]diazepine)

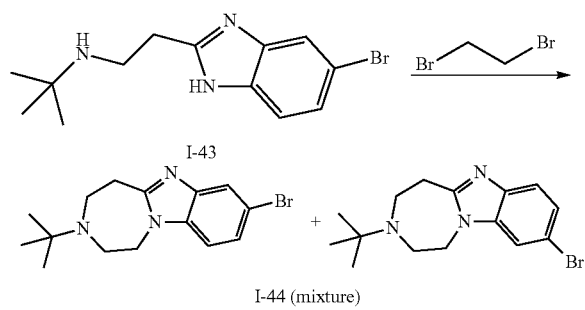

Intermediate I-43 (550 mg, 1.9 mmol, 1.0 eq) was dissolved in neat 1,2-dibromoethane (2 mL) and solid NaH (220 mg, 5.6 mmol, 60% dispersion in mineral oil, 3.0 eq) was added portion wise. The reaction mixture was stirred at 80° C. for 16 hours and quenched by addition of water (5 mL). The crude reaction mixture was extracted with CH$_2$Cl$_2$ and washed with brine. The combined organic layers were dried over anhydrous Na$_2$SO$_4$, the solids were removed by filtration and the filtrate was concentrated by evaporation. The crude reaction product was purified by preparative thin layer chromatography to give intermediate I-44 (60 mg, 10%) as pale yellow solid. $^1$H-NMR (400 MHz, DMSO-d$_6$) δ: 7.81-7.73 (d, 1H, J=1.6 Hz), 7.50-7.49 (d, 1H, J=8.4 Hz), 7.35-7.29 (dd, 1H, J$_1$=1.6 Hz, J$_2$=8.4 Hz), 4.27 (t, 2H, J=4.0 Hz), 3.12 (t, 2H, J=4.0 Hz), 2.82 (m, 4H), 1.08 (s, 9H). MS (ESI): m/z 322.1, 324.1 (M+H$^+$).

276. Intermediate I-45: (3-cyclobutyl-8-(piperidin-3-yl)-2,3,4,5-tetrahydro-1H-benzo[4,5]imidazo[1,2-d][1,4]diazepine)

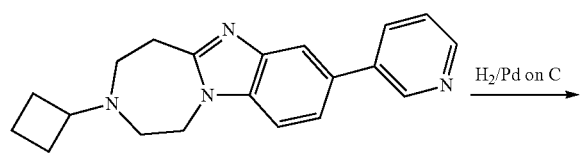

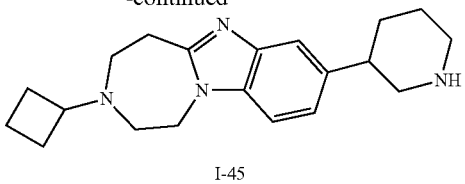

Compound 115 (400 mg, 1.3 mmol, 1.0 eq) and Pd/C (10% wt/wt, 20 mg) were dissolved in acetic acid (10 mL) and the reaction mixture was stirred under a hydrogen atmosphere (1 atm) at 70° C. for 12 hours. The solids were removed by filtration, the residue was dissolved in water (15 mL) and pH was adjusted to ~8 by adding an aqueous solution of NaHCO$_3$. The crude reaction mixture was extracted with ethyl acetate, the combined organic layers were dried over anhydrous Na$_2$SO$_4$, the solids were removed by filtration and the filtrate was concentrated by evaporation. The crude reaction product was purified by silica gel column chromatography to give intermediate I-45 (200 mg, 49%). MS (ESI): m/z 325 (M+H$^+$).

277. Intermediate I-46: ((E)-3-cyclobutyl-8-(2-nitrovinyl)-2,3,4,5-tetrahydro-1H-benzo[4,5]imidazo[1,2-d][1,4]diazepine)

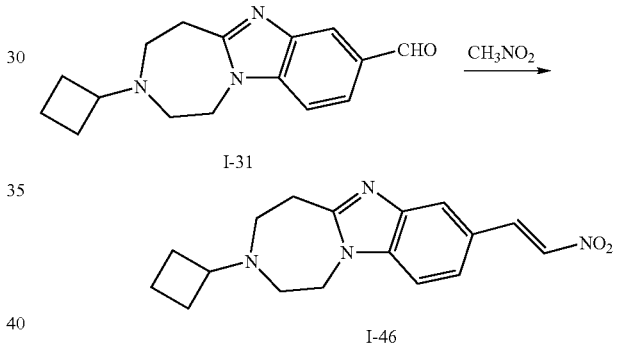

Intermediate I-31 (300 mg, 1.1 mmol. 1.0 eq) and NH$_4$OAc (120 mg, 1.5 mmol, 1.4 eq) were suspended in CH$_3$NO$_2$ (10 mL) and the reaction mixture was stirred at 100° C. for 4 hours. Excess solvent was removed by evaporation and the crude reaction product was purified by silica gel column chromatography to give intermediate 1-46 (300 mg, 86%) as yellow solid. $^1$H-NMR (400 MHz, CDCl$_3$) δ: 8.09 (d, 1H, J=13.6 Hz), 7.82 (d, 1H, J=1.2 Hz), 7.56 (d, 1H, J=13.6 Hz), 7.40 (dd, 1H, J=8.8 Hz), 7.23 (d, 1H, J=8.8 Hz), 4.23 (s, 2H), 3.23 (s, 2H), 2.91 (s, 1H), 2.61 (s, 4H), 2.09 (s, 2H), 1.93 (s, 1H), 1.70 (s, 1H), 1.58 (m, 2H). MS (ESI): m/z 313.0 (M+H$^+$).

278. Intermediate I-49: (tert-butyl 4-(hydroxyimino)piperidine-1-carboxylate)

To a solution of I-48 (50 g, 0.25 mol, 1.0 eq) in ethanol (300 mL) hydroxylamine hydrochloride (35 g, 0.50 mol, 2.0 eq) was added followed by sodium acetate (41 g, 0.50 mol, 2.0 eq) and the reaction mixture was stirred at 100° C. for 7 hours. Solids were removed by filtration and the filtrate was concentrated by evaporation. Water was added to the residue; the reaction mixture was extracted with ethyl acetate and washed with aqueous sodium bicarbonate and brine. The combined organic layers were dried on anhydrous $MgSO_4$, the solids were removed by filtration and the filtrate was concentrated to give intermediate I-49 (54 g, 100%) as white solid that was used in the following step without further purification. MS (ESI): m/z 159.1 (M+H$^+$).

279. Intermediate I-50: (tert-butyl 5-oxo-1,4-diazepane-1-carboxylate)

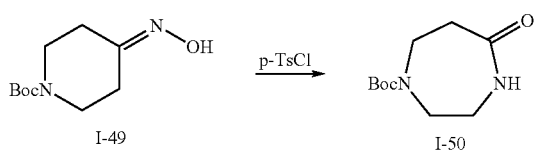

To a solution of intermediate I-49 (11 g, 50 mmol, 1.0 eq) in acetone (60 mL) was added a solution of $Na_2CO_3$ (16 g, 150 mmol, 3.0 eq) in water (80 mL) and the reaction mixture was stirred for 5 minutes. A solution of p-toluenesulfonyl chloride (14 g, 75 mmol, 1.5 eq) in acetone (20 mL) was added slowly and the reaction mixture was stirred at room temperature for 3 hours. Excess solvent was removed by evaporation, water was added and the reaction mixture was extracted with dichloromethane. The combined organic layers were dried over anhydrous $MgSO_4$, the solids were removed by filtration and the filtrate was concentrated by evaporation. The crude reaction product was purified by silica gel column chromatography to give intermediate I-50 (5.0 g, 48%). MS (ESI): m/z 159.1 (M+H$^+$).

280. Intermediate I-52: (1-cyclobutyl-1,4-diazepan-5-one)

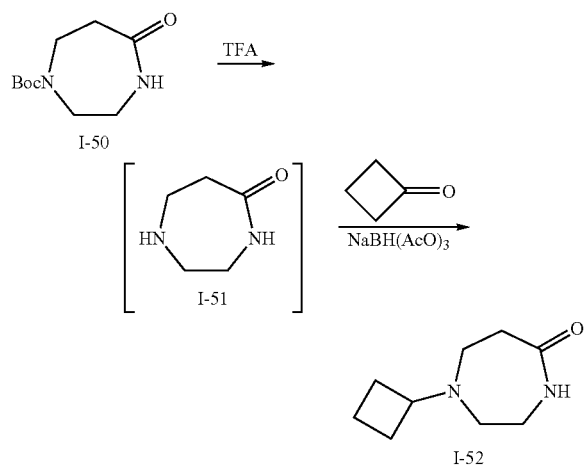

Intermediate I-50 (2.1 g, 10 mmol, 1.0 eq) was dissolved with dichloromethane (20 mL) and neat TFA (4 mL) was added. The reaction mixture was stirred at room temperature for 3 hours and excess solvent and TFA were removed by evaporation. The resulting crude intermediate I-51 (MS (ESI): m/z 115.1 (M+H$^+$)), cyclobutanone (1.1 g, 15 mmol, 1.5 eq) and acetic acid (0.5 mL, 0.8 eq) were dissolved in dichloromethane (20 mL) and the reaction mixture was stirred at room temperature for 60 minutes. Solid NaBH(OAc)$_3$ (4.2 g, 20 mmol, 2.0 eq) was added and the reaction mixture was stirred at room temperature for additional 3 hours. The reaction mixture was neutralized by adding an aqueous solution of $K_2CO_3$ and extracted with dichloromethane. The combined organic layers were dried over anhydrous $MgSO_4$, the solids were removed by filtration and the filtrate was concentrated by evaporation to give the crude intermediate I-52 (1.6 g, 98%) as white solid that was used in the following reaction without further purification. $^1$H-NMR (400 MHz, CDCl$_3$) δ: 6.15 (s, 1H), 3.30 (q, J=4.8 Hz, 2H), 2.81 (q, J=4.4 Hz, 1H), 2.61-2.63 (m, 2H), 2.45-2.50 (m, 4H), 2.03-2.10 (m, 2H), 1.79-1.88 (m, 2H), 1.62-1.74 (m, 2H). MS (ESI): m/z 169.1 (M+H$^+$).

281. Intermediate I-54: (5-bromoisobenzofuran-1,3-dione)

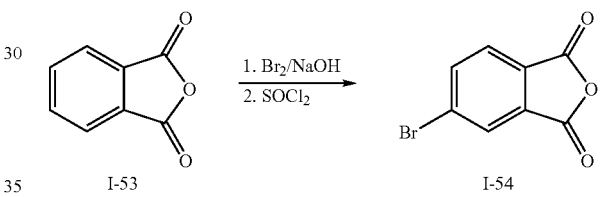

To a solution of intermediate I-53 (22 g, 0.15 mol, 1.0 eq) in water (150 mL) was added solid NaOH (12 g, 0.30 mol, 2.0 eq) and neat Br$_2$ (8.5 mL, 0.17 mol, 1.1 eq) and the reaction mixture was stirred at 90° C. for 6 hours. The crude reaction mixture was cooled slowly to 0° C. in a refrigerator and the light yellow solids were collected by filtration, washed with cold water and dissolved in neat SOCl$_2$ (60 mL). The reaction mixture was refluxed for 2.5 hours and concentrated by evaporation. The crude reaction product was crystallized from ethyl acetate to give intermediate I-54 (22 g, 79%). MS (ESI): m/z 228 (M+H$^+$).

282. Intermediate I-55: (5-bromoisoindoline-1,3-dione)

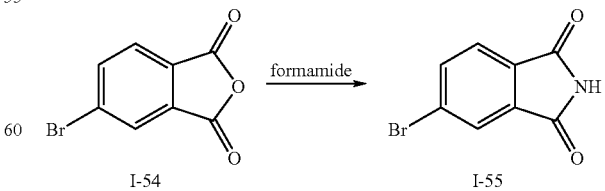

A mixture of intermediate I-54 (6.6 g, 0.30 mol, 1.0 eq) and formamide (10 mL, 2.4 mol, 8.0 eq) was stirred at 200° C. for 2 hours and poured onto a mixture of ice and water. The

283. Intermediate I-56: (5-bromo-6-nitroisoindoline-1,3-dione)

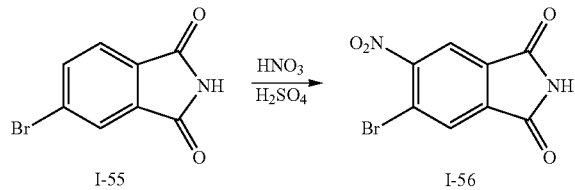

To fuming nitric acid (9.2 mL, 0.22 mol, 1.0 eq) pre-cooled at 0° C. was added drop wise concentrated sulfuric acid (21 mL, 0.40 mol, 1.8 eq) followed by portion-wise addition of intermediate I-55 (10 g, 44 mmol, 2.0 eq) and the resulting suspension was warmed to room temperature over 1 hour and stirred for a additional 24 hours at room temperature. The crude reaction mixture was poured onto a mixture of ice and water and the solids were collected by filtration and dried in vacuo to give intermediate I-56 (11.8 g, 98%). MS (ESI): m/z 272 (M+H$^+$).

284. Intermediate I-57: (2-benzyl-5-bromo-6-nitroisoindoline-1,3-dione)

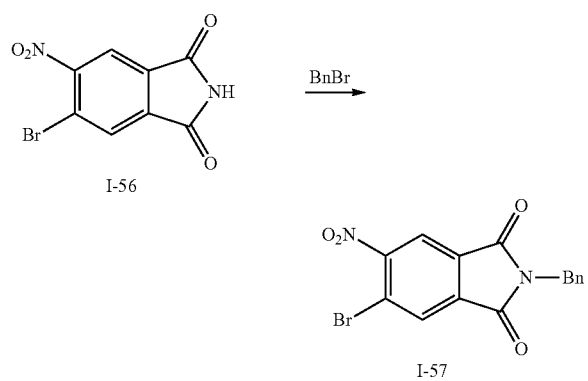

To a mixture intermediate I-56 (10 g, 37 mmol, 1.0 eq) in DMF (30 mL) was added solid K$_2$CO$_3$ (13 g, 93 mmol, 2.5 eq) and neat BnBr (6.6 mL, 55 mmol, 1.5 eq) and the reaction mixture was stirred at room temperature for 16 hours. The crude reaction mixture was extracted with ethyl acetate and the organic layer was washed with water and brine. The combined organic layers were dried over anhydrous MgSO$_4$, the solids were removed by filtration and the filtrate was concentrated. The crude reaction product was purified by silica gel column chromatography to give intermediate I-57 (12 g, 90%). MS (ESI): m/z 362 (M+H$^+$).

285. Intermediate I-58: (2-benzyl-5-(4-cyclobutyl-7-oxo-1,4-diazepan-1-yl)-6-nitroisoindoline-1,3-dione)

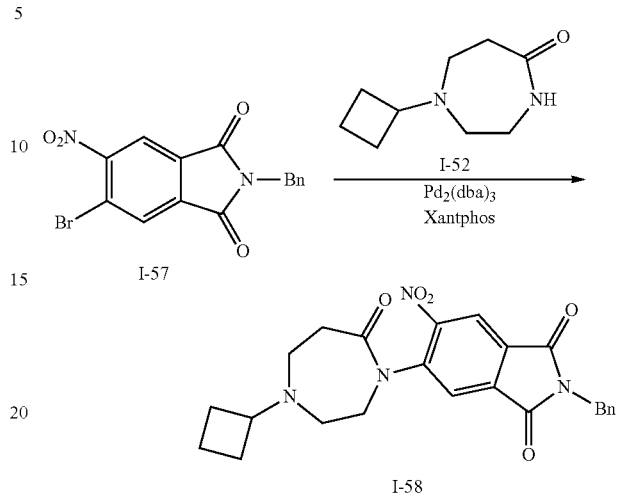

A dried, three-necked flask was charged with Pd$_2$(dba)$_3$ (0.28 g, 0.30 mmol, 0.1 eq), Xantphos (0.28 g, 0.50 mmol, 0.16 eq), intermediate I-52 (0.50 g, 3.0 mmol, 1.0 eq), Cs$_2$CO$_3$ (1.2 g, 6.0 mmol, 2.0 eq), intermediate I-57 (1.1 g, 3.0 mmol, 1.0 eq) and 1,4-dioxane (15 mL) and the reaction mixture was degassed by bubbling N$_2$. The reaction mixture was stirred at 80° C. for 5 hours, diluted with dichloromethane (50 mL), the solids were removed by filtration and the filtrate was concentrated in vacuo. The crude reaction product was purified by silica gel column chromatography to give intermediate I-58 (0.6 g, 36%) as a pale yellow solid. MS (ESI): m/z 449.0 (M+H$^+$).

286. Intermediate I-60: (2-(3-bromophenyl)ethanamine)

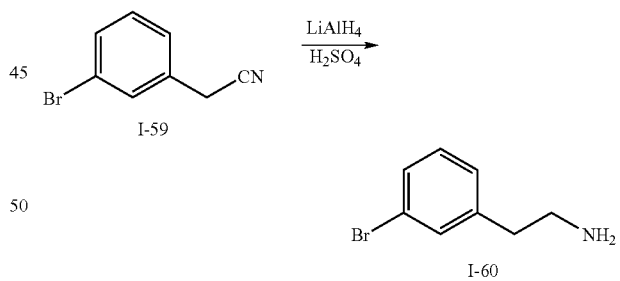

A suspension of LiAH$_4$ (2.5 g, 66 mmol, 1.6 eq) in dry THF (100 mL) was cooled to −5° C. and concentrated H$_2$SO$_4$ (3.2 g, 33 mmol, 0.8 eq) was added drop wise while the temperature was maintained below 3° C. The reaction mixture was stirred at 5° C. for 40 minutes and a solution of intermediate I-59 (8.0 g, 41 mmol, 1.0 eq) in THF was added drop wise. The reaction mixture was warmed to room temperature and stirred for additional 60 minutes. The reaction mixture was cooled to 0° C. and quenched by adding a mixture of THF (5 mL) and water (5 mL). Ether was added followed by a solution of sodium hydroxide (20 mL, 3.6M in water) and the crude reaction mixture was filtered through short plug of Celite. The combined organic layers were dried over anhyresulting crystals were collected by filtration and dried in vacuo to give intermediate I-55 (7.0 g, 99%). MS (ESI): m/z 227 (M+H$^+$).

drous MgSO₄, the solids were removed by filtration and the filtrate was concentrated by evaporation to give intermediate I-60 (8.0 g, 93%). MS (ESI): m/z 200 (M+H⁺).

287. Intermediate I-61:
(N-(3-bromophenethyl)-2,2,2-trifluoroacetamide)

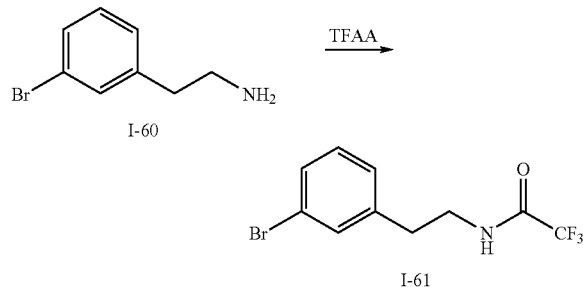

A mixture of intermediate I-60 (8.0 g, 40 mmol, 1.0 eq) and 2,6-lutidine(4.8 mL, 41 mmol, 1.03 eq) in dry dichloromethane (160 mL) was cooled to 0° C. and neat TFAA (5.6 mL, 39.6 mmol, 0.99 eq) was added drop wise. The reaction mixture was warmed to room temperature and stirred for 16 hours. Water (150 mL) was added, the aqueous layer was extracted with dichloromethane and the combined organic layers were washed with aqueous HCl (1.0 M in water) and a saturated aqueous solution of NaHCO₃. The combined organic layers were dried over anhydrous Na₂SO₄, the solids were removed by filtration and the filtrate was concentrated by evaporation to give intermediate I-61 (11 g, 92%). ¹H-NMR (400 MHz, CDCl₃) δ: δ 7.40 (d, 1H, J=8.0 Hz), 7.35 (t, 1H, J=1.6 Hz), 7.20 (t, 1H, J=7.6 Hz), 7.12 (d, 1H, J=8.0 Hz), 6.55 (brs, 1H), 3.59 (q, 2H, J₁=6.4 Hz, J₂=13.2 Hz), 2.86 (t, 2H, J=6.8 Hz). MS (ESI): m/z 296 (M+H⁺).

288. Intermediate I-62: (1-(6-bromo-3,4-dihydroisoquinolin-2(1H)-yl)-2,2,2-trifluoroethanone)

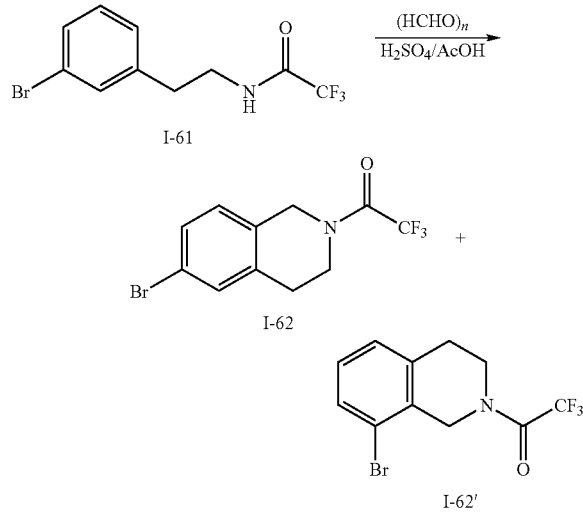

A mixture of acetic acid (61 mL) and concentrated H₂SO₄ (40 mL) was added to a mixture of intermediate I-61 (11 g, 37 mmol, 1.0 eq) and paraformaldehyde (1.8 g, 59 mmol, 1.6 eq) and the reaction mixture was stirred at room temperature for 72 hours. The crude reaction mixture was poured onto a mixture of ice and water and extracted with ethyl acetate. The combined organic layer was washed with a saturated aqueous solution of NaHCO₃ and water and the combined organic layers were dried over anhydrous Na₂SO₄, the solids were removed by filtration and the filtrate was concentrated by evaporation. The crude reaction product was purified by silica gel column chromatography to give pure intermediate I-62 (3.8 g, 33%) and a mixture of intermediates I-62 and I-62' (4.0 g, 36%) that was discarded. ¹H-NMR (400 MHz, CDCl₃) δ: 7.33~7.37 (m, 2H), 7.00 (d, 1H, J=8.4 Hz), 7.02 (d, 1H, J=8.4 Hz), 4.72 (m, 2H), 3.84 (m, 2H), 2.91~2.96 (m, 2H). MS (ESI): m/z 308 (M+H⁺).

289. Intermediate I-63: (1-(6-bromo-7-nitro-3,4-dihydroisoquinolin-2(1H)-yl)-2,2,2-trifluoroethanone)

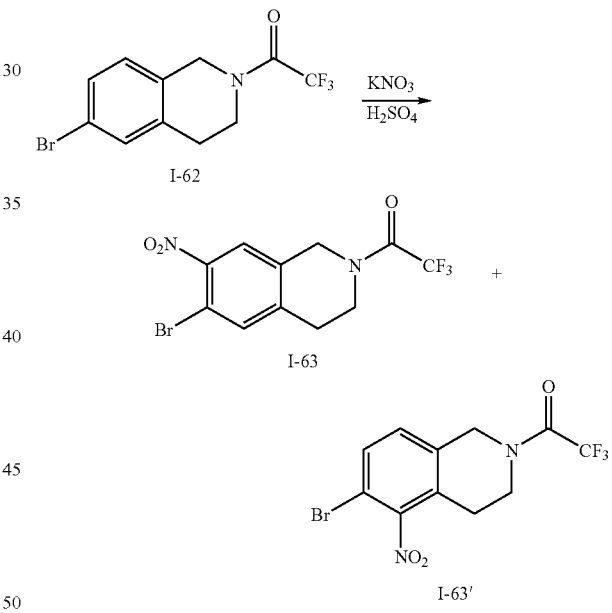

A solution of intermediate I-62 (1.5 g, 5 mmol, 1.0 eq) in dichloromethane (25 mL) was cooled to −15° C., a solution of KNO₃ (505 mg, 5 mmol, 1.0 eq) in concentrated H₂SO₄ (2 mL) was added and the reaction mixture was stirred for 30 minutes. The reaction mixture was carefully diluted with ice and extracted with dichloromethane. The combined organic layers were dried over anhydrous Na₂SO₄, the solids were removed by filtration and the filtrate was concentrated by evaporation. The crude reaction product was purified by silica gel column chromatography to give pure intermediate I-63 (800 mg, 45%), intermediate I-63' (110 mg, 6%), and a mixture of intermediates I-63 and I-63' (600 mg, 35%). ¹H-NMR (400 MHz, CDCl₃) δ: 7.72 (s, 1H), 7.60 (s, 1H), 4.77 (m, 2H), 3.94 (m, 2H), 2.99~3.04 (m, 2H). MS (ESI): m/z 353 (M+H⁺).

290. Intermediate I-64: (1-(9-cyclobutyl-3,4,8,9,10,11-hexahydro-1H-[1,4]diazepino[7',1':2,3]imidazo[4,5-g]isoquinolin-2(7H)-yl)-2,2,2-trifluoroethanone)

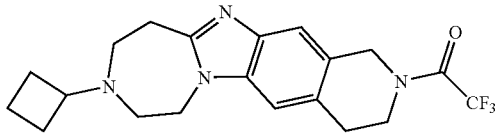

This intermediate was prepared in 63% yield (110 mg) by using a reaction sequence described for intermediate I-58 and compound 143 but using intermediate I-63 as the starting material. MS (ESI): m/z 393 (M+H$^+$).

291. Intermediate I-65: (1-(10-cyclobutyl-9,10,11,12-tetrahydro-1H-[1,4]diazepino[1',7':1,2]imidazo[4,5-f]isoquinolin-3(2H,4H,8H)-yl)-2,2,2-trifluoroethanone)

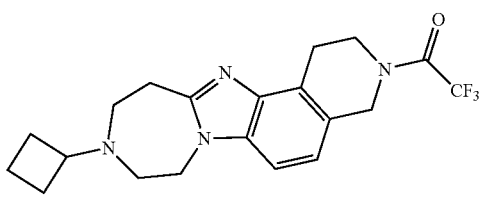

This intermediate was prepared in 51% yield by using a reaction sequence described for intermediate I-58 and compound 143 but using intermediate I-63' as the starting material. MS (ESI): m/z 393 (M+H$^+$).

292. Intermediate I-67: ((E)-1-bromo-4-(2-nitrovinyl)benzene)

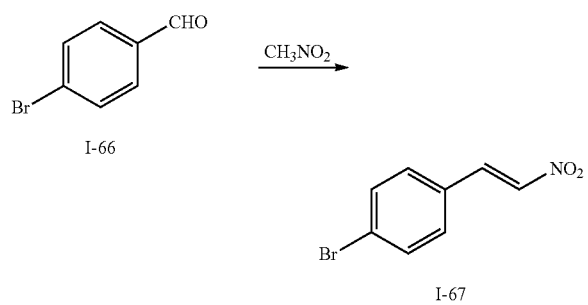

A mixture of intermediate I-66 (23 g, 100 mmol, 1.0 eq.), NH$_4$OAc (18 g, 220 mmol, 2.2 eq), CH$_3$NO$_2$ (70 mL) and acetic acid (17 mL) was stirred at 50° C. for 5 hours. The precipitate was collected by filtration and washed with a mixture of ethanol (50 mL) and H$_2$O (50 mL) and air dried to give intermediate I-67 (14 g, 50%) as yellow solid. $^1$H-NMR (400 MHz, DMSO-d$_6$) δ: 7.95 (d, J=13.6 Hz, 1H), 7.60 (m, 3H), 7.42 (m, 2H).

293. Intermediate I-68: (2-(4-bromophenyl)ethanaminium chloride)

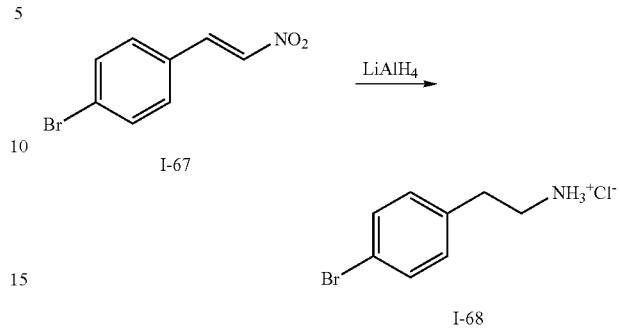

To a stirred suspension of LiAlH$_4$ (7.7 g, 203 mmol, 3.5 eq.) in THF (40 mL) was added drop wise a solution of intermediate I-67 (13 g, 59 mmol, 1.0 eq.) in THF (40 mL) and the reaction mixture was stirred at room temperature for 2 hours and quenched by adding a solution of NaOH (30% in water). Ethyl acetate (100 mL) was added and the crude reaction mixture was stirred for another 30 minutes. The organic layer was separated and dried over anhydrous Na$_2$SO$_4$. Gaseous HCl was bubbled through the ethyl acetate solution at 0° C. and the white precipitate was collected by filtration to give intermediate I-68 (3.2 g, 23%). $^1$H-NMR (400 MHz, DMSO-d$_6$) δ: 7.52 (m, 2H), 7.24 (m, 2H), 3.18 (m, 2H), 2.95 (m, 2H). MS (ESI): m/z 198.1, 200.1 (M+H$^+$).

294. Intermediate I-69: (N-(4-bromophenethyl)-2,2,2-trifluoroacetamide)

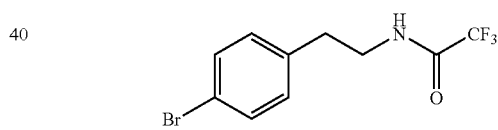

This intermediate was prepared in 77% yield (3.2 g) as described for intermediate I-61 but using intermediate I-68 as the starting material. $^1$H-NMR (400 MHz, CDCl$_3$) δ: 9.48 (m, 1H), 7.49 (m, 2H), 7.17 (m, 2H), 3.41 (m, 2H), 2.78 (m, 2H). MS (ESI): m/z 296.0, 298.0 (M+H$^+$).

295. Intermediate I-70: (N 1-(7-bromo-3,4-dihydroisoquinolin-2(1H)-yl)-2,2,2-trifluoroethanone)

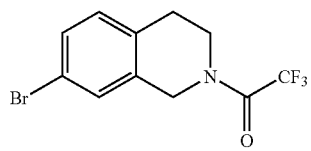

This intermediate was prepared in 78% yield (1.9 g) as described for intermediate I-62 but using intermediate I-69 as the starting material. $^1$H-NMR (400 MHz, CDCl$_3$) δ: 7.34 (m, 2H), 7.05 (m, 1H), 4.75 (m, 2H), 3.86 (m, 2H), 2.91 (m, 2H). MS (ESI): m/z 308.0, 310.1 (M+H⁺).

296. Intermediate I-71: (mixture of 1-(7-bromo-6-nitro-3,4-dihydroisoquinolin-2(1H)-yl)-2,2,2-trifluoroethanone and 1-(7-bromo-8-nitro-3,4-dihydroisoquinolin-2(1H)-yl)-2,2,2-trifluoroethanone)

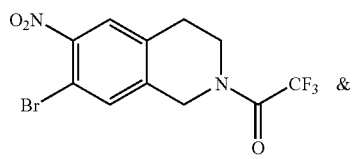

This intermediate was prepared in 87% yield (1.9 g) as described for intermediate I-63 and I-63' but using intermediate I-70 as the starting material. MS (ESI): m/z 353.0, 355.1 (M+H⁺).

297. Intermediate I-72: (7-bromo-6-nitro-1,2,3,4-tetrahydroisoquinoline)

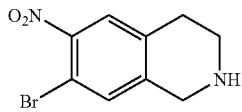

This intermediate was prepared in 44% yield (0.8 g) as described for compound 183 but using intermediate I-71 as the starting material. ¹H-NMR (400 MHz, CDCl₃) δ: 7.65 (s, 1H), 7.38 (s, 1H), 4.03 (s, 2H), 3.14 (m, 2H), 2.81 (m, 2H). MS (ESI): m/z 257.0, 259.1 (M+H⁺).

298. Intermediate I-73: (1-cyclobutyl-4-(6-nitro-1,2,3,4-tetrahydroisoquinolin-7-yl)-1,4-diazepan-5-one)

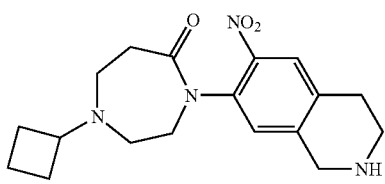

This intermediate was prepared in 71% yield (380 mg) as described for intermediate I-58 but using intermediate I-72 as the starting material. MS (ESI): m/z 345.4 (M+H⁺).

299. Intermediate I-75: (6-bromo-2-methylimidazo[1,2-a]pyridine)

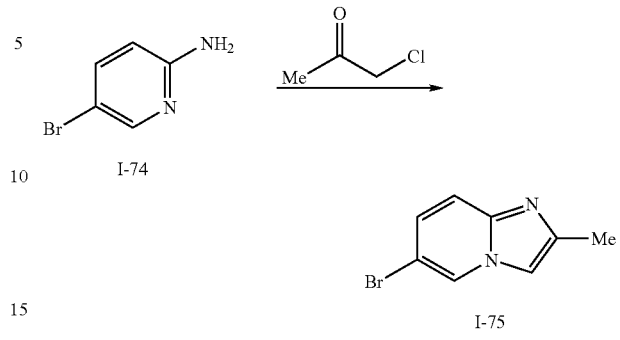

Intermediate I-74 (800 mg, 4.2 mmol, 1.0 eq) and chloroacetone (3.0 g, 13 mmol, 3.0 eq) were mixed in ethanol (10 mL) and the reaction mixture was refluxed for 24 hours. The crude reaction mixture was concentrated by evaporation; the residue was dissolved in ethyl acetate and washed with water. The combined organic layers were dried over anhydrous Na₂SO₄, the solids were removed by filtration and the filtrate was concentrated by evaporation. The crude reaction product was purified by silica gel column chromatography to give intermediate I-75 (188 mg, 19%). MS (ESI): m/z 212 (M+H⁺).

300. Intermediate I-77: (3,3,5-tribromo-1H-pyrrolo[2,3-b]pyridin-2(3H)-one)

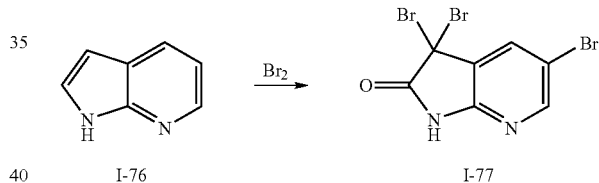

Intermediate I-76 (5.0 g, 42 mmol, 1.0 eq) was dissolved in a mixture of water (330 mL) and t-butanol (330 mL), neat bromine (27 mL, 530 mmol, 13 eq) was added drop wise at room temperature and the reaction mixture was stirred for 24 hours. t-Butanol was removed by evaporation and the pH was adjusted to ~9 by adding an aqueous saturated solution of NaHCO₃. The precipitate was collected by filtration and dried in vacuo to give intermediate I-77 (13 g, 83%) as brown solid that was used in the following step without further purification. MS (ESI): m/z 372 (M+H⁺).

301. Intermediate I-78: (5-bromo-1H-pyrrolo[2,3-b]pyridin-2(3H)-one)

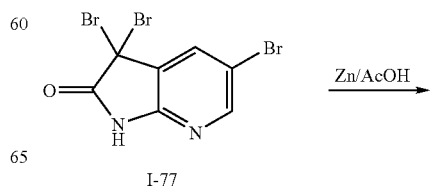

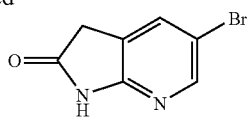

I-78

Elemental zinc (4.0 g, 61 mmol, 10 eq) was added to a solution of intermediate I-77 (2.3 g, 6.1 mmol, 1.0 eq) in acetic acid (50 mL) and the solution was purged by bubbling nitrogen. The reaction mixture was stirred at room temperature for 5 hours and concentrated by evaporation. The residue was dissolved in water and extracted with ethyl acetate. The combined organic layers were dried over anhydrous $Na_2SO_4$, the solids were removed by filtration and the filtrated was concentrated by evaporation and azeotropic distillation with toluene. The crude reaction product was purified by silica gel column chromatography to give intermediate I-78 (0.3 g, 23%) as an orange solid. MS (ESI): m/z 214 (M+H$^+$).

302. Intermediate I-79: (5-bromo-1H-pyrrolo[2,3-b]pyridine)

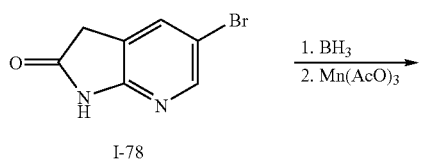

I-78

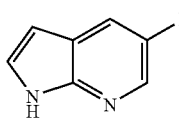

I-79

To a $N_2$-purged solution of intermediate I-78 (0.30 g, 1.4 mmol, 1.0 eq) in anhydrous THF (10 mL) at 0° C. was added a solution of $BH_3$ (5.7 mL, 1.0 M in THF, 5.7 mmol, 4.0 eq) and the reaction mixture was stirred at room temperature for 50 minutes. The crude reaction mixture was concentrated by evaporation and the residue was dissolved in a solution of HCl (6.0 M in water) and the reaction mixture was stirred heated until a complete dissolution of all solids. After cooling to room temperature, the pH was adjusted to ~9 by adding a solution of NaOH (6.0 M in water) and the crude reaction mixture was extracted with ethyl acetate. The combined organic layers were dried over anhydrous $Na_2SO_4$, the solids were removed by filtration and the filtrate was concentrated by evaporation. The residue was dissolved in acetic acid (4 mL), added to a suspension of manganese(III) acetate (0.61 g, 2.3 mmol, 1.6 eq) in acetic acid (5 mL) and the reaction mixture was stirred at 75° C. for 50 minutes. The crude reaction mixture was concentrated by azeotropic distillation with toluene; the residue was dissolved in water and extracted with ethyl acetate. The combined organic layers were dried over anhydrous $Na_2SO_4$, the solids were removed by filtration and the filtrate was concentrated by evaporation. The crude reaction product was purified by silica gel column chromatography to give intermediate I-79 (17 mg, 6%, over 2 steps) as a yellowish solid. MS (ESI): m/z 198 (M+H$^+$).

303. Intermediate I-81: (6-bromoimidazo[1,5-a]pyridine)

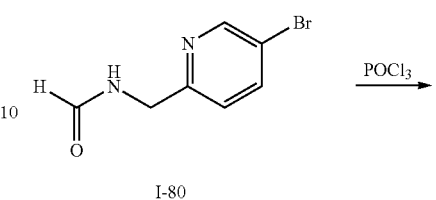

I-80

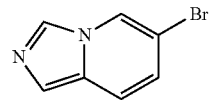

I-81

Neat $POCl_3$ (3 mL) was added drop wise to a solution of intermediate I-80 (360 mg, 1.7 mmol, 1.0 eq) in benzene (20 mL), the reaction mixture was refluxed for 14 hours and quenched with ice. The crude reaction mixture was basified with an aqueous saturated solution of $NaHCO_3$ and extracted with ethyl acetate. The combined organic layers were dried over anhydrous $Na_2SO_4$, the solids were removed by filtration and the filtrate was concentrated by evaporation. The crude reaction product was purified by silica gel column chromatography to give intermediate I-81 (140 mg, 14%) as a yellow solid. MS (ESI): m/z 198 (M+H$^+$).

304. Intermediate I-83: (5-bromo-3-((trimethylsilyl)ethynyl)pyrazin-2-amine)

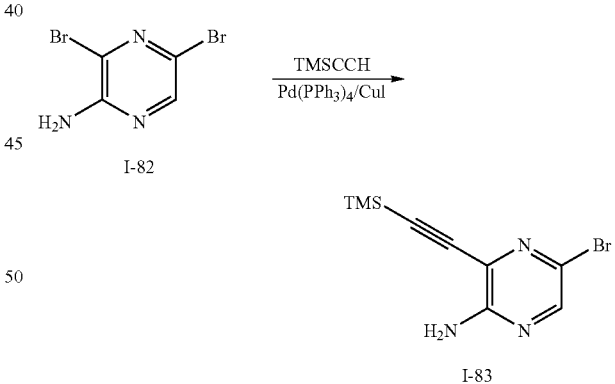

I-82

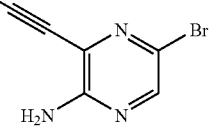

I-83

To a solution of intermediate I-82 (10 g, 40 mmol, 1.0 eq) in DMF (115 mL) was added neat triethylamine (53 mL), $Pd(PPh_3)_4$ (2.3 g, 2.0 mmol, 0.05 eq) and CuI (0.90 g, 4.7 mmol, 0.12 eq) followed by drop wise addition of ethynyltrimethylsilane (6.7 mL, 48 mmol, 1.2 eq) and the reaction mixture was stirred for 30 minutes at 120° C. The crude reaction mixture was concentrated by evaporation and the crude reaction product was purified by silica gel column chromatography to give intermediate I-83 (3.0 g, 17%) as yellow oil. MS (ESI): m/z 271 (M+H$^+$).

305. Intermediate I-84: (N-(5-bromo-3-((trimethylsilyl)ethynyl)pyrazin-2-yl)acetamide)

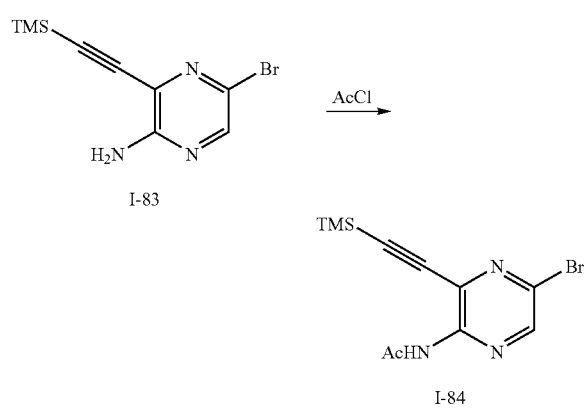

To a solution of intermediate I-83 (3.0 g, 11 mmol, 1.0 eq) in anhydrous THF (45 mL) was added neat pyridine(2.2 g, 28 mmol, 2.5 eq) followed by AcCl (22 mmol, 2.0 eq) and the reaction mixture was stirred at room temperature for 16 hours and at 60° C. for additional 5 hours. The crude reaction mixture was concentrated by evaporation and the crude reaction product was purified by silica gel column chromatography to give intermediate I-84 (1.0 g, 29%) as yellow solid. MS (ESI): m/z 314 (M+H$^+$).

306. Intermediate I-85: (2-bromo-5H-pyrrolo[2,3-b]pyrazine)

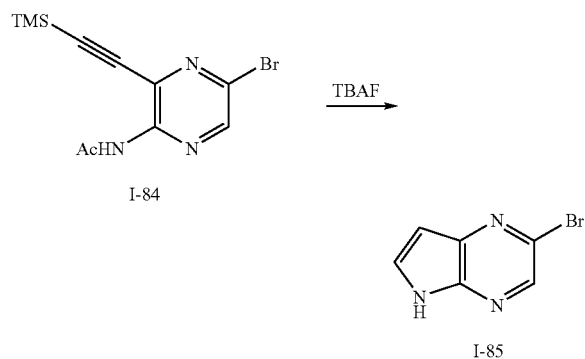

To a solution of intermediate I-84 (1.0 g, 3.2 mmol, 1.0 eq) in THF (8.5 mL) was added drop wise a solution TBAF (7.1 mL, 1.0 M in THF, 7.1 mmol, 2.2 eq) and the reaction mixture was refluxed for 15 hours. The crude reaction was concentrated by evaporation; the residue was dissolved in water and extracted with ethyl acetate. The combined organic layers were dried over anhydrous Na$_2$SO$_4$, the solids were removed by filtration and the filtrate was concentrated by evaporation. The crude reaction product was purified by silica gel column chromatography to give intermediate I-85 (100 mg, 16%) as yellow solid. MS (ESI): m/z 199 (M+H$^+$).

307. Intermediate I-87: (1-benzyl 2-tert-butyl hydrazine-1,2-dicarboxylate)

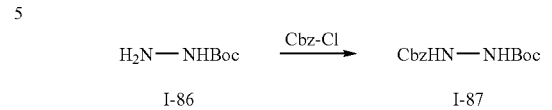

To a solution of intermediate I-86 (20 g, 150 mmol, 1 eq) in dichloromethane (400 mL) was added drop wise neat CbzCl (28 g, 166 mmol, 1.1 eq) over the period of 20 minutes and the reaction mixture was stirred at room temperature overnight. Excess solvent was removed by evaporation and the residue was diluted with water and extracted with ether. pH of the aqueous layer was adjusted to ~8 and the aqueous layer was extracted with dichloromethane. The combined organic layers were dried over anhydrous Na$_2$SO$_4$, the solids were removed by filtration. The filtrate was concentrated to give intermediate I-87 (38 g, 94%) that was used in the following step without further purification. MS (ESI): m/z 167 (M+H$^+$).

308. Intermediate I-88: (1-benzyl 2-tert-butyl pyrazolidine-1,2-dicarboxylate)

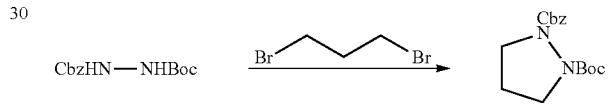

A suspension of sodium hydride (60% dispersion in mineral oil, 3.0 g, 75 mmol, 2.0 eq) in anhydrous DMF (120 mL) was cooled under nitrogen atmosphere to 0° C. on an ice/water bath. Intermediate I-87 (10 g, 38 mmol, 1.0 eq) was added portion wise and the reaction mixture was stirred for 20 minutes. 1,3-Dibromopropane (7.5 g, 38 mmol, 1.0 eq) was added drop wise and the reaction mixture was allowed to stir at room temperature overnight. Glacial acetic acid (0.5 mL) was added and excess solvent was removed by evaporation. The residue was diluted with 50% saturated aqueous brine and extracted with diethyl ether. The combined organic layers were washed with brine, dried over anhydrous MgSO$_4$; the solids were removed by filtration. The filtrate was concentrated by evaporation to give the crude intermediate I-88 (11 g, 95%) which was used in the following step without further purification. MS (ESI): m/z 307 (M+H$^+$).

309. Intermediate I-89: (benzyl pyrazolidine-1-carboxylate)

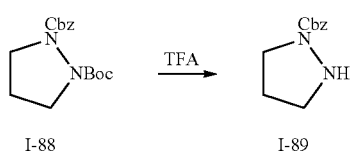

Intermediate I-88 (11 g, 35 mmol, 1.0 eq) was dissolved in neat trifluoroacetic acid (10 mL) under nitrogen atmosphere at room temperature and the reaction mixture was stirred vigorously for 10 minutes. Excess solvent was removed by evaporation and the residue was dissolved in water and extracted with a 1:1 mixture of ethyl acetate and hexane. The organic phase was back-extracted with aqueous hydrochloric acid (1.0 M) and the combined aqueous phases were basified with aqueous NaOH (50%). The basified aqueous layer was extracted with dichloromethane, the combined organic layers were dried over anhydrous Na$_2$SO$_4$ and the solids were removed by filtration. The filtrate was concentrated by evaporation to give intermediate I-89 (5.5 g, 74%) that was used in the following step without further purification. MS (ESI): m/z 207 (M+H$^+$).

310. Intermediate I-90: (benzyl 2-(3-chloropropanoyl)pyrazolidine-1-carboxylate)

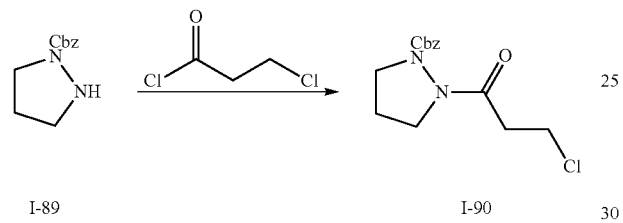

I-89                            I-90

A solution of intermediate I-89 (8.6 g, 41 mmol, 1.0 eq) and diisoproylethylamine (5.3 g, 41 mmol, 1.0 eq) in dichloromethane (100 mL) was cooled under nitrogen atmosphere to 0° C. on an ice/water bath. A solution of 3-chloropropionyl chloride (5.2 g, 41 mmol, 1.0 eq) in dichloromethane (30 mL) was added drop wise over 45 minutes and the reaction mixture was stirred for additional 60 minutes. The reaction was quenched by addition of aqueous hydrochloric acid (1.0 M) and the reaction mixture was extracted with dichloromethane. The combined organic layers were washed with aqueous HCl (1.0 M), dried over anhydrous MgSO$_4$ and the solids were removed by filtration. The filtrate was concentrated by evaporation and the crude reaction product was purified by silica gel column chromatography to give intermediate I-90 (10 g, 81%). MS (ESI): m/z 297 (M+H$^+$).

311. Intermediate I-91: (tetrahydropyrazolo[1,2-a]pyrazol-1(5H)-one)

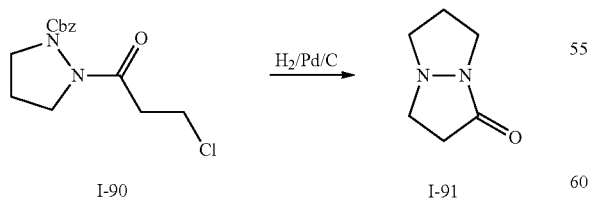

I-90                            I-91

To a solution of intermediate I-90 (10 g, 34 mmol, 1.0 eq) in absolute ethanol (200 mL) was added palladium on carbon (10 wt %, 1.0 g) and the reaction mixture was stirred under atmosphere of hydrogen (1 atm) overnight. The solids were removed by filtration and the filtrate was concentrated by evaporation to give intermediate I-91 as the HCl salt (5.3 g, 97%). MS (ESI): m/z 127 (M+H$^+$).

312. Intermediate I-92: (1,5-diazocan-2-one)

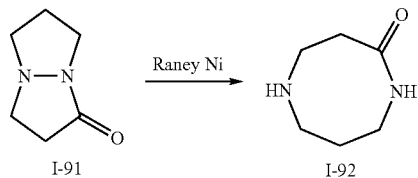

I-91                            I-92

To a solution of intermediate I-91 (5.0 g, 31.6 mmol, 1.0 eq) in absolute ethanol (25 mL) was added a slurry of Raney nickel (4 g, wet weight) and the reaction mixture was stirred under atmosphere of hydrogen (1 atm) for 4 days. The solids were removed by filtration and the filtrate was concentrated by evaporation to give intermediate I-92 as the HCl salt (5.1 g, 99%). MS (ESI): m/z 129 (M+H$^+$).

313. Intermediate I-93: (5-cyclobutyl-1,5-diazocan-2-one)

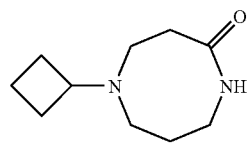

This intermediate was prepared in 60% yield (4.4 g) as described for compound 8 but using intermediate I-92 as the starting material. MS (ESI): m/z 183 (M+H$^+$).

314. Intermediate I-94: (1-(4-chloro-2-nitrophenyl)-5-cyclobutyl-1,5-diazocan-2-one)

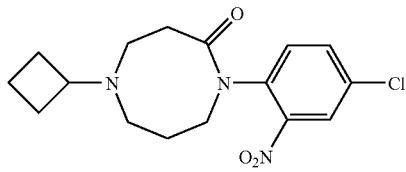

This intermediate was prepared in 65% yield (1.2 g) as described for intermediate I-58 but using intermediate I-93 and 1-bromo-4-chloro-2-nitrobenzene as the starting material. MS (ESI): m/z 338 (M+H$^+$).

315. Intermediate I-95: (3-cyclobutyl-10-(4,4,5,5-tetramethyl-1,3,2-dioxaborolan-2-yl)-1,2,3,4,5,6-hexahydrobenzo[4,5]imidazo[1,2-a][1,5]diazocine)

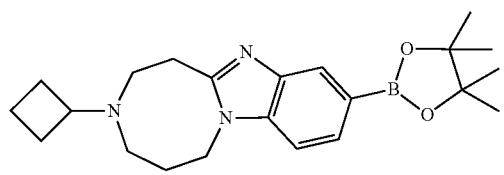

This intermediate was prepared in 37% yield (50 mg) as described for intermediate I-17 but using compound 218 as the starting material. MS (ESI): m/z 381 (M+H⁺).

316. Intermediate I-96: (4-(5-cyclobutyl-2-oxo-1,5-diazocan-1-yl)-3-nitrobenzonitrile)

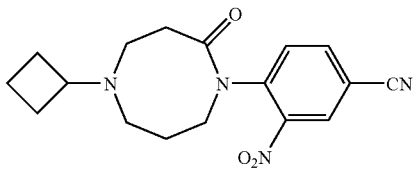

This intermediate was prepared in 36% yield (6.8 g) as described for intermediate I-58 but using intermediate I-93 and 4-bromo-3-nitrobenzonitrile as the starting materials. MS (ESI): m/z 329 (M+H⁺).

317. Intermediate I-97: (3-cyclobutyl-1,2,3,4,5,6-hexahydrobenzo[4,5]imidazo[1,2-a][1,5]diazocine-10-carbonitrile)

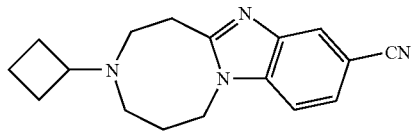

This intermediate was prepared in 75% yield (6.8 g) as described for compound 143 but using intermediate I-96 as the starting material. MS (ESI): m/z 281 (M+H⁺).

318. Intermediate I-98: (3-cyclobutyl-1,2,3,4,5,6-hexahydrobenzo[4,5]imidazo[1,2-a][1,5]diazocine-10-carbaldehyde)

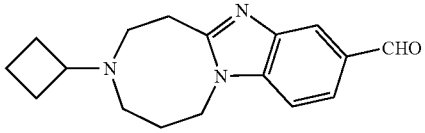

This intermediate was prepared in 65% yield (2.9 g) as described for intermediate I-39 but using intermediate I-97 as the starting material. MS (ESI): m/z 284 (M+H⁺).

319. Intermediate I-100: (5-bromo-3-nitropyridin-2-ol)

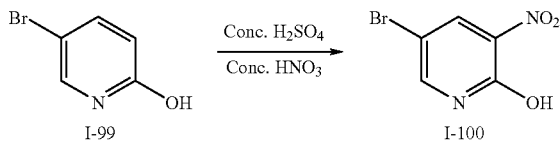

A mixture of 5-bromopyridin-2-ol (I-99, Aldrich, Wis.; 53 g, 0.30 mol) in concentrated.H₂SO₄ (250 mL) was stirred with ice bath cooling and concentrated HNO₃ (105 mL) was added slowly to the mixture. The reaction mixture was stirred for 4 hours at room temperature and then poured onto ice and stirred for additional 30 minutes. A yellow precipitate was filtered off used in the following step without further purification (45 g, 68%). MS (ESI): m/z 220 (M+1)⁺.

320. Intermediate I-101: (5-bromo-2-chloro-3-nitropyridine)

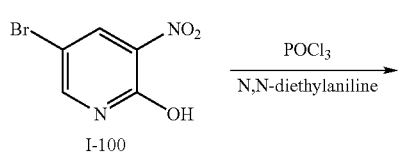

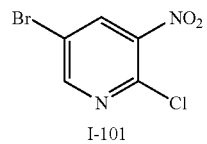

A mixture of I-100 (8.0 g, 36.7 mmol) and N,N-diethylaniline (7 mL) in POCl₃ (30 mL) was refluxed for 4 hours. The reaction mixture was cooled to room temperature, poured onto ice and stirred for additional 30 minutes. A yellow precipitate was filtered off used in the following step without further purification (7.2 g, 83%). MS (ESI): m/z 238 (M+1)⁺.

321. Intermediate I-102: (2-(5-bromo-3-nitropyridin-2-ylamino)ethanol)

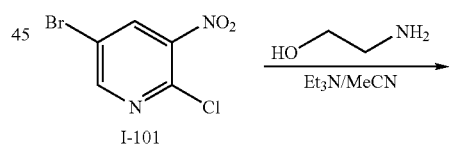

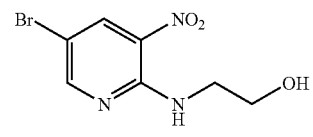

I-101 (3.2 g, 13.6 mmol), 2-aminoethanol (1 mL, 16.3 mmol) and Et₃N (3.8 mL, 27.1 mmol) were dissolved in CH₃CN (10 mL) and the reaction mixture was refluxed for 3 h. The reaction mixture was concentrated and the residue was dissolved in ethyl acetate and washed with brine. The combined organic layers were dried over Na₂SO₄, the solids were filtered and the filtrated was concentrated to give I-102 (3.2 g, 90%). MS (ESI): m/z 263 (M+1)⁺.

322. Intermediate I-103: (2-(5-bromo-3-nitropyridin-2-ylamino)ethanol)

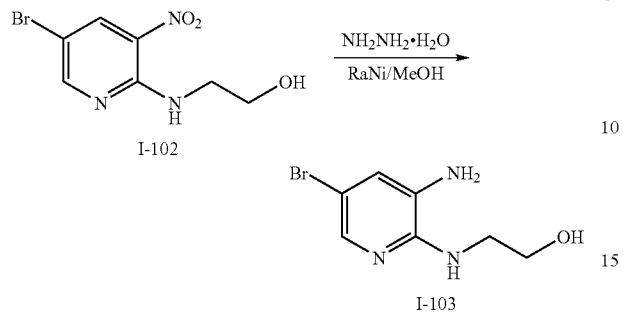

I-102 (3.2 g, 12.3 mmol) and NH$_2$NH$_2$.H$_2$O (2.5 g, 49 mmol) were dissolved MeOH (40 mL) and the reaction mixture was stirred at room temperature while a suspension of Raney Ni was being added slowly. The reaction mixture was stirred for 1 hour at room temperature and filtered through a short plug of Celite, the filtrate was dried over Na$_2$SO$_4$, the solids were filtered and the filtrate was concentrated to give I-103 (2.8 g, 100%). MS (ESI): m/z 233 (M+1)$^+$.

323. Intermediate I-104: (2-(5-bromo-3-nitropyridin-2-ylamino)ethanol)

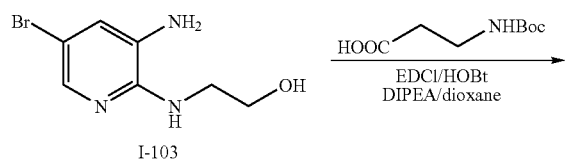

I-103 (36 g, 0.156 mol), EDCI (60 g, 0.31 mol), HOBt (44 g, 0.33 mol), DIPEA (60 g, 0.47 mol) and N-Boc-3-aminopropanoic acid (44 g, 0.23 mol) were dissolved in dioxane (50 mL) and the reaction mixture was stirred at 80° C. for 16 h. The reaction mixture was concentrated and the residue was dissolved in ethyl acetate and washed with brine. The combined organic layers were dried over Na$_2$SO$_4$, solids were filtered, and the filtrate was concentrated. The crude reaction mixture was purified by flash chromatography to give I-104 (23 g, 37%). MS (ESI): m/z 404 (M+1)$^+$.

324. Intermediate I-105: (2-(5-bromo-3-(3-(tert-butoxycarbonyl-amino)propanamido)pyridin-2-ylamino)ethyl 3-(tert-butoxy-carbonylamino)propanoate)

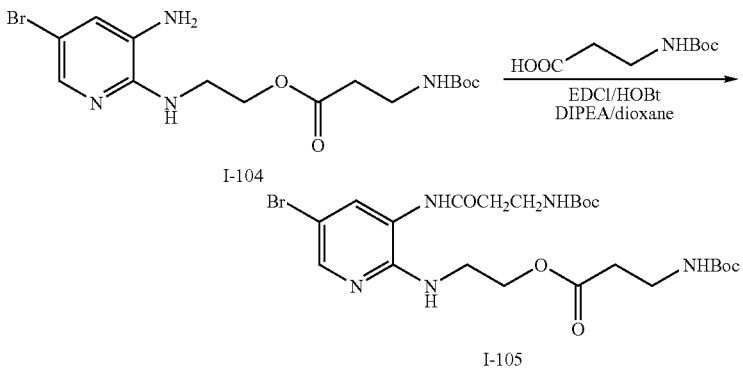

I-104 (16.6 g, 41.3 mmol), EDCI (11.9 g, 61.9 mmol), HOBt (11.1 g, 82.6 mmol), DIPEA (16 g, 124 mmol) and N-Boc-3-aminopropanoic acid (11.7 g, 61.9 mmol) were dissolved in dioxane (50 mL) and the reaction mixture was stirred at 80° C. for 16 h. The reaction mixture was concentrated and the residue was dissolved in ethyl acetate and washed with brine. The combined organic layers were dried over Na$_2$SO$_4$, the solids were filtered and the filtrate was concentrated. The crude reaction mixture was purified by flash chromatography to give I-105 (11.8 g, 50%). MS (ESI): m/z 575 (M+1)$^+$.

325. Intermediate I-106: (2-(6-bromo-2-(2-(tert-butoxycarbonyl-amino)ethyl)-3H-imidazo[4,5-b]pyridin-3-yl)ethyl 3-(tert-butoxycarbonylamino)propanoate)

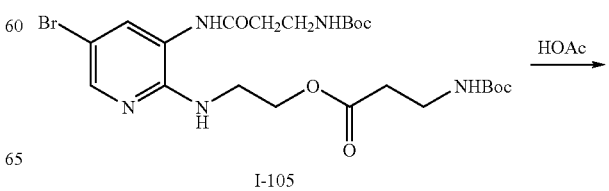

-continued

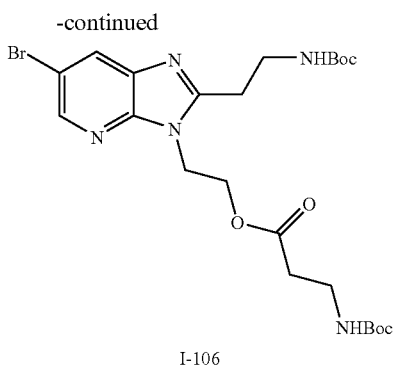

I-105 (4.20 g, 7.3 mmol) was dissolved in acetic acid (20 mL) stirred at 80° C. for 16 h. The reaction mixture was concentrated and the residue was dissolved in ethyl acetate and washed with brine. The combined organic layers were dried over $Na_2SO_4$, the solids were filtered and the filtrate was concentrated to give crude I-106 that was used in the following step without further purification (3.2 g, 79%). MS (ESI): m/z 557 (M+1)$^+$.

326. Intermediate I-107: (tert-butyl 2-(6-bromo-3-(2-hydroxyethyl)-3H-imidazo[4,5-b]pyridin-2-yl)ethyl-carbamate)

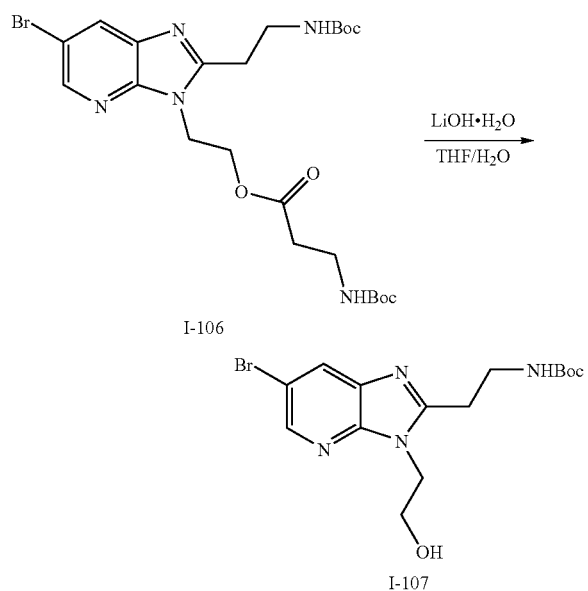

I-106 (3.2 g, 5.77 mmol) and LiOH.$H_2O$ (0.73 g, 17.3 mmol) were dissolved in a 1:1 mixture of THF and $H_2O$ (10 mL) and the reaction mixture was stirred for 2 hours at room temperature. The reaction mixture was concentrated and the residue was dissolved ethyl acetate and washed with water. The combined organic layers were dried over $Na_2SO_4$, the solids were filtered and the filtrate was concentrated. The crude reaction mixture was purified by flash chromatography to give I-107 (0.65 g, 30%). MS (ESI): m/z 386 (M+1)$^+$.

327. Intermediate I-108: (2-(6-bromo-2-(2-(tert-butoxycarbonylamino) ethyl)-3H-imidazo[4,5-b]pyridin-3-yl)ethyl) 4-methylbenzene-sulfonate)

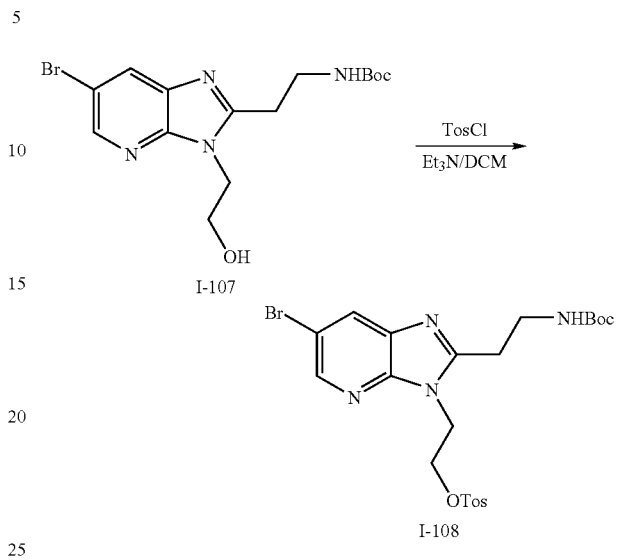

I-107 (0.65 g, 1.69 mmol), TosCl (0.65 g, 3.39 mmol) and $Et_3N$ (0.6 mL, 4.23 mmol) were dissolved in dichloromethane and the reaction mixture was stirred for 16 hours at room temperature. The reaction mixture was concentrated and the residue was dissolved in ethyl acetate and washed with brine. The combined organic layers were dried over $Na_2SO_4$, the solids were filtered and the filtrate was concentrated. Excess TosCl was removed by washing the residue with petrol ether to give I-108 (0.79 g, 87%). MS (ESI): m/z 540 (M+1)$^+$.

328. Intermediate I-109: (2-(2-(2-aminoethyl)-6-bromo-3H-imidazo[4,5-b]pyridin-3-yl)ethyl 4-methylbenzenesulfonate)

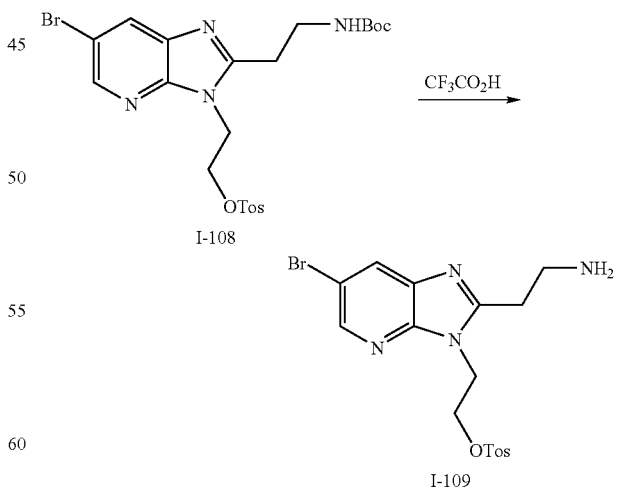

I-108 (0.79 g, 1.47 mmol) was dissolved in trifluoroacetic acid (5 mL) and the reaction mixture was stirred for 60 minutes at room temperature. The reaction mixture was concentrated and the residue was dissolved in ethyl acetate and washed with aqueous saturated.NaHCO₃ and brine. The combined organic layers were dried over Na₂SO₄, the solids were filtered and the filtrate was concentrated to give I-109 (0.60 g, 94%). MS (ESI): m/z 440 (M+1)⁺.

329. Intermediate I-110: (7-Aza-9-bromo-2,3,4,5-tetrahydro-1H-[1,4]diazepino[1,7-a]benzimidazole)

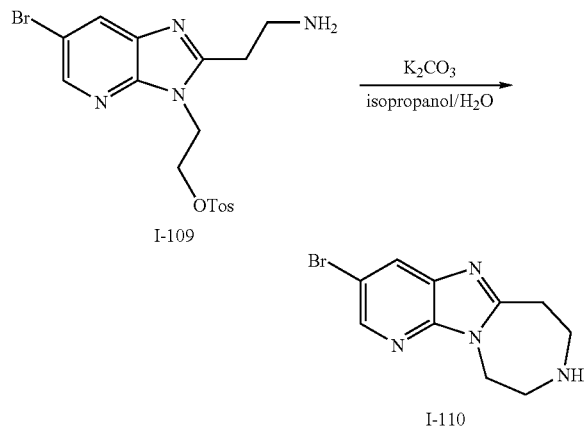

I-109 (0.60 g, 1.37 mmol) and K₂CO₃ (0.47 g, 3.42 mmol) were dissolved in a 1:1 mixture of isopropanol and H₂O (4 mL) and the reaction mixture was stirred at 80° C. for 2 hours. The reaction mixture was concentrated and the residue was dissolved in ethyl acetate and washed with brine. The combined organic layers were dried over Na₂SO₄, the solids were filtered and the filtrate was concentrated by evaporation to give I-110 (0.30 g, 83%). MS (ESI): m/z 268 (M+1)⁺.

330. Intermediate I-111: (7-Aza-3-cyclobutyl-9-(4,4,5,5-tetramethyl-1,3,2-dioxaborolan-2-yl) 2,3,4,5-tetrahydro-1H-[1,4]diazepino-[1,7-a]benzimidazole)

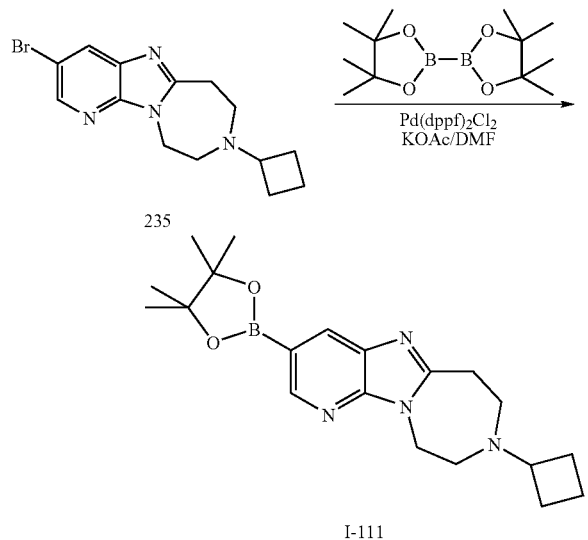

Compound 235 (0.20 g, 0.63 mmol), Pd(dppf)₂Cl₂(0.10 g, 0.125 mmol), KOAc (0.21 g, 2.19 mmol) and 4,4,5,5-tetramethyl-2-(4,4,5,5-tetramethyl-1,3,2-dioxaborolan-2-yl)-1,3,2-dioxaborolane (0.24 g, 0.94 mmol) were dissolved in DMF (1 mL) in a microwave tube that was filled with argon. The reaction mixture was stirred at 100° C. for 1 hour under microwave irradiation. The reaction mixture was diluted with ethyl acetate and filtered through a short plug of Celite. The filtrate was washed with brine and the combined organic layers were dried over Na₂SO₄, the solids were filtered and the filtrate was concentrated. The crude reaction mixture was purified by preparative TLC to give I-111 (0.08 g, 48%). MS (ESI): m/z 369 (M+1)⁺.

B. Histamine H3 In Vitro Assay

H3 GTPγS assay (SPA method) was performed at EuroScreen (Belgium, ES-392-C) using conventional methods. Briefly, cells expressing the human histamine H3 receptor were homogenized in 15 mM Tris-HCl pH 7.5, 2 mM MgCl₂, 0.3 mM EDTA, and 1 mM EGTA. Membranes were washed twice in the above tris buffer, collected by centrifugation (40,000×g, 25 min), and re-suspended in 75 mM Tris-HCl pH 7.5, 12.5 mM MgCl₂, 0.3 mM EDTA, 1 mM EGTA, and 250 mM sucrose. Membranes were frozen in liquid nitrogen until use. On the day of the assay, membranes were thawed and diluted in assay buffer (20 mM HEPES pH 7.4, 100 mM NaCl, 10 ng/ml saponin, 1 mM MgCl₂) to give 500 μg/ml and mixed (v/v) with GDP in assay buffer for a final GDP concentration of 10 μM and incubated on ice for at least 15 min. PVT-WGA beads (Amersham, RPNQ001) were diluted in assay buffer at 50 mg/mL and mixed with GTPγ[³⁵S] (Amersham, SJ1308) diluted in assay buffer to give ~25,000 dpm/10 μL and mixed vol/vol just before the start of the reaction. The reaction was started by adding 50 μL of test compound, 20 μl, of the membranes:GDP mix, 10 μL of buffer, and 20 μL of the GTPγ[³⁵S]:beads mix in a 96 well plate Optiplate™ (PerkinElmer, 6005299) covered with topseal (TopCount™, PerkinElmer), mixed with an orbital shaker for 2 min, incubated for 1 hour at room temperature, centrifuged for 10 mM at 2000 rpm, incubated for 1 h at room temperature, and counted for 1 min in a TopCount™ reader (PerkinElmer). Dose response curves and IC₅₀ values (concentration to inhibit the reaction by 50%) were calculated by nonlinear regression using XLfit software (IDBS).

For antagonists testing, 10 μl of a reference agonist (R-γ-Me-Histamine) instead of 10 μL buffer was added at a concentration corresponding to the EC₈₀ (30 nM). Control ligands were R-γ-Me-Histamine (Tocris, 0569), Imetit (Sigma, I-135), Thioperamide (Tocris, 0644), and Clobenpropit (Tocris, 0754) diluted in assay buffer.

The compounds provided herein were tested in the histamine H3 in vitro assay. In one embodiment, the respective HCl salts of the compounds provided herein were prepared using standard chemical procedures and tested in the histamine H3 in vitro assay. The functional potency of the compounds (as indicated by their IC₅₀s) are shown in Table 1.

TABLE 1

| Compound | Potency |
|---|---|
| 1 | (++++) |
| 2 | (++++) |
| 3 | (++++) |
| 4 | (+++) |
| 5 | (+++) |
| 6 | (+++) |
| 7 | (++) |
| 8 | (++) |
| 9 | (++) |
| 10 | (+) |
| 11 | (+) |
| 12 | (+) |

TABLE 1-continued

| Compound | Potency |
|---|---|
| 13 | (+) |
| 14 | (+) |
| 15 | (+) |
| 16 | (+) |
| 17 | (+) |
| 18 | (+) |
| 19 | (+) |
| 20 | (+) |
| 21 | (++) |
| 22 | (++++) |
| 23 | (++++) |
| 24 | (++++) |
| 25 | (++) |
| 26 | (++) |
| 27 | (++++) |
| 28 | (++++) |
| 29 | (+++) |
| 30 | (+++) |
| 31 | (++++) |
| 32 | (+++) |
| 33 | (+++) |
| 34 | (+++) |
| 35 | (++++) |
| 36 | (++) |
| 37 | (+) |
| 38 | (+++) |
| 39 | (+++) |
| 40 | (+++) |
| 41 | (++) |
| 42 | (++) |
| 43 | (++) |
| 44 | (+++) |
| 45 | (++) |
| 46 | (++) |
| 47 | (++) |
| 48 | (++) |
| 49 | (++) |
| 50 | (++++) |
| 51 | (+++) |
| 52 | (+++) |
| 53 | (++++) |
| 54 | (++) |
| 55 | (+++) |
| 56 | (+++) |
| 57 | (++) |
| 58 | (++) |
| 59 | (+++) |
| 60 | (+++) |
| 61 | (+++) |
| 62 | (+++) |
| 63 | (+++) |
| 64 | (+++) |
| 65 | (+++) |
| 66 | (++++) |
| 67 | (+++) |
| 68 | (++++) |
| 69 | (+++) |
| 70 | (+++) |
| 71 | (++) |
| 72 | (+++) |
| 73 | (++++) |
| 74 | (++++) |
| 75 | (++++) |
| 76 | (+) |
| 77 | (++) |
| 78 | (++) |
| 79 | (++) |
| 80 | (++) |
| 81 | (+++) |
| 82 | (+) |
| 83 | (++++) |
| 84 | (++) |
| 85 | (+) |
| 86 | (++) |
| 87 | (++++) |
| 88 | (++++) |
| 89 | (++++) |
| 90 | (++) |
| 91 | (+++) |
| 92 | (++++) |
| 93 | (+++) |
| 94 | (+++) |
| 95 | (++++) |
| 96 | (++++) |
| 97 | (++++) |
| 98 | (++++) |
| 99 | (++++) |
| 100 | (++++) |
| 101 | (++++) |
| 102 | (++++) |
| 103 | (++++) |
| 104 | (++++) |
| 105 | (+++) |
| 106 | (++) |
| 107 | (+++) |
| 108 | (+++) |
| 109 | (++++) |
| 110 | (++) |
| 111 | (++) |
| 112 | (++) |
| 113 | (++) |
| 114 | (+++) |
| 115 | (+++) |
| 116 | (++++) |
| 117 | (++++) |
| 118 | (++++) |
| 119 | (+++) |
| 120 | (+++) |
| 121 | (+++) |
| 122 | (+++) |
| 123 | (+++) |
| 124 | (+++) |
| 125 | (+++) |
| 126 | (++++) |
| 127 | (+++) |
| 128 | (++++) |
| 129 | (++++) |
| 130 | (+++) |
| 131 | (++++) |
| 132 | (+++) |
| 133 | (+++) |
| 134 | (+++) |
| 135 | (+++) |
| 136 | (+++) |
| 137 | (+++) |
| 138 | (+++) |
| 139 | (+++) |
| 140 | (+++) |
| 141 | (+++) |
| 142 | (+++) |
| 143 | (+) |
| 144 | (++++) |
| 145 | (++++) |
| 146 | (++++) |
| 147 | (++++) |
| 148 | (+++) |
| 149 | (+) |
| 150 | (+++) |
| 151 | (+++) |
| 152 | (+++) |
| 153 | (++++) |
| 154 | (+++) |
| 155 | (++++) |
| 156 | (+++) |
| 157 | (+++) |
| 158 | (++++) |
| 159 | (++++) |
| 160 | (++++) |
| 161 | (++++) |
| 162 | (++++) |
| 163 | (++++) |
| 164 | (++++) |
| 165 | (+++) |
| 166 | (++++) |
| 167 | (++++) |
| 168 | (++++) |

TABLE 1-continued

| Compound | Potency |
| --- | --- |
| 169 | (+++) |
| 170 | (++++) |
| 171 | (++++) |
| 172 | (+++) |
| 173 | (+++) |
| 174 | (++++) |
| 175 | (++++) |
| 176 | (++++) |
| 177 | (++++) |
| 178 | (+++) |
| 179 | (++++) |
| 180 | (++++) |
| 181 | (+++) |
| 182 | (+++) |
| 183 | (+++) |
| 184 | (++) |
| 185 | (++++) |
| 186 | (+++) |
| 187 | (++++) |
| 188 | (++) |
| 189 | (+++) |
| 190 | (++++) |
| 191 | (+++) |
| 192 | (+++) |
| 193 | (+++) |
| 194 | (+++) |
| 195 | (++++) |
| 196 | (+++) |
| 197 | (++++) |
| 198 | (++++) |
| 199 | (+++) |
| 200 | (++++) |
| 201 | (++++) |
| 202 | (++++) |
| 203 | (+++) |
| 204 | (++++) |
| 205 | (+++) |
| 206 | (+++) |
| 207 | (++++) |
| 208 | (++++) |
| 209 | (++++) |
| 210 | (++++) |
| 211 | (+++) |
| 212 | (++++) |
| 213 | (+++) |
| 214 | (+++) |
| 215 | (+++) |
| 216 | (++++) |
| 217 | (+++) |
| 218 | (+++) |
| 219 | (++++) |
| 220 | (++++) |
| 221 | (++++) |
| 222 | (++++) |
| 223 | (++++) |
| 224 | (++++) |
| 225 | (++++) |
| 226 | (+++) |
| 227 | (+++) |
| 228 | (++++) |
| 229 | (++++) |
| 230 | (++++) |
| 231 | (++++) |
| 232 | (++++) |
| 233 | (++++) |
| 234 | (+++) |
| 235 | (+) |
| 236 | (++) |
| 237 | (+++) |
| 238 | (++) |
| 239 | (+++) |

(++++) <=10 nM
(+++) <=100 nM
(++) <=1 μM
(+) >=1 μM

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed:
1. A compound of formula (Ia):

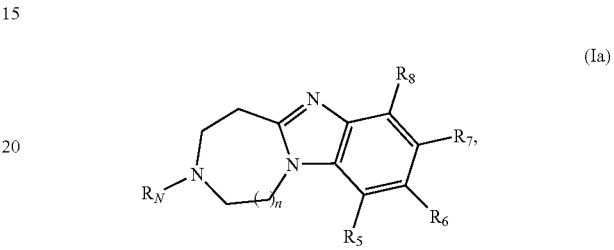

(Ia)

or a pharmaceutically acceptable salt, non-stoichiometric hydrate, or stereoisomer thereof, wherein
$R_N$ is hydrogen, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, or (5 to 10 membered)heteroaryl, each of which is optionally substituted with one or more R';

each occurrence of R' is independently hydrogen, halogen, cyano, $(C_1-C_{10})$alkyl, $C_{10}$)alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_2$; or two R' substituents together may form a 3 to 10 membered ring optionally substituted with one or more $R_2$;

$R_5$, $R_6$, $R_7$, and $R_8$ are each independently (i) hydrogen, halogen, or cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; (iii) hydroxyl substituted with $R_1$'; or (iv) two adjacent $R_5$, $R_6$, $R_7$, and $R_8$ together form a 3 to 10 membered ring optionally substituted with one or more $R_1$;

each occurrence of $R_1$ is independently hydrogen, halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_2NR_3R_4$, $(C_1-C_{10})$alkyl optionally substituted with one or more $R_2$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$;

each occurrence of $R_1$' is independently —$C(O)NR_3R_4$, —$C(O)R_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$ heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$;

each occurrence of $R_2$ is independently hydrogen, $(C_1-C_6)$ alkyl optionally substituted with one or more $R_3$, $(C_3-C_6)$cycloalkyl optionally substituted with one or more $R_3$, halogen, cyano, =O, —$OR_3$, —$NR_3R_4$, —$N(R_3)C(O)R_4$, —$C(O)NR_3R_4$, —$C(O)R_3$, —$C(O)OR_3$, —$OC(O)R_3$, —$S(O)_mR_3$, or —$S(O)_2NR_3R_4$;

$R_3$ and $R_4$ are each independently hydrogen, $(C_1-C_6)$alkyl, $(C_3-C_6)$cycloalkyl, $(C_7-C_{10})$aralkyl; $(C_1-C_6)$heteroalkyl, $(C_3-C_6)$heterocycloalkyl, (6 to 10 membered) aryl, or (5 to 10 membered)heteroaryl; or $R_3$ and $R_4$ together may form a 3 to 10 membered ring;

m is 0, 1, or 2;

n is 1, 2, or 3; and provided that when n is 1, (i) $R_5$, $R_6$, $R_7$, and $R_8$ cannot all be hydrogen; (ii) when one of $R_5$, $R_6$, $R_7$, and $R_8$ is halogen, the other three of $R_5$, $R_6$, $R_7$, and $R_8$ cannot all be hydrogen; and (iii) when $R_6$ is $(C_1-C_4)$alkyl or $(C_1-C_4)$alkoxyl optionally substituted with one or more halogen, $R_5$, $R_7$, and $R_8$ cannot all be hydrogen.

2. The compound of claim 1, or a pharmaceutically acceptable salt, non-stoichiometric hydrate, or stereoisomer thereof, having formula (IIa):

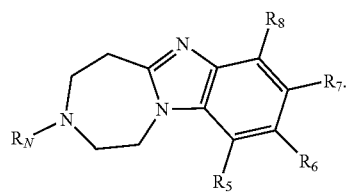

3. The compound of claim 2, wherein two adjacent $R_5$, $R_6$, $R_7$, and $R_8$ together form a 3 to 10 membered ring optionally substituted with one or more $R_1$.

4. The compound of claim 3, wherein the compound is:

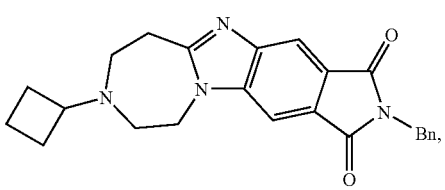

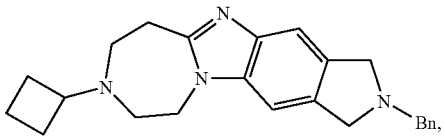

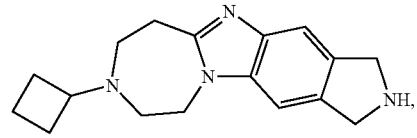

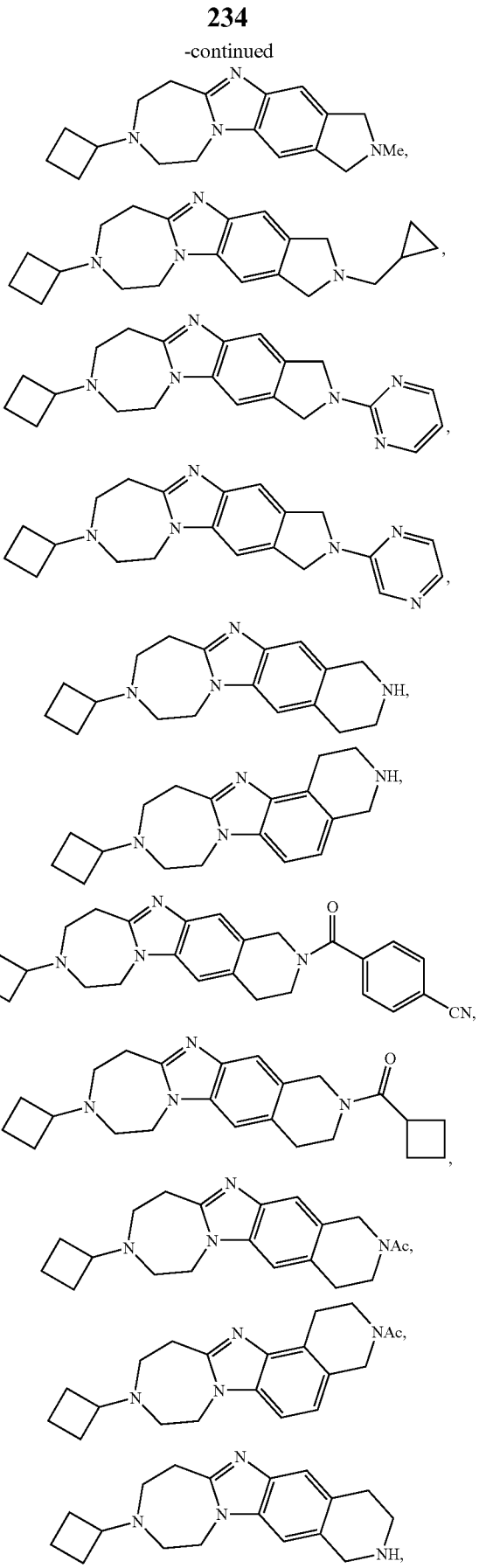

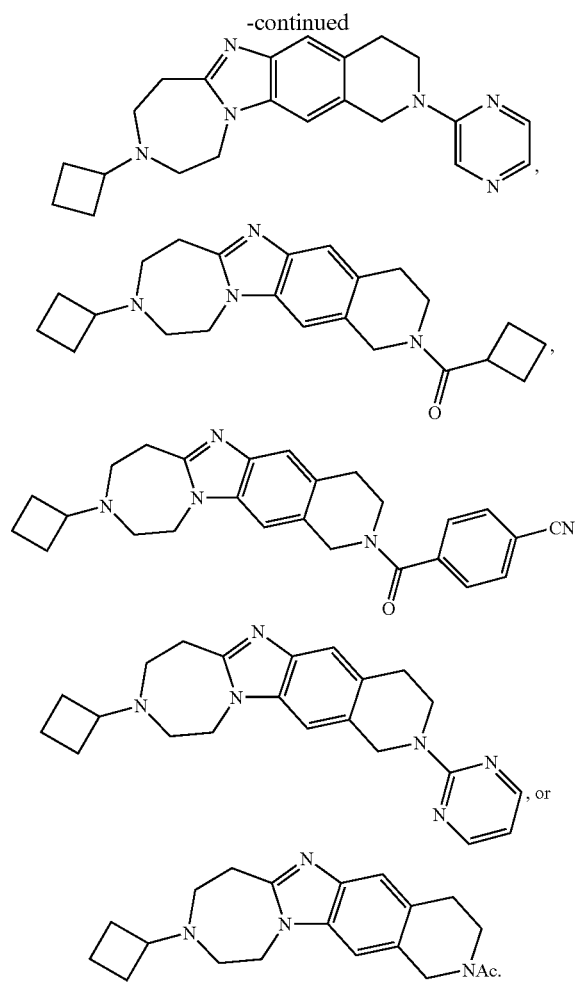

5. The compound of claim 2, or a pharmaceutically acceptable salt, non-stoichiometric hydrate, or stereoisomer thereof, having formula (IIIa):

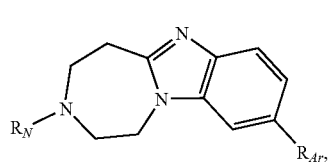

(IIIa)

wherein $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with $R_1$'; and provided that $R_{Ar}$ is not $(C_1-C_4)$alkyl or $(C_1-C_4)$alkoxyl optionally substituted with one or more halogen.

6. The compound of claim 5, wherein $R_N$ is $(C_3-C_{10})$cycloalkyl or $(C_1-C_{10})$alkyl, each of which is optionally substituted with one or more R'; and $R_{Ar}$ is (i) cyano; (ii) (6 to 10 membered)aryl, $(C_1-C_{10})$heteroalkyl, $(C_3-C_{10})$heterocycloalkyl, (5 to 10 membered)heteroaryl, aminoalkyl, amino, amido, or carbonyl, each of which is optionally substituted with one or more $R_1$; (iii) $(C_1-C_{10})$alkyl or alkoxyl, each of which is substituted with one or more $R_1$'; or (iv) hydroxyl substituted with $R_1$'.

7. The compound of claim 5, wherein $R_N$ is optionally substituted cyclobutyl.

8. The compound of claim 5, wherein $R_{Ar}$ is cyano, optionally substituted phenyl, optionally substituted six-membered heteroaryl, optionally substituted five-membered heteroaryl, optionally substituted (8 to 10)membered heteroaryl, optionally substituted six-membered heterocycloalkyl, optionally substituted five-membered heterocycloalkyl, —$OR_1$', —$OCH_2R_1$', —$NHR_1$, 13 $NHCH_2R_1$, —$N(R_1)_2$, —$C(O)R_1$, —$C(O)N(R_1)_2$, —$CH_2R_1$', —$CH_2N(R_1)_2$, —$CH_2OH$, or —$CH_2OR_1$'.

9. The compound of claim 5, or a pharmaceutically acceptable salt, non-stoichiometric hydrate, or stereoisomer thereof, having formula (IVa):

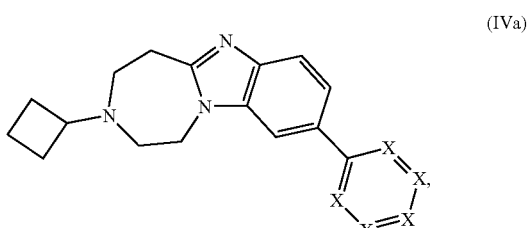

(IVa)

wherein each X is independently N, CH, or $CR_1$.

10. The compound of claim 5, wherein the compound is:

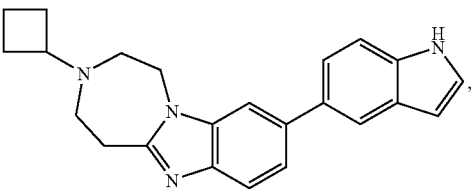

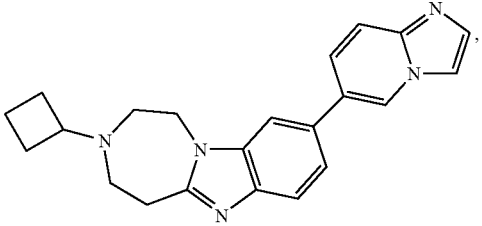

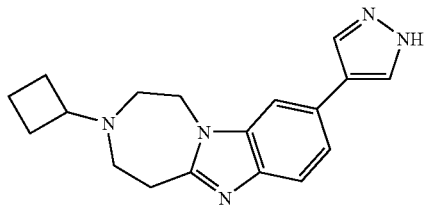

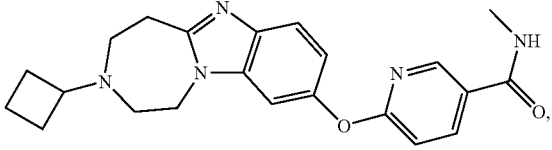

237
-continued
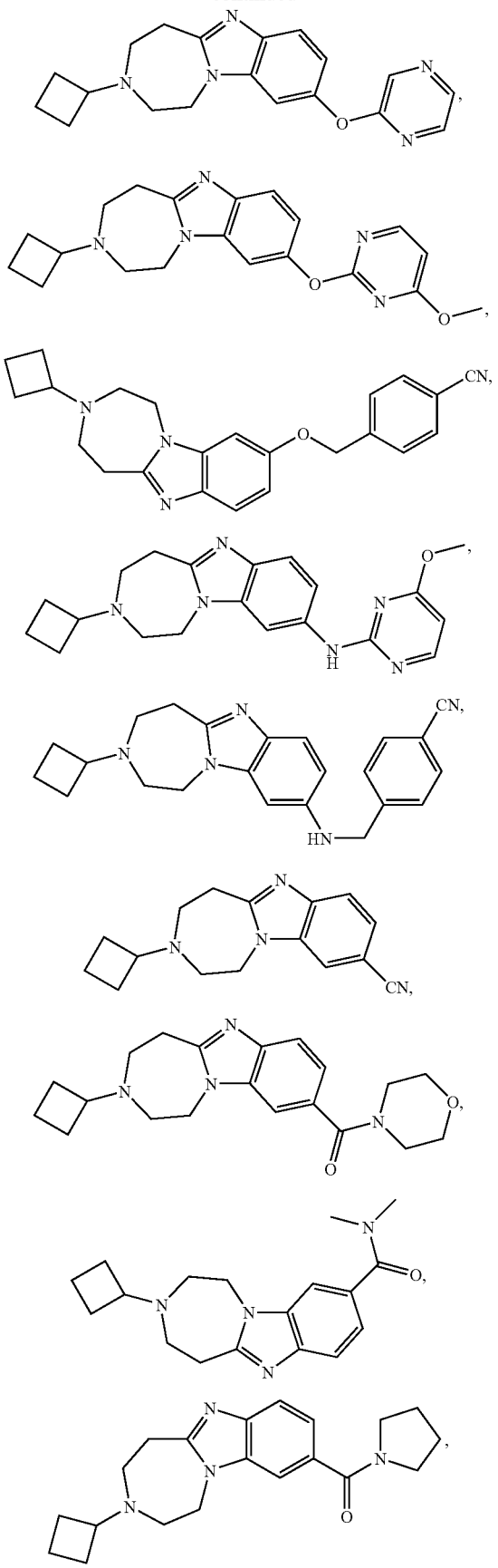
238
-continued
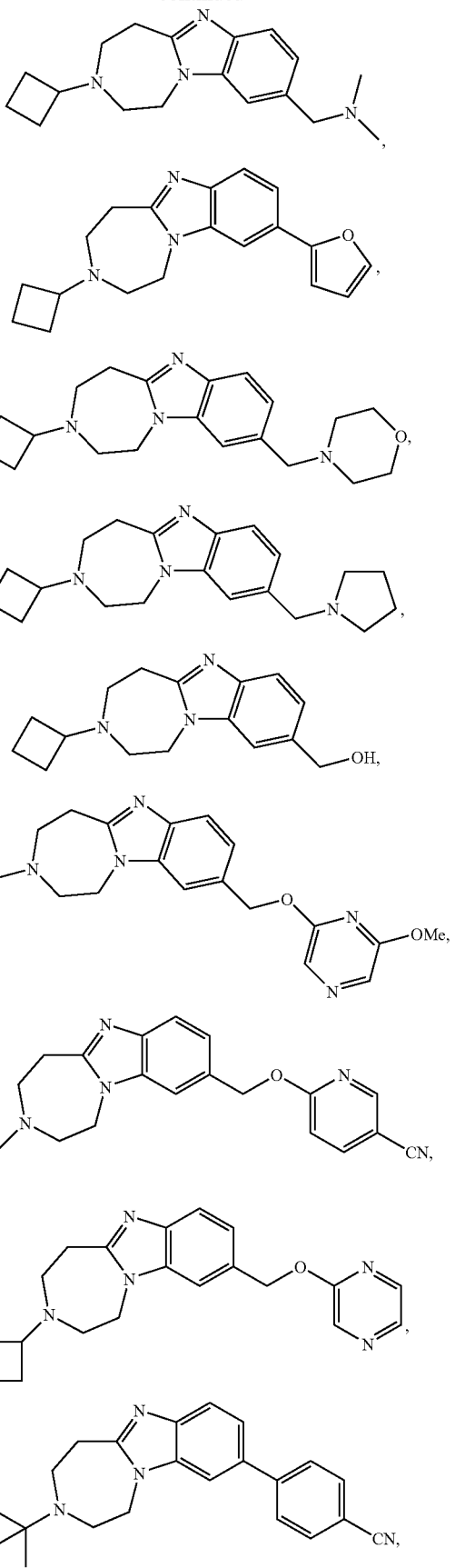

-continued

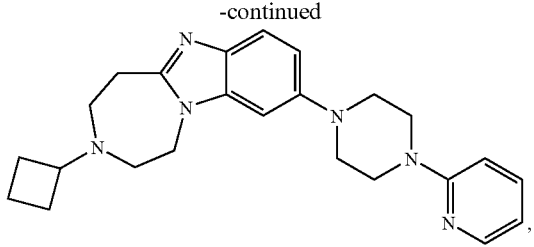

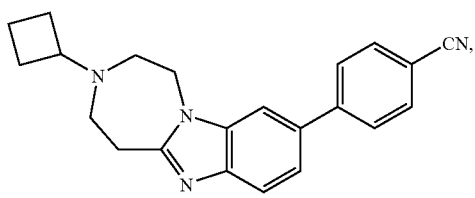

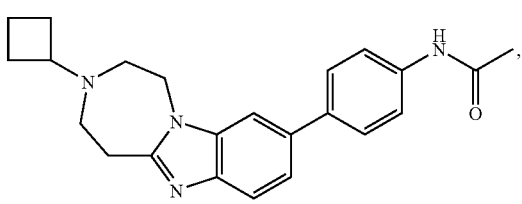

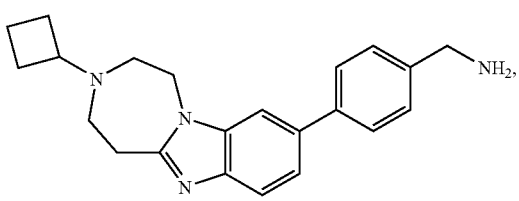

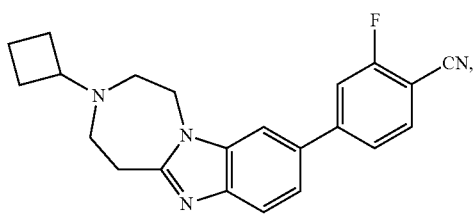

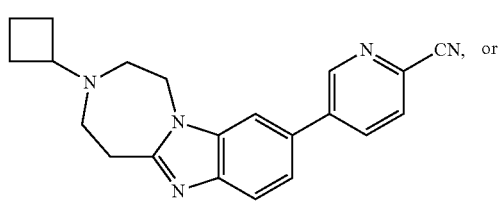

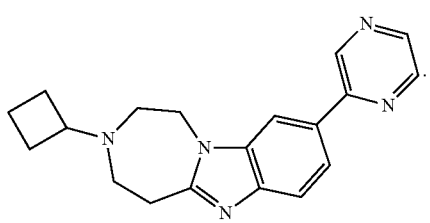

11. The compound of claim 2, or a pharmaceutically acceptable salt, non-stoichiometric hydrate, or stereoisomer thereof, having formula (IIIb):

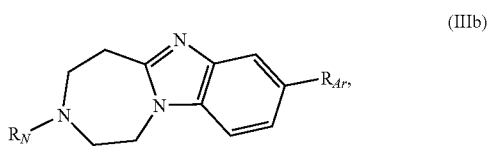

(IIIb)

wherein $R_{Ar}$ is (i) cyano; (ii) $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered) heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with $R_1'$.

12. The compound of claim 11, wherein $R_N$ is $(C_1-C_{10})$ alkyl optionally substituted with one or more R'.

13. The compound of claim 11, wherein $R_N$ is $(C_3-C_{10})$ heterocycloalkyl optionally substituted with one or more R'.

14. The compound of claim 11, wherein $R_N$ is $(C_3-C_{10})$ cycloalkyl optionally substituted with one or more R'.

15. The compound of claim 14, wherein $R_N$ is cyclobutyl optionally substituted with one or more.

16. The compound of claim 11, wherein $R_{Ar}$ is phenyl or naphthyl optionally substituted with one or more $R_1$.

17. The compound of claim 11, wherein $R_{Ar}$ is six-membered heteroaryl optionally substituted with one or more $R_1$.

18. The compound of claim 11, wherein $R_{Ar}$ is five-membered heteroaryl optionally substituted with one or more $R_1$.

19. The compound of claim 11, wherein $R_{Ar}$ is 8 to 10 membered heteroaryl optionally substituted with one or more $R_1$.

20. The compound of claim 11, wherein $R_{Ar}$ is $(C_3-C_{10})$ heterocycloalkyl optionally substituted with one or more $R_1$.

21. The compound of claim 11, wherein $R_{Ar}$ is $(C_1-C_{10})$ alkyl or alkoxyl, each of which is optionally substituted with one or more $R_1$.

22. The compound of claim 11, wherein $R_{Ar}$ is hydroxyl substituted with $R_1'$.

23. The compound of claim 11, wherein $R_{Ar}$ is amino, amido, or carbonyl, each of which is optionally substituted with one or more $R_1$.

24. The compound of claim 11, having formula (IVb):

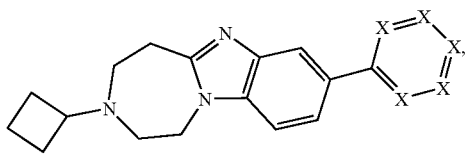

or a pharmaceutically acceptable salt, non-stoichiometric hydrate, or stereoisomer thereof, wherein each X is independently N, CH, or $CR_1$.

25. The compound of claim 11, wherein the compound is:
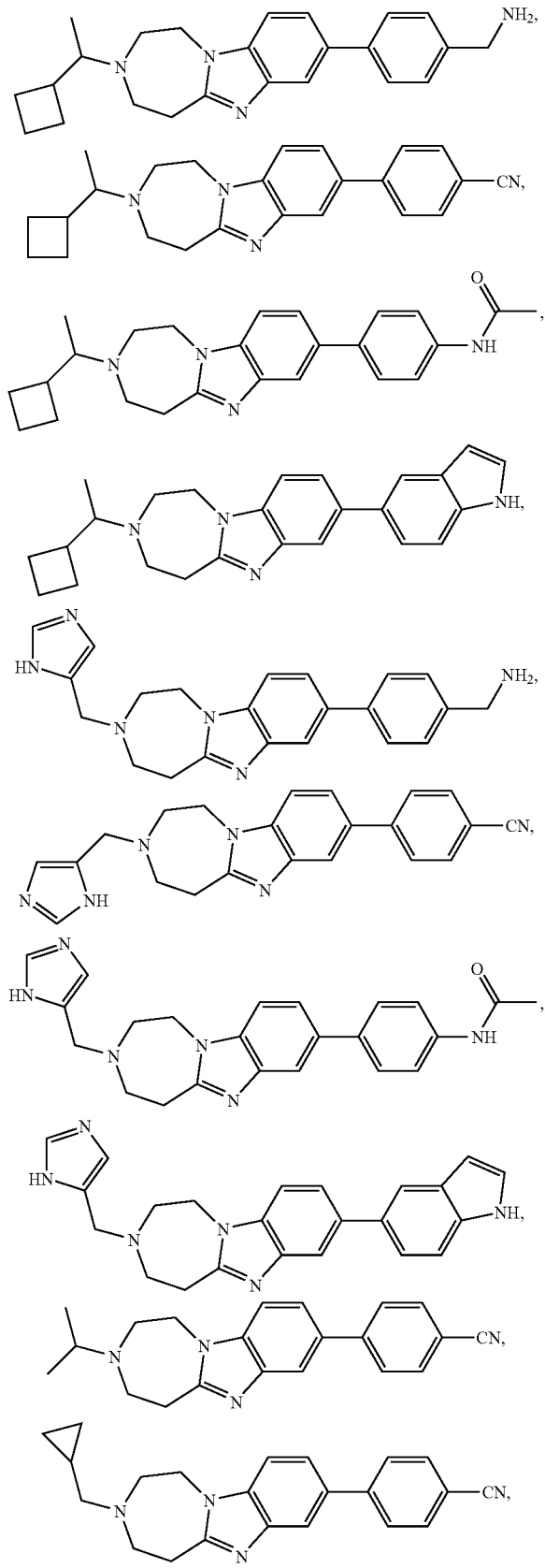
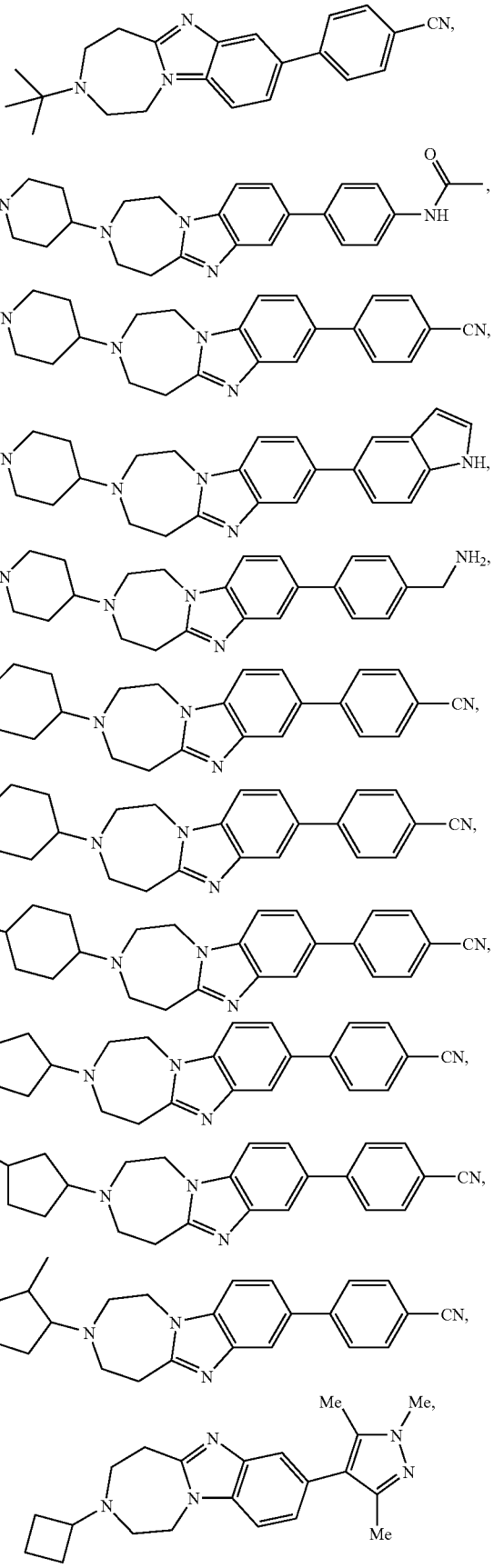

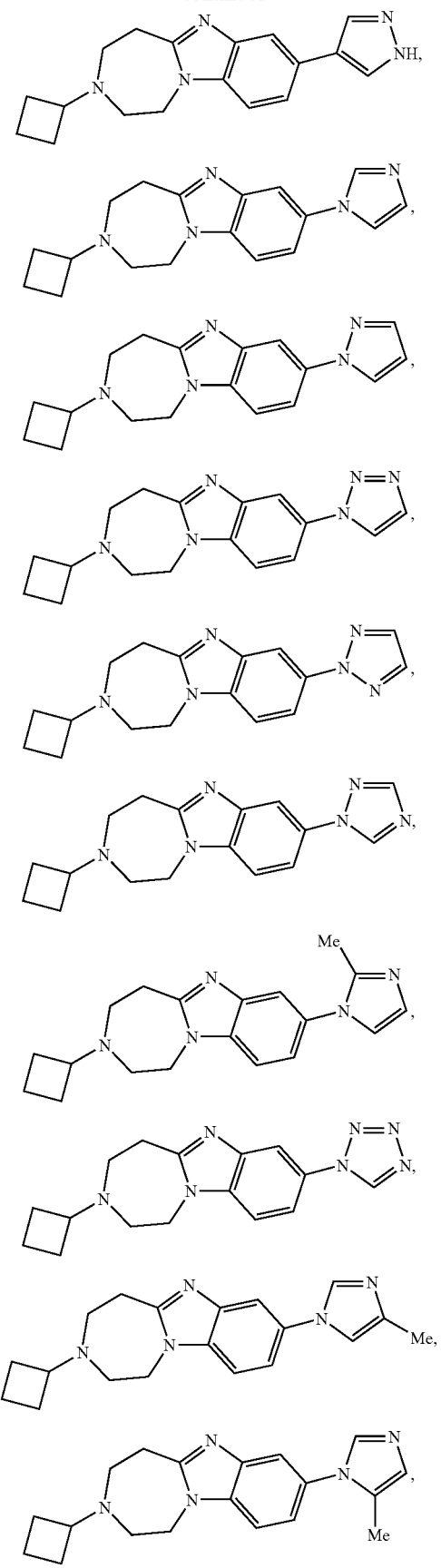
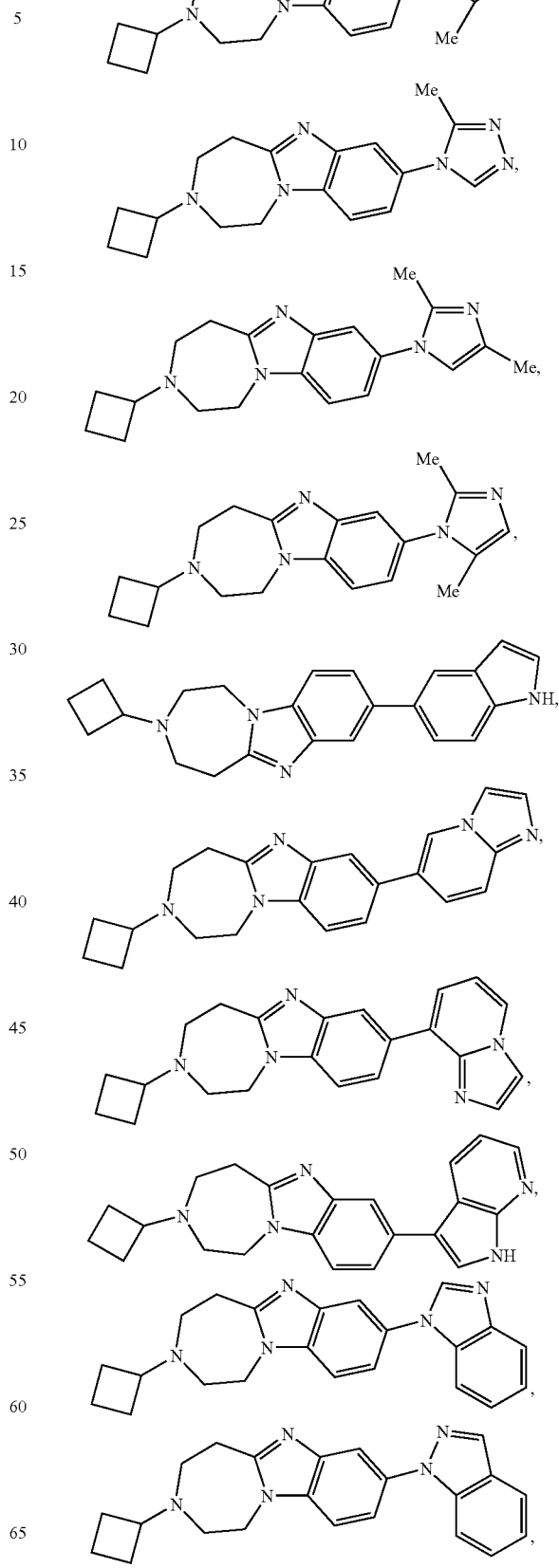

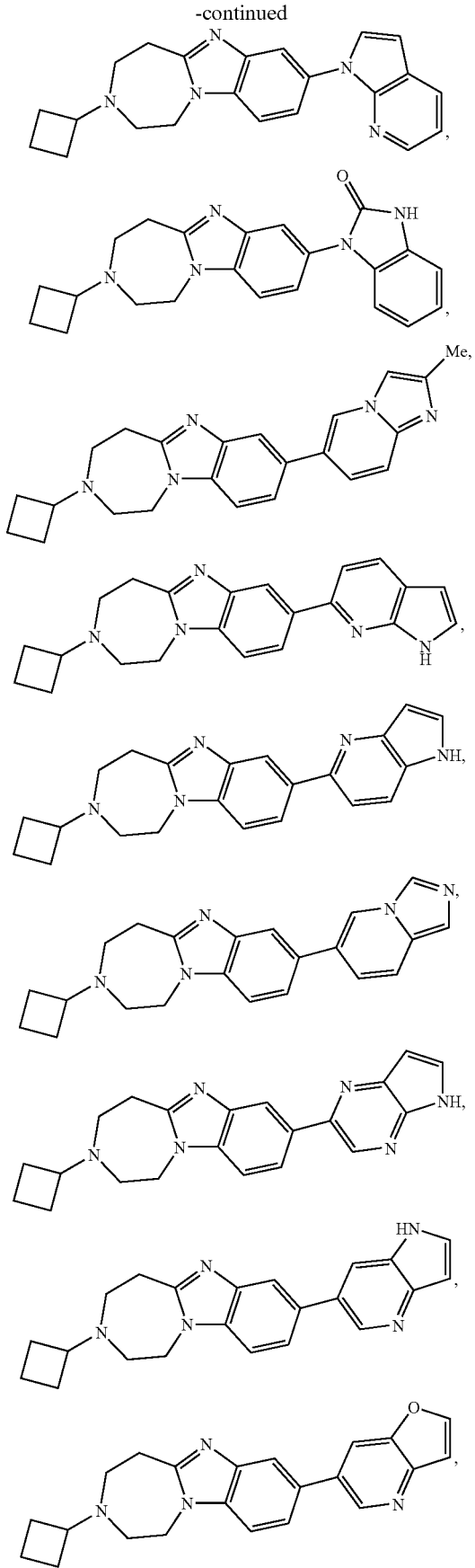
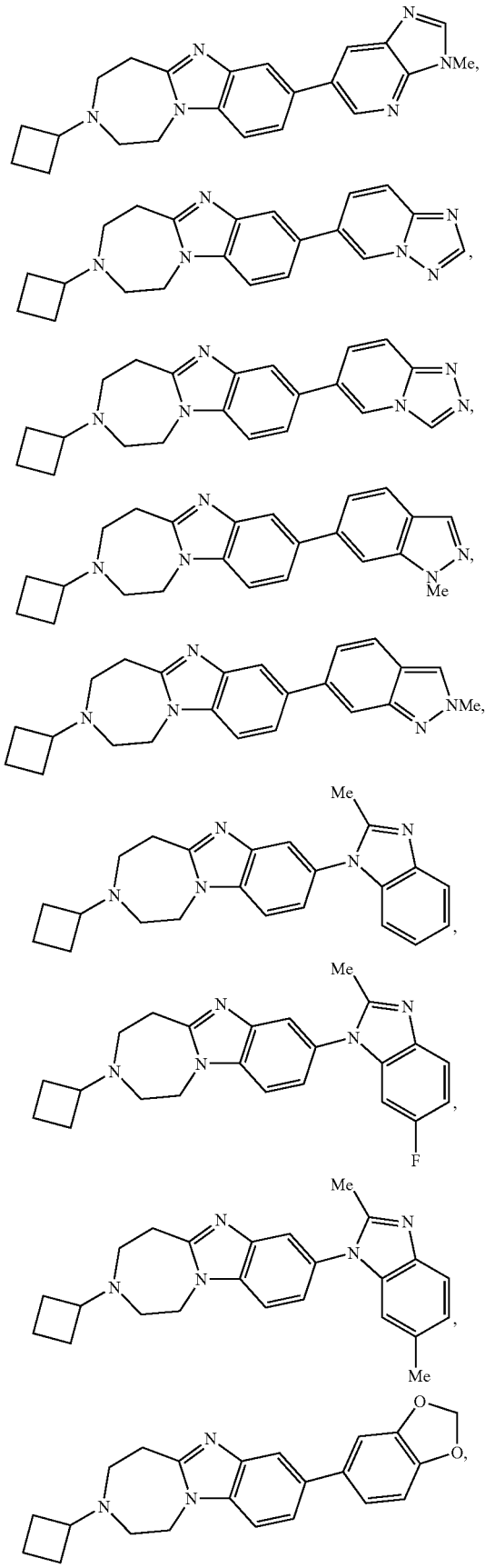

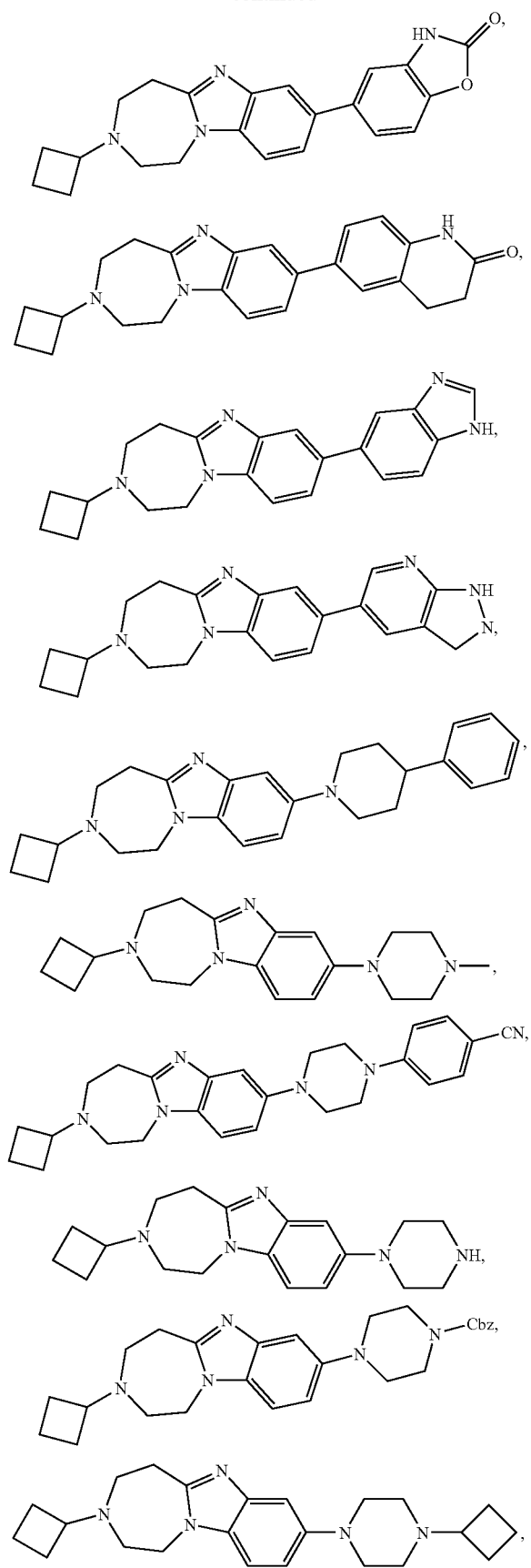
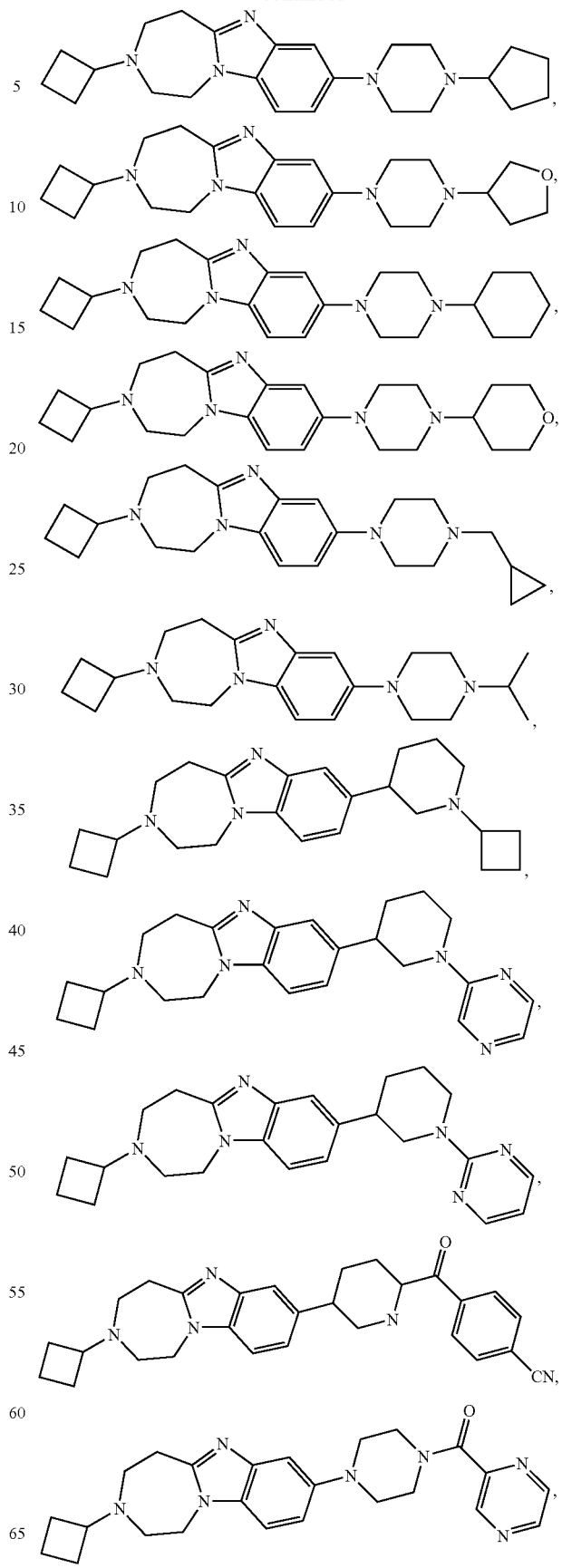

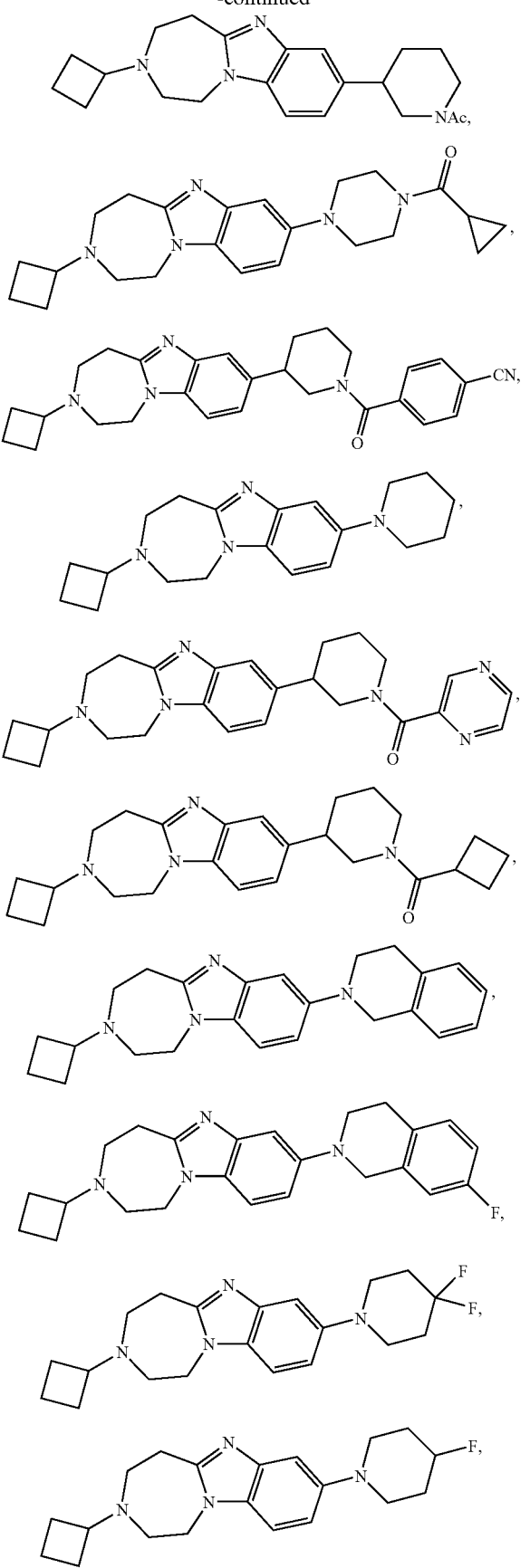
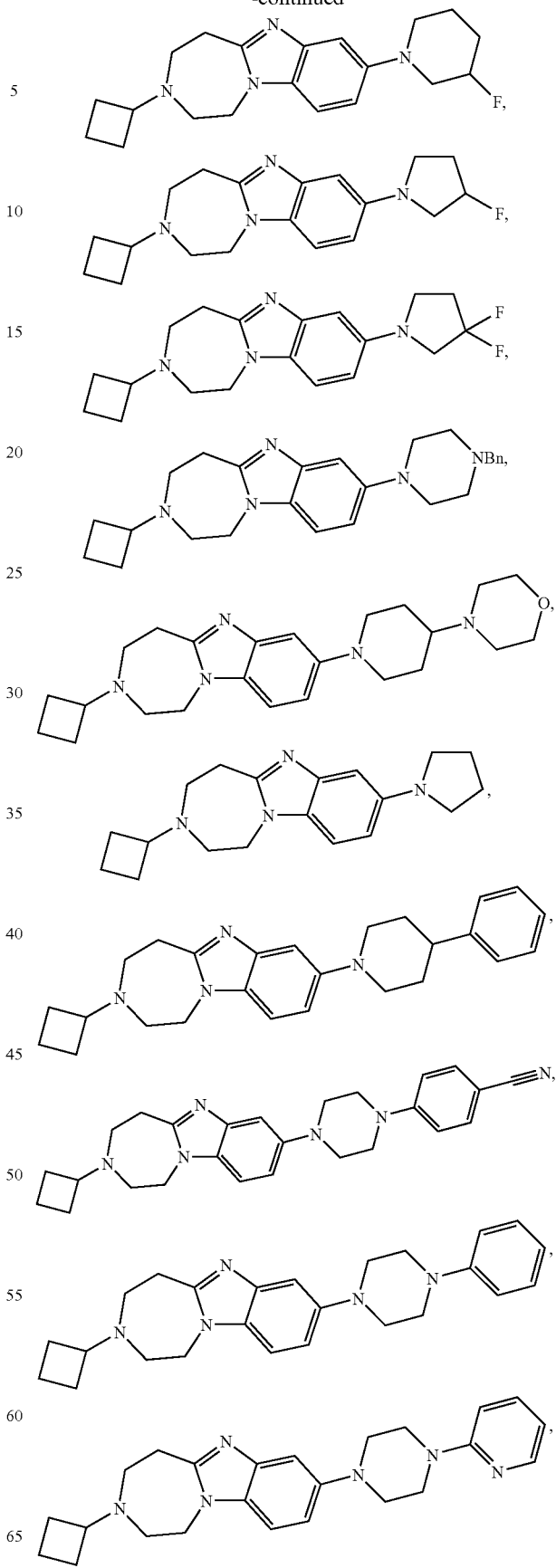

251
-continued
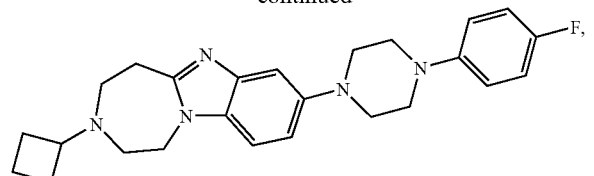
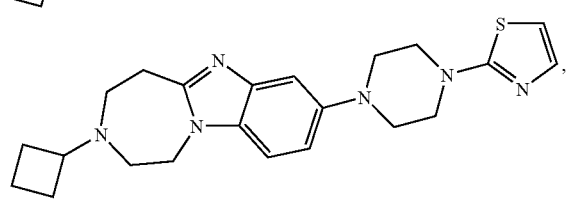
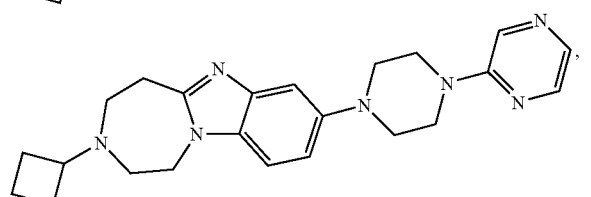
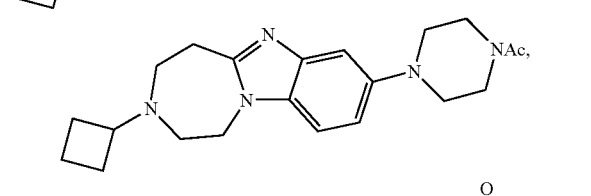
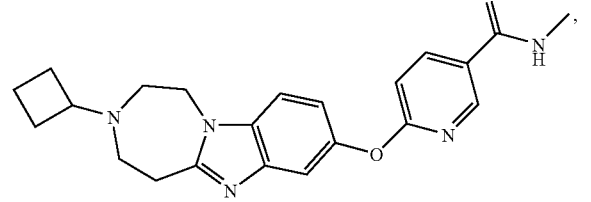
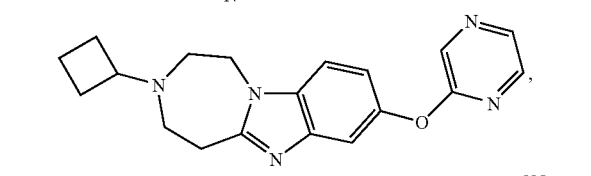
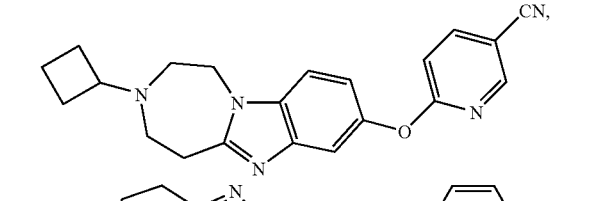
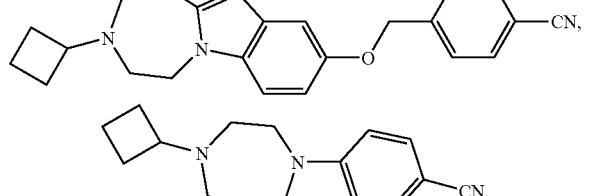
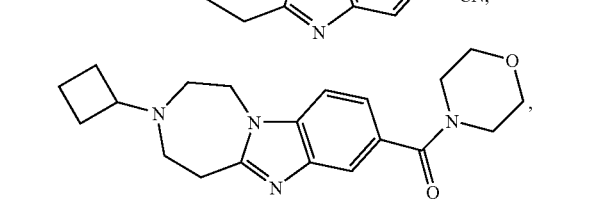
252
-continued
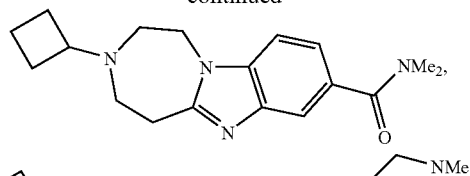
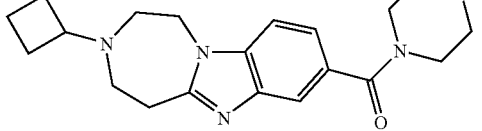
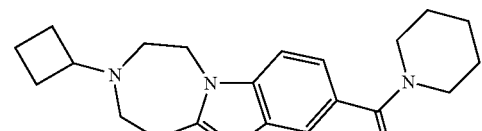
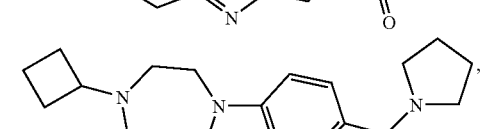
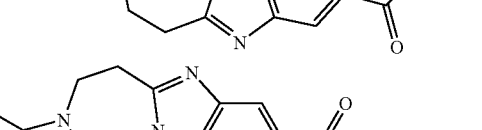
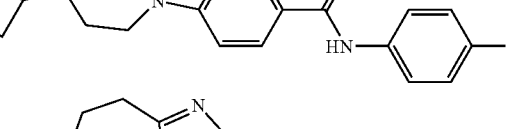
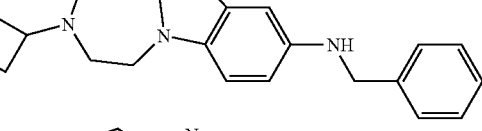
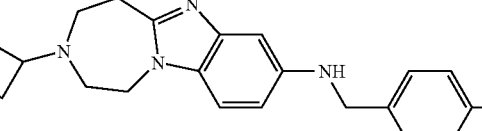
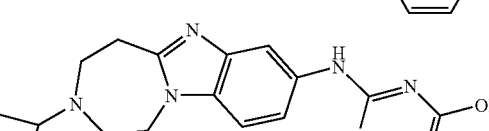
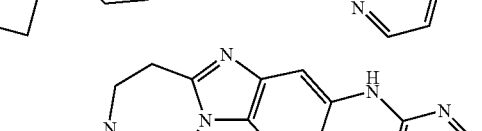
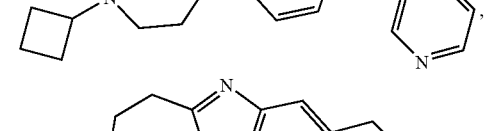
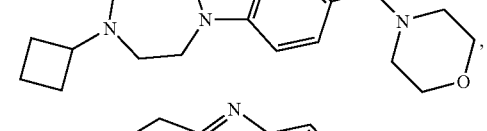
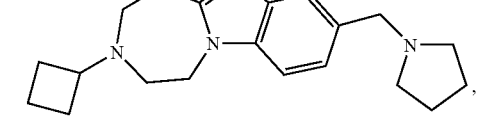

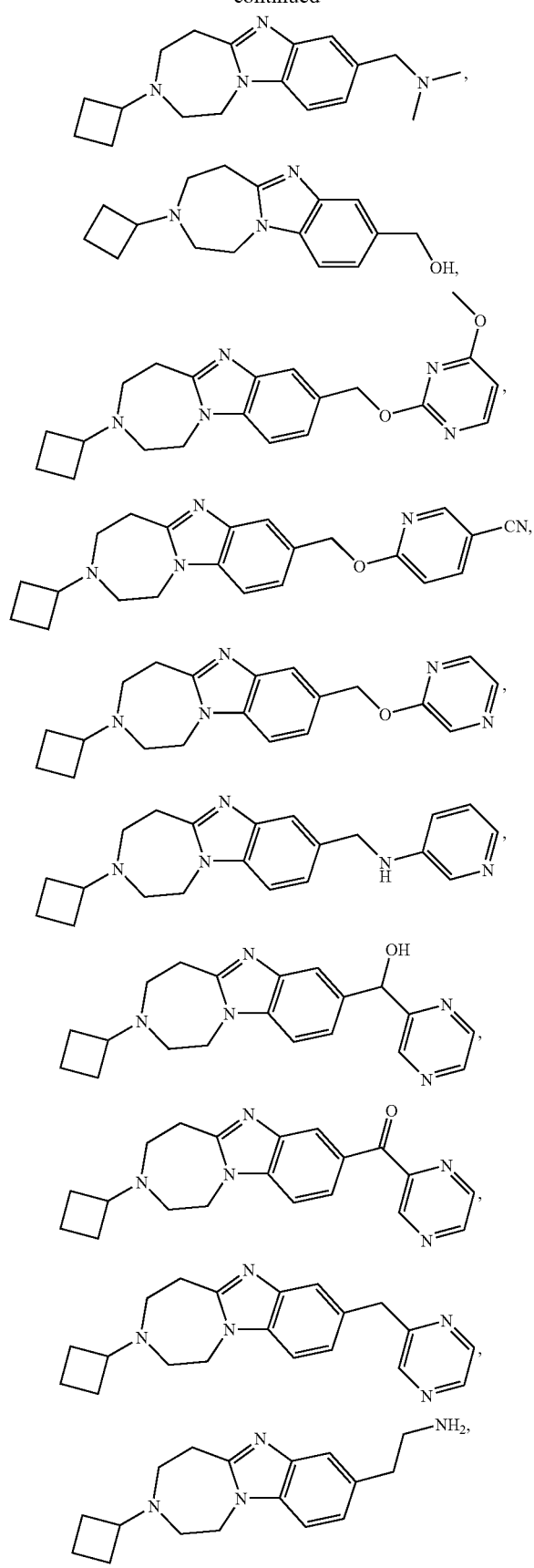
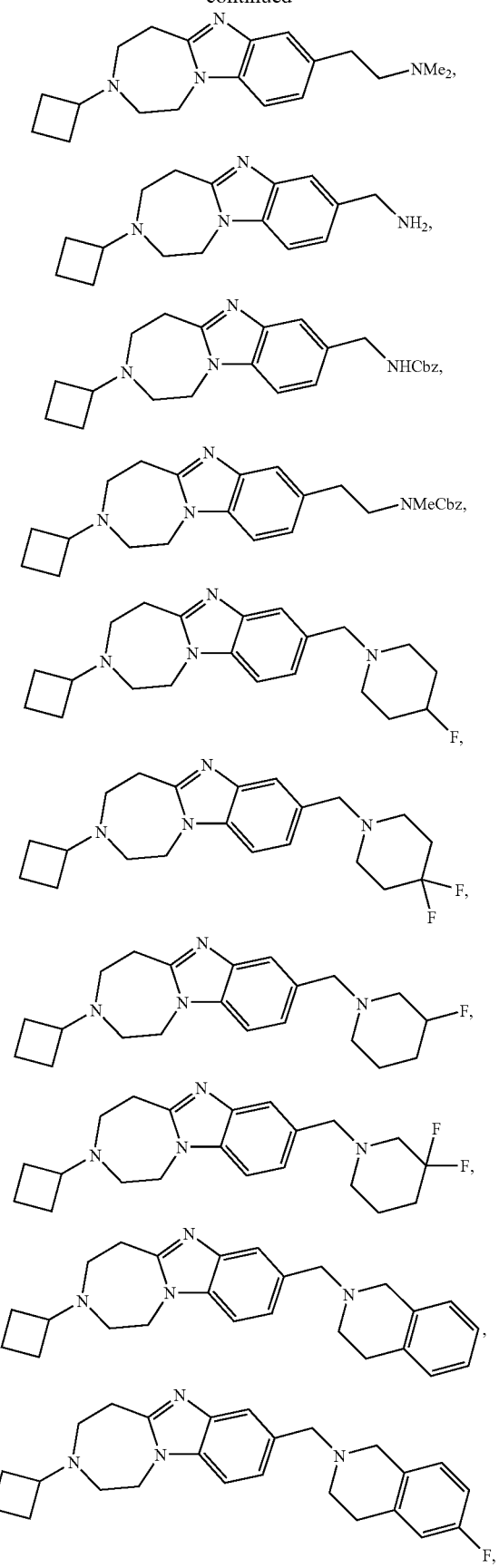

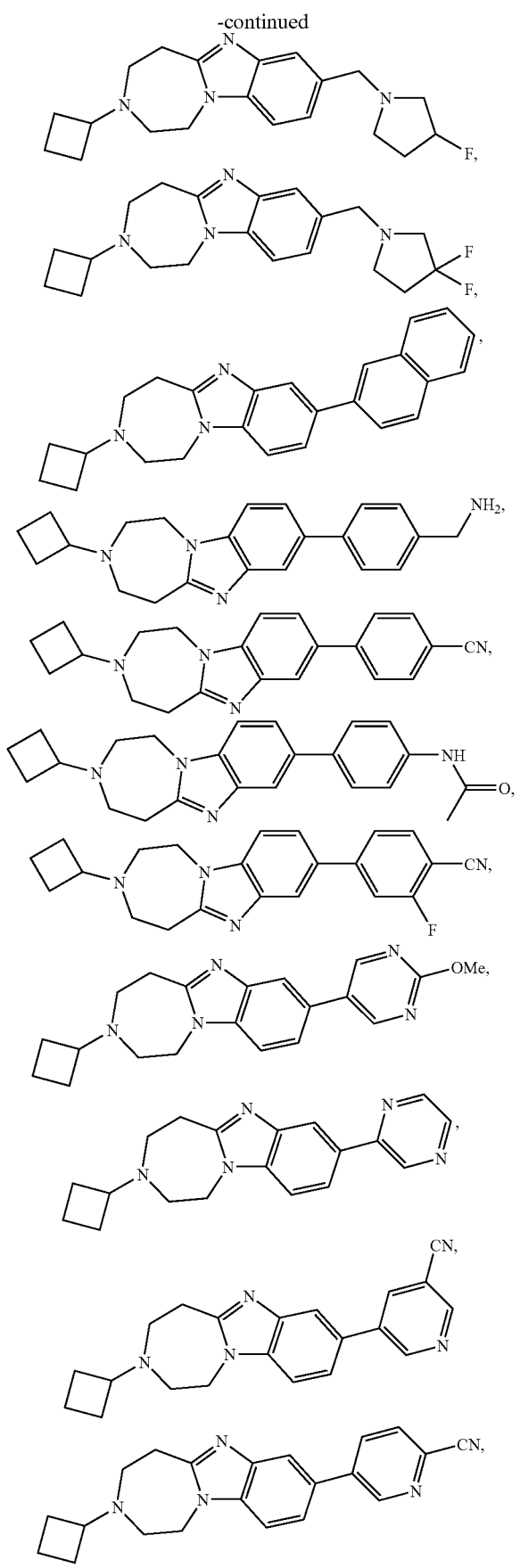

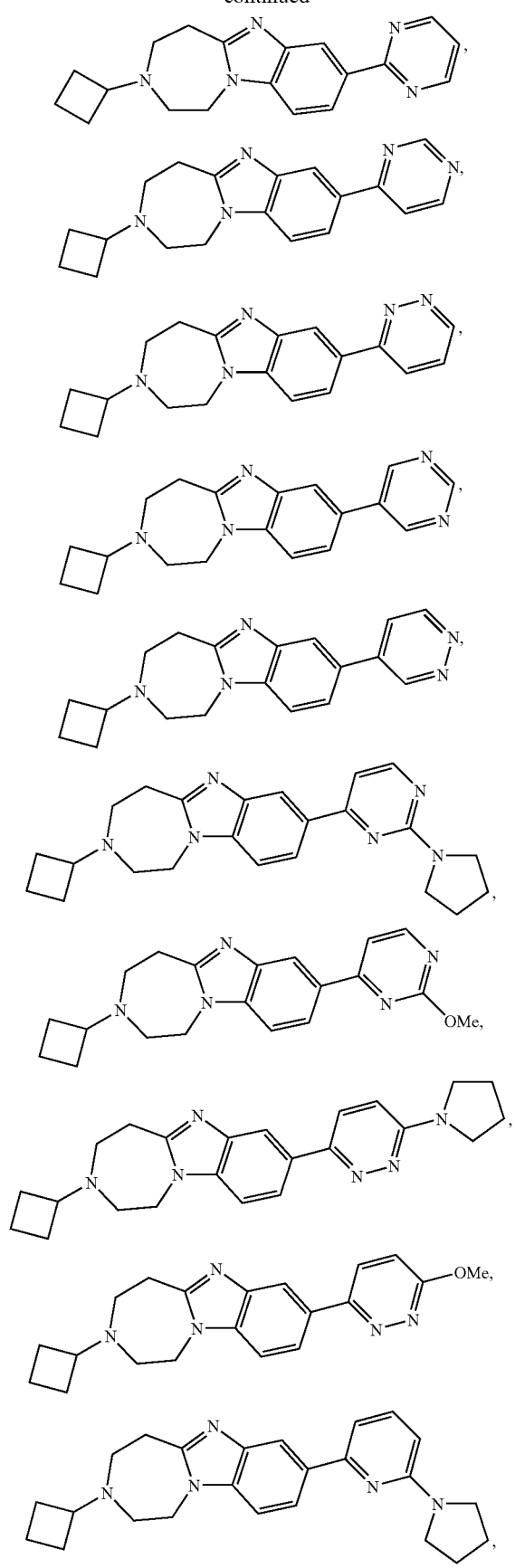

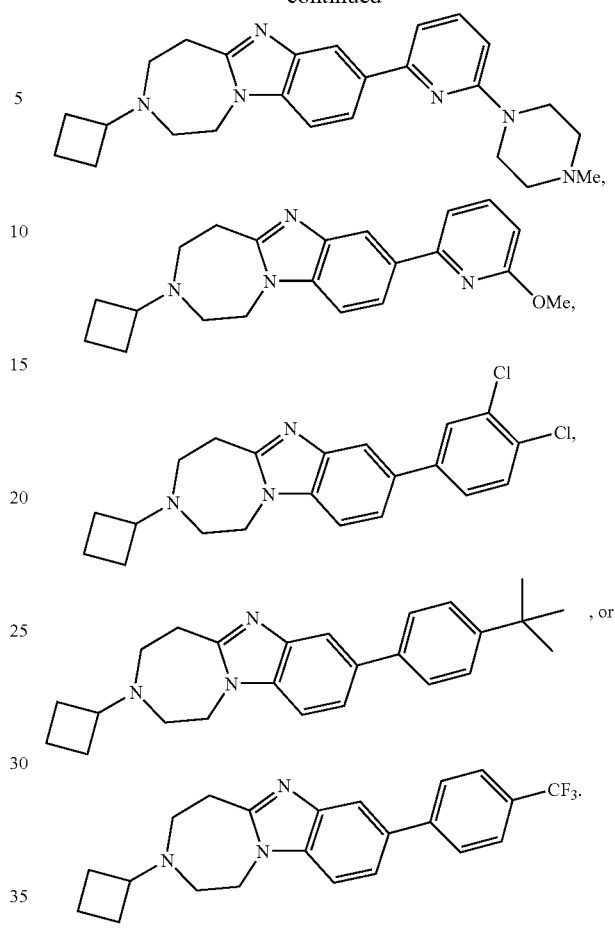

26. The compound of claim 1, or a pharmaceutically acceptable salt, non-stoichiometric hydrate, or stereoisomer thereof, having formula (V):

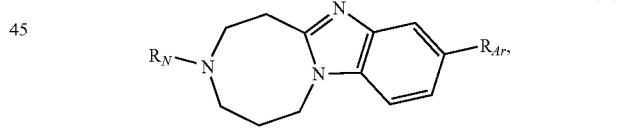

wherein $R_{Ar}$ is (i) hydrogen, halogen, or cyano; (ii) ($C_1$-$C_{10}$)alkyl, ($C_1$-$C_{10}$)alkenyl, ($C_3$-$C_{10}$)cycloalkyl, (6 to 10 membered)aryl, ($C_1$-$C_{10}$)heteroalkyl, ($C_3$-$C_{10}$)heterocycloalkyl, (5 to 10 membered)heteroaryl, alkoxyl, aminoalkyl, amino, imino, amido, carbonyl, thiol, sulfinyl, or sulfonyl, each of which is optionally substituted with one or more $R_1$; or (iii) hydroxyl substituted with $R_1'$.

27. The compound of claim 26, wherein the compound is:

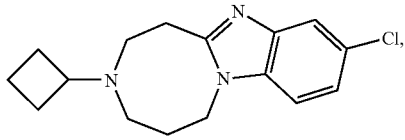

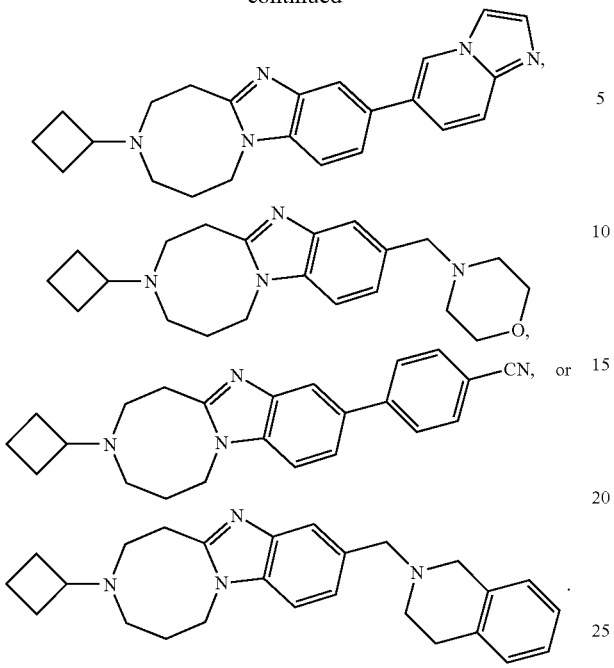

28. A compound of formula (IIb):

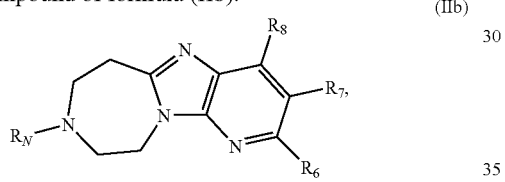

(IIb)

or a pharmaceutically acceptable salt, non-stoichiometric hydrate, or stereoisomer thereof, wherein $R_N$ is hydrogen, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, or (5 to 10 membered)heteroaryl, each of which is optionally substituted with one or more R';

each occurrence of R' is independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$heterocycloalkyl, (5 to 10 membered)heteroaryl, hydroxyl, alkoxyl, aminoalkyl, amino, imino, amido, carbonyl, thiol, sulfinyl, or sulfonyl, each of which is optionally substituted with one or more $R_2$; or two R' substituents together may form a 3 to 10 membered ring optionally substituted with one or more $R_2$;

$R_6$, $R_7$, and $R_8$ are independently hydrogen, halogen, cyano, $(C_1-C_{10})$alkyl, $(C_1-C_{10})$alkenyl, $(C_3-C_{10})$cycloalkyl, (6 to 10 membered)aryl, $(C_1-C_{10})$heteroalkyl, $(C_3-C_{10})$-heterocycloalkyl, (5 to 10 membered)heteroaryl, hydroxyl, alkoxyl, aminoalkyl, amino, imino, amido, carbonyl, thiol, sulfinyl, or sulfonyl, each of which may be optionally substituted with one or more $R_1$; or two adjacent $R_6$, $R_7$, and $R_8$ may together form a 3 to 10 membered ring;

each occurrence of $R_1'$ is independently —C(O)NR$_3$R$_4$, —C(O)R$_3$, $(C_3-C_{10})$cycloalkyl optionally substituted with one or more $R_2$, $(C_6-C_{12})$aralkyl optionally substituted with one or more $R_2$, (6 to 10 membered)aryl optionally substituted with one or more $R_2$, $(C_1-C_{10})$heteroalkyl optionally substituted with one or more $R_2$, $(C_3-C_{10})$heterocycloalkyl optionally substituted with one or more $R_2$, or (5 to 10 membered)heteroaryl optionally substituted with one or more $R_2$;

each occurrence of $R_2$ is independently hydrogen, $(C_1-C_6)$alkyl optionally substituted with one or more $R_3$, $(C_3-C_6)$cycloalkyl optionally substituted with one or more $R_3$, halogen, cyano, =O, —OR$_3$, —NR$_3$R$_4$, —N(R$_3$)C(O)R$_4$, —C(O)NR$_3$R$_4$, —C(O)R$_3$, —C(O)OR$_3$, —OC(O)R$_3$, —S(O)$_m$R$_3$, or —S(O)$_2$NR$_3$R$_4$;

$R_3$ and $R_4$ are each independently hydrogen, $(C_1-C_6)$alkyl, $(C_3-C_6)$cycloalkyl, $(C_7-C_{10})$aralkyl; $(C_1-C_6)$heteroalkyl, $(C_3-C_6)$heterocycloalkyl, (6 to 10 membered)aryl, or (5 to 10 membered)heteroaryl; or $R_3$ and $R_4$ together may form a 3 to 10 membered ring;

m is 0, 1, or 2.

29. The compound of claim 28, wherein $R_6$ and $R_8$ are hydrogen, and $R_N$ is $(C_3-C_{10})$cycloalkyl optionally substituted with one or more R'.

30. The compound of claim 28, wherein $R_7$ is halogen, (6 to 10 membered) aryl optionally substituted with one or more $R_1$, or (5 to 10 membered)heteroaryl optionally substituted with one or more $R_1$.

31. The compound of claim 28, wherein the compound is:

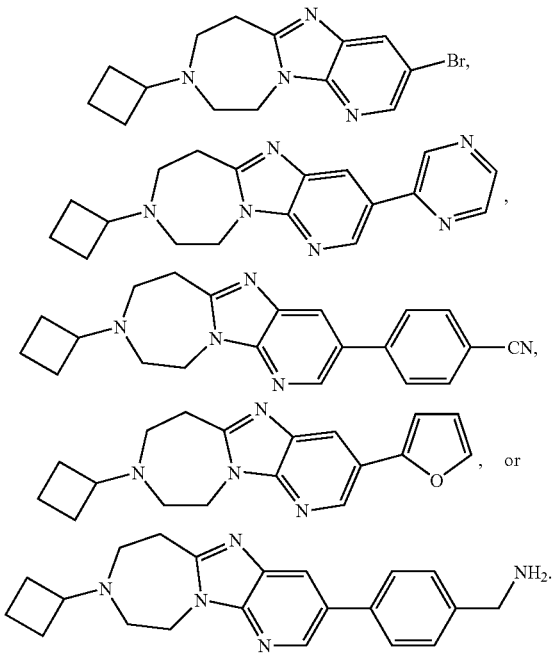

32. A pharmaceutical composition comprising a compound of claim 1, and one or more excipients.

33. The pharmaceutical composition of claim 32, which further comprises one or more additional active agents.

34. The compound of claim 11, wherein $R_N$ is cyclobutyl optionally substituted with one or more R; and $R_{Ar}$ is $(C_1-C_{10})$alkyl or alkoxyl, each of which is optionally substituted with one or more $R_1$.

35. The compound of claim 34, wherein $R_1$ is $(C_3-C_{10})$heterocycloalkyl optionally substituted with one or more $R_2$.

36. The compound of claim 34, wherein $R_{Ar}$ is —CH$_2$R$_1$.

37. The compound of claim 36, wherein R$_1$ is (C$_3$-C$_{10}$) heterocycloalkyl optionally substituted with one or more R$_2$.

38. The compound of claim 11, wherein the compound is:

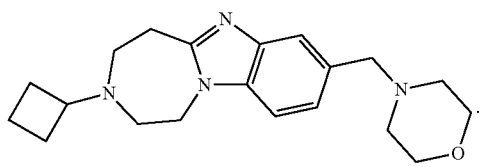

39. The compound of claim 26, wherein R$_N$ is cyclobutyl optionally substituted with one or more R'.

40. The compound of claim 26, wherein R$_{Ar}$ is (C$_1$-C$_{10}$) alkyl or alkoxyl, each of which is optionally substituted with one or more R$_1$.

41. The compound of claim 26, wherein R$_N$ is cyclobutyl optionally substituted with one or more R'; and R$_{Ar}$ is (C$_1$-C$_{10}$)alkyl or alkoxyl, each of which is optionally substituted with one or more R$_1$.

42. The compound of claim 41, wherein R$_1$ is (C$_3$-C$_{10}$) heterocycloalkyl optionally substituted with one or more R$_2$.

43. The compound of claim 41, wherein R$_{Ar}$ is —CH$_2$R$_1$.

44. The compound of claim 43, wherein R$_1$ is (C$_3$-C$_{10}$) heterocycloalkyl optionally substituted with one or more R$_2$.

45. The compound of claim 26, wherein the compound is:

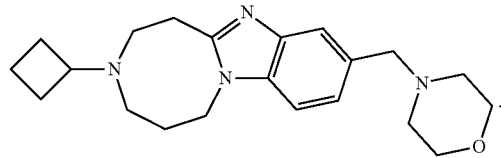

46. The compound of claim 26, wherein the compound is:

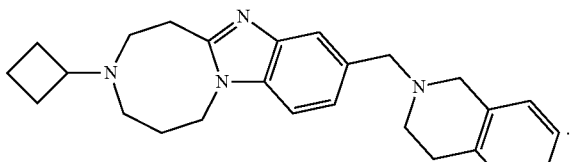

47. The compound of claim 11, wherein the compound is:

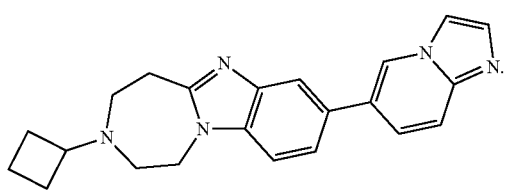

48. The compound of claim 11, wherein the compound is:

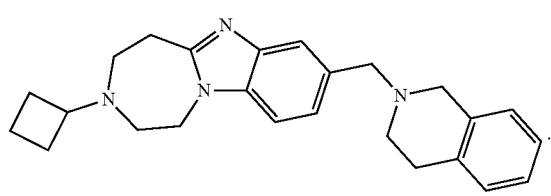

49. A compound having the following structure, or a pharmaceutically acceptable salt thereof:

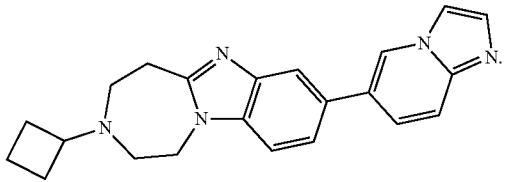

50. A pharmaceutical composition comprising a compound of claim 49, and one or more excipients.

51. A compound having the following structure, or a pharmaceutically acceptable salt thereof:

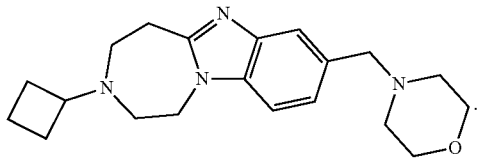

52. A pharmaceutical composition comprising a compound of claim 51, and one or more excipients.

53. A compound having the following structure, or a pharmaceutically acceptable salt thereof:

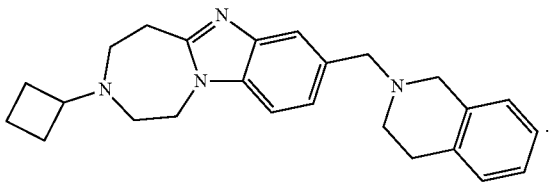

54. A pharmaceutical composition comprising a compound of claim 53, and one or more excipients.

55. A compound having the following structure, or a pharmaceutically acceptable salt thereof:

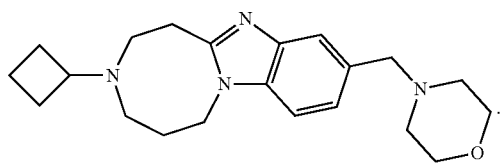

56. A pharmaceutical composition comprising a compound of claim 55, and one or more excipients.

57. A compound having the following structure, or a pharmaceutically acceptable salt thereof:

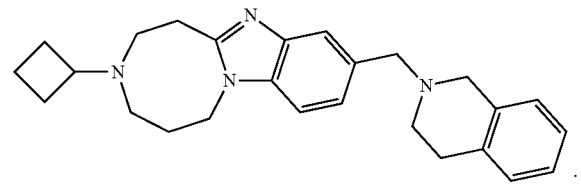

58. A pharmaceutical composition comprising a compound of claim 57, and one or more excipients.

* * * * *